United States Patent
Kwong

(10) Patent No.: US 9,318,710 B2
(45) Date of Patent: Apr. 19, 2016

(54) ORGANIC ELECTROLUMINESCENT MATERIALS AND DEVICES

(71) Applicant: Universal Display Corporation, Ewing, NJ (US)

(72) Inventor: Raymond Kwong, Ewing, NJ (US)

(73) Assignee: UNIVERSAL DISPLAY CORPORATION, Ewing, NJ (US)

(*) Notice: Subject to any disclaimer, the term of this patent is extended or adjusted under 35 U.S.C. 154(b) by 136 days.

(21) Appl. No.: 13/788,741

(22) Filed: Mar. 7, 2013

(65) Prior Publication Data

US 2014/0027734 A1 Jan. 30, 2014

Related U.S. Application Data

(60) Provisional application No. 61/677,310, filed on Jul. 30, 2012.

(51) Int. Cl.
  H01L 51/00 (2006.01)
  H01L 51/50 (2006.01)
  C07F 5/02 (2006.01)

(52) U.S. Cl.
  CPC .............. *H01L 51/0071* (2013.01); *C07F 5/02* (2013.01); *H01L 51/008* (2013.01); *H01L 51/0052* (2013.01); *H01L 51/0058* (2013.01); *H01L 51/5012* (2013.01); *H01L 51/5016* (2013.01)

(58) Field of Classification Search
  CPC ... C07F 5/02; H01L 51/0052; H01L 51/0058; H01L 51/0071; H01L 51/008; H01L 51/5012; H01L 51/5016
  USPC .............. 564/11; 257/40; 546/13; 548/110; 549/4
  See application file for complete search history.

(56) References Cited

U.S. PATENT DOCUMENTS

| | | | |
|---|---|---|---|
| 4,769,292 A | 9/1988 | Tang et al. | |
| 5,061,569 A | 10/1991 | VanSlyke et al. | |
| 5,077,142 A * | 12/1991 | Sakon et al. | 428/690 |
| 5,247,190 A | 9/1993 | Friend et al. | |
| 5,703,436 A | 12/1997 | Forrest et al. | |
| 5,707,745 A | 1/1998 | Forrest et al. | |
| 5,834,893 A | 11/1998 | Bulovic et al. | |
| 5,844,363 A | 12/1998 | Gu et al. | |
| 6,013,982 A | 1/2000 | Thompson et al. | |
| 6,087,196 A | 7/2000 | Sturm et al. | |
| 6,091,195 A | 7/2000 | Forrest et al. | |
| 6,097,147 A | 8/2000 | Baldo et al. | |
| 6,294,398 B1 | 9/2001 | Kim et al. | |
| 6,303,238 B1 | 10/2001 | Thompson et al. | |
| 6,337,102 B1 | 1/2002 | Forrest et al. | |
| 6,468,819 B1 | 10/2002 | Kim et al. | |
| 6,528,187 B1 | 3/2003 | Okada | |
| 6,687,266 B1 | 2/2004 | Ma et al. | |
| 6,835,469 B2 | 12/2004 | Kwong et al. | |
| 6,921,915 B2 | 7/2005 | Takiguchi et al. | |
| 7,087,321 B2 | 8/2006 | Kwong et al. | |
| 7,090,928 B2 | 8/2006 | Thompson et al. | |
| 7,154,114 B2 | 12/2006 | Brooks et al. | |
| 7,250,226 B2 | 7/2007 | Tokito et al. | |
| 7,279,704 B2 | 10/2007 | Walters et al. | |
| 7,332,232 B2 | 2/2008 | Ma et al. | |
| 7,338,722 B2 | 3/2008 | Thompson et al. | |
| 7,393,599 B2 | 7/2008 | Thompson et al. | |
| 7,396,598 B2 | 7/2008 | Takeuchi et al. | |
| 7,431,968 B1 | 10/2008 | Shtein et al. | |
| 7,445,855 B2 | 11/2008 | Mackenzie et al. | |
| 7,534,505 B2 | 5/2009 | Lin et al. | |
| 2002/0034656 A1 | 3/2002 | Thompson et al. | |

(Continued)

FOREIGN PATENT DOCUMENTS

| | | |
|---|---|---|
| EP | 0650955 | 5/1995 |
| EP | 1725079 | 11/2006 |

(Continued)

OTHER PUBLICATIONS

Hatakeyama, et al., "Synthesis of BN-fused Polycyclic Aromatics via Tandem Intramolecular Electrophilic Arene Borylation," J. Am. Chem. Soc., 133, 18614-18617, 2011.*

(Continued)

*Primary Examiner* — Paul A Zucker
*Assistant Examiner* — Mark Luderer
(74) *Attorney, Agent, or Firm* — Duane Morris LLP

(57) ABSTRACT

Boron-nitrogen polyaromatic compounds having a fused aromatic ring system are provided, where the compounds include a [1,2]azaborino[1,2-a][1,2]azaborine

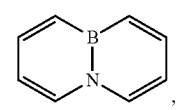

which is optionally fused to one or more aromatic rings or fused aromatic rings; wherein the fused aromatic ring system is substituted by one or more substituents, R, that are not fused to the aromatic ring system, selected from deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof; and wherein any two adjacent substituents, R, are optionally joined to form one or more non-aromatic rings. Devices, such as organic light emitting devices (OLEDs) that comprise light emitting materials are also provided.

33 Claims, 4 Drawing Sheets

(56) References Cited

U.S. PATENT DOCUMENTS

| | | |
|---|---|---|
| 2002/0134984 A1 | 9/2002 | Igarashi |
| 2002/0158242 A1 | 10/2002 | Son et al. |
| 2003/0138657 A1 | 7/2003 | Li et al. |
| 2003/0151042 A1 | 8/2003 | Hueschen |
| 2003/0152802 A1 | 8/2003 | Tsuboyama et al. |
| 2003/0175553 A1 | 9/2003 | Thompson et al. |
| 2003/0230980 A1 | 12/2003 | Forrest et al. |
| 2004/0036077 A1 | 2/2004 | Ise |
| 2004/0137267 A1 | 7/2004 | Igarashi et al. |
| 2004/0137268 A1 | 7/2004 | Igarashi et al. |
| 2004/0174116 A1 | 9/2004 | Lu et al. |
| 2005/0025993 A1 | 2/2005 | Thompson et al. |
| 2005/0112407 A1 | 5/2005 | Ogasawara et al. |
| 2005/0238919 A1 | 10/2005 | Ogasawara |
| 2005/0244673 A1 | 11/2005 | Satoh et al. |
| 2005/0260441 A1 | 11/2005 | Thompson et al. |
| 2005/0260449 A1 | 11/2005 | Walters et al. |
| 2006/0008670 A1 | 1/2006 | Lin et al. |
| 2006/0202194 A1 | 9/2006 | Jeong et al. |
| 2006/0240279 A1 | 10/2006 | Adamovich et al. |
| 2006/0251923 A1 | 11/2006 | Lin et al. |
| 2006/0263635 A1 | 11/2006 | Ise |
| 2006/0280965 A1 | 12/2006 | Kwong et al. |
| 2007/0048545 A1* | 3/2007 | Hatwar et al. ............... 428/690 |
| 2007/0190359 A1 | 8/2007 | Knowles et al. |
| 2007/0278938 A1 | 12/2007 | Yabunouchi et al. |
| 2008/0015355 A1 | 1/2008 | Schafer et al. |
| 2008/0018221 A1 | 1/2008 | Egen et al. |
| 2008/0106190 A1 | 5/2008 | Yabunouchi et al. |
| 2008/0124572 A1 | 5/2008 | Mizuki et al. |
| 2008/0157657 A1* | 7/2008 | Matsunami et al. ........... 313/504 |
| 2008/0220265 A1 | 9/2008 | Xia et al. |
| 2008/0297033 A1 | 12/2008 | Knowles et al. |
| 2009/0008605 A1 | 1/2009 | Kawamura et al. |
| 2009/0009065 A1 | 1/2009 | Nishimura et al. |
| 2009/0017330 A1 | 1/2009 | Iwakuma et al. |
| 2009/0030202 A1 | 1/2009 | Iwakuma et al. |
| 2009/0039776 A1 | 2/2009 | Yamada et al. |
| 2009/0045730 A1 | 2/2009 | Nishimura et al. |
| 2009/0045731 A1 | 2/2009 | Nishimura et al. |
| 2009/0101870 A1 | 4/2009 | Prakash et al. |
| 2009/0108737 A1 | 4/2009 | Kwong et al. |
| 2009/0115316 A1 | 5/2009 | Zheng et al. |
| 2009/0165846 A1 | 7/2009 | Johannes et al. |
| 2009/0167162 A1 | 7/2009 | Lin et al. |
| 2009/0179554 A1 | 7/2009 | Kuma et al. |
| 2011/0284899 A1* | 11/2011 | Hack et al. .................. 257/98 |

FOREIGN PATENT DOCUMENTS

| | | |
|---|---|---|
| EP | 2034538 | 3/2009 |
| EP | 2112214 | * 10/2009 ............ C09K 11/06 |
| JP | 2005011610 | 1/2005 |
| JP | 2007123392 | 5/2007 |
| JP | 2007254297 | 10/2007 |
| JP | 2008074939 | 4/2008 |
| WO | 0139234 | 5/2001 |
| WO | 0202714 | 1/2002 |
| WO | 0215645 | 2/2002 |
| WO | 03040257 | 5/2003 |
| WO | 03060956 | 7/2003 |
| WO | 2004093207 | 10/2004 |
| WO | 2004107822 | 12/2004 |
| WO | 2005014551 | 2/2005 |
| WO | 2005019373 | 3/2005 |
| WO | 2005030900 | 4/2005 |
| WO | 2005089025 | 9/2005 |
| WO | 2005123873 | 12/2005 |
| WO | 2006009024 | 1/2006 |
| WO | 2006056418 | 6/2006 |
| WO | 2006072002 | 7/2006 |
| WO | 2006082742 | 8/2006 |
| WO | 2006098120 | 9/2006 |
| WO | 2006100298 | 9/2006 |
| WO | 2006103874 | 10/2006 |
| WO | 2006114966 | 11/2006 |
| WO | 2006132173 | 12/2006 |
| WO | 2007002683 | 1/2007 |
| WO | 2007004380 | 1/2007 |
| WO | 2007063754 | 6/2007 |
| WO | 2007063796 | 6/2007 |
| WO | 2008056746 | 5/2008 |
| WO | 2008101842 | 8/2008 |
| WO | 2008132085 | 11/2008 |
| WO | 2009000673 | 12/2008 |
| WO | 2009003898 | 1/2009 |
| WO | 2009008311 | 1/2009 |
| WO | 2009018009 | 2/2009 |
| WO | 2009050290 | 4/2009 |
| WO | 2009021126 | 5/2009 |
| WO | 2009062578 | 5/2009 |
| WO | 2009063833 | 5/2009 |
| WO | 2009066778 | 5/2009 |
| WO | 2009066779 | 5/2009 |
| WO | 2009086028 | 7/2009 |
| WO | 2009100991 | 8/2009 |

OTHER PUBLICATIONS

Davis et al., "New Heteroaromatic Compounds. XXVII. Boron-11 Chemical Shifts of Some Heteroaromatic Boron Compounds," J. Am. Chem. Soc., 90(3), 706-708, 1968.*

Xie et al, "Tuning spectral properties of fullerenes by substitutional doping," Physical Review B 69, 201403(R)-201403-4, 2004.*

Adachi, Chihaya et al., "Organic Electroluminescent Device Having a Hole Conductor as an Emitting Layer," Appl. Phys. Lett., 55(15): 1489-1491 (1989).

Adachi, Chihaya et al., "Nearly 100% Internal Phosphorescence Efficiency in an Organic Light Emitting Device," J. Appl. Phys., 90(10): 5048-5051 (2001).

Adachi, Chihaya et al., "High-Efficiency Red Electrophosphorescence Devices," Appl. Phys. Lett., 78(11)1622-1624 (2001).

Aonuma, Masaki et al., "Material Design of Hole Transport Materials Capable of Thick-Film Formation in Organic Light Emitting Diodes," Appl. Phys. Lett., 90:183503-1-183503-3.

Baldo et al., Highly Efficient Phosphorescent Emission from Organic Electroluminescent Devices, Nature, vol. 395, 151-154, (1998).

Baldo et al., Very high-efficiency green organic light-emitting devices based on electrophosphorescence, Appl. Phys. Lett., vol. 75, No. 3, 4-6 (1999).

Gao, Zhiqiang et al., "Bright-Blue Electroluminescence From a Silyl-Substituted ter-(phenylene-vinylene) derivative," Appl. Phys. Lett., 74(6): 865-867 (1999).

Guo, Tzung-Fang et al., "Highly Efficient Electrophosphorescent Polymer Light-Emitting Devices," Organic Electronics, 115-20 (2000).

Hamada, Yuji et al., "High Luminance in Organic Electroluminescent Devices with Bis(10-hydroxybenzo[h]quinolinato) beryllium as an Emitter," Chem. Lett., 905-906 (1993).

Holmes, R.J. et al., "Blue Organic Electrophosphorescence Using Exothermic Host-Guest Energy Transfer," Appl. Phys. Lett., 82(15):2422-2424 (2003).

Hu, Nan-Xing et al., "Novel High Tg Hole-Transport Molecules Based on Indolo[3,2-b]carbazoles for Organic Light-Emitting Devices," Synthetic Metals, 111-112:421-424 (2000).

Huang, Jinsong et al., "Highly Efficient Red-Emission Polymer Phosphorescent Light-Emitting Diodes Based on Two Novel Tris(1-phenylisoquinolinato-C2,N)iridium(III) Derivates," Adv. Mater, 19:739-743 (2007).

Huang, Wei-Sheng et al., "Highly Phosphorescent Bis-Cyclometalated Iridium Complexes Containing Benzoimidazole-Based Ligands," Chem. Mater, 16(12):2480-2488 (2004).

Hung, L.S. et al., "Anode Modification in Organic Light-Emitting Diodes by Low-Frequency Plasma Polymerization of CHF3," Appl. Phys. Lett., 78(5):673-675 (2001).

Ikai, Masamichi and Tokito, Shizuo, "Highly Efficient Phosphorescence From Organic Light-Emitting Devices with an Exciton-Block Layer," Appl. Phys. Lett., 79(2):156-158 (2001).

(56) References Cited

OTHER PUBLICATIONS

Ikeda, Hisao et al., "P-185 Low-Drive-Voltage OLEDs with a Buffer Layer Having Molybdenum Oxide," SID Symposium Digest, 37:923-926 (2006).

Inada, Hiroshi and Shirota, Yasuhiko, "1,3,5-Tris[4-(diphenylamino)phenyl]benzene and its Methylsubstituted Derivatives as a Novel Class of Amorphous Molecular Materials," J. Mater. Chem., 3(3):319-320 (1993).

Kanno, Hiroshi et al., "Highly Efficient and Stable Red Phosphorescent Organic Light-Emitting Device Using bis[2-(2-benzothiazoyl)phenolato]zinc(II) as host material," Appl. Phys. Lett., 90:123509-1-123509-3 (2007).

Kido, Junji et al., 1,2,4-Triazole Derivative as an Electron Transport Layer in Organic Electroluminescent Devices, Jpn. J. Appl. Phys., 32:L917-L920 (1993).

Kuwabara, Yoshiyuki et al., "Thermally Stable Multilayered Organic Electroluminescent Devices Using Novel Starburst Molecules, 4,4',4"-Tri(N-carbazolyl)triphenylamine (TCTA) and 4,4',4"-Tris(3-methylphenylphenyl-amino) triphenylamine (m-MTDATA), as Hole-Transport Materials," Adv. Mater., 6(9):677-679 (1994).

Kwong, Raymond C. et al., "High Operational Stability of Electrophosphorescent Devices," Appl. Phys. Lett., 81(1) 162-164 (2002).

Lamansky, Sergey et al., "Synthesis and Characterization of Phosphorescent Cyclometalated Iridium Complexes," Inorg. Chem., 40(7):1704-1711 (2001).

Lee, Chang-Lyoul et al., "Polymer Phosphorescent Light-Emitting Devices Doped with Tris(2-phenylpyridine) Iridium as a Triplet Emitter," Appl. Phys. Lett., 77(15)2280-2282 (2000).

Lo, Shih-Chun et al., "Blue Phosphorescence from Indium(III) Complexes at Room Temperature," Chem. Mater., 18(21)5119-5129 (2006).

Ma, Yuguang et al., "Triplet Luminescent Dinuclear-Gold(I) Complex-Based Light-Emitting Diodes with Low Turn-On voltage," Appl. Phys. Lett., 74(10):1361-1363 (1999).

Mi, Bao-Xiu et al., "Thermally Stable Hole-Transporting Material for Organic Light-Emitting Diode an Isoindole Derivative," Chem. Mater., 15(16):3148-3151 (2003).

Nishida, Jun-ichi et al., "Preparation, Characterization, and Electroluminescence Characteristics of α-Diimine-type Platinum(II) Complexes with Perfluorinated Phenyl Groups as Ligands," Chem. Lett., 34(4): 592-593 (2005).

Niu, Yu-Hua et al., "Highly Efficient Electrophosphorescent Devices with Saturated Red Emission from a Neutral Osmium Complex," Chem. Mater., 17(13):3532-3536 (2005).

Noda, Tetsuya and Shirota,Yasuhiko, "5,5'-Bis(dimesitylboryl)-2,2'-bithiophene and 5,5'-Bis(dimesitylboryl)-2,2'5',2"-terthiophene as a Novel Family of Electron-Transporting Amorphous Molecular Materials," J. Am. Chem. Soc., 120 (37):9714-9715 (1998).

Okumoto, Kenji et al., "Green Fluorescent Organic Light-Emitting Device with External Quantum Efficiency of Nearly 10%," Appl. Phys. Lett., 89:063504-1-063504-3 (2006).

Palilis, Leonidas C., "High Efficiency Molecular Organic Light-Emitting Diodes Based on Silole Derivatives and Their Exciplexes," Organic Electronics, 4:113-121 (2003).

Paulose, Betty Marie Jennifer S. et al., "First Examples of Alkenyl Pyridines as Organic Ligands for Phosphorescent Iridium Complexes," Adv. Mater., 16(22):2003-2007 (2004).

Ranjan, Sudhir et al., "Realizing Green Phosphorescent Light-Emitting Materials from Rhenium(I) Pyrazolato Diimine Complexes," Inorg. Chem., 42(4):1248-1255 (2003).

Sakamoto,Youichi et al., "Synthesis, Characterization, and Electron-Transport Property of Perfluorinated Phenylene Dendrimers," J. Am. Chem. Soc., 122(8):1832-1833 (2000).

Salbeck, J. et al., "Low Molecular Organic Glasses for Blue Electroluminescence," Synthetic Metals, 91209-215 (1997).

Shirota, Yasuhiko et al., "Starburst Molecules Based on p-Electron Systems as Materials for Organic Electroluminescent Devices," Journal of Luminescence, 72-74:985-991 (1997).

Sotoyama, Wataru et al., "Efficient Organic Light-Emitting Diodes with Phosphorescent Platinum Complexes Containing $N^{\wedge}C^{\wedge}N$-Coordinating Tridentate Ligand," Appl. Phys. Lett., 86:153505-1-153505-3 (2005).

Sun, Yiru and Forrest, Stephen R., "High-Efficiency White Organic Light Emitting Devices with Three Separate Phosphorescent Emission Layers," Appl. Phys. Lett., 91:263503-1-263503-3 (2007).

T. Östergaård et al., "Langmuir-Blodgett Light-Emitting Diodes of Poly(3-Hexylthiophene) Electro-Optical Characteristics Related to Structure," Synthetic Metals, 87:171-177 (1997).

Takizawa, Shin-ya et al., "Phosphorescent Iridium Complexes Based on 2-Phenylimidazo[1,2-α]pyridine Ligands Tuning of Emission Color toward the Blue Region and Application to Polymer Light-Emitting Devices," Inorg. Chem., 46(10):4308-4319 (2007).

Tang, C.W. and VanSlyke, S.A., "Organic Electroluminescent Diodes," Appl. Phys. Lett., 51(12):913-915 (1987).

Tung, Yung-Liang et al., "Organic Light-Emitting Diodes Based on Charge-Neutral Ru II PHosphorescent Emitters," Adv. Mater., 17(8)1059-1064 (2005).

Van Slyke, S. A. et al., "Organic Electroluminescent Devices with Improved Stability," Appl. Phys. Lett., 69(15):2160-2162 (1996).

Wang, Y. et al., "Highly Efficient Electroluminescent Materials Based on Fluorinated Organometallic Iridium Compounds," Appl. Phys. Lett., 79(4):449-451 (2001).

Wong, Keith Man-Chung et al., A Novel Class of Phosphorescent Gold(III) Alkynyl-Based Organic Light-Emitting Devices with Tunable Colour, Chem. Commun., 2906-2908 (2005).

Wong, Wai-Yeung, "Multifunctional Iridium Complexes Based on Carbazole Modules as Highly Efficient Electrophosphors," Angew. Chem. Int. Ed., 45:7800-7803 (2006).

\* cited by examiner

ORGANIC ELECTROLUMINESCENT MATERIALS AND DEVICES

CROSS-REFERENCE TO RELATED APPLICATIONS

This application claims priority to U.S. Provisional Application Ser. No. 61/677,310, filed Jul. 30, 2012, the entire contents of which are incorporated herein by reference.

JOINT RESEARCH AGREEMENT

The claimed invention was made by, on behalf of, and/or in connection with one or more of the following parties to a joint university corporation research agreement: Regents of the University of Michigan, Princeton University, University of Southern California, and the Universal Display Corporation. The agreement was in effect on and before the date the claimed invention was made, and the claimed invention was made as a result of activities undertaken within the scope of the agreement.

FIELD OF THE INVENTION

The present invention relates to organic light emitting devices (OLEDs). More specifically, the invention relates to light emitting materials that may have improved photoluminescence and electroluminescence stability.

BACKGROUND

Opto-electronic devices that make use of organic materials are becoming increasingly desirable for a number of reasons. Many of the materials used to make such devices are relatively inexpensive, so organic opto-electronic devices have the potential for cost advantages over inorganic devices. In addition, the inherent properties of organic materials, such as their flexibility, may make them well suited for particular applications such as fabrication on a flexible substrate. Examples of organic opto-electronic devices include organic light emitting devices (OLEDs), organic phototransistors, organic photovoltaic cells, and organic photodetectors. For OLEDs, the organic materials may have performance advantages over conventional materials. For example, the wavelength at which an organic emissive layer emits light may generally be readily tuned with appropriate dopants.

OLEDs make use of thin organic films that emit light when voltage is applied across the device. OLEDs are becoming an increasingly interesting technology for use in applications such as flat panel displays, illumination, and backlighting. Several OLED materials and configurations are described in U.S. Pat. Nos. 5,844,363, 6,303,238, and 5,707,745, which are incorporated herein by reference in their entirety.

One application for phosphorescent emissive molecules is a full color display. Industry standards for such a display call for pixels adapted to emit particular colors, referred to as "saturated" colors. In particular, these standards call for saturated red, green, and blue pixels. Color may be measured using CIE coordinates, which are well known to the art.

One example of a green emissive molecule is tris(2-phenylpyridine) iridium, denoted Ir(ppy)$_3$, which has the following structure:

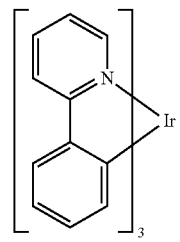

In this, and later figures herein, we depict the dative bond from nitrogen to metal (here, Ir) as a straight line.

As used herein, the term "organic" includes polymeric materials as well as small molecule organic materials that may be used to fabricate organic opto-electronic devices. "Small molecule" refers to any organic material that is not a polymer, and "small molecules" may actually be quite large. Small molecules may include repeat units in some circumstances. For example, using a long chain alkyl group as a substituent does not remove a molecule from the "small molecule" class. Small molecules may also be incorporated into polymers, for example as a pendent group on a polymer backbone or as a part of the backbone. Small molecules may also serve as the core moiety of a dendrimer, which consists of a series of chemical shells built on the core moiety. The core moiety of a dendrimer may be a fluorescent or phosphorescent small molecule emitter. A dendrimer may be a "small molecule," and it is believed that all dendrimers currently used in the field of OLEDs are small molecules.

As used herein, "top" means furthest away from the substrate, while "bottom" means closest to the substrate. Where a first layer is described as "disposed over" a second layer, the first layer is disposed further away from substrate. There may be other layers between the first and second layer, unless it is specified that the first layer is "in contact with" the second layer. For example, a cathode may be described as "disposed over" an anode, even though there are various organic layers in between.

As used herein, "solution processible" means capable of being dissolved, dispersed, or transported in and/or deposited from a liquid medium, either in solution or suspension form.

A ligand may be referred to as "photoactive" when it is believed that the ligand directly contributes to the photoactive properties of an emissive material. A ligand may be referred to as "ancillary" when it is believed that the ligand does not contribute to the photoactive properties of an emissive material, although an ancillary ligand may alter the properties of a photoactive ligand.

As used herein, and as would be generally understood by one skilled in the art, a first "Highest Occupied Molecular Orbital" (HOMO) or "Lowest Unoccupied Molecular Orbital" (LUMO) energy level is "greater than" or "higher than" a second HOMO or LUMO energy level if the first energy level is closer to the vacuum energy level. Since ionization potentials (IP) are measured as a negative energy relative to a vacuum level, a higher HOMO energy level corresponds to an IP having a smaller absolute value (an IP that is less negative). Similarly, a higher LUMO energy level corresponds to an electron affinity (EA) having a smaller absolute value (an EA that is less negative). On a conventional energy level diagram, with the vacuum level at the top, the LUMO energy level of a material is higher than the HOMO energy level of the same material. A "higher" HOMO or LUMO energy level appears closer to the top of such a diagram than a "lower" HOMO or LUMO energy level.

As used herein, and as would be generally understood by one skilled in the art, a first work function is "greater than" or "higher than" a second work function if the first work function has a higher absolute value. Because work functions are generally measured as negative numbers relative to vacuum level, this means that a "higher" work function is more negative. On a conventional energy level diagram, with the vacuum level at the top, a "higher" work function is illustrated as further away from the vacuum level in the downward direction. Thus, the definitions of HOMO and LUMO energy levels follow a different convention than work functions.

More details on OLEDs, and the definitions described above, can be found in U.S. Pat. No. 7,279,704, which is incorporated herein by reference in its entirety.

SUMMARY OF THE INVENTION

A new type of material is provided, which includes boron-nitrogen polyaromatic compounds having a fused aromatic ring system that includes a [1,2]azaborino[1,2-a]-[1,2]azaborine which is optionally fused to one or more aromatic rings or fused aromatic rings; wherein the fused aromatic ring system is substituted by one or more substituents, R, that are not fused to the aromatic ring system, selected from the group consisting of deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof; and wherein any two adjacent substituents, R, are optionally joined to form one or more non-aromatic rings.

In some such embodiments, the fused aromatic ring system is selected from the group consisting of:

Compound 1-1

Compound 1-2

Compound 1-3

Compound 2-1

Compound 2-2

Compound 2-3

Compound 2-4

Compound 2-5

Compound 2-6

Compound 2-7

Compound 2-8

Compound 2-9

Compound 2-10
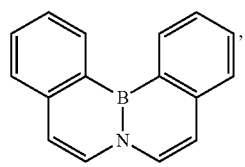
Compound 2-11
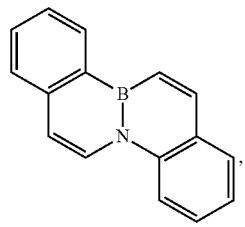
Compound 2-12
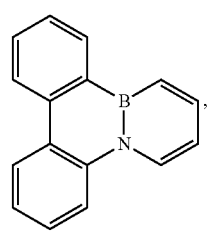
Compound 2-13
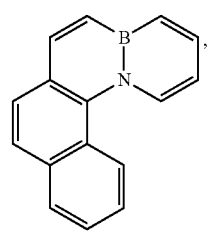
Compound 2-14
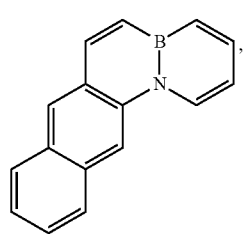
Compound 2-15
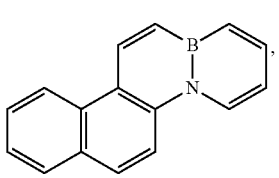
Compound 2-16
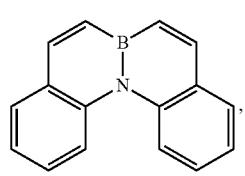
Compound 2-17
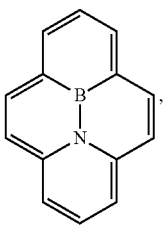
Compound 3-1
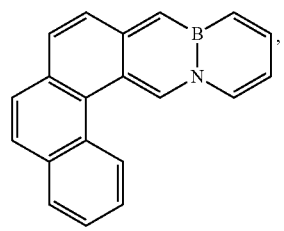
Compound 3-2
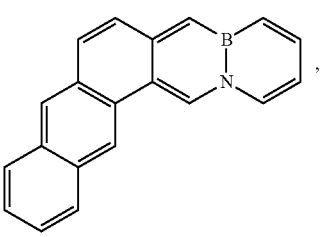
Compound 3-3
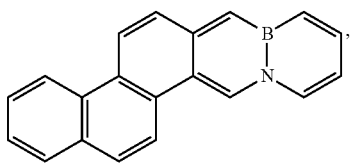
Compound 3-4
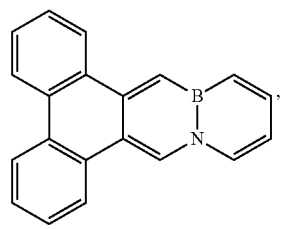
Compound 3-5
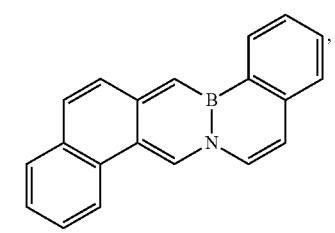
Compound 3-6
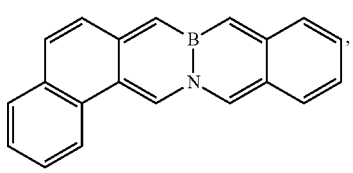

-continued
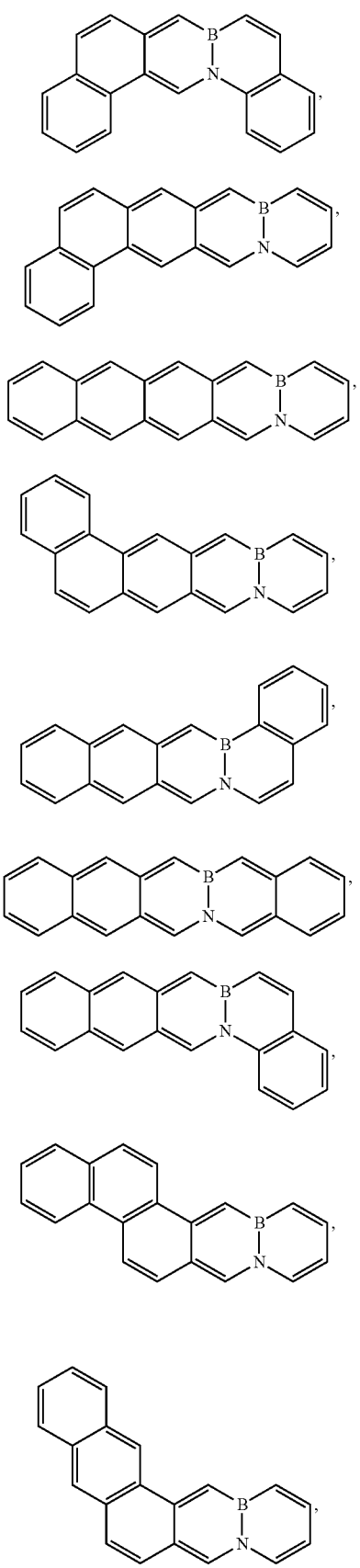
Compound 3-7
Compound 3-8
Compound 3-9
Compound 3-10
Compound 3-11
Compound 3-12
Compound 3-13
Compound 3-14
Compound 3-15
-continued
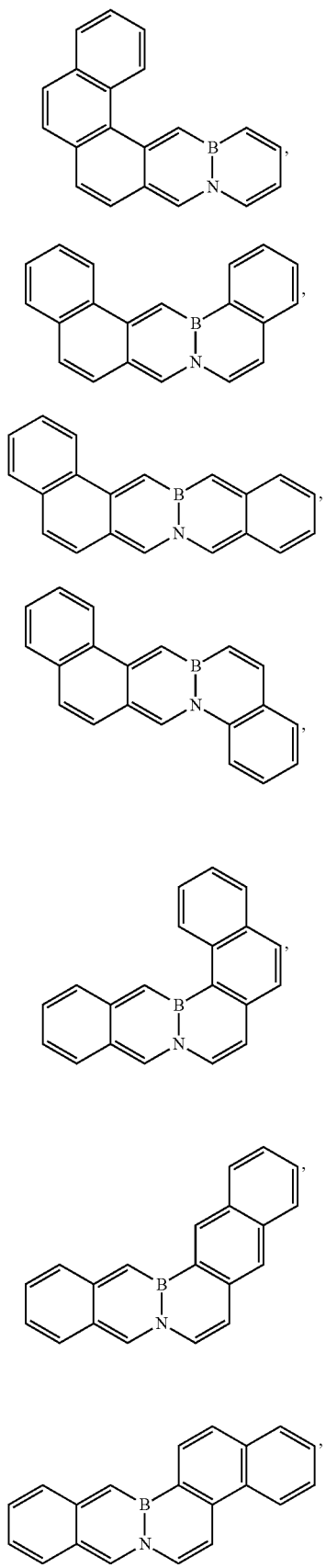
Compound 3-16
Compound 3-17
Compound 3-18
Compound 3-19
Compound 3-20
Compound 3-21
Compound 3-22

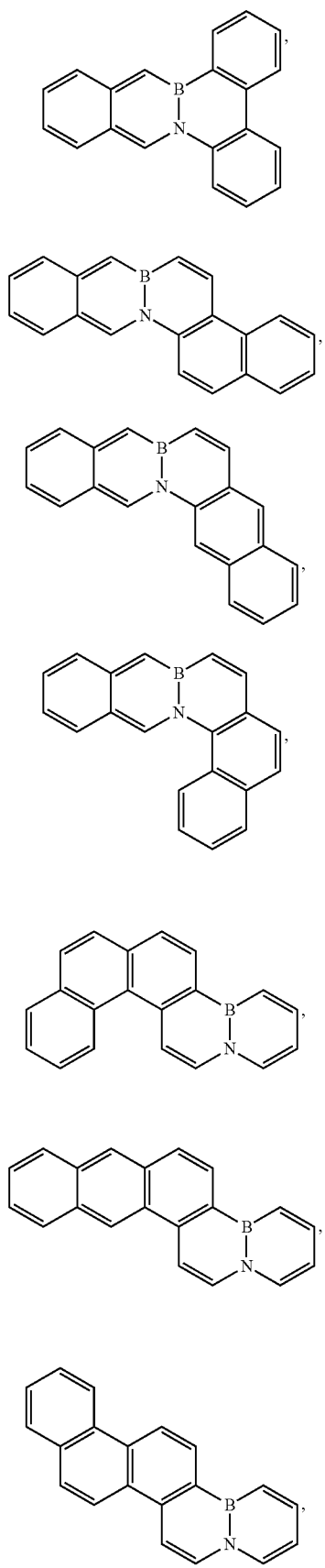

-continued
Compound 3-36
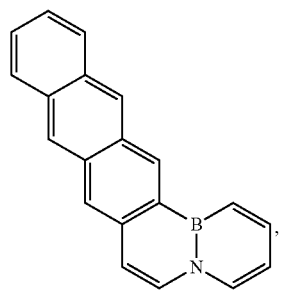
Compound 3-37
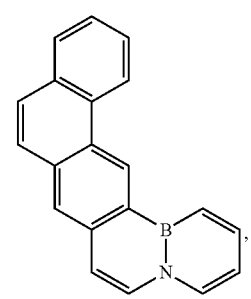
Compound 3-38
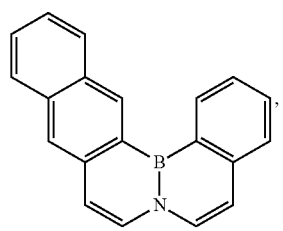
Compound 3-39
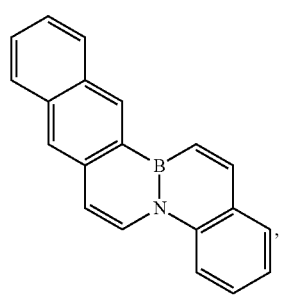
Compound 3-40
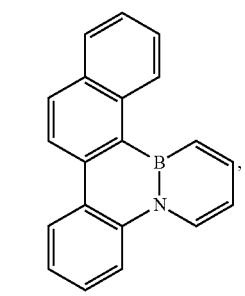
-continued
Compound 3-41
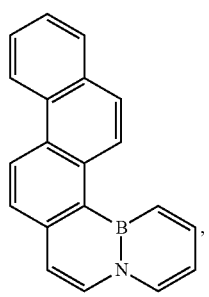
Compound 3-42
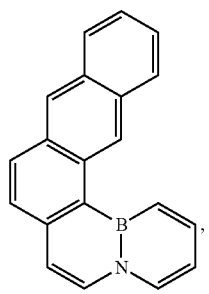
Compound 3-43
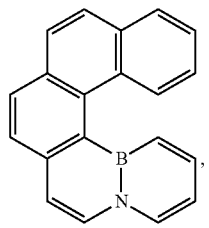
Compound 3-44
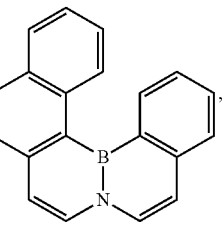
Compound 3-45
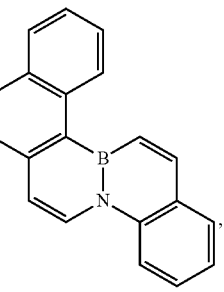
Compound 3-46
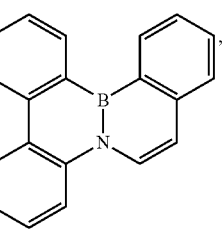

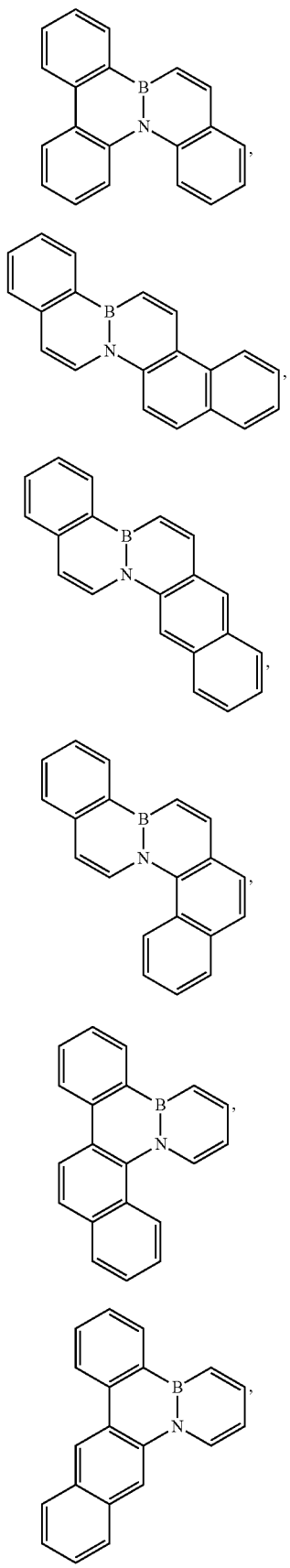
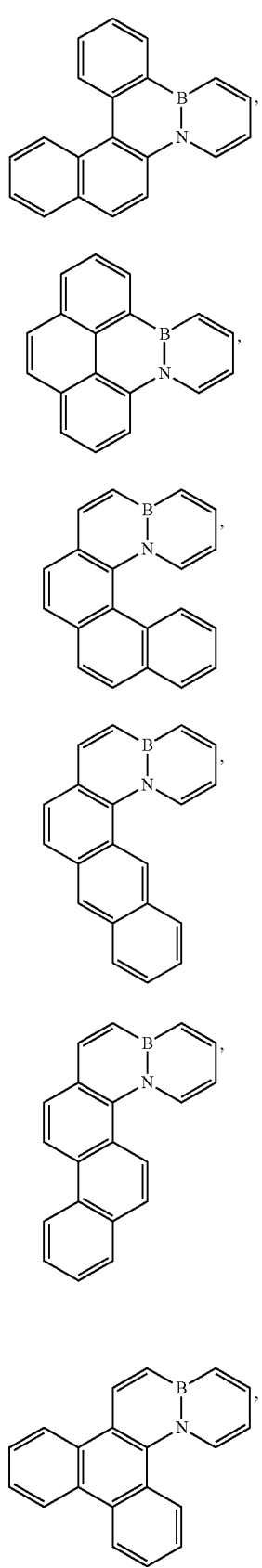

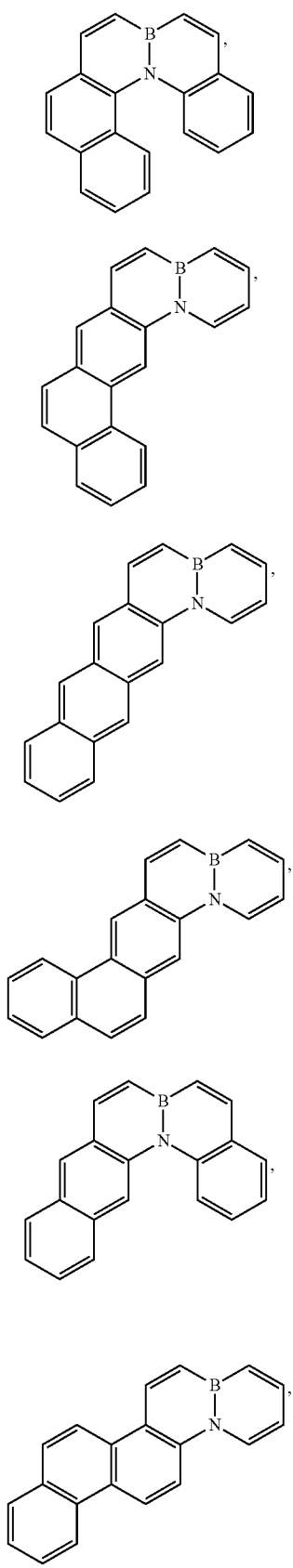
Compound 3-59
Compound 3-60
Compound 3-61
Compound 3-62
Compound 3-63
Compound 3-64
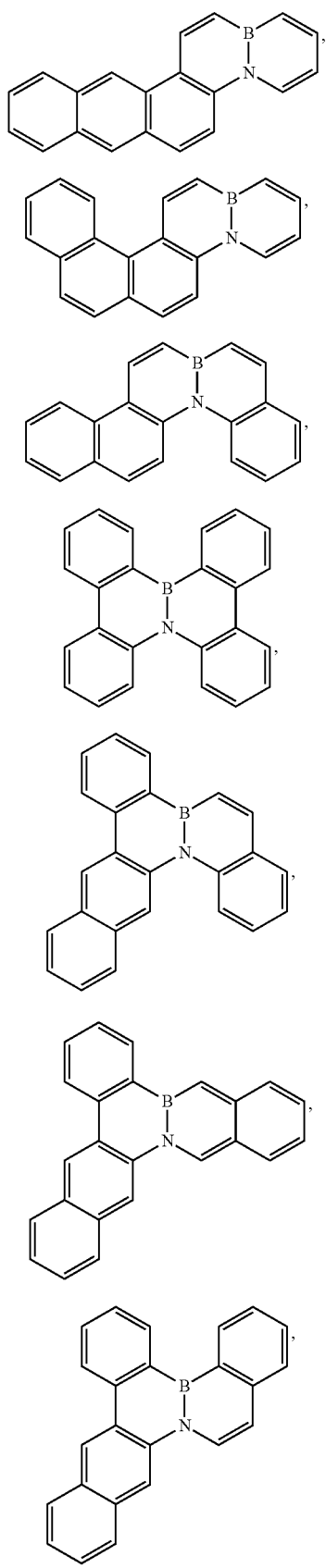
Compound 3-65
Compound 3-66
Compound 3-67
Compound 4-1
Compound 4-2
Compound 4-3
Compound 4-4

-continued
Compound 4-5
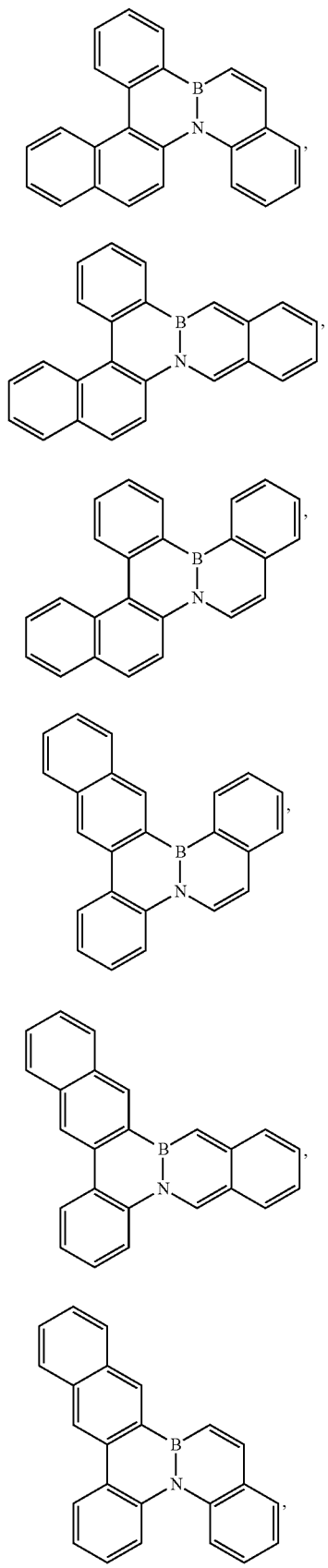
Compound 4-6
Compound 4-7
Compound 4-8
Compound 4-9
Compound 4-10
-continued
Compound 4-11
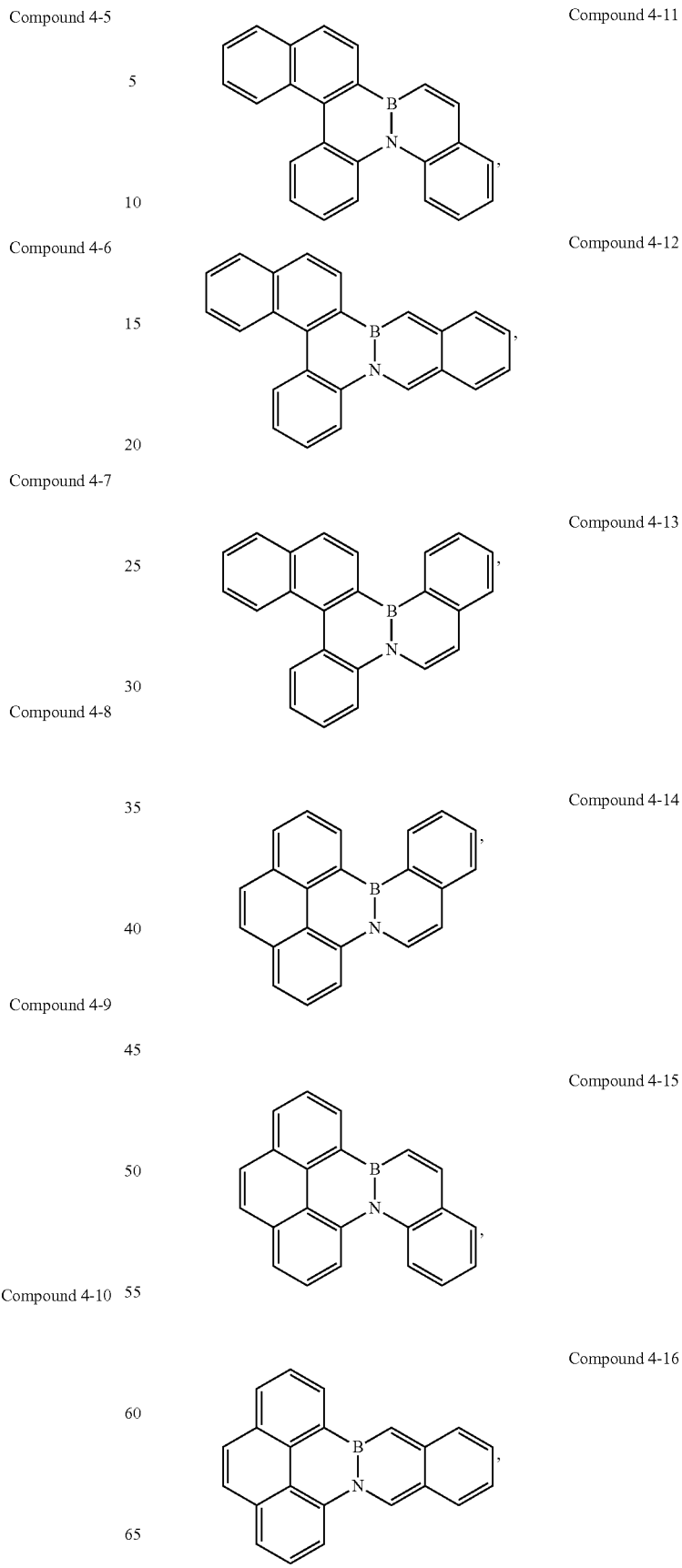
Compound 4-12
Compound 4-13
Compound 4-14
Compound 4-15
Compound 4-16

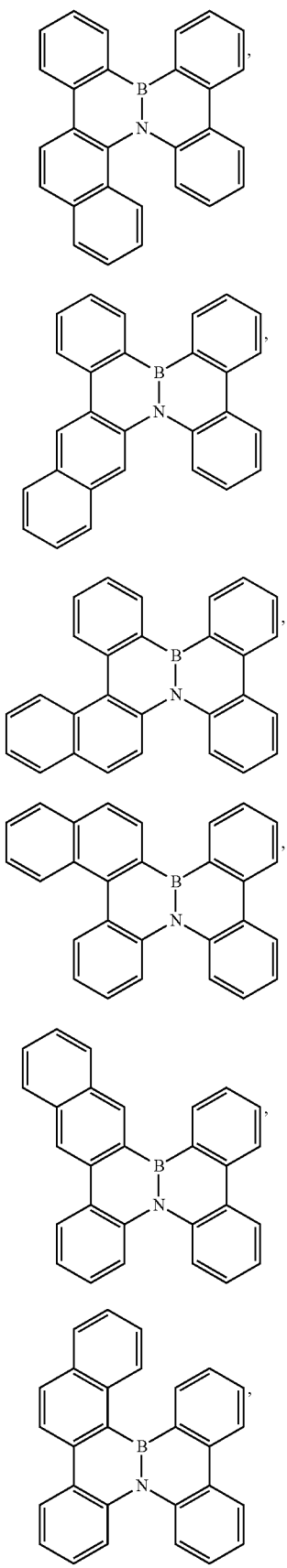
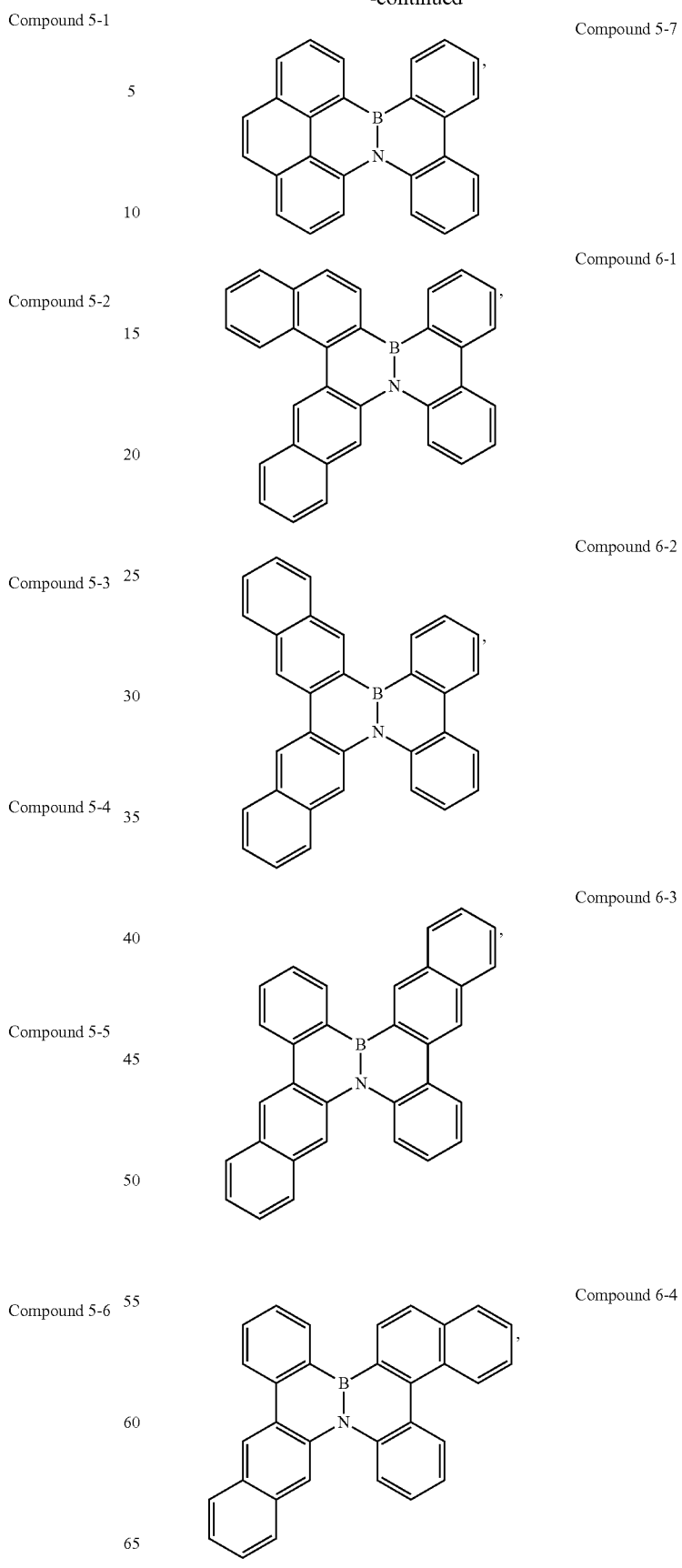

-continued
Compound 6-5
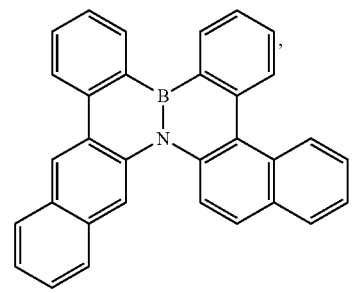
Compound 6-6
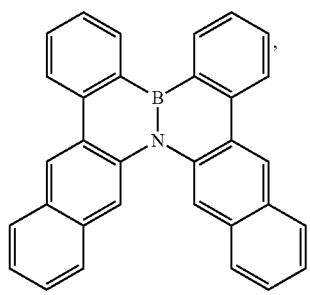
Compound 6-7
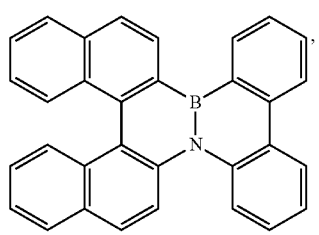
Compound 6-8
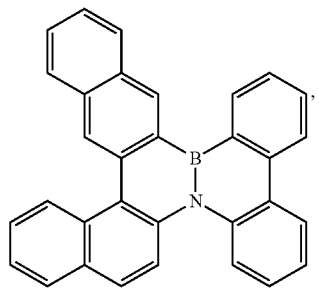
Compound 6-9
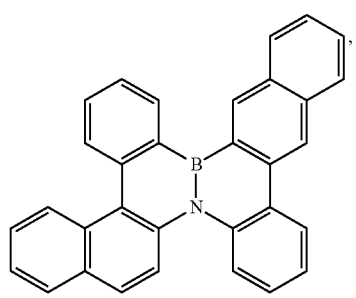
Compound 6-10
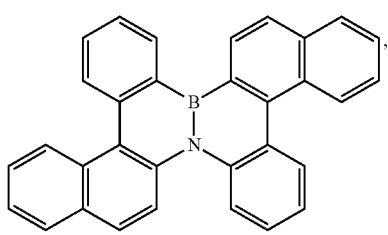
-continued
Compound 6-11
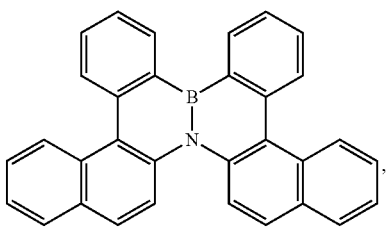
Compound 6-12
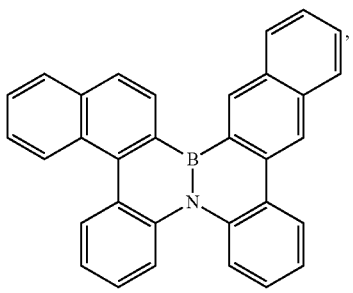
Compound 6-13
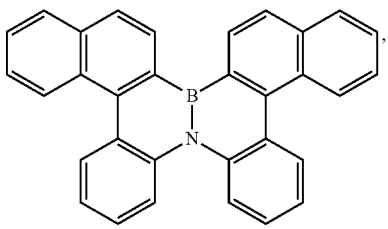
Compound 6-14
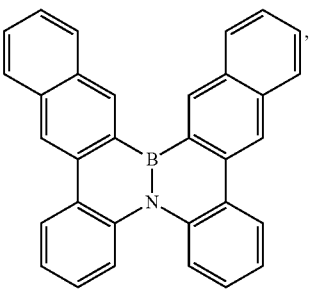
Compound 6-15
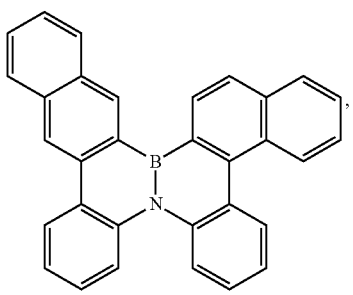

Compound 6-16
Compound 6-17
Compound 6-18
Compound 6-19
Compound 7-1
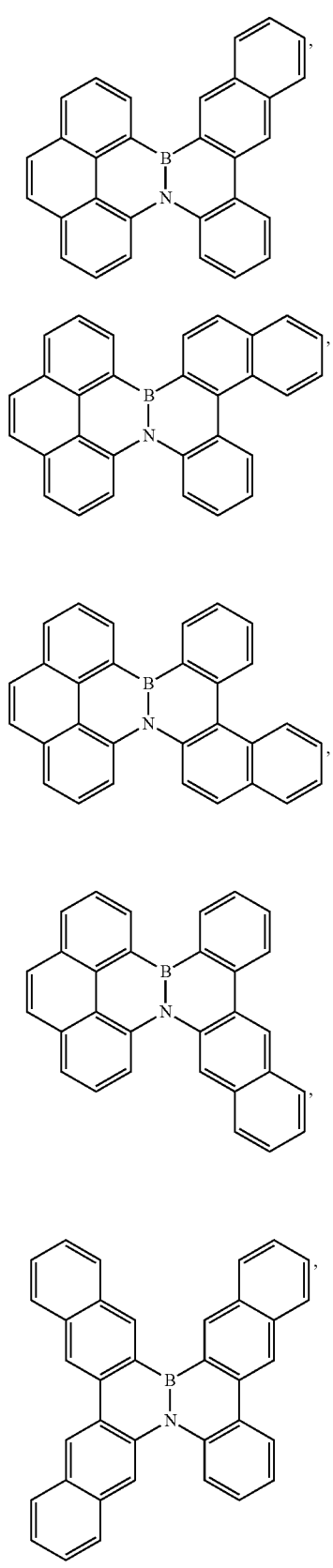
Compound 7-2
Compound 7-3
Compound 7-4
Compound 7-5
Compound 7-6
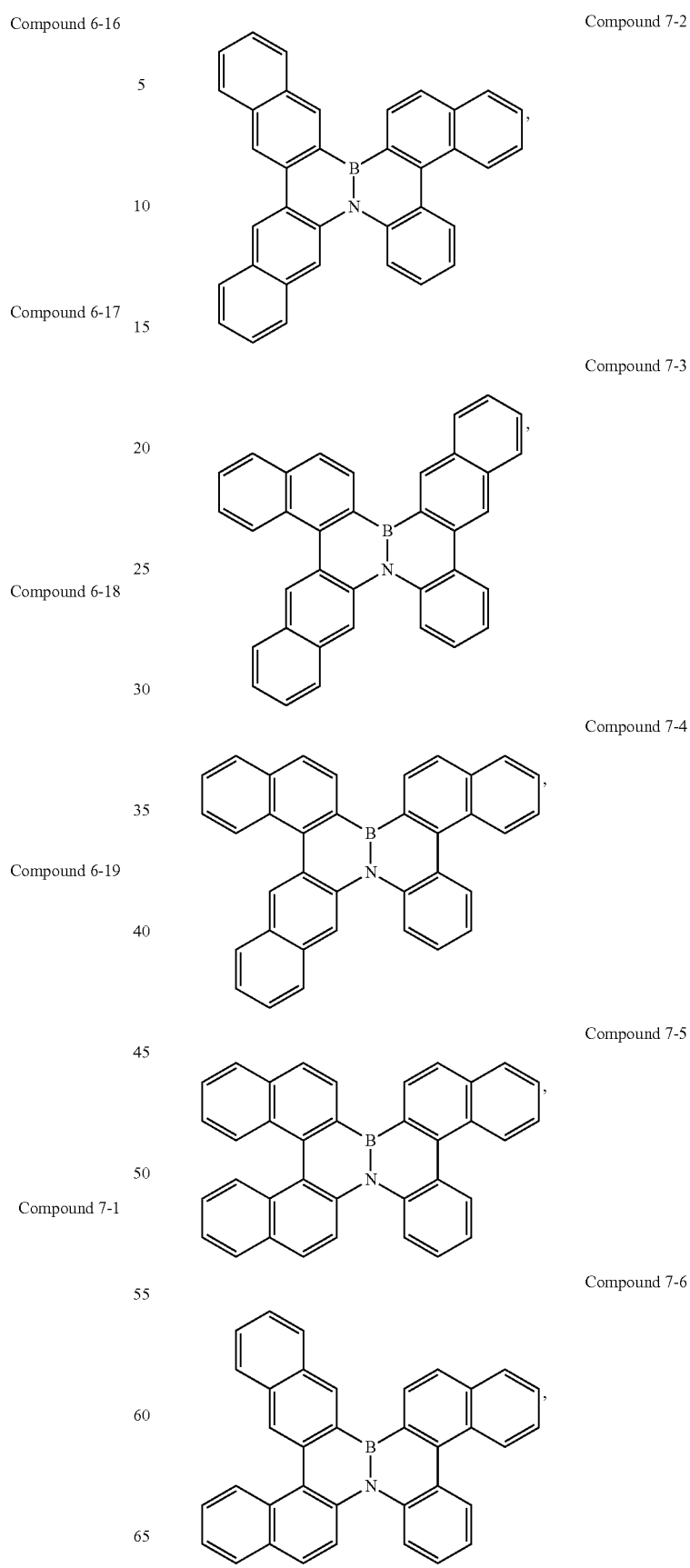

Compound 7-7
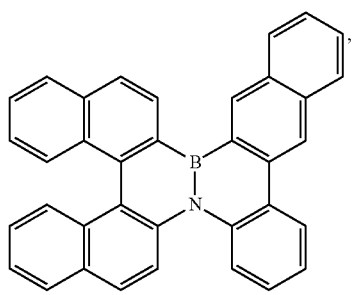
Compound 7-8
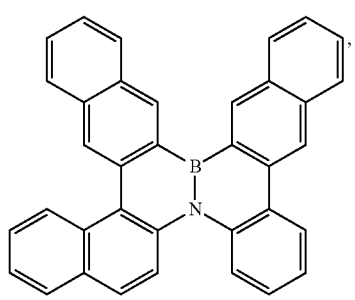
Compound 7-8
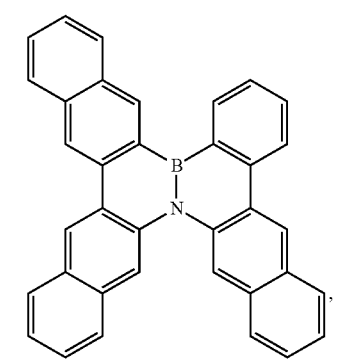
Compound 7-9
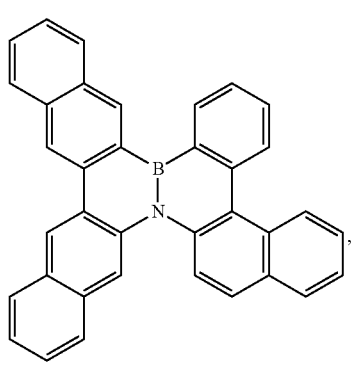
Compound 7-10
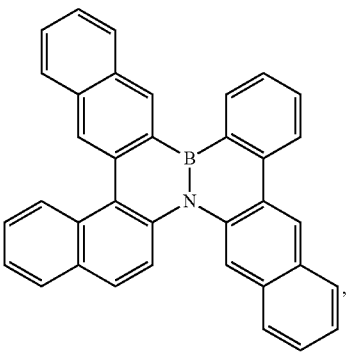
Compound 7-11
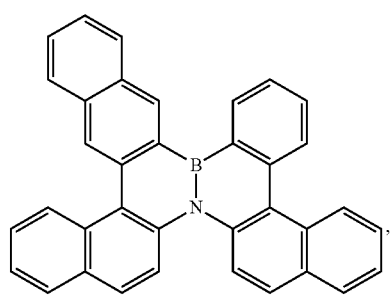
Compound 7-12
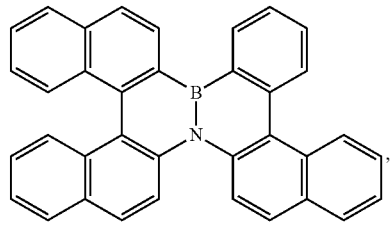
Compound 7-13
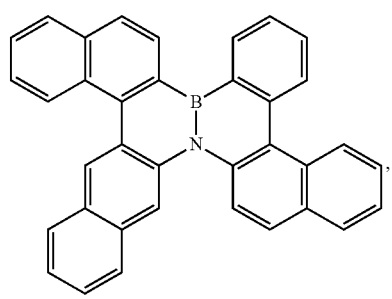
Compound 7-14
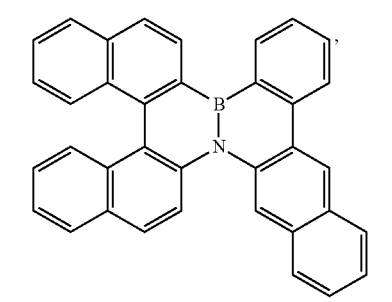

Compound 7-15
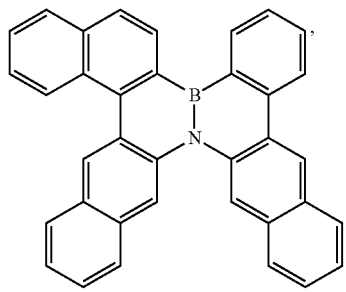
Compound 8-1
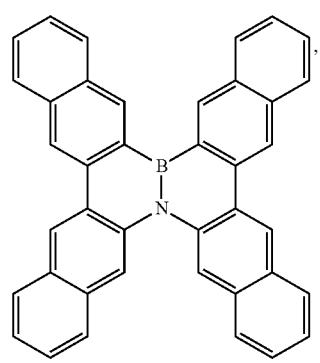
Compound 8-2
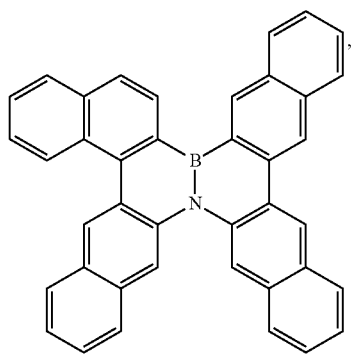
Compound 8-3
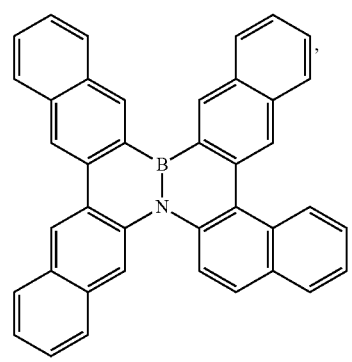
Compound 8-4
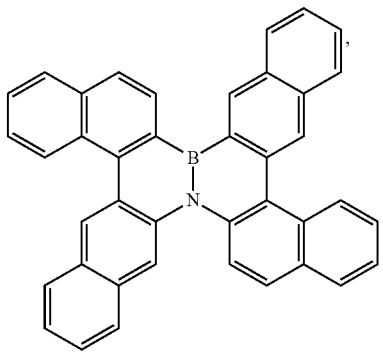
Compound 8-5
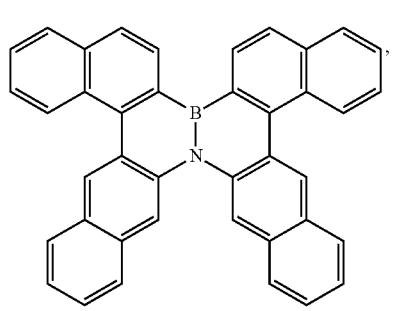
Compound 8-6
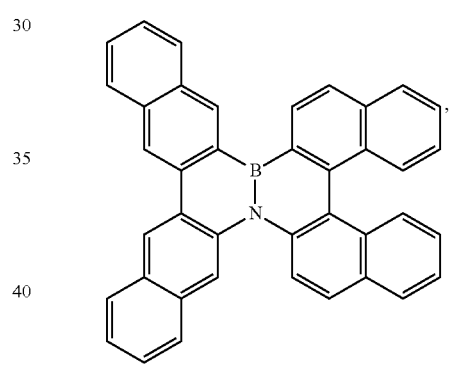
Compound 8-7
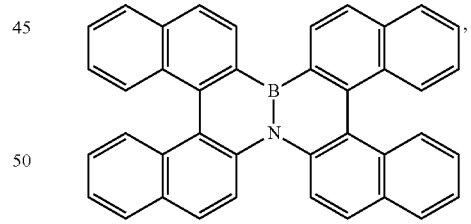
Compound 8-8
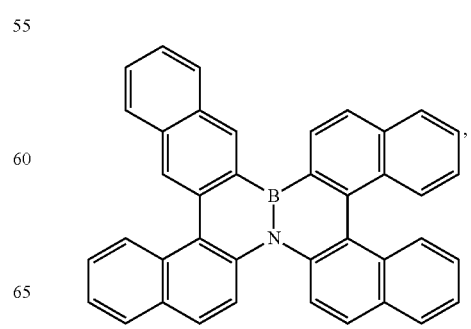

Compound 8-9

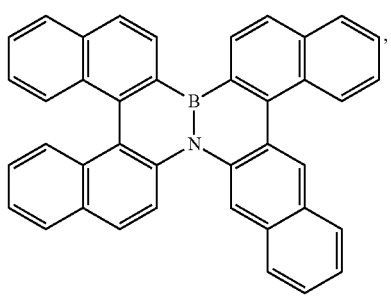

and

Compound 8-10

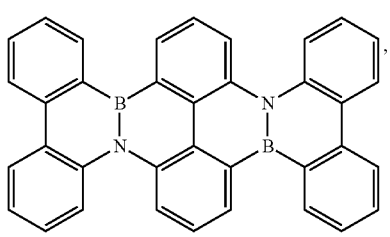

wherein the fused aromatic ring system is substituted by one or more substituents, R, that are not fused to the aromatic ring system, selected from the group consisting of deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof; and wherein any two adjacent substituents, R, are optionally joined to form one or more non-aromatic rings.

In some further such embodiments, the fused aromatic ring system is selected from the group consisting of:

Compound 1-1

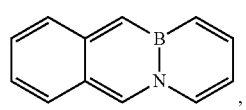

Compound 1-3

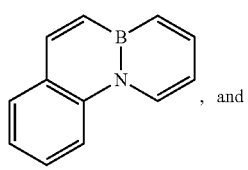

, and

Compound 2-12

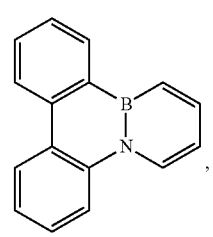

, each of which is substituted by one or more substituents, R, that are not fused to the aromatic ring system, selected from the group consisting of deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof; and wherein any two adjacent substituents, R, are optionally joined to form one or more non-aromatic rings.

In some embodiments, the fused aromatic ring system is:

Compound 1-1

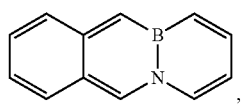

which is substituted by one or more substituents, R, that are not fused to the aromatic ring system, selected from the group consisting of deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof; and wherein any two adjacent substituents, R, are optionally joined to form one or more non-aromatic rings.

In some embodiments, the fused aromatic ring system is

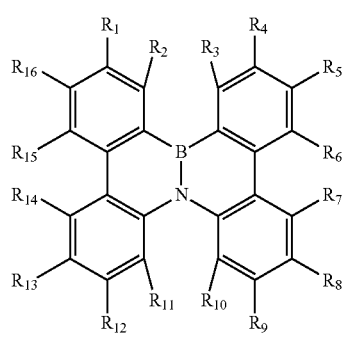

which is substituted by one or more substituents, R, that are not fused to the aromatic ring system, selected from the group consisting of deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof; and wherein any two adjacent substituents, R, are optionally joined to form one or more non-aromatic rings.

In some embodiments of the invention, the substituent, R, is selected from the group consisting of alkyl, cycloalkyl, amino, silyl, aryl, heteroaryl, and combinations thereof.

In some such embodiments, the boron-nitrogen polyaromatic compound is a compound of Formula (II), Formula (III), or Formula (IV):

(II)

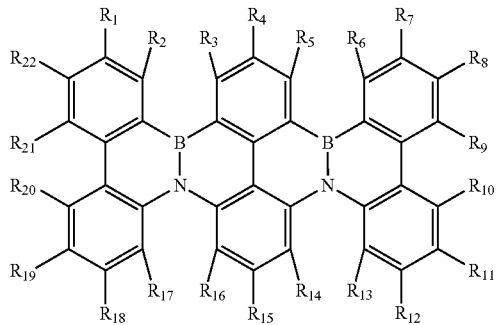

(III)

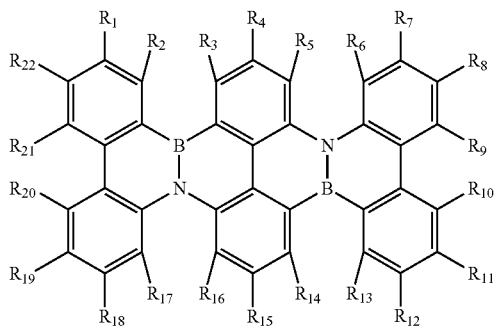

(IV)

wherein R$_1$ to R$_{22}$ are each independently selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof, wherein any two adjacent substituents are optionally joined to form a ring. In some such embodiments, the boron-nitrogen polyaromatic compound is a compound of Formula (II). In other such embodiments, the boron-nitrogen polyaromatic compound is a compound of Formula (III). In other such embodiments, the boron-nitrogen polyaromatic compound is a compound of Formula (IV). In some embodiments, the substituents, R$_1$ to R$_{22}$, are selected independently from the group consisting of aryl, heteroaryl, and NR$_a$R$_b$; wherein R$_a$ and R$_b$ are aryl or heteroaryl, which can be further substituted.

In some embodiments, the boron-nitrogen polyaromatic compound is a compound of Formula (II), and at least one of R$_5$, R$_8$, R$_{13}$, or R$_{16}$ is not hydrogen or deuterium. In some further such embodiments, at least one of R$_5$, R$_8$, R$_{13}$, or R$_{16}$ is aryl, heteroaryl or NR$_a$R$_b$; wherein R$_a$ and R$_b$ are aryl or heteroaryl, which can be further substituted. In some further such embodiments, R$_5$ and R$_{13}$ are phenyl or NR$_a$R$_b$. In some further such embodiments, R$_a$ and R$_b$ are phenyl.

In some embodiments, the boron-nitrogen polyaromatic compound is a compound of Formula (II), and at least one of R$_1$, R$_4$, R$_9$, or R$_{12}$ is not hydrogen or deuterium. In some further such embodiments, at least one of R$_1$, R$_4$, R$_9$, or R$_{12}$ is aryl, heteroaryl or NR$_a$R$_b$; wherein R$_a$ and R$_b$ are aryl or heteroaryl, which can be further substituted. In some further such embodiments, R$_1$ and R$_9$ are phenyl or NR$_a$R$_b$. In some further such embodiments, R$_a$ and R$_b$ are phenyl.

In some embodiments, the boron-nitrogen polyaromatic compound is a compound of Formula (III) or Formula (IV), and at least one of R$_8$, R$_{11}$, R$_{19}$, or R$_{22}$ is not hydrogen or deuterium. In some further such embodiments, at least one of R$_8$, R$_{11}$, R$_{19}$, or R$_{22}$ is aryl, heteroaryl or NR$_a$R$_b$; wherein R$_a$ and R$_b$ are aryl or heteroaryl, which can be further substituted. In some further such embodiments, R$_8$ and R$_{19}$ are phenyl or NR$_a$R$_b$. In some further such embodiments R$_a$ and R$_b$ are phenyl.

In some embodiments, the boron-nitrogen polyaromatic compound is a compound of Formula (II), and at least one of R$_1$, R$_4$, R$_7$, R$_{12}$, R$_{15}$ or R$_{18}$ is not hydrogen or deuterium. In some further such embodiments, at least one of R$_1$, R$_4$, R$_7$, R$_{12}$, R$_{15}$ or R$_{18}$ is aryl, heteroaryl or NR$_a$R$_b$; wherein R$_a$ and R$_b$ are aryl or heteroaryl, which can be further substituted. In some further such embodiments, R$_1$ and R$_{12}$ are phenyl or NR$_a$R$_b$. In some further such embodiments, R$_a$ and R$_b$ are phenyl.

Boron-nitrogen polyaromatic compounds are provided, where the compounds are selected from the group consisting of:

Compound 0-1

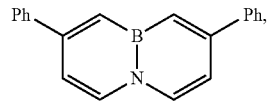

Compound 0-2

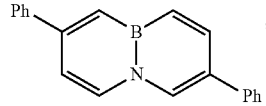

Compound 0-3

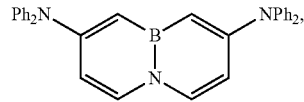

Compound 0-4

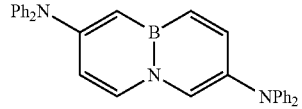

Compound 0-5

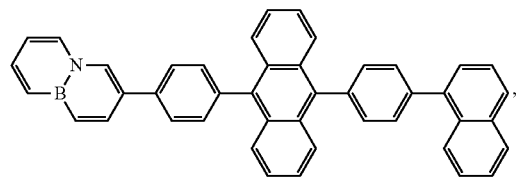

Compound 0-6

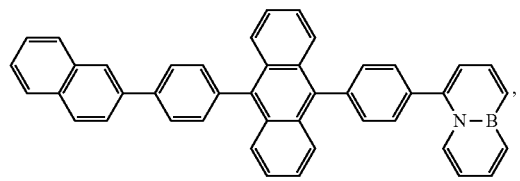

-continued
Compound 0-7
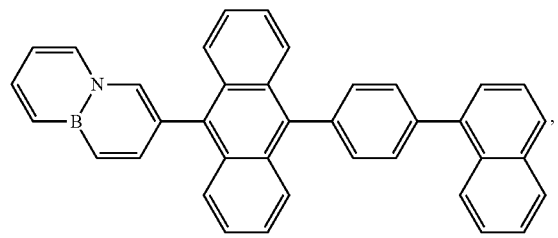
Compound 1-1-1
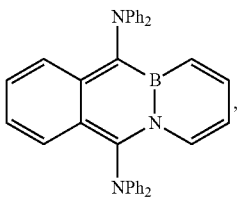
Compound 1-1-2
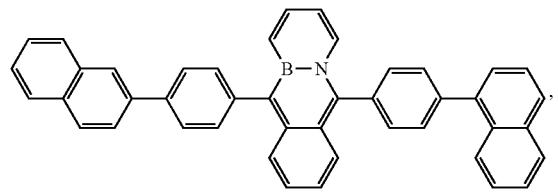
Compound 1-1-3
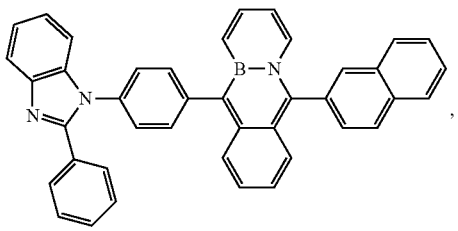
Compound 1-2-1
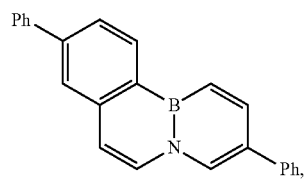
Compound 1-2-2
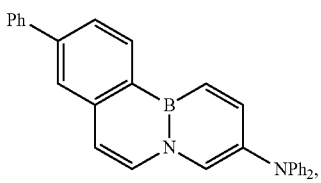
Compound 1-3-1
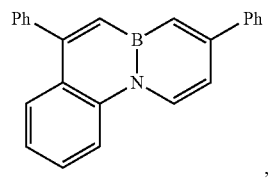
Compound 1-3-2
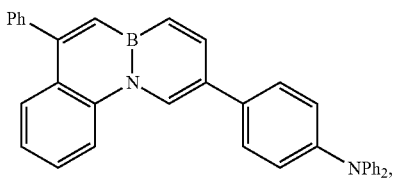
Compound 2-7-1
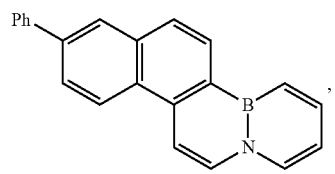
Compound 2-7-2
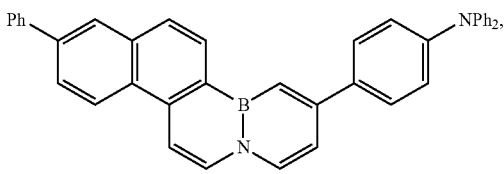
Compound 2-11-1
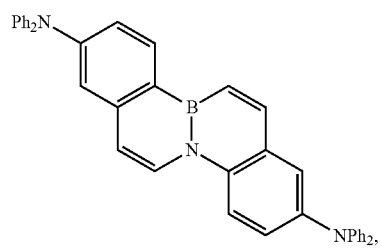
Compound 2-12-1
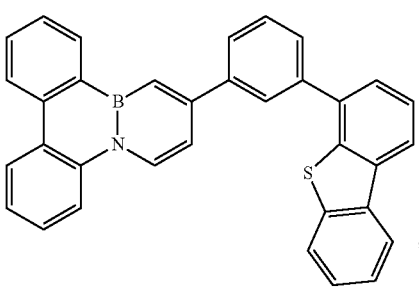
Compound 2-12-2
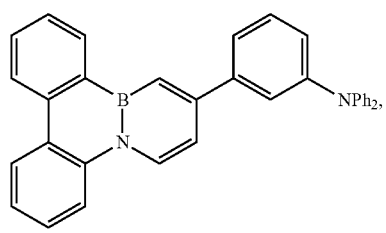
Compound 2-15-1
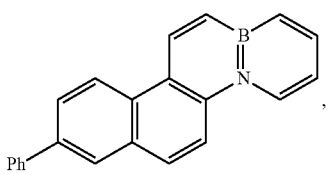

-continued
Compound 2-15-2
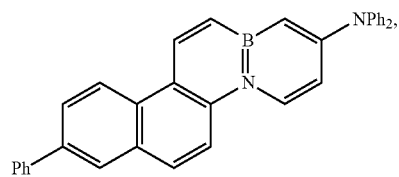
Compound 2-15-3
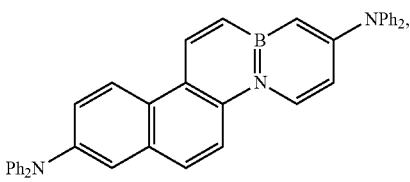
Compound 2-15-4
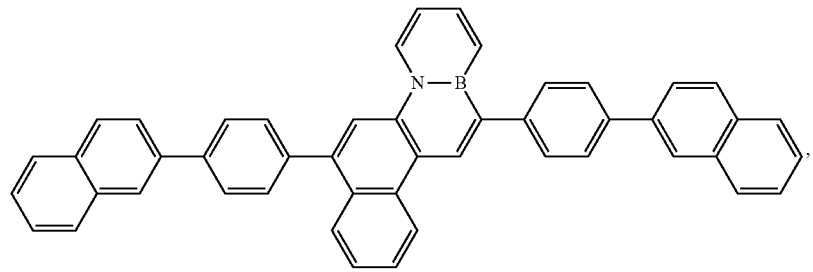
Compound 3-30-1
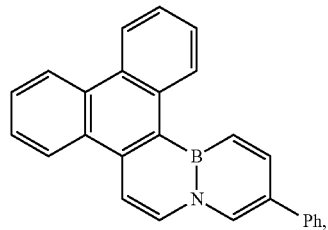
Compound 3-33-1
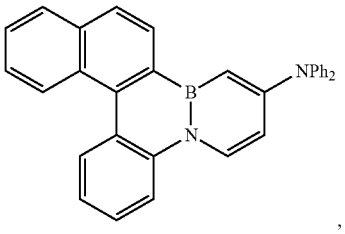
Compound 3-46-1
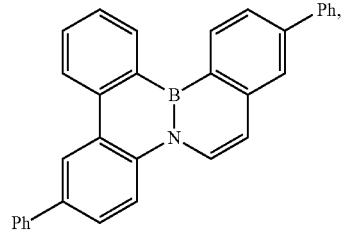
Compound 5-2-1
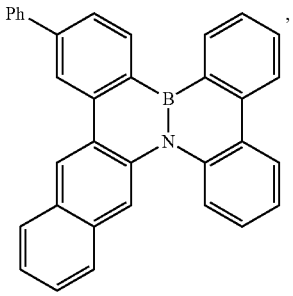
Compound 5-3-1
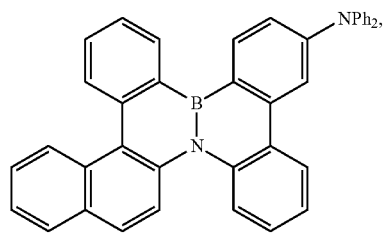
Compound 5-4-1
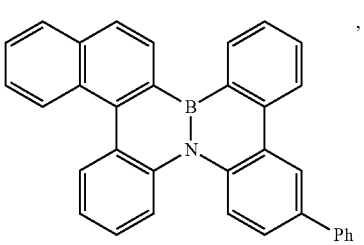
Compound 6-3-1
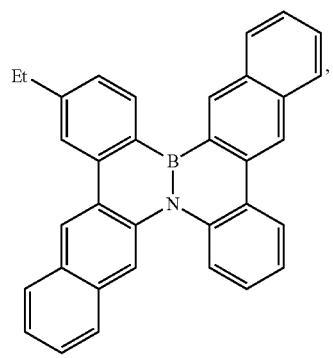
Compound 6-4-1
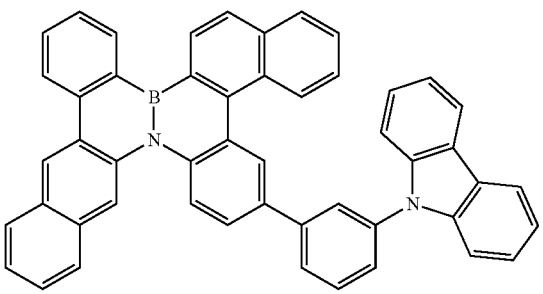

-continued
Compound 7-4-1
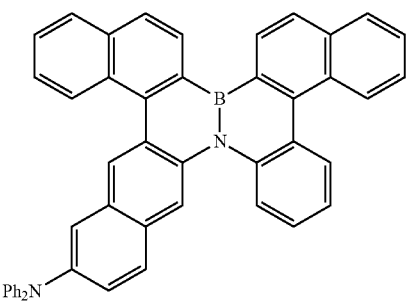
, and
Compound 8-4-1
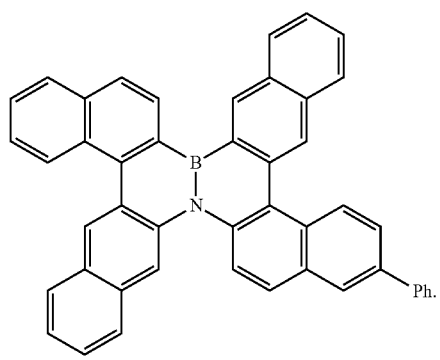
Boron-nitrogen polyaromatic compounds are provided, where the compounds are compounds of Formula (II) and are selected from the group consisting of:
Compound 4-4-1
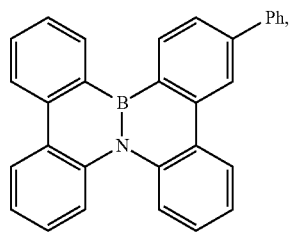
Compound 4-1-2
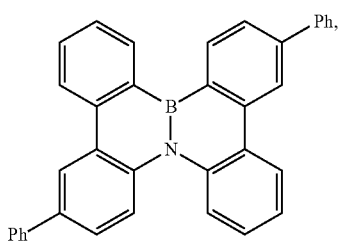
Compound 4-1-3
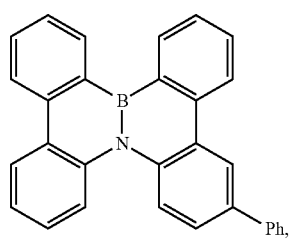
Compound 4-1-4
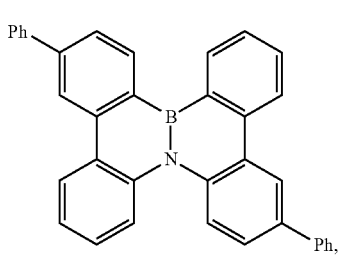
-continued
Compound 4-1-5
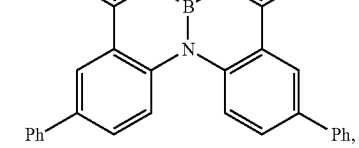
Compound 4-1-21
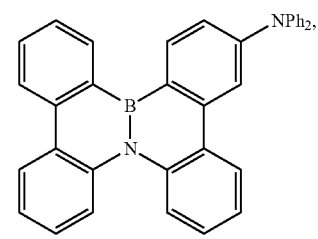
Compound 4-1-22
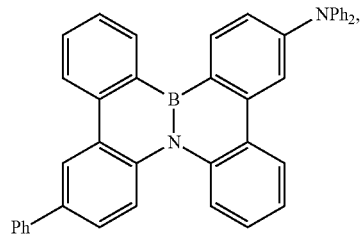
Compound 4-1-23
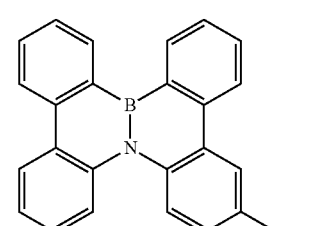

-continued
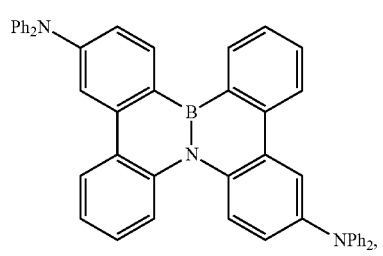
Compound 4-1-24

Compound 4-1-25
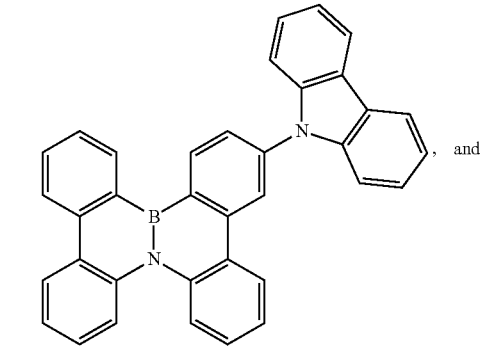
Compound 4-1-26, and
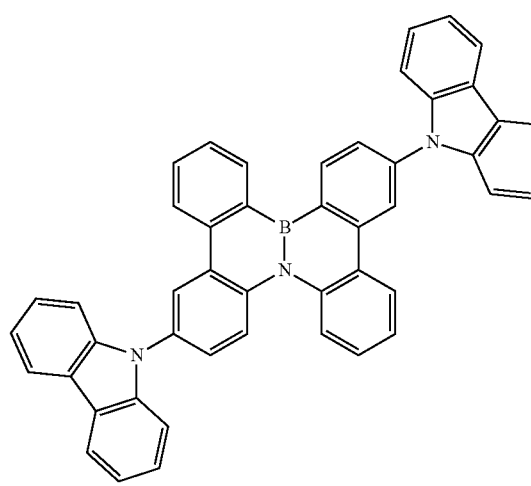
Compound 4-1-27
Boron-nitrogen polyaromatic compounds are provided, where the compounds are compounds of Formula (II) and are selected from the group consisting of:
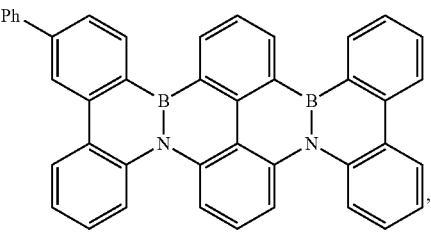
Compound 8-10-1
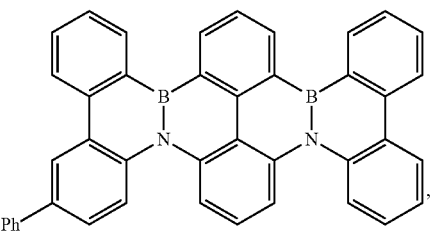
Compound 8-10-2
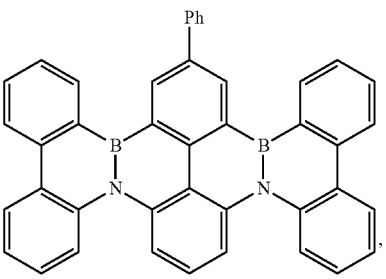
Compound 8-10-3
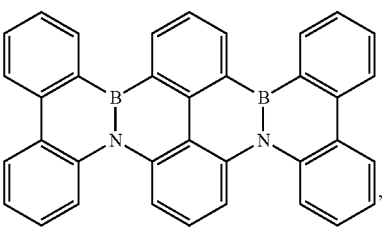
Compound 8-10-4
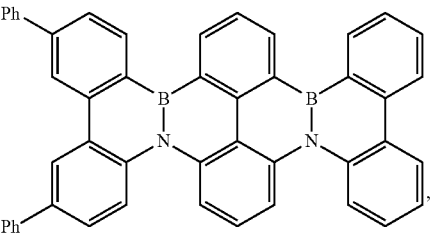
Compound 8-10-5
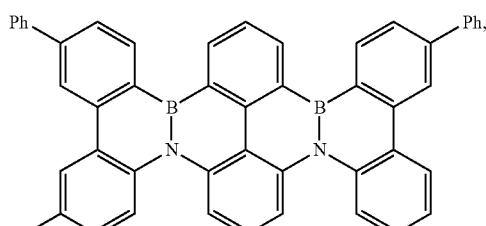
Compound 8-10-6

Compound 8-10-7
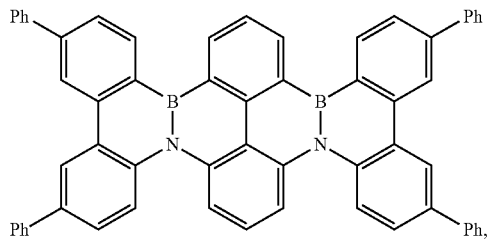
Compound 8-10-8
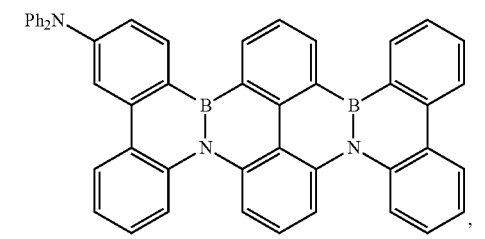
Compound 8-10-9
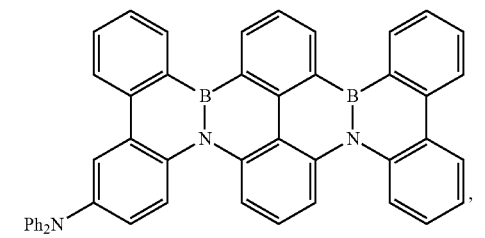
Compound 8-10-10
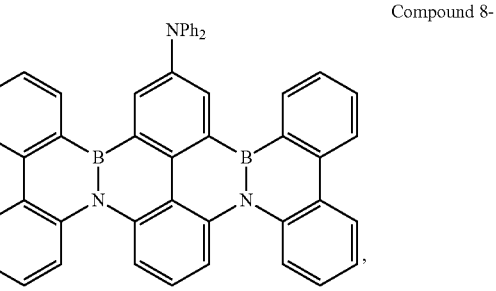
Compound 8-10-11
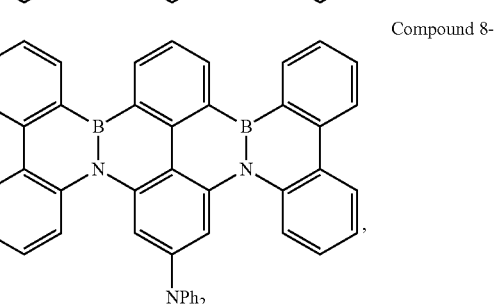
Compound 8-10-12
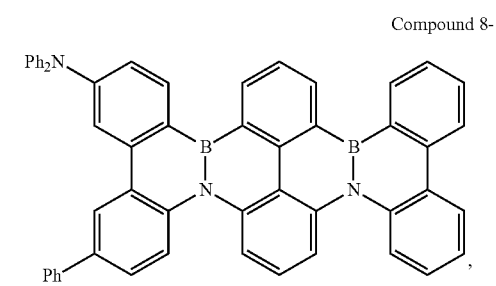
Compound 8-10-13
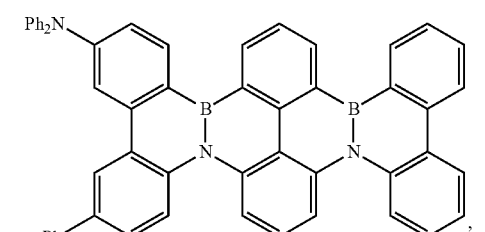
Compound 8-10-14
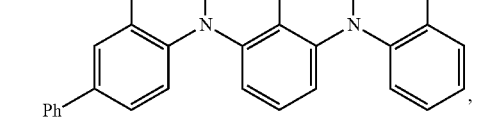
Compound 8-10-15
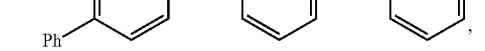
Boron-nitrogen polyaromatic compounds are provided, where the compounds are compounds of Formula (IV) and are selected from the group consisting of:
Compound 8-11-1
Compound 8-11-2

Compound 8-11-3
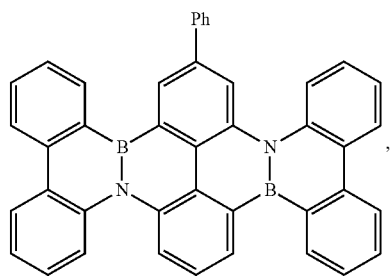
Compound 8-11-4
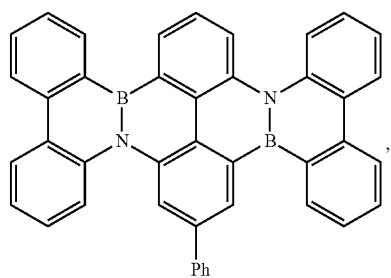
Compound 8-11-5
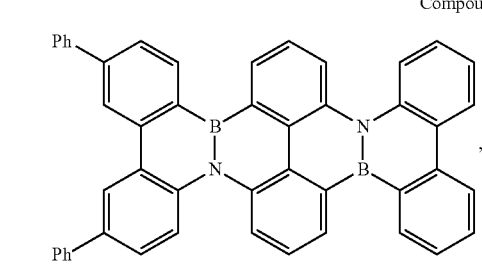
Compound 8-10-6
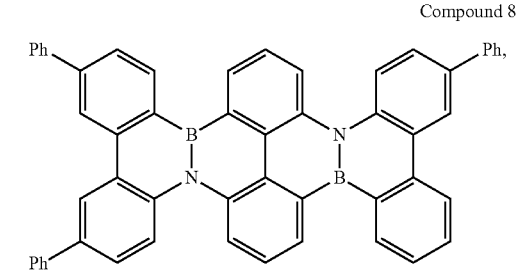
Compound 8-10-7
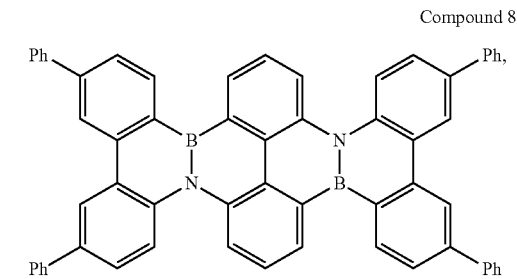
Compound 8-11-8
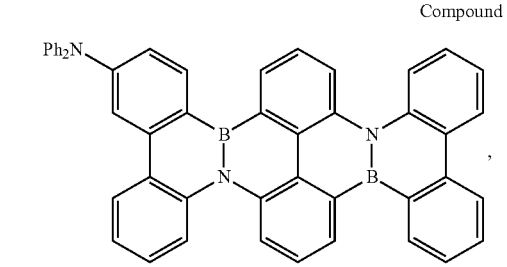
Compound 8-11-9
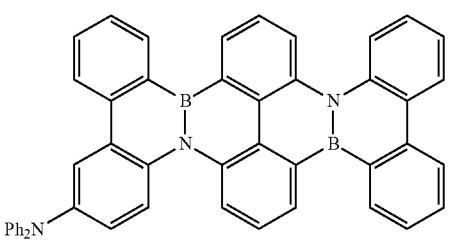
Compound 8-11-10
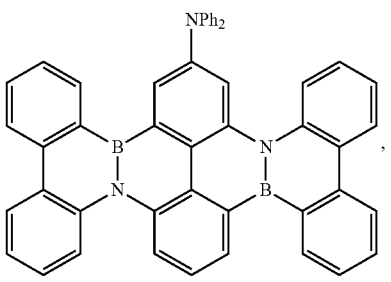
Compound 8-11-11
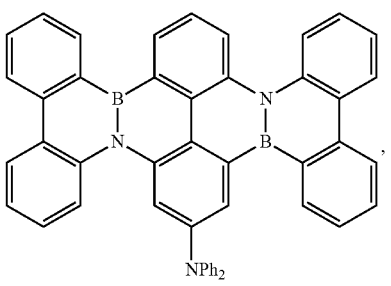
Compound 8-11-12
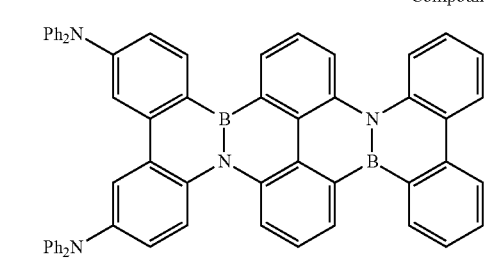
Compound 8-11-13
Compound 8-11-14
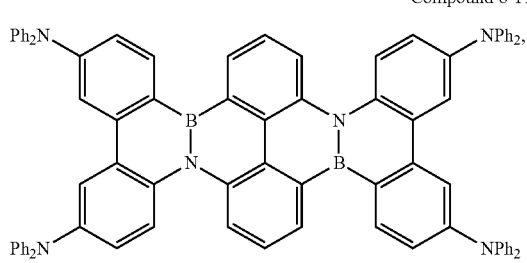

-continued and

Compound 8-11-15

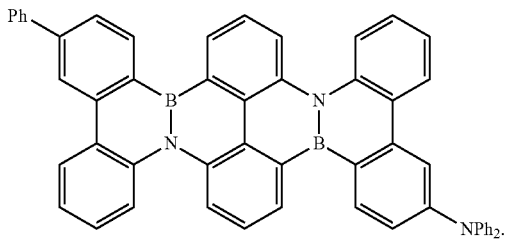

A device is also provided. The device may include an anode, a cathode, and an organic layer disposed between the anode and the cathode, where the organic layer comprises a boron-nitrogen polyaromatic compound of any of the foregoing embodiments.

The invention is not limited to any particular type of device. In some embodiments, the device is a consumer product. In some embodiments, the device is an organic light emitting device (OLED). In some embodiments, the device is a delayed fluorescence device. In other embodiments, the device comprises a lighting panel.

In some embodiments, the organic layer of the device is an emissive layer. In some such embodiments, the boron-nitrogen polyaromatic compound is an emissive dopant. In some other embodiments, the boron-nitrogen polyaromatic compound is a host.

In some embodiments, the organic layer of the device is a hole injecting layer or a hole transporting layer. In some other embodiments, the organic layer of the device is an electron injecting layer or an electron transporting layer. In some embodiments, the organic layer of the device is an exciton blocking layer.

DETAILED DESCRIPTION

Generally, an OLED comprises at least one organic layer disposed between and electrically connected to an anode and a cathode. When a current is applied, the anode injects holes and the cathode injects electrons into the organic layer(s). The injected holes and electrons each migrate toward the oppositely charged electrode. When an electron and hole localize on the same molecule, an "exciton," which is a localized electron-hole pair having an excited energy state, is formed. Light is emitted when the exciton relaxes via a photoemissive mechanism. In some cases, the exciton may be localized on an excimer or an exciplex. Non-radiative mechanisms, such as thermal relaxation, may also occur, but are generally considered undesirable.

The initial OLEDs used emissive molecules that emitted light from their singlet states ("fluorescence") as disclosed, for example, in U.S. Pat. No. 4,769,292, which is incorporated by reference in its entirety. Fluorescent emission generally occurs in a time frame of less than 10 nanoseconds.

More recently, OLEDs having emissive materials that emit light from triplet states ("phosphorescence") have been demonstrated. Baldo et al., "Highly Efficient Phosphorescent Emission from Organic Electroluminescent Devices," Nature, vol. 395, 151-154, 1998; ("Baldo-I") and Baldo et al., "Very high-efficiency green organic light-emitting devices based on electrophosphorescence," Appl. Phys. Lett., vol. 75, No. 3, 4-6 (1999) ("Baldo-II"), which are incorporated by reference in their entireties. Phosphorescence is described in more detail in U.S. Pat. No. 7,279,704 at cols. 5-6, which are incorporated by reference.

Figure 1:
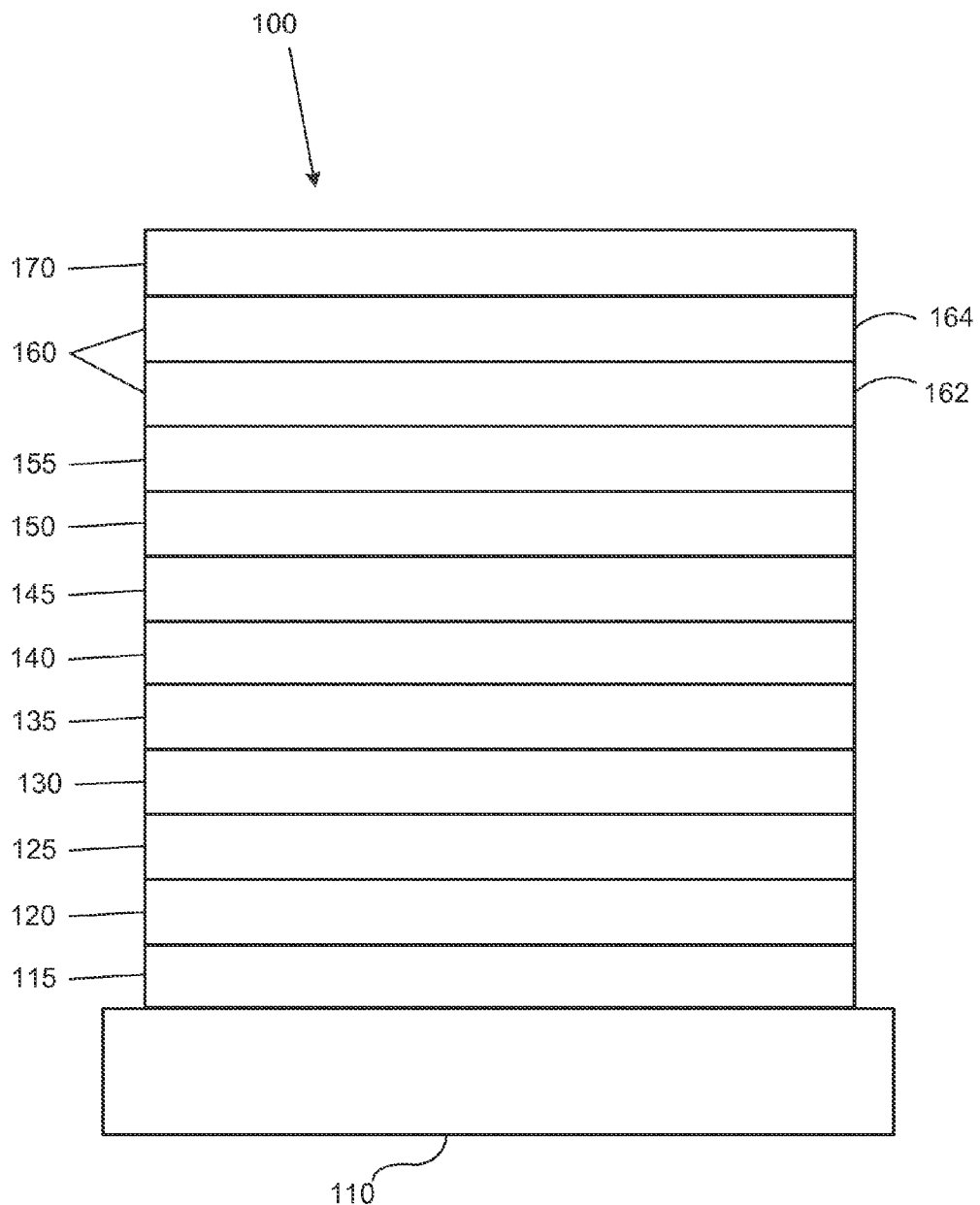
FIG. 1 shows an organic light emitting device.

FIG. 1 shows an organic light emitting device 100. The figures are not necessarily drawn to scale. Device 100 may include a substrate 110, an anode 115, a hole injection layer 120, a hole transport layer 125, an electron blocking layer 130, an emissive layer 135, a hole blocking layer 140, an electron transport layer 145, an electron injection layer 150, a protective layer 155, a cathode 160, and a barrier layer 170. Cathode 160 is a compound cathode having a first conductive layer 162 and a second conductive layer 164. Device 100 may be fabricated by depositing the layers described, in order. The properties and functions of these various layers, as well as example materials, are described in more detail in U.S. Pat. No. 7,279,704 at cols. 6-10, which are incorporated by reference.

More examples for each of these layers are available. For example, a flexible and transparent substrate-anode combination is disclosed in U.S. Pat. No. 5,844,363, which is incorporated by reference in its entirety. An example of a p-doped hole transport layer is m-MTDATA doped with F.sub.4-TCNQ at a molar ratio of 50:1, as disclosed in U.S. Patent Application Publication No. 2003/0230980, which is incorporated by reference in its entirety. Examples of emissive and host materials are disclosed in U.S. Pat. No. 6,303,238 to Thompson et al., which is incorporated by reference in its entirety. An example of an n-doped electron transport layer is BPhen doped with Li at a molar ratio of 1:1, as disclosed in U.S. Patent Application Publication No. 2003/0230980, which is incorporated by reference in its entirety. U.S. Pat. Nos. 5,703,436 and 5,707,745, which are incorporated by reference in their entireties, disclose examples of cathodes including compound cathodes having a thin layer of metal such as Mg:Ag with an overlying transparent, electrically-conductive, sputter-deposited ITO layer. The theory and use of blocking layers is described in more detail in U.S. Pat. No. 6,097,147 and U.S. Patent Application Publication No 2003/0230980, which are incorporated by reference in their entireties. Examples of injection layers are provided in U.S. Patent Application Publication No. 2004/0174116, which is incorporated by reference in its entirety. A description of protective layers may be found in U.S. Patent Application Publication No. 2004/0174116, which is incorporated by reference in its entirety.

Figure 2:
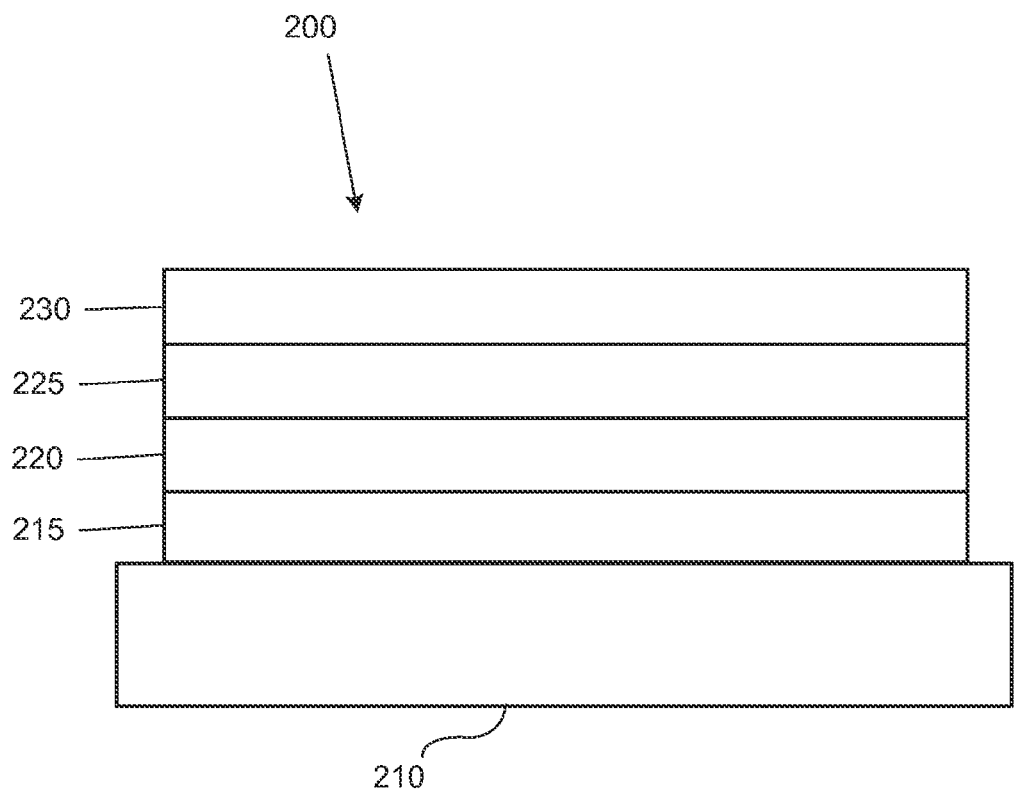
FIG. 2 shows an inverted organic light emitting device that does not have a separate electron transport layer.
Figure 3:
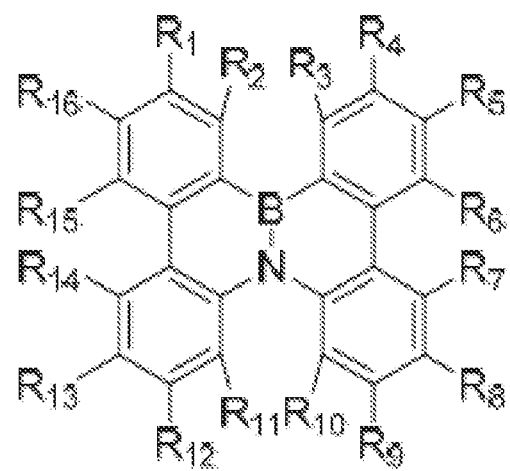
FIG. 3 shows a chemical structure that represents at least some embodiments of the boron-nitrogen polyaromatic compound, as disclosed herein.

FIG. 2 shows an inverted OLED 200. The device includes a substrate 210, a cathode 215, an emissive layer 220, a hole transport layer 225, and an anode 230. Device 200 may be fabricated by depositing the layers described, in order. Because the most common OLED configuration has a cathode disposed over the anode, and device 200 has cathode 215 disposed under anode 230, device 200 may be referred to as an "inverted" OLED. Materials similar to those described with respect to device 100 may be used in the corresponding layers of device 200. FIG. 2 provides one example of how some layers may be omitted from the structure of device 100.

The simple layered structure illustrated in FIGS. 1 and 2 is provided by way of non-limiting example, and it is understood that embodiments of the invention may be used in connection with a wide variety of other structures. The specific materials and structures described are exemplary in nature, and other materials and structures may be used. Functional OLEDs may be achieved by combining the various layers described in different ways, or layers may be omitted entirely, based on design, performance, and cost factors. Other layers not specifically described may also be included. Materials other than those specifically described may be used. Although many of the examples provided herein describe various layers as comprising a single material, it is understood that combinations of materials, such as a mixture of host and dopant, or more generally a mixture, may be used. Also, the layers may have various sublayers. The names given to the various layers herein are not intended to be strictly limiting. For example, in device 200, hole transport layer 225 transports holes and injects holes into emissive layer 220, and may be described as a hole transport layer or a hole injection layer. In one embodiment, an OLED may be described as having an "organic layer" disposed between a cathode and an anode. This organic layer may comprise a single layer, or may further comprise multiple layers of different organic materials as described, for example, with respect to FIGS. 1 and 2.

Structures and materials not specifically described may also be used, such as OLEDs comprised of polymeric materials (PLEDs) such as disclosed in U.S. Pat. No. 5,247,190 to Friend et al., which is incorporated by reference in its entirety. By way of further example, OLEDs having a single organic layer may be used. OLEDs may be stacked, for example as described in U.S. Pat. No. 5,707,745 to Forrest et al, which is incorporated by reference in its entirety. The OLED structure may deviate from the simple layered structure illustrated in FIGS. 1 and 2. For example, the substrate may include an angled reflective surface to improve out-coupling, such as a mesa structure as described in U.S. Pat. No. 6,091,195 to Forrest et al., and/or a pit structure as described in U.S. Pat. No. 5,834,893 to Bulovic et al., which are incorporated by reference in their entireties.

Unless otherwise specified, any of the layers of the various embodiments may be deposited by any suitable method. For the organic layers, preferred methods include thermal evaporation, ink-jet, such as described in U.S. Pat. Nos. 6,013,982 and 6,087,196, which are incorporated by reference in their entireties, organic vapor phase deposition (OVPD), such as described in U.S. Pat. No. 6,337,102 to Forrest et al., which is incorporated by reference in its entirety, and deposition by organic vapor jet printing (OVJP), such as described in U.S. patent application Ser. No. 10/233,470, which is incorporated by reference in its entirety. Other suitable deposition methods include spin coating and other solution based processes. Solution based processes are preferably carried out in nitrogen or an inert atmosphere. For the other layers, preferred methods include thermal evaporation. Preferred patterning methods include deposition through a mask, cold welding such as described in U.S. Pat. Nos. 6,294,398 and 6,468,819, which are incorporated by reference in their entireties, and patterning associated with some of the deposition methods such as ink-jet and OVJD. Other methods may also be used. The materials to be deposited may be modified to make them compatible with a particular deposition method. For example, substituents such as alkyl and aryl groups, branched or unbranched, and preferably containing at least 3 carbons, may be used in small molecules to enhance their ability to undergo solution processing. Substituents having 20 carbons or more may be used, and 3-20 carbons is a preferred range. Materials with asymmetric structures may have better solution processibility than those having symmetric structures, because asymmetric materials may have a lower tendency to recrystallize. Dendrimer substituents may be used to enhance the ability of small molecules to undergo solution processing.

Devices fabricated in accordance with embodiments of the present invention may further optionally comprise a barrier layer. One purpose of the barrier layer is to protect the electrodes and organic layers from damaging exposure to harmful species in the environment including moisture, vapor and/or gases, etc. The barrier layer may be deposited over, under or next to a substrate, an electrode, or over any other parts of a device including an edge. The barrier layer may comprise a single layer, or multiple layers. The barrier layer may be formed by various known chemical vapor deposition techniques and may include compositions having a single phase as well as compositions having multiple phases. Any suitable material or combination of materials may be used for the barrier layer. The barrier layer may incorporate an inorganic or an organic compound or both. The preferred barrier layer comprises a mixture of a polymeric material and a non-polymeric material as described in U.S. Pat. No. 7,968,146, PCT Pat. Application Nos. PCT/US2007/023098 and PCT/US2009/042829, which are herein incorporated by reference in their entireties. To be considered a "mixture", the aforesaid polymeric and non-polymeric materials comprising the barrier layer should be deposited under the same reaction conditions and/or at the same time. The weight ratio of polymeric to non-polymeric material may be in the range of 95:5 to 5:95. The polymeric material and the non-polymeric material may be created from the same precursor material. In one example, the mixture of a polymeric material and a non-polymeric material consists essentially of polymeric silicon and inorganic silicon.

Devices fabricated in accordance with embodiments of the invention may be incorporated into a wide variety of consumer products, including flat panel displays, computer monitors, medical monitors, televisions, billboards, lights for interior or exterior illumination and/or signaling, heads up displays, fully transparent displays, flexible displays, laser printers, telephones, cell phones, personal digital assistants (PDAs), laptop computers, digital cameras, camcorders, viewfinders, micro-displays, vehicles, a large area wall, theater or stadium screen, or a sign. Various control mechanisms may be used to control devices fabricated in accordance with the present invention, including passive matrix and active matrix. Many of the devices are intended for use in a temperature range comfortable to humans, such as 18 degrees C. to 30 degrees C., and more preferably at room temperature (20-25 degrees C.).

The materials and structures described herein may have applications in devices other than OLEDs. For example, other optoelectronic devices such as organic solar cells and organic photodetectors may employ the materials and structures. More generally, organic devices, such as organic transistors, may employ the materials and structures.

The terms halo, halogen, alkyl, cycloalkyl, alkenyl, alkynyl, arylkyl, heterocyclic group, aryl, aromatic group, and heteroaryl are known to the art, and are defined in U.S. Pat. No. 7,279,704 at cols. 31-32, which are incorporated herein by reference.

Boron-nitrogen polyaromatic compounds are provided. Such materials can be used as emitters in fluorescent devices, such as delayed fluorescent devices. They can also be used as host materials or charge transport materials in phosphorescent or fluorescent devices, including both single-color and multiple-color devices. Such materials can be vapor evaporated or solution processed. One of the more challenging problems in OLED fabrication related to achieving efficiency and stability for blue OLEDs. To achieve stable blue OLEDs, polyaromatic compounds, such as antracene, chrysene, pyrene, and their derivatives are often used because these polyaromatics can emit in the blue region despite their high π-conjugation. The high π-conjugation may be used to stabilize charges when the materials are oxidized or reduced. Such properties render these compounds suitable for OLED use. However, these materials are purely fluorescent materials, which means that the maximum device efficiency is limited to the singlet excitation ratio, i.e., about 25%. P-type delayed fluorescence resulting from triplet-triplet annihilation may exist in some devices employing these materials, which would lead to an efficiency that is higher than the theoretical limit for purely fluorescent OLEDs. Nevertheless, triplet-triplet annihilation can only produce, at most, one singlet exciton out of two triplet excitons. Thus, device efficiency is still limited. On the other hand, if E-type delayed fluorescence can be employed, e.g., via thermal conversion of triplet to singlet, there would be no loss of triplet exciton, which may lead to improved electroluminescent efficiency. To achieve thermal conversion of triplet to singlet, a small S1-T1 gap is generally required. Some highly polarized compounds can exhibit a small S1-T1 gap, but these compounds may not be suitable for use in OLEDs because their polarity may reduce stability and quantum efficiency. Boron-nitrogen polyaromatic compounds can have small S1-T1 gaps due to the reduced aromatic character at the center of the ring(s), which can somewhat isolate outer π-system and enhances resonance. This can lead to an increase in energy, particularly triplet energy. However, the overall polyaromatic π-conjugation may still be able to stabilize charge and lead to high stability.

A new type of material is provided, which includes boron-nitrogen polyaromatic compounds having a fused aromatic ring system that includes a [1,2]azaborino[1,2-a]-[1,2]azaborine

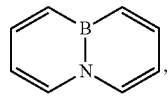

which is optionally fused to one or more aromatic rings or fused aromatic rings; wherein the fused aromatic ring system is substituted by one or more substituents, R, that are not fused to the aromatic ring system, selected from the group consisting of deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof; and wherein any two adjacent substituents, R, are optionally joined to form one or more non-aromatic rings.

Figure 4:
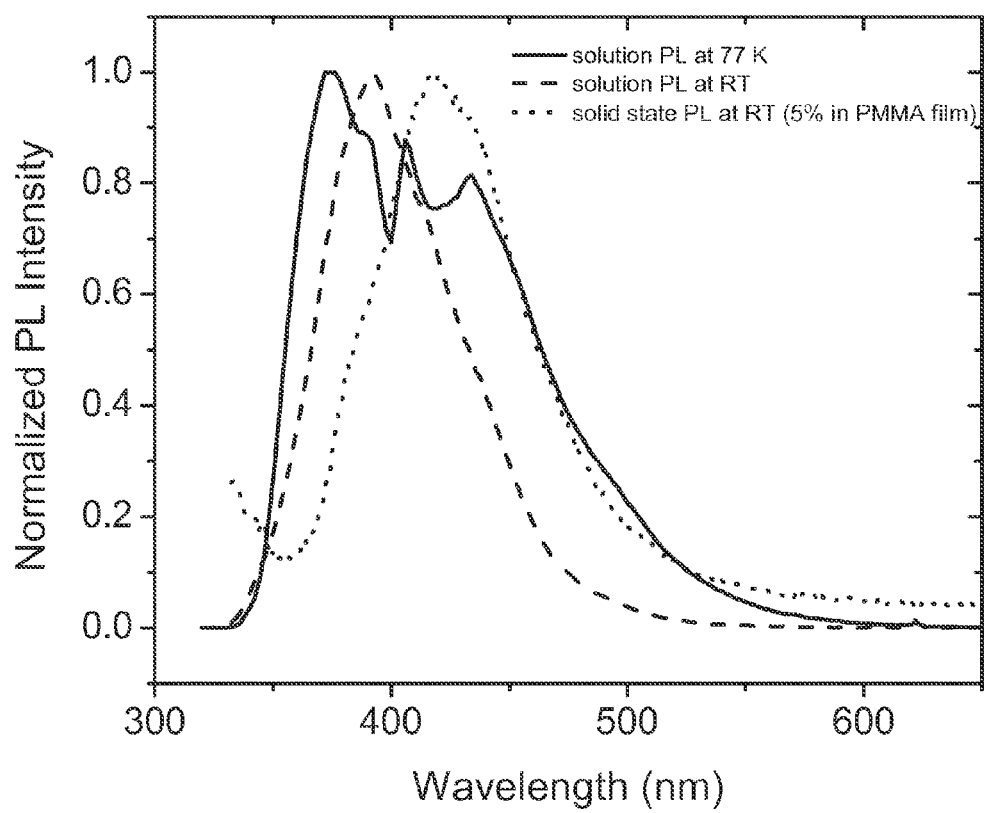
FIG. 4 shows the photoluminescence (PL) of Compound 4-1. The solution PL was obtained in 2-MeTHF solution.

Substitution(s) on the compounds can tune the electronic properties such as absorption, emission, HOMO/LUMO level and thermal properties such as melting point, evaporation temperature, etc. For example, as shown in FIG. 4, the emission of Compound 4-1 is mostly in the UV region. Red shifting by substituting with phenyl, biphenyl, diphenylamino and/or N-carbazolyl groups which provide increased π-conjugation in the system can lead to emission in the visible region, rendering the compounds useful as the emitters in OLEDs. Substitutions can also result in increased solubilities which may make the compounds useful in solution processed devices.

In some such embodiments, the fused aromatic ring system is selected from the group consisting of:

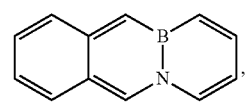

Compound 1-1

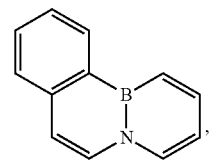

Compound 1-2

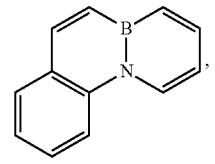

Compound 1-3

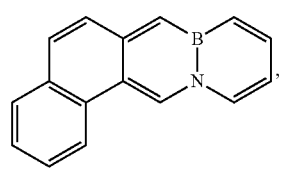

Compound 2-1

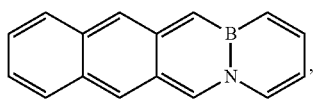

Compound 2-2

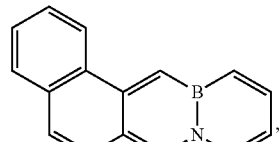

Compound 2-3

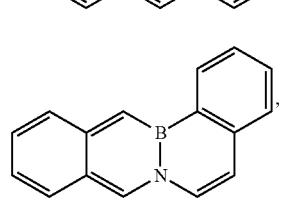

Compound 2-4

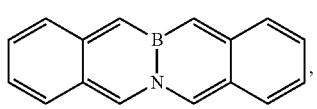

Compound 2-5

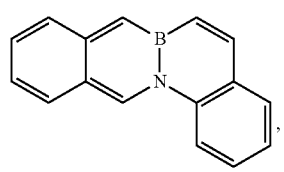

Compound 2-6

-continued
Compound 2-7
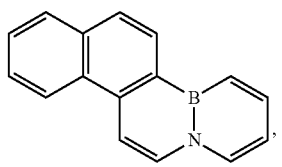
Compound 2-8
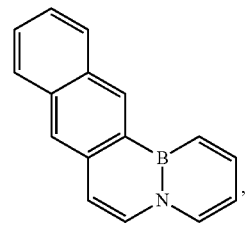
Compound 2-9
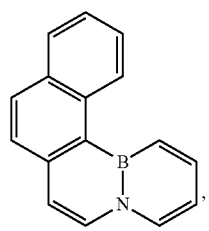
Compound 2-10
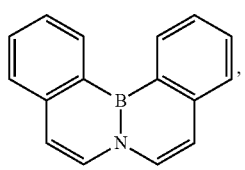
Compound 2-11
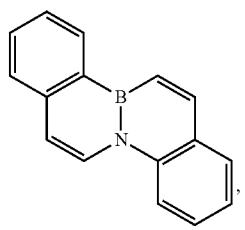
Compound 2-12
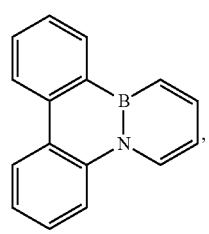
Compound 2-13
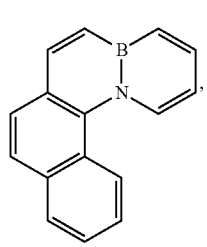
-continued
Compound 2-14
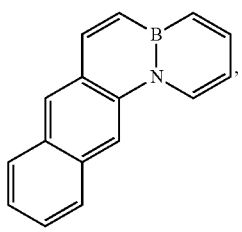
Compound 2-15
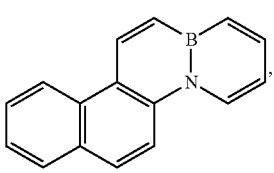
Compound 2-16
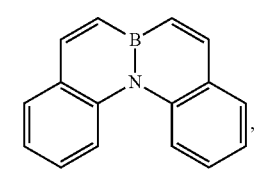
Compound 2-17
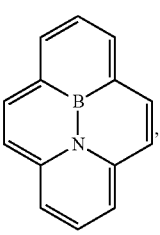
Compound 3-1
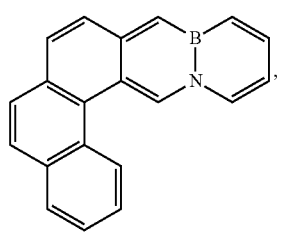
Compound 3-2
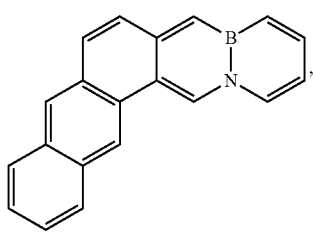
Compound 3-3
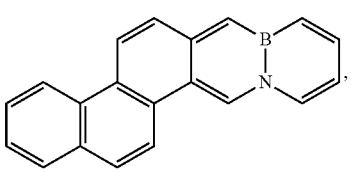

-continued
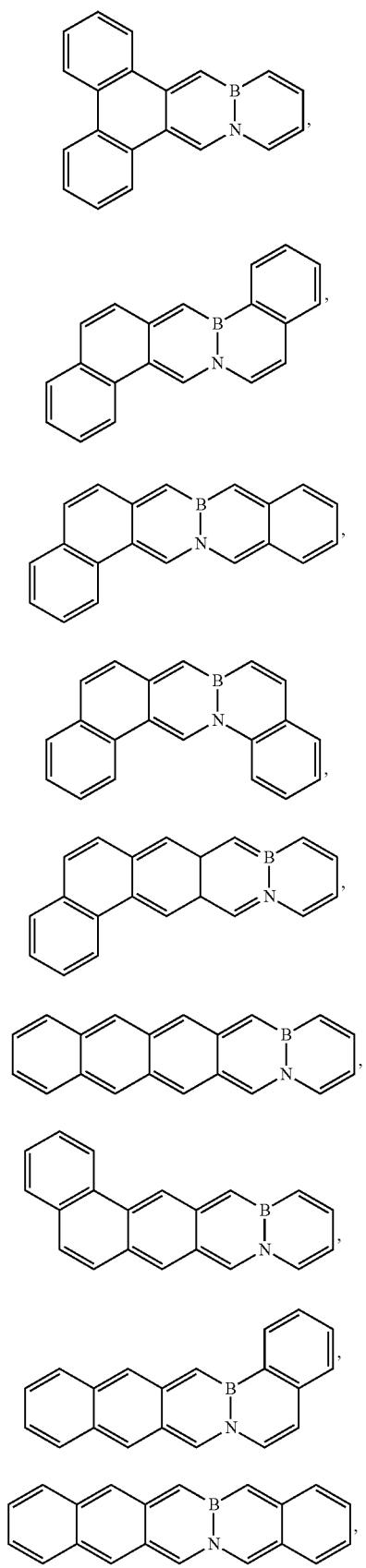
Compound 3-4
Compound 3-5
Compound 3-6
Compound 3-7
Compound 3-8
Compound 3-9
Compound 3-10
Compound 3-11
Compound 3-12
-continued
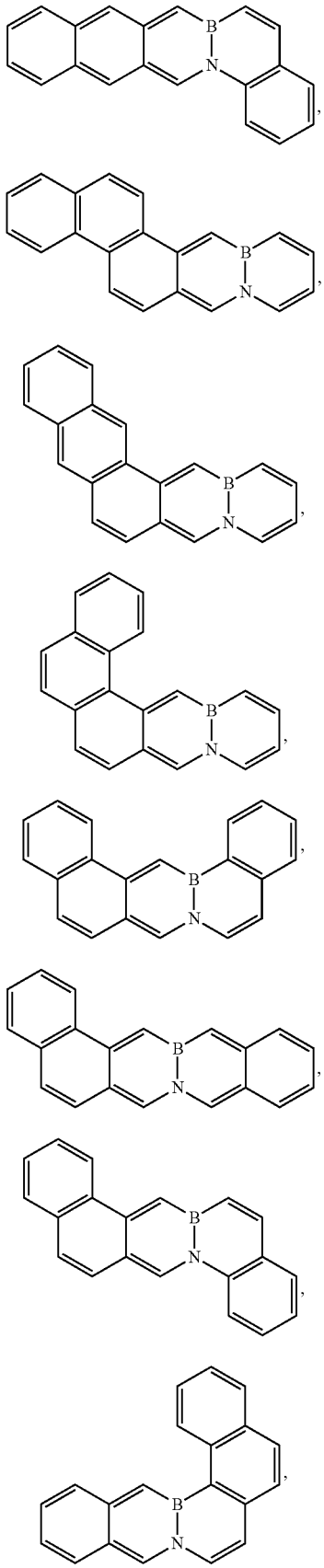
Compound 3-13
Compound 3-14
Compound 3-15
Compound 3-16
Compound 3-17
Compound 3-18
Compound 3-19
Compound 3-20

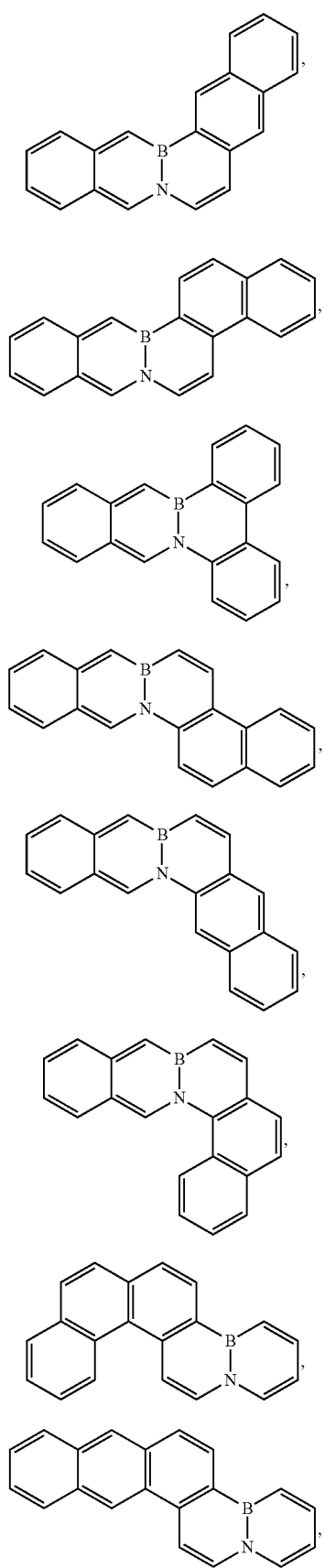
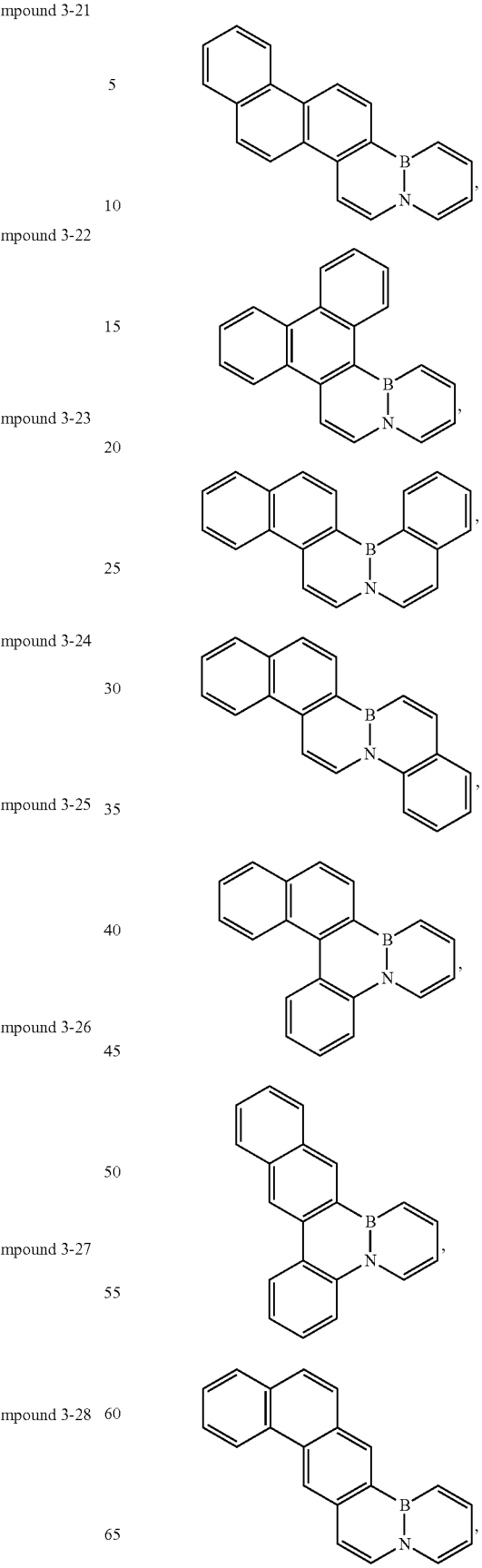

Compound 3-36
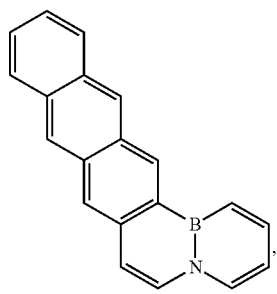
Compound 3-37
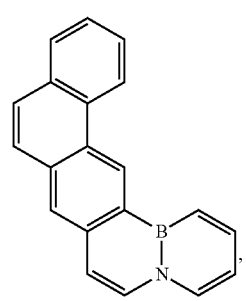
Compound 3-38
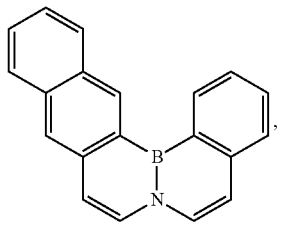
Compound 3-39
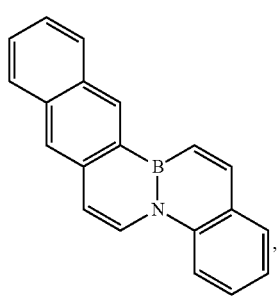
Compound 3-40
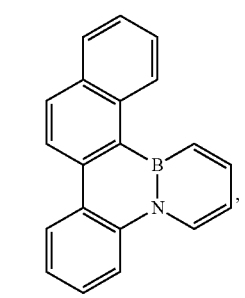
Compound 3-41
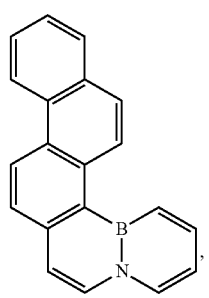
Compound 3-42
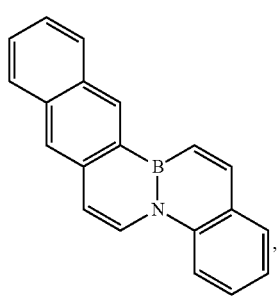
Compound 3-43
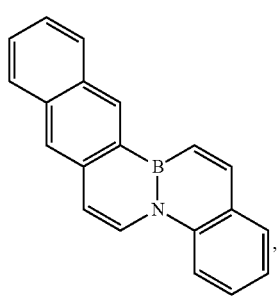
Compound 3-44
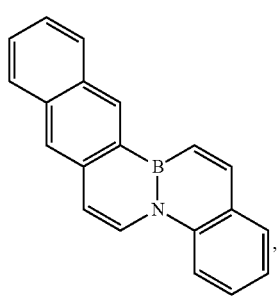
Compound 3-45
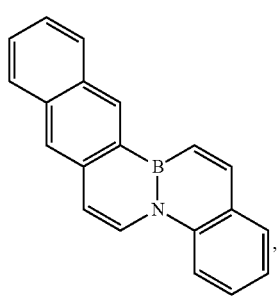
Compound 3-46
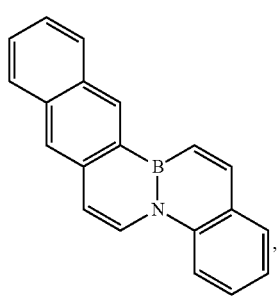

Compound 3-47
Compound 3-48
Compound 3-49
Compound 3-50
Compound 3-51
Compound 3-52
Compound 3-53
Compound 3-54
Compound 3-55
Compound 3-56
Compound 3-57
Compound 3-58
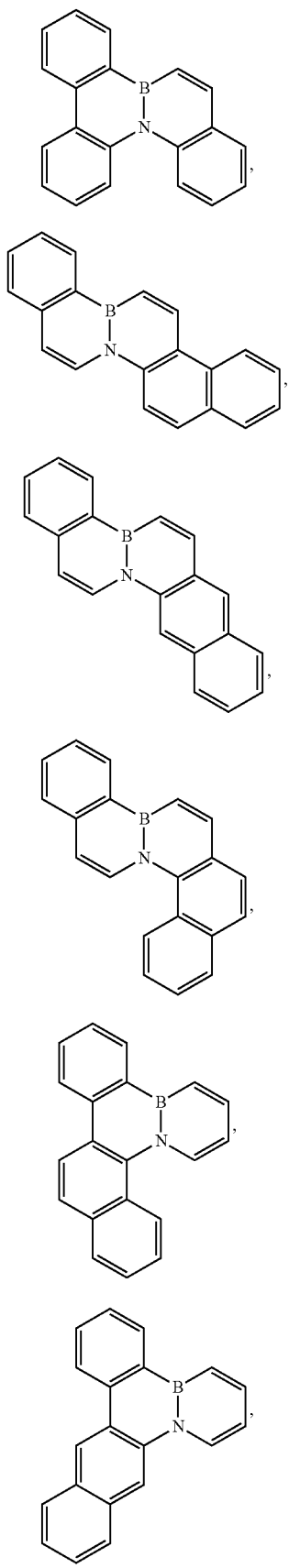
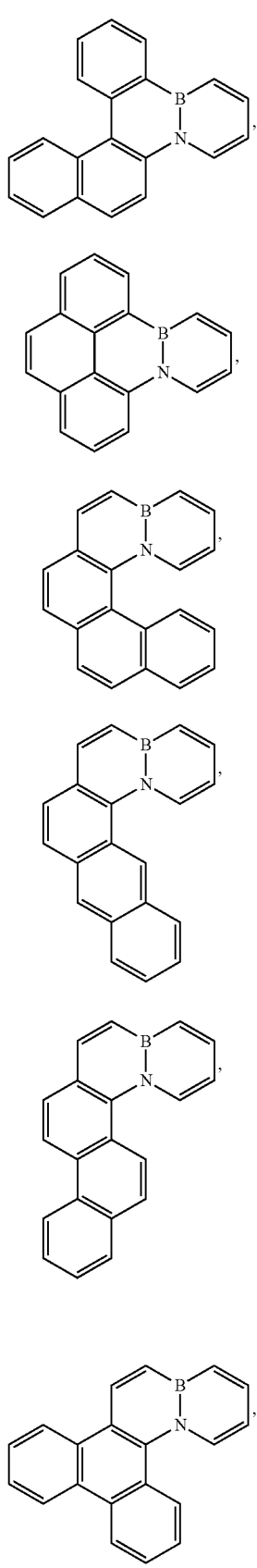

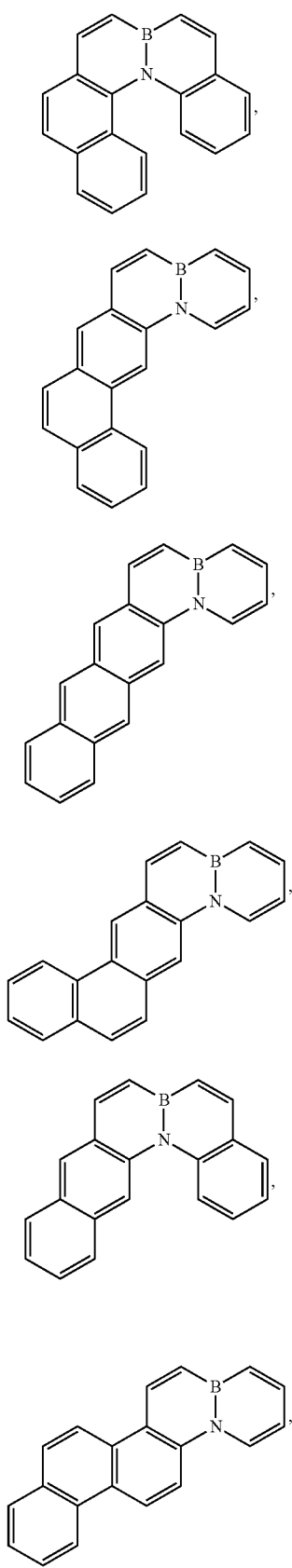
Compound 3-59
Compound 3-60
Compound 3-61
Compound 3-62
Compound 3-63
Compound 3-64
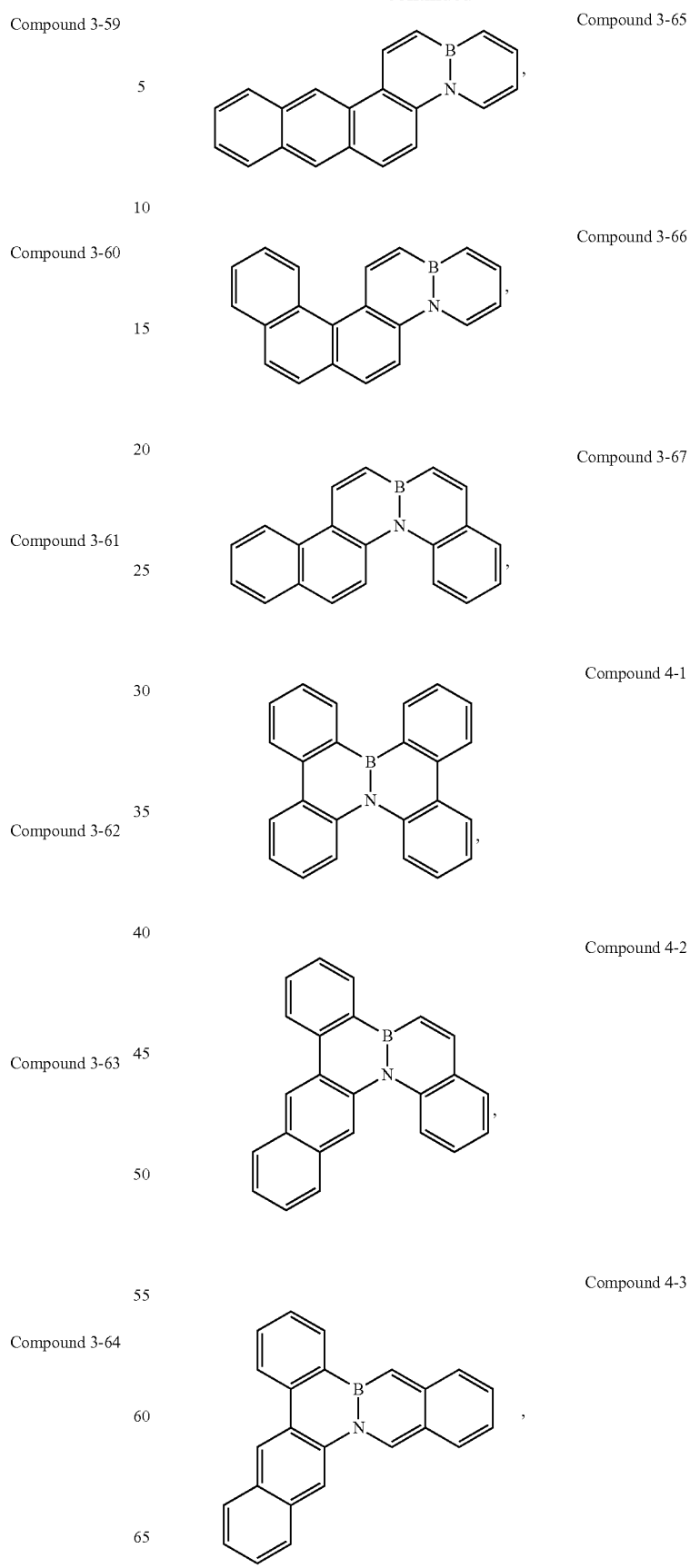
Compound 3-65
Compound 3-66
Compound 3-67
Compound 4-1
Compound 4-2
Compound 4-3

Compound 4-4
Compound 4-5
Compound 4-6
Compound 4-7
Compound 4-8
Compound 4-9
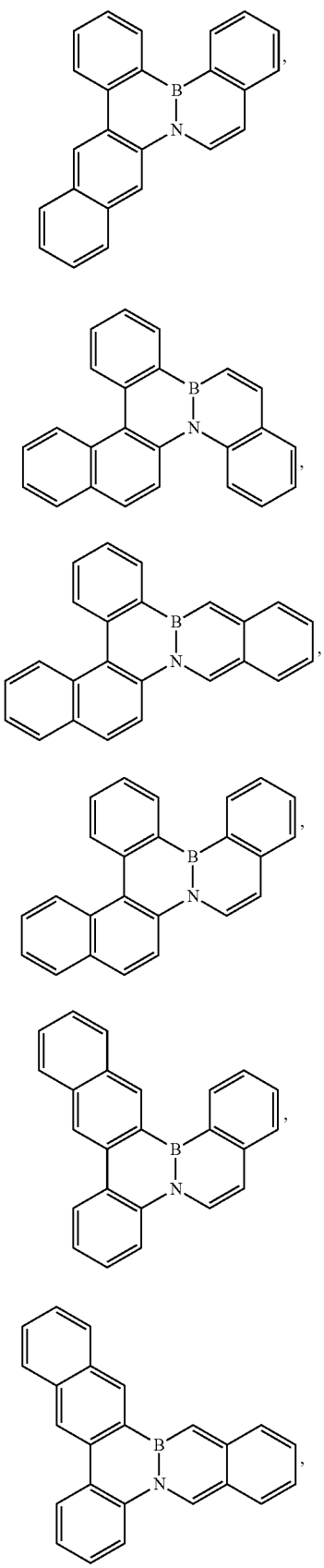
Compound 4-10
Compound 4-11
Compound 4-12
Compound 4-13
Compound 4-14
Compound 4-15
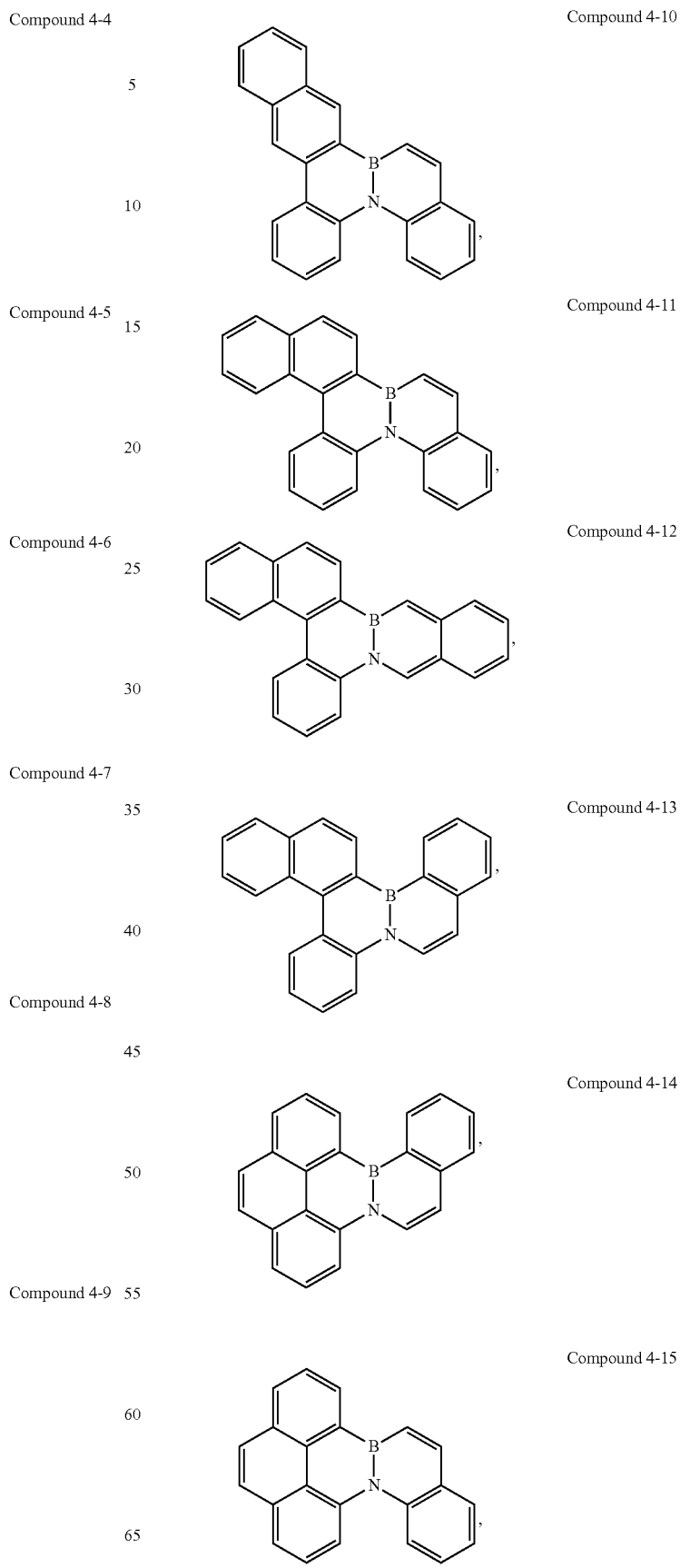

Compound 4-16
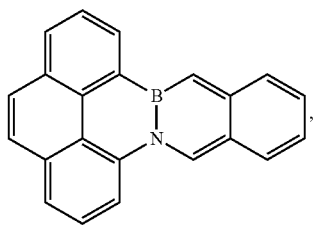
Compound 5-1
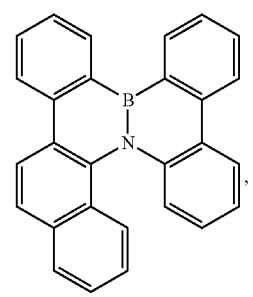
Compound 5-2
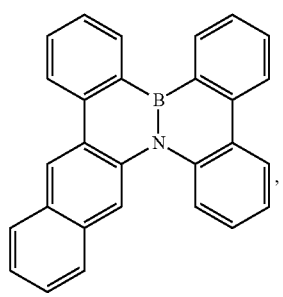
Compound 5-3
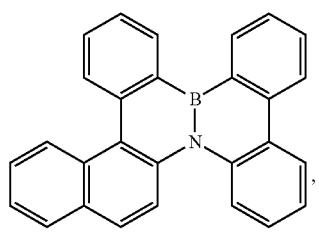
Compound 5-4
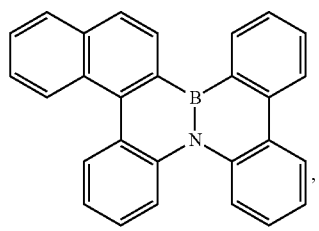
Compound 5-5
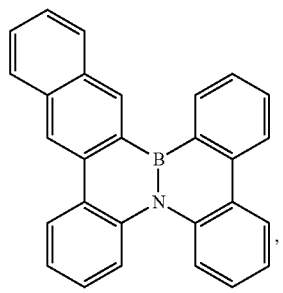
Compound 5-6
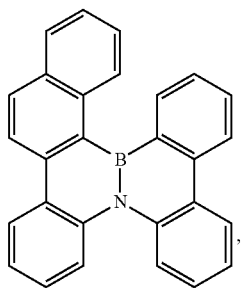
Compound 5-7
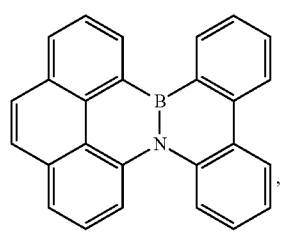
Compound 6-1
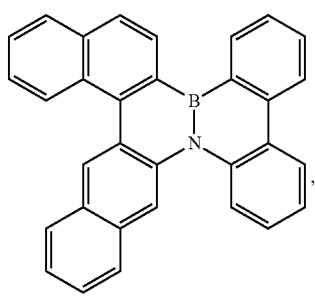
Compound 6-2
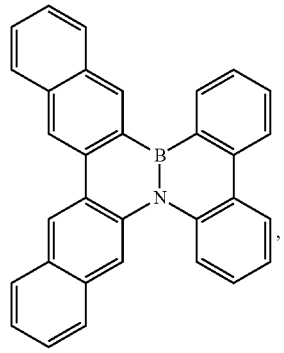
Compound 6-3
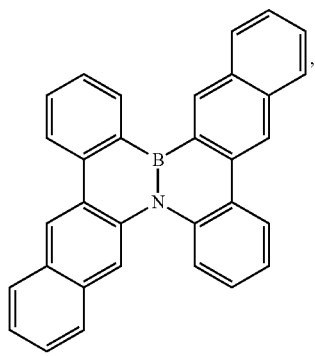

Compound 6-4
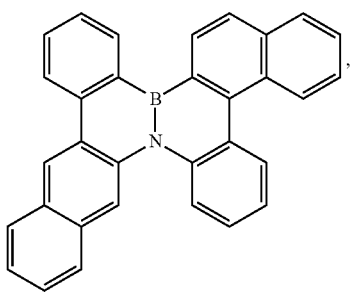
Compound 6-5
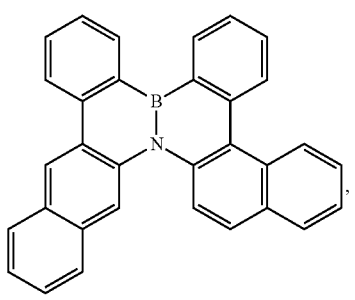
Compound 6-6
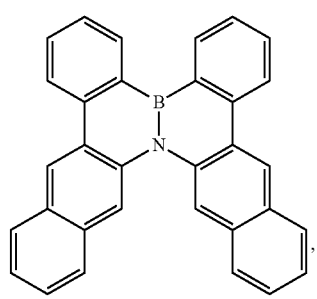
Compound 6-7
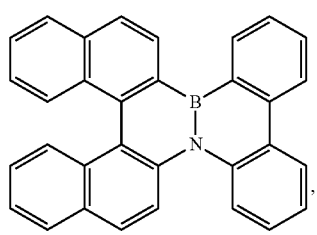
Compound 6-8
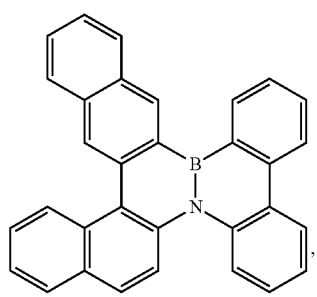
Compound 6-9
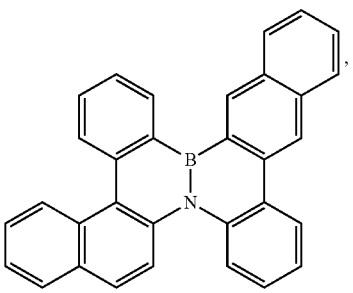
Compound 6-10
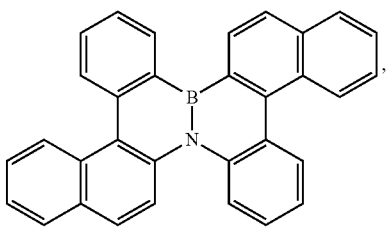
Compound 6-11
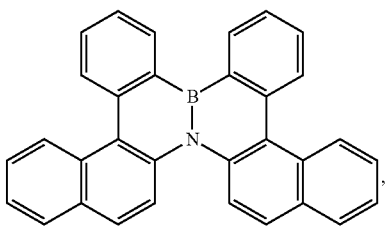
Compound 6-12
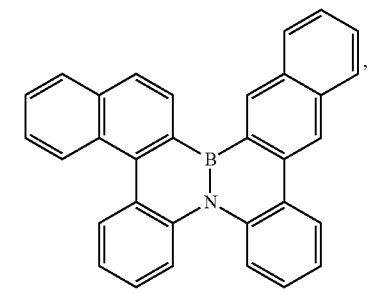
Compound 6-13
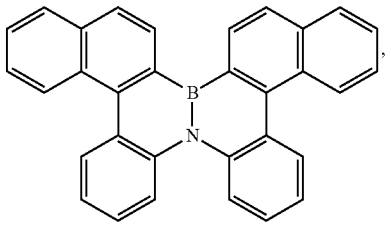
Compound 6-14
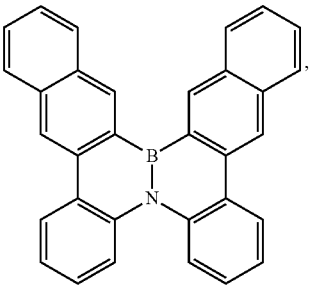

Compound 6-15
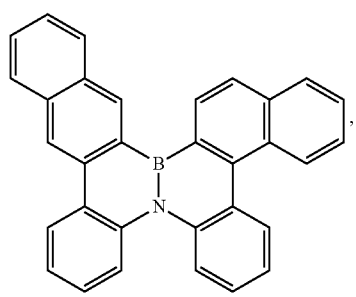
Compound 6-16
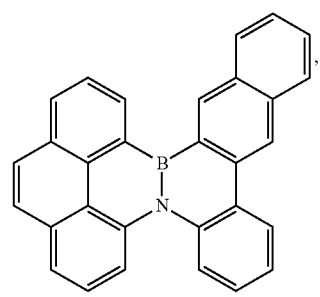
Compound 6-17
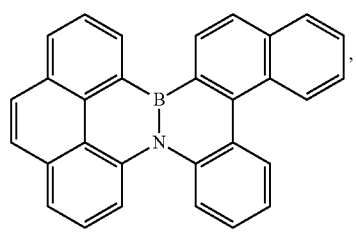
Compound 6-18
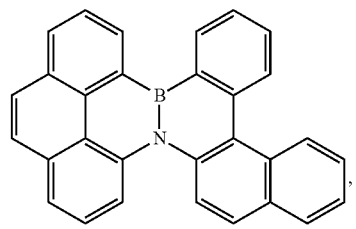
Compound 6-19
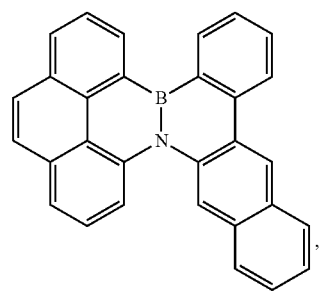
Compound 7-1
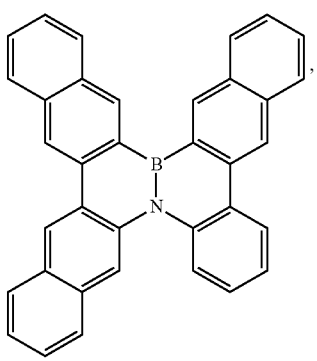
Compound 7-2
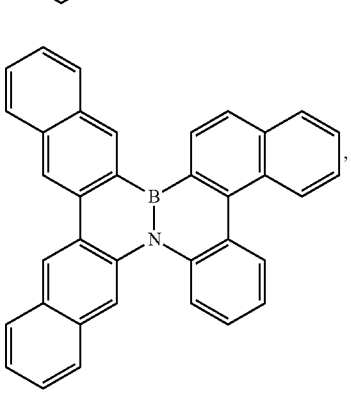
Compound 7-3
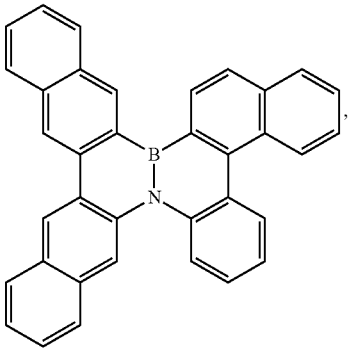
Compound 7-4
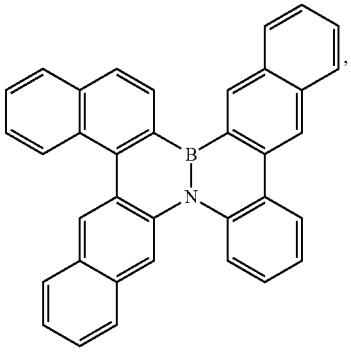
Compound 7-5
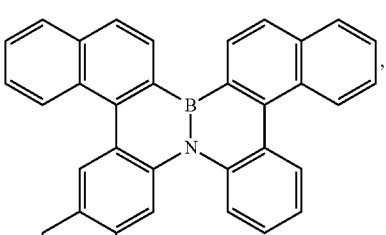

Compound 7-6
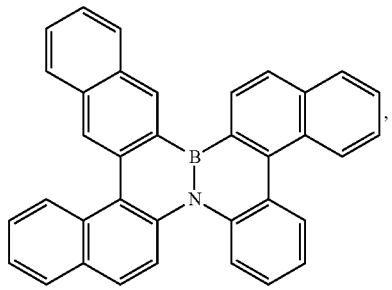
Compound 7-7
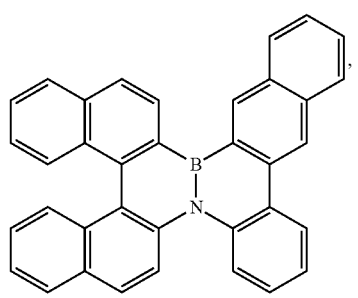
Compound 7-8
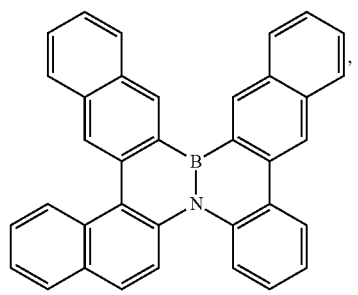
Compound 7-8
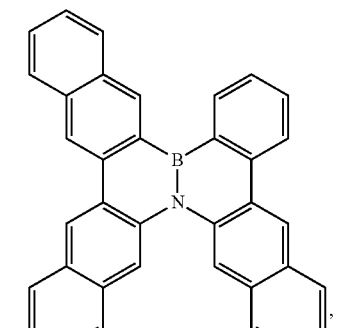
Compound 7-9
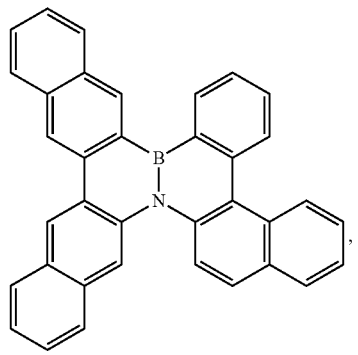
Compound 7-10
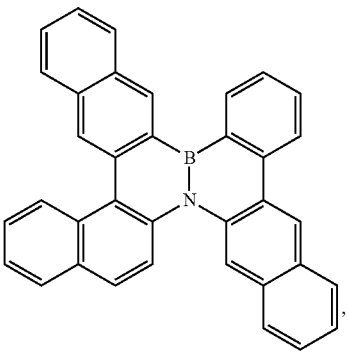
Compound 7-11
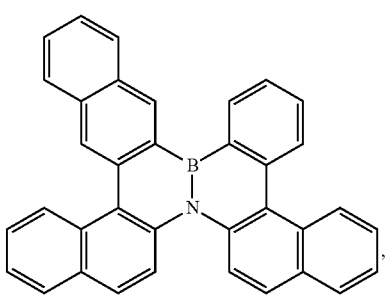
Compound 7-12
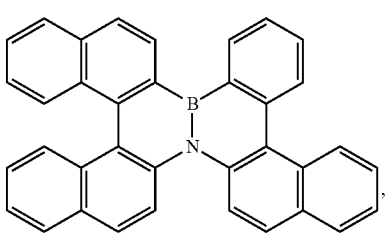
Compound 7-13
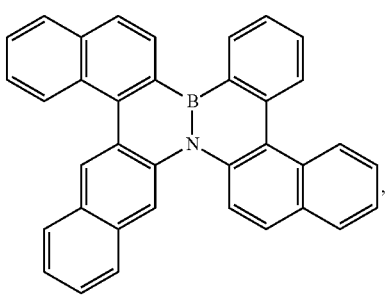
Compound 7-14
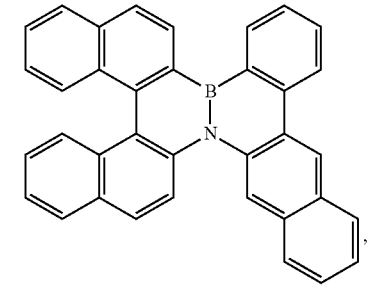

-continued
Compound 7-15
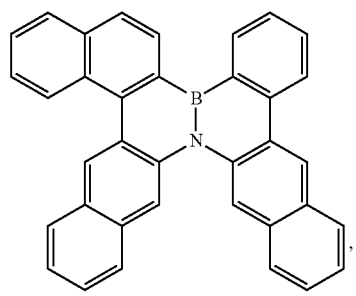
Compound 8-1
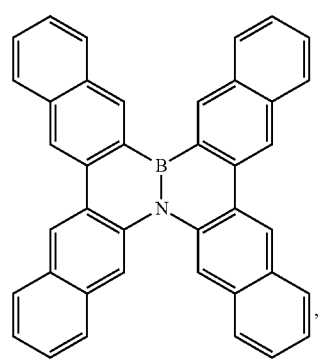
Compound 8-2
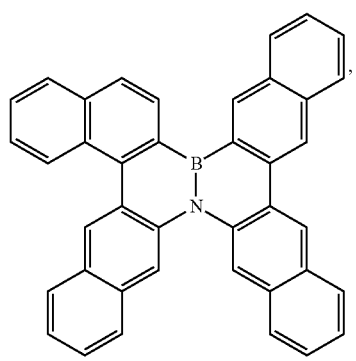
Compound 8-3
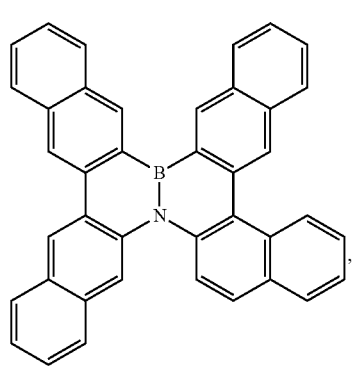
Compound 8-4
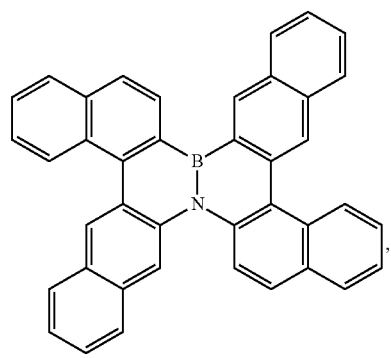
Compound 8-5
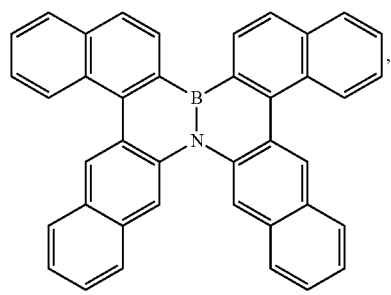
Compound 8-6
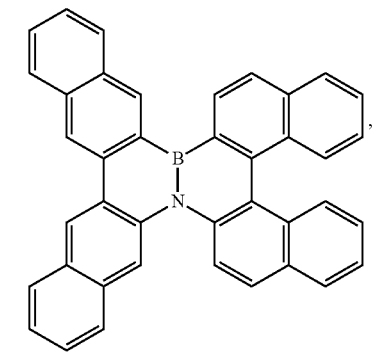
Compound 8-7
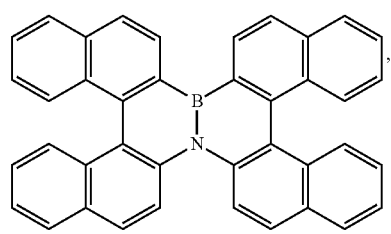
Compound 8-8
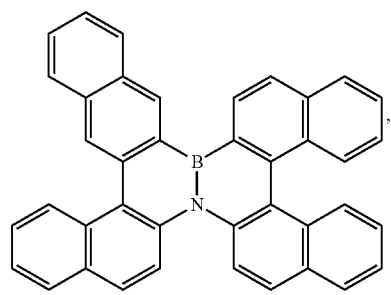

-continued

Compound 8-9

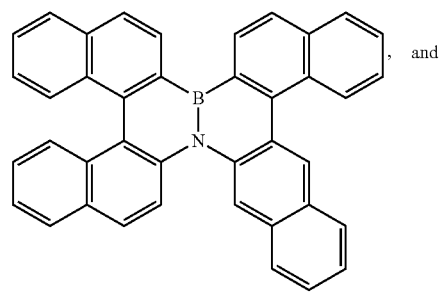
, and

Compound 8-10

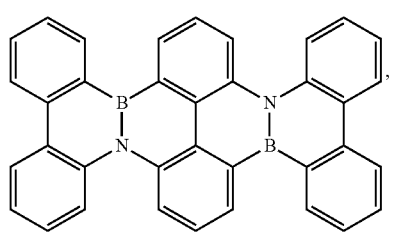
, wherein the fused aromatic ring system is substituted by one or more substituents, R, that are not fused to the aromatic ring system, selected from the group consisting of deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof; and wherein any two adjacent substituents, R, are optionally joined to form one or more non-aromatic rings.

In some further such embodiments, the fused aromatic ring system is selected from the group consisting of:

Compound 1-1

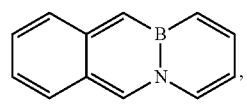
,

Compound 1-3

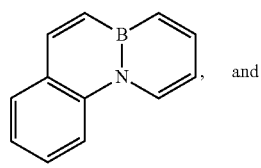
, and

Compound 2-12

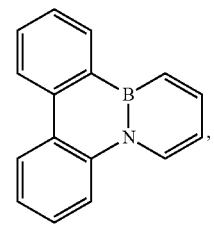
, each of which is substituted by one or more substituents, R, that are not fused to the aromatic ring system, selected from the group consisting of deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof; and wherein any two adjacent substituents, R, are optionally joined to form one or more non-aromatic rings.

In some embodiments, the fused aromatic ring system is:

Compound 1-1

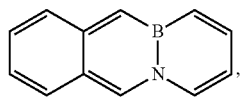
, which is substituted by one or more substituents, R, that are not fused to the aromatic ring system, selected from the group consisting of deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof; and wherein any two adjacent substituents, R, are optionally joined to form one or more non-aromatic rings.

In some embodiments, the fused aromatic ring system is

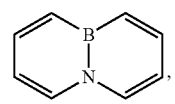
, which is substituted by one or more substituents, R, that are not fused to the aromatic ring system, selected from the group consisting of deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof; and wherein any two adjacent substituents, R, are optionally joined to form one or more non-aromatic rings.

In some embodiments of the invention, the substituent, R, is selected from the group consisting of alkyl, cycloalkyl, amino, silyl, aryl, heteroaryl, and combinations thereof.

In some embodiments of the invention, the substituent, R, is selected from the group consisting of:

S1

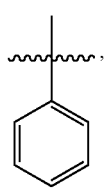
,

S2

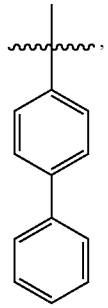
,

77
-continued
S3
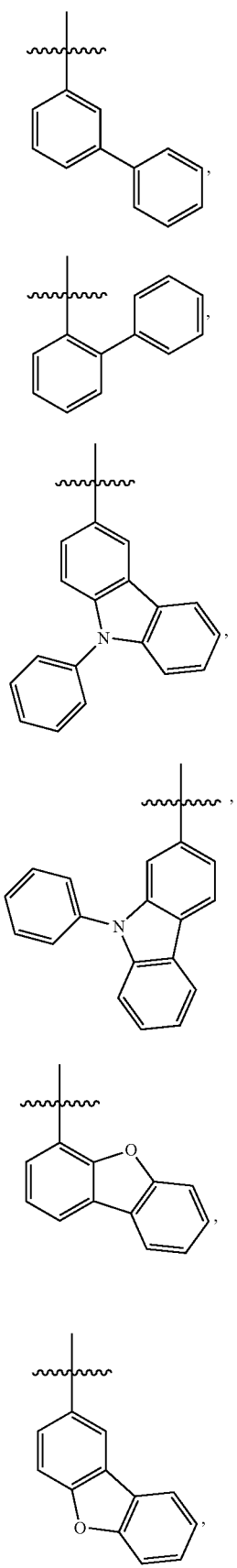
S4
S5
S6
S7
S8
78
-continued
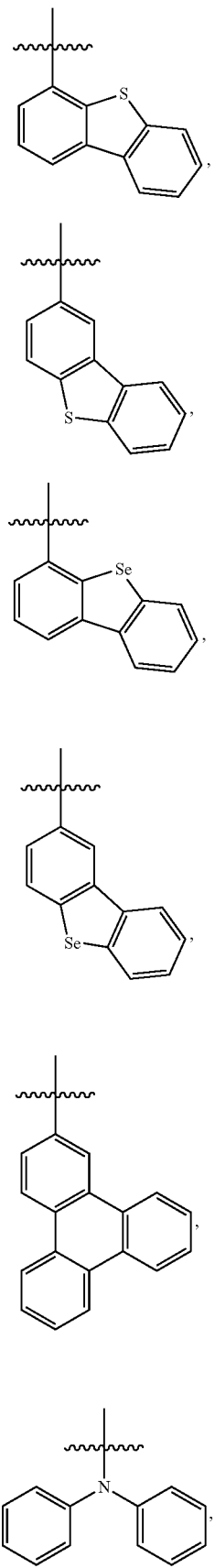
S9
S10
S11
S12
S13
S14

-continued
S15
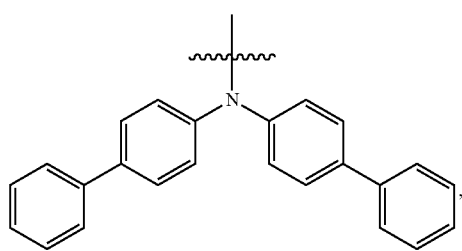
S16
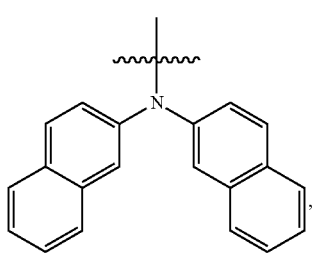
S17
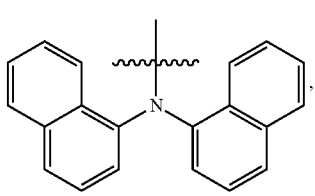
S18
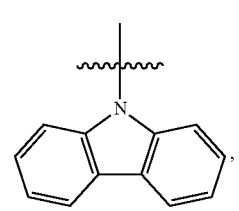
S19
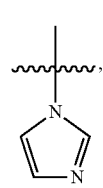
S20
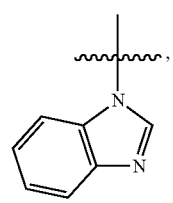
S21
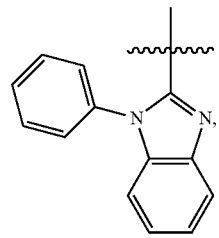
-continued
S22
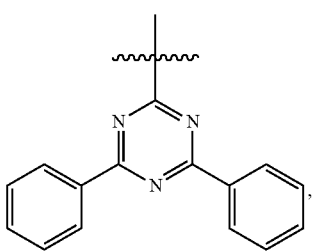
S23
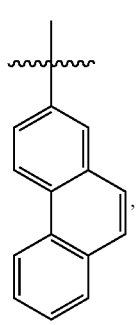
S24
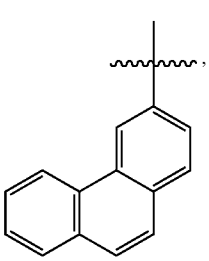
S25
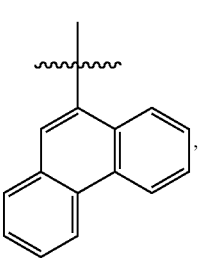
S26
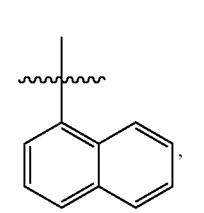
S27
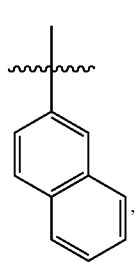

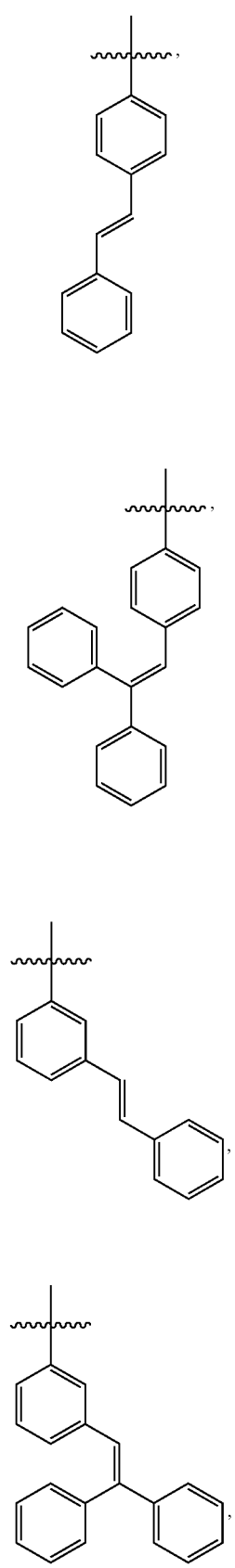
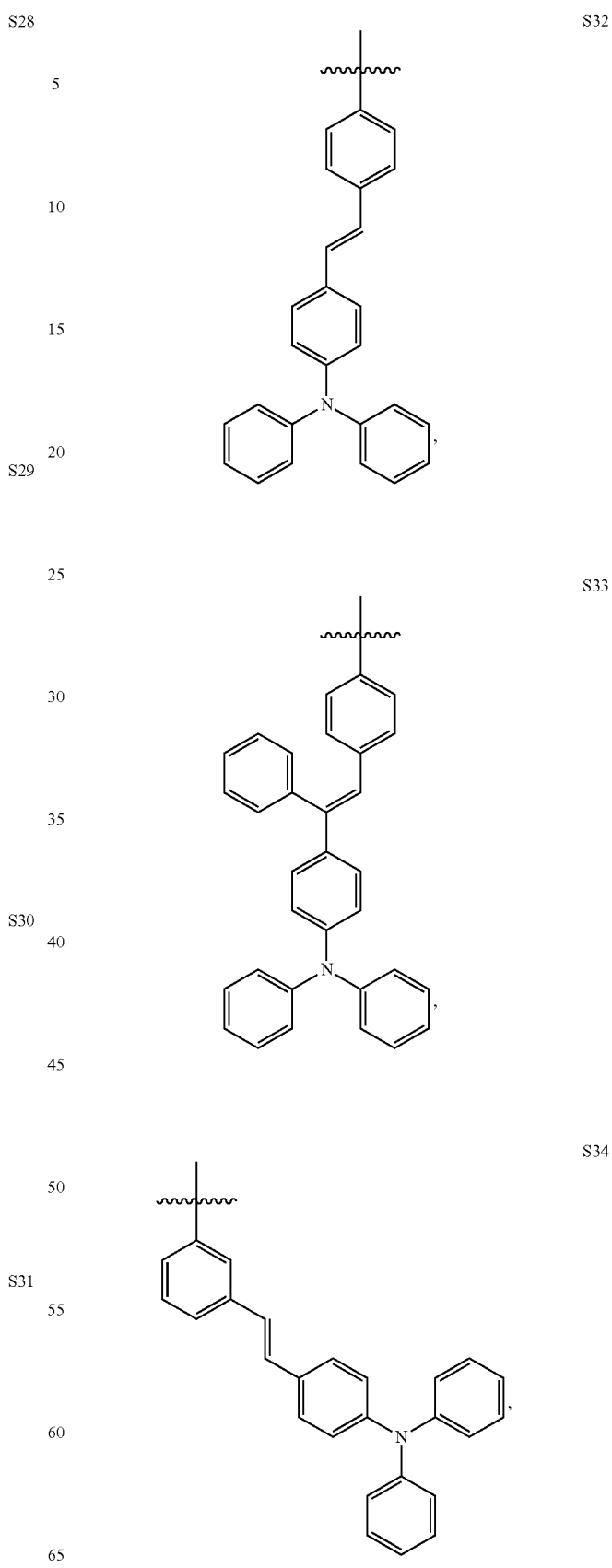

S35
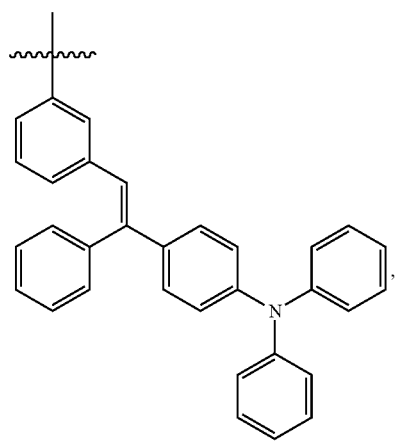
S36
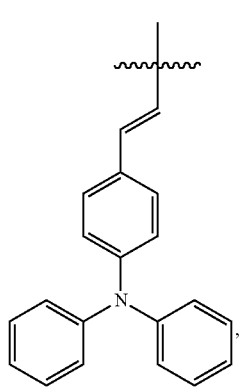
S37
S38
S39
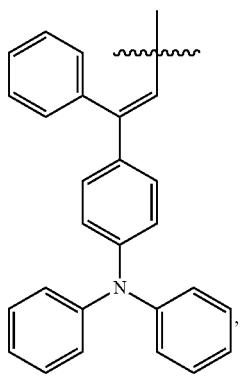
S40
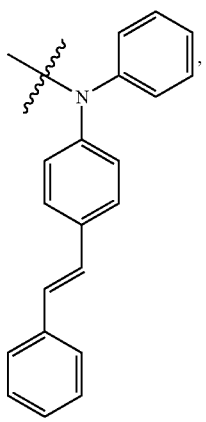
S41
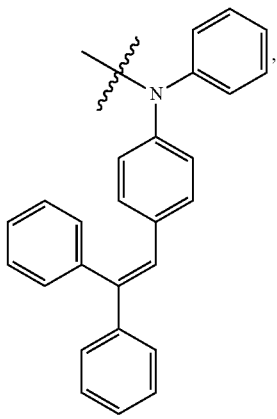
S42
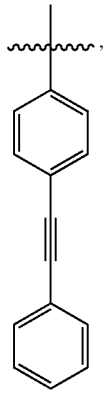

-continued
S43
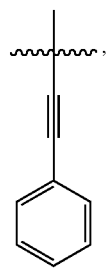
S44
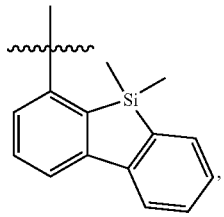
S45
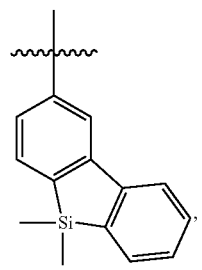
S46
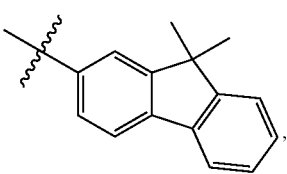
S47
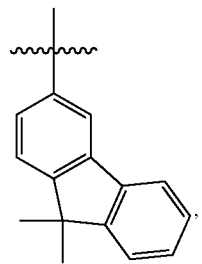
S48
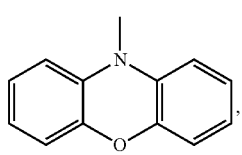
S49
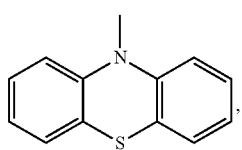
S50
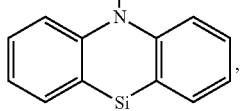
S51
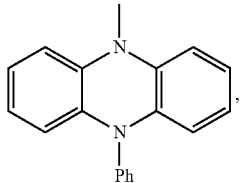
S52
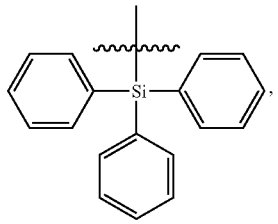
S53
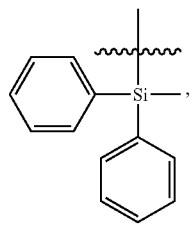
S54
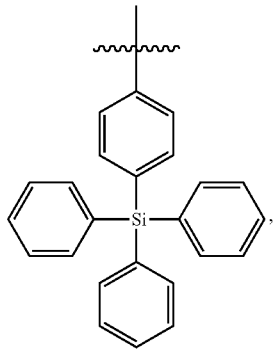
S55
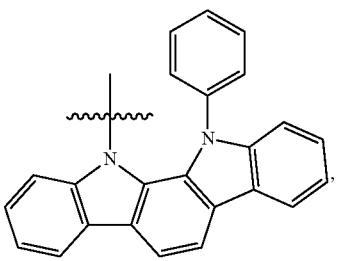

S56
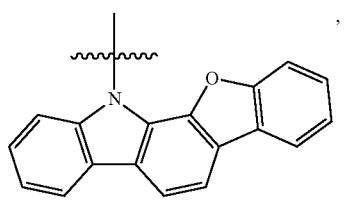
S57
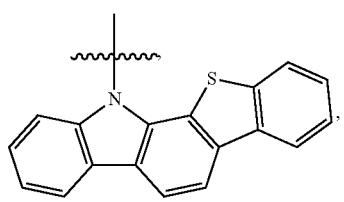
S58
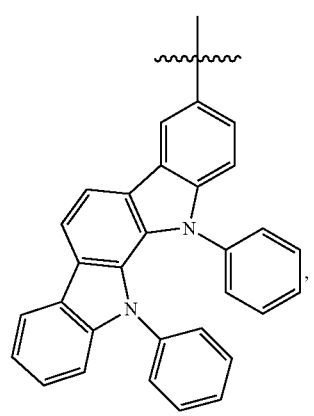
S59
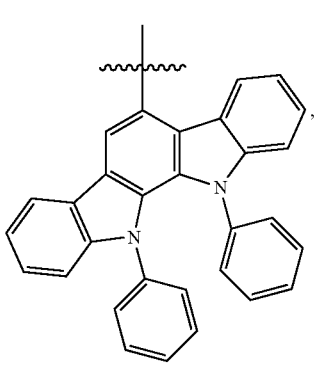
S60
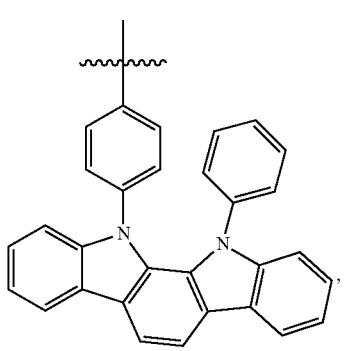
S61
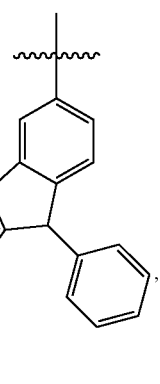
S62
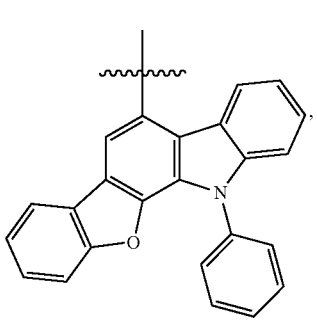
S63
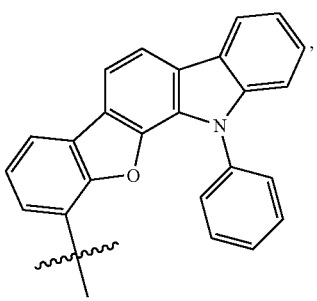
S64

-continued
S65
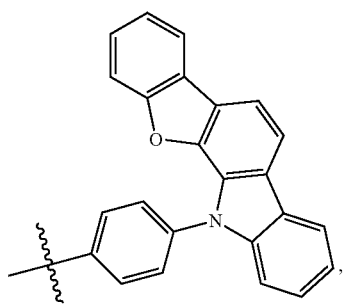
S66
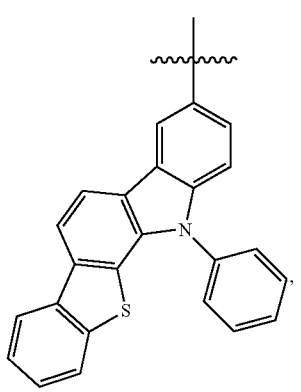
S67
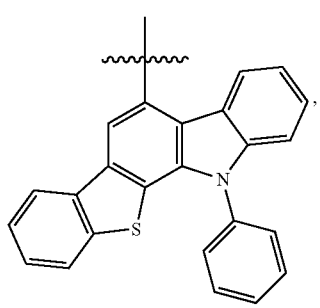
S68
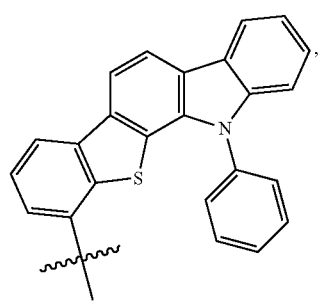
-continued
S69
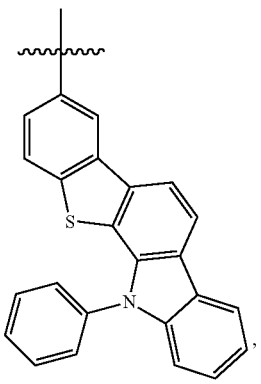
S70
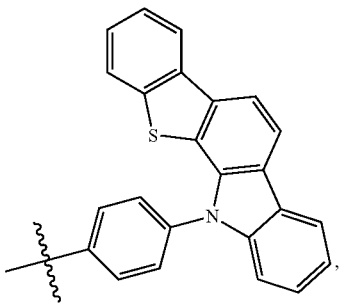
S71
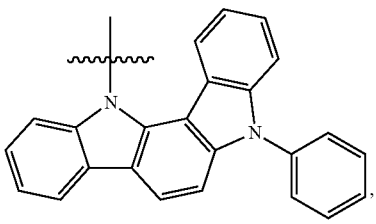
S72
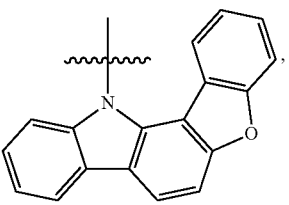
S73
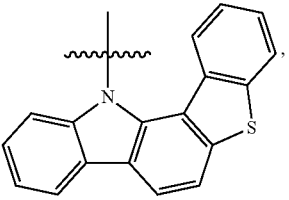
S74
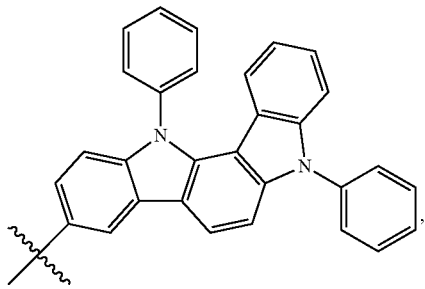

-continued
S75
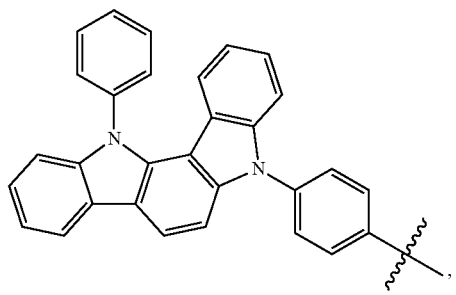
S76
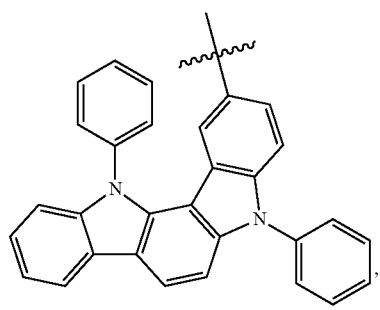
S77
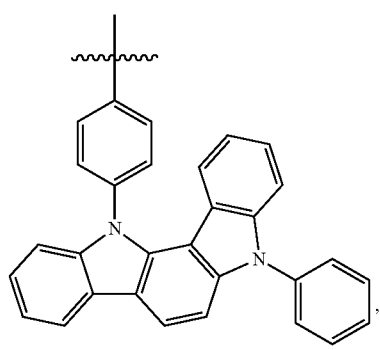
S78
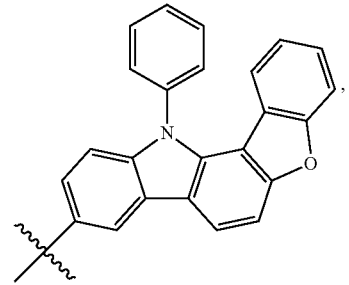
S79
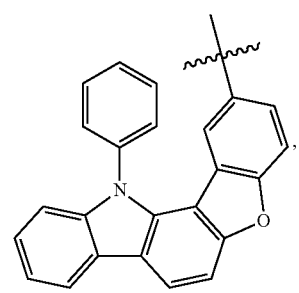
-continued
S80
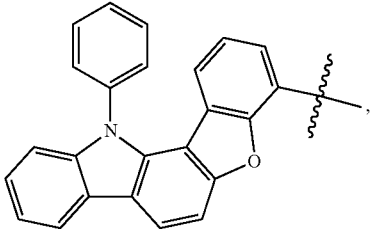
S81
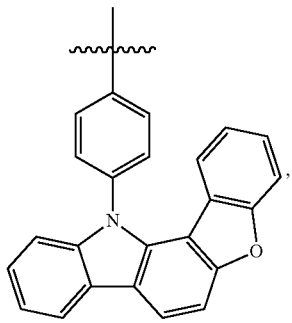
S82
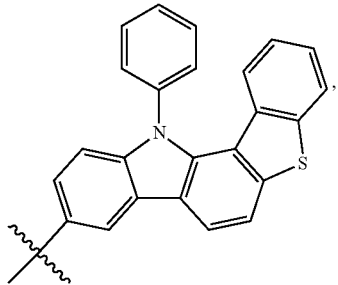
S83
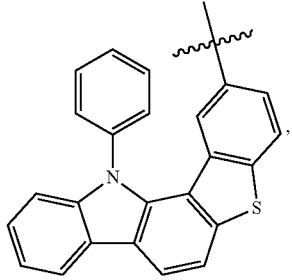
S84
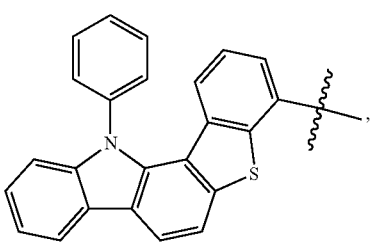

S85
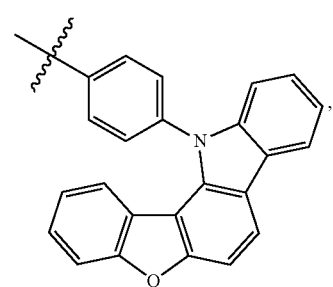
S86
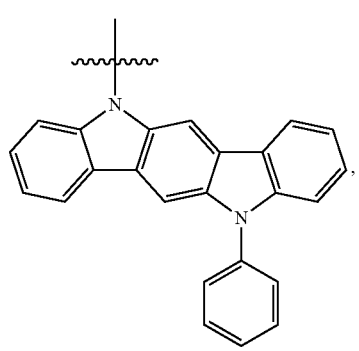
S87
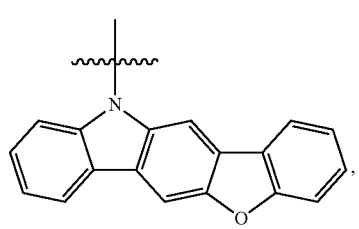
S88
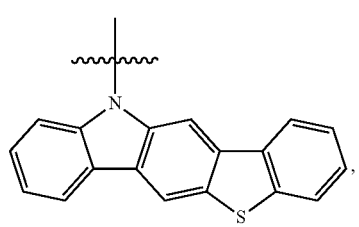
S89
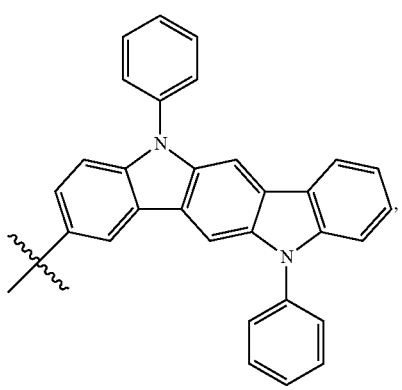
S90
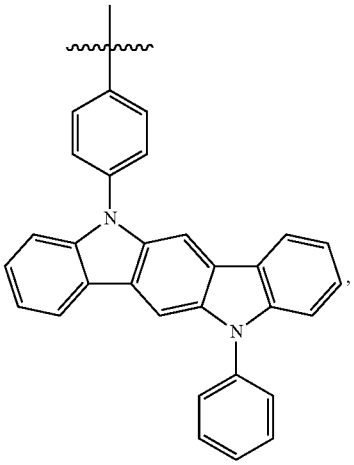
S91
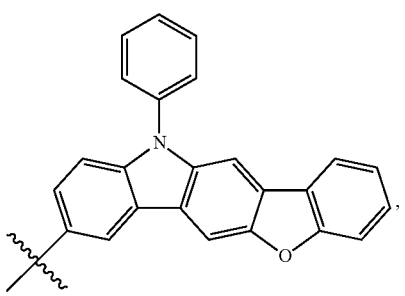
S92
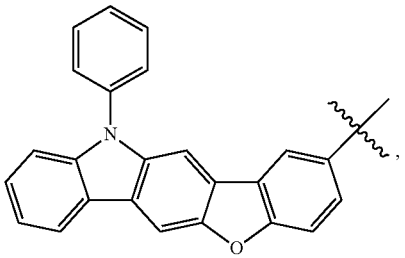
S93
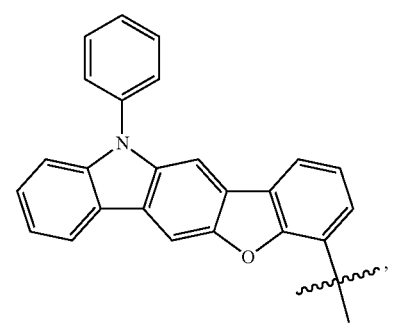

-continued
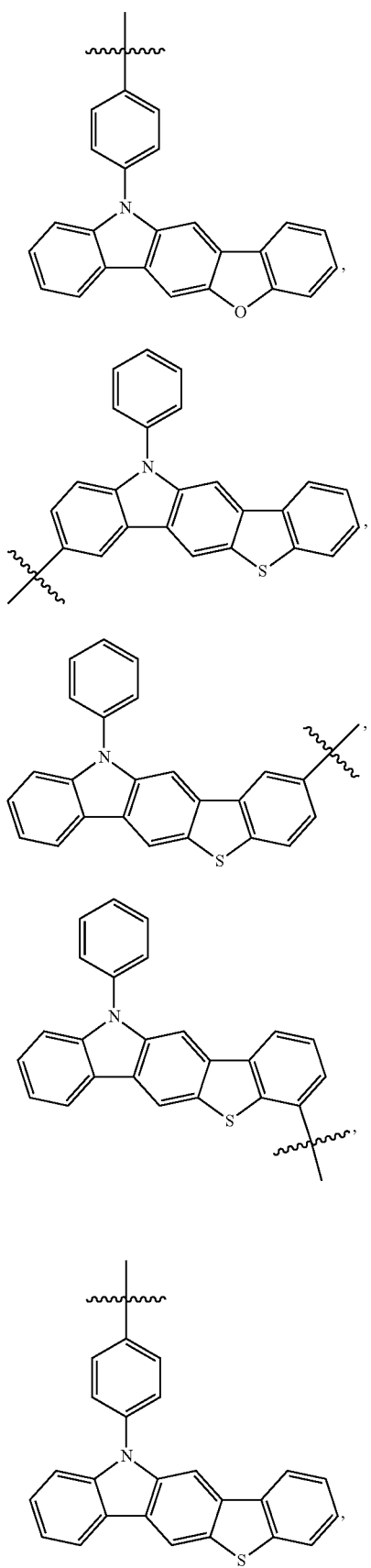
S94
S95
S96
S97
S98
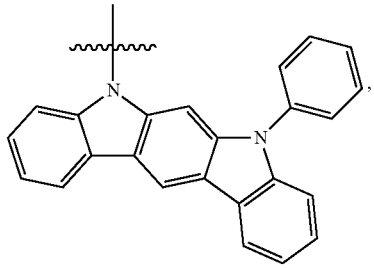
S99
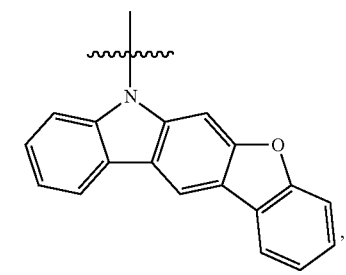
S100
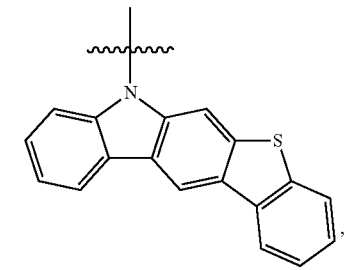
S101
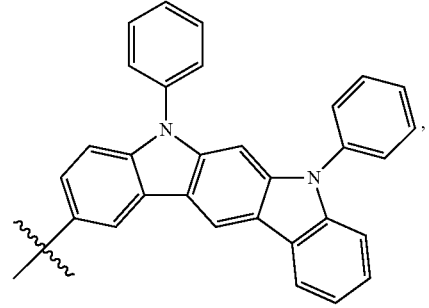
S102
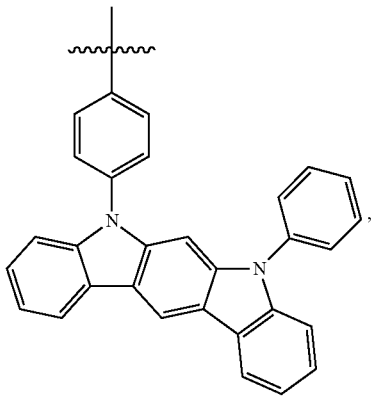
S103

S104
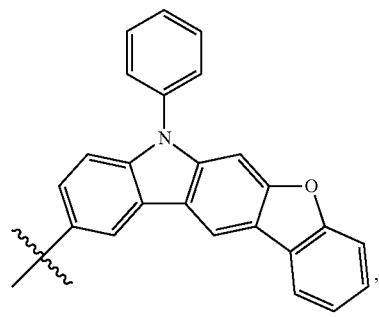
S105
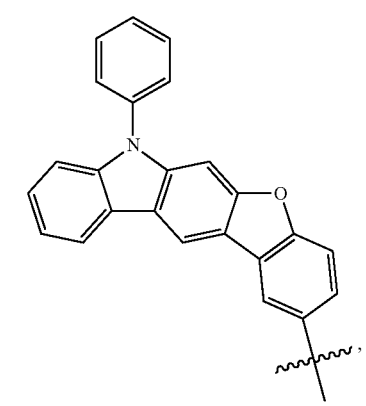
S106
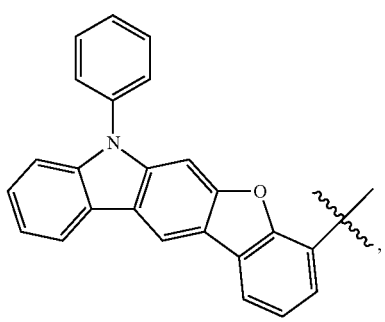
S107
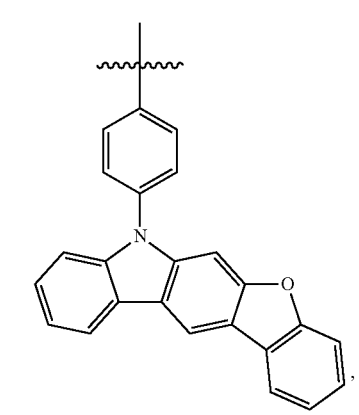
S108
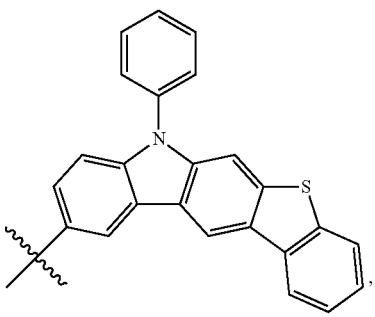
S109
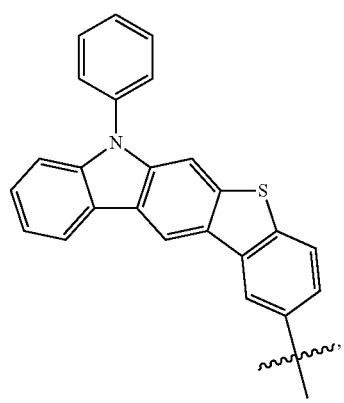
S110
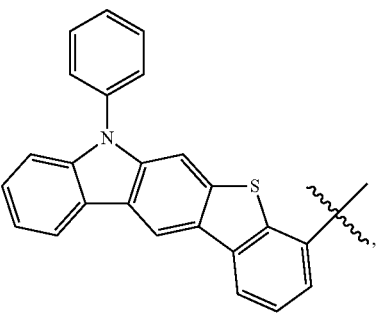
S111
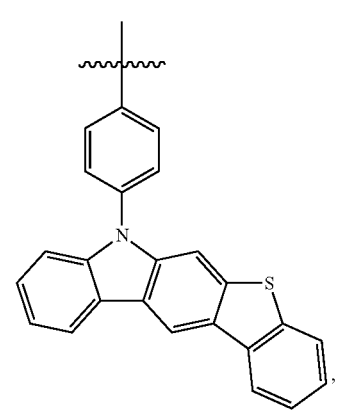

-continued
S112
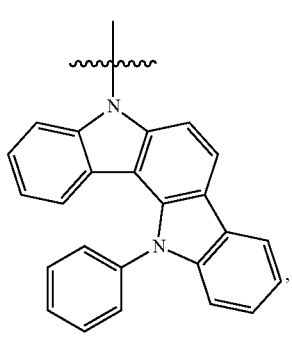
S113
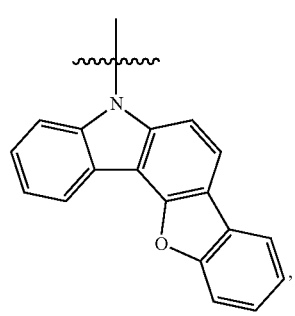
S114
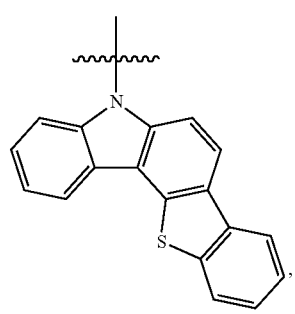
S115
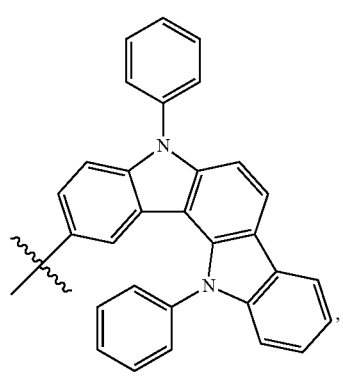
-continued
S116
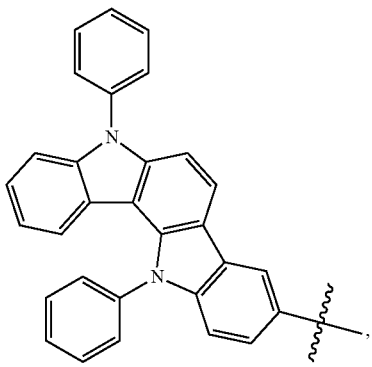
S117
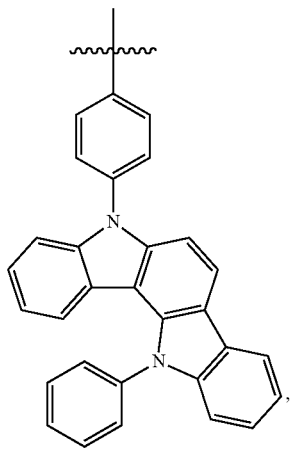
S118
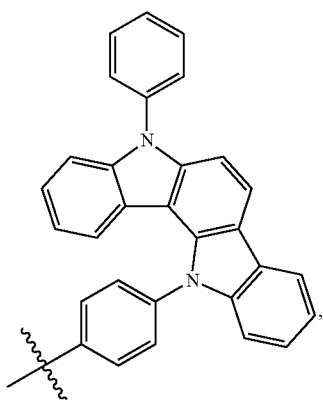
S119
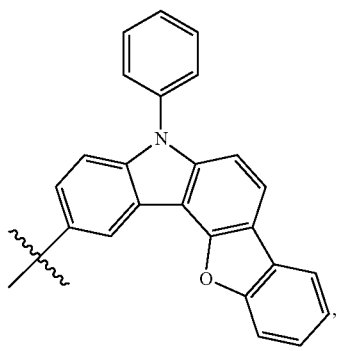

-continued
S120
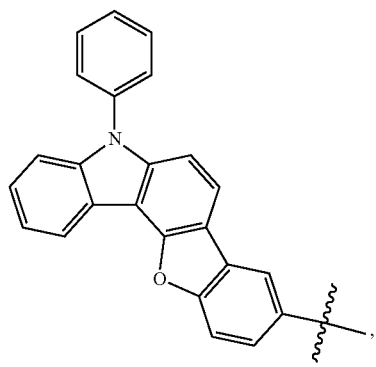
S121
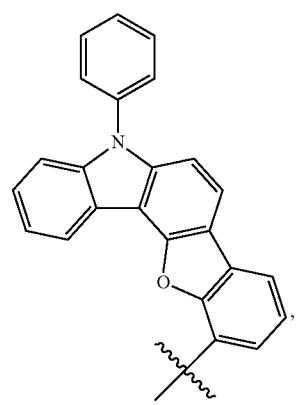
S122
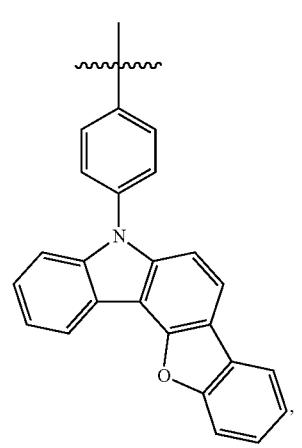
S123
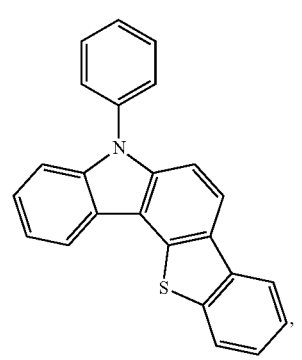
S124
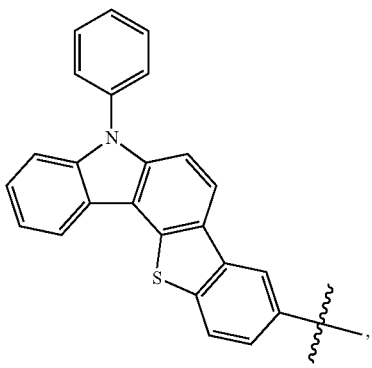
S125
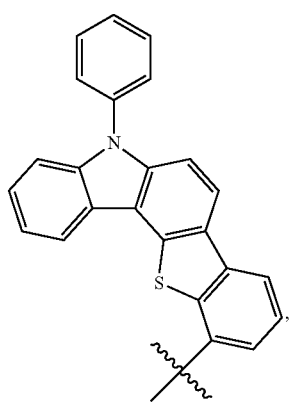
S126
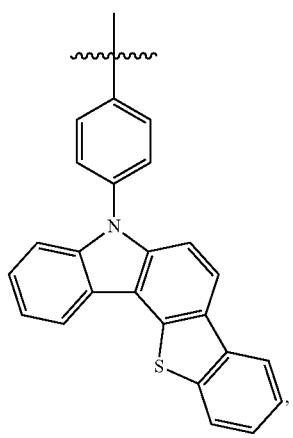
S127
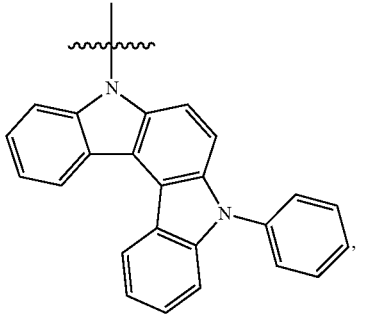

-continued
S128
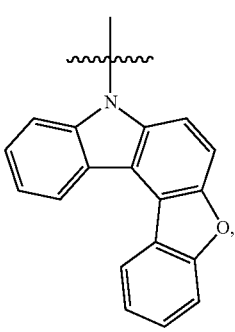
S129
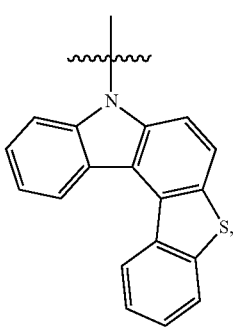
S130
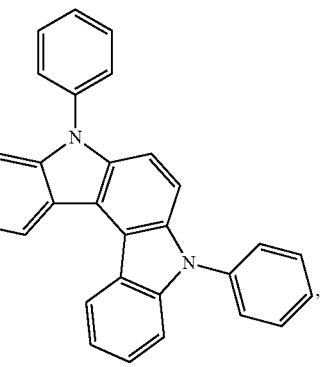
S131
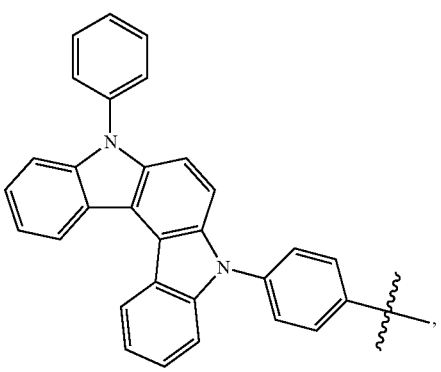
-continued
S132
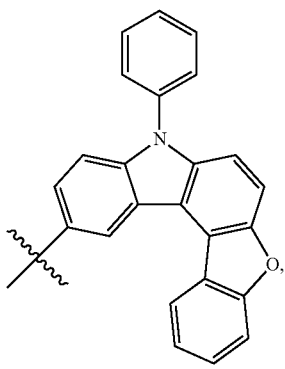
S133
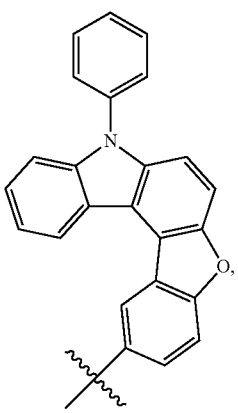
S134
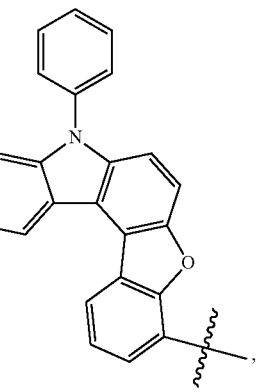
S135
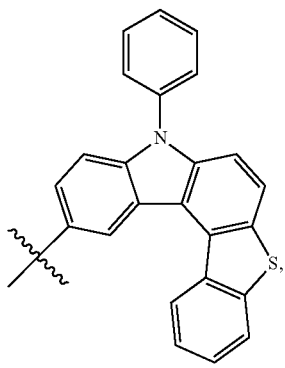

-continued
S136
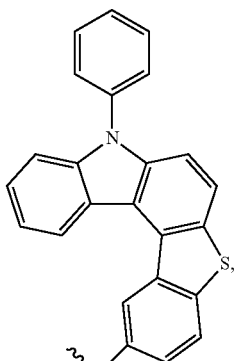
S137
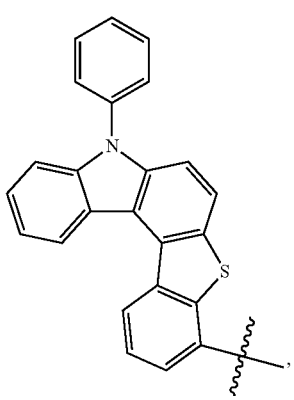
S138
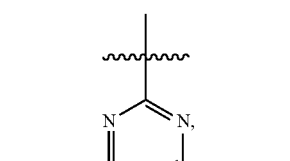
S139
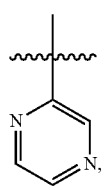
S140
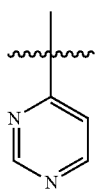
S141
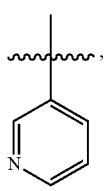
-continued
S142
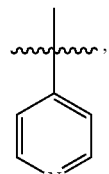
S143
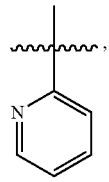
S145
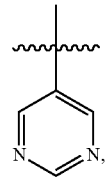
S146
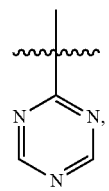
S147
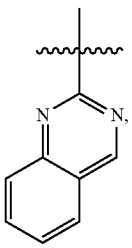
S148
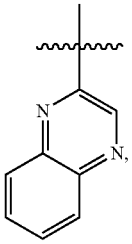
S149
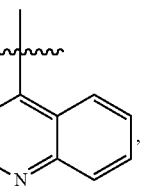

S150 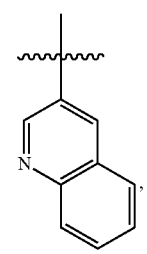

S151 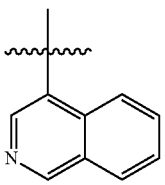

S152 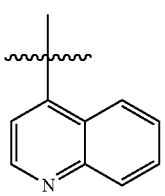

S153 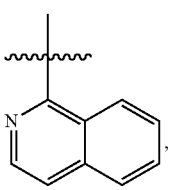

S154 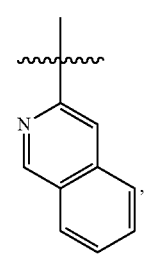

S155 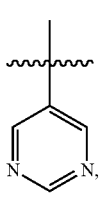

S156 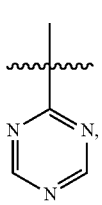

S157 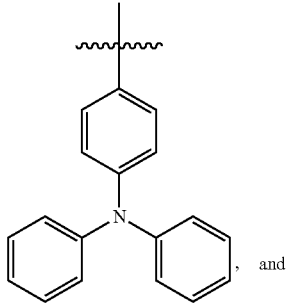, and

S158 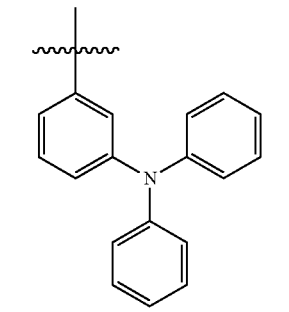

In some embodiments, any of the foregoing substituents is optionally further substituted with one or more substituents selected independently from the group consisting of with deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof.

In some such embodiments, the boron-nitrogen polyaromatic compound is a compound of Formula (II), Formula (III), or Formula (IV):

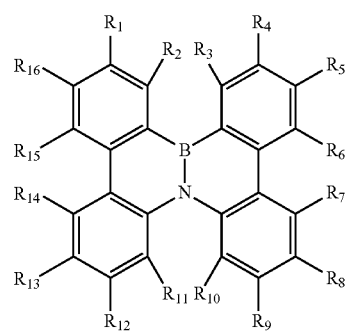
(II)

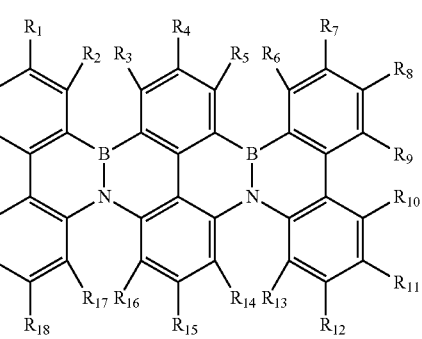
(III)

-continued

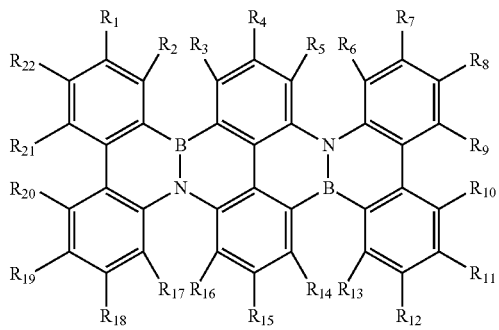

wherein $R_1$ to $R_{22}$ are each independently selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof, wherein any two adjacent substituents are optionally joined to form a ring. In some such embodiments, the boron-nitrogen polyaromatic compound is a compound of Formula (II). In other such embodiments, the boron-nitrogen polyaromatic compound is a compound of Formula (III). In other such embodiments, the boron-nitrogen polyaromatic compound is a compound of Formula (IV). In some embodiments, the substituents, $R_1$ to $R_{22}$, are selected independently from the group consisting of aryl, heteroaryl, and $NR_aR_b$; wherein $R_a$ and $R_b$ are aryl or heteroaryl, which can be further substituted.

In some embodiments, the boron-nitrogen polyaromatic compound is a compound of Formula (II), and at least one of $R_5$, $R_8$, $R_{13}$, or $R_{16}$ is not hydrogen or deuterium. In some further such embodiments, at least one of $R_5$, $R_8$, $R_{13}$, or $R_{16}$ is aryl, heteroaryl or $NR_aR_b$; wherein $R_a$ and $R_b$ are aryl or heteroaryl, which can be further substituted. In some further such embodiments, $R_5$ and $R_{13}$ are phenyl or $NR_aR_b$. In some further such embodiments, $R_a$ and $R_b$ are phenyl.

In some embodiments, the boron-nitrogen polyaromatic compound is a compound of Formula (II), and at least one of $R_1$, $R_4$, $R_9$, or $R_{12}$ is not hydrogen or deuterium. In some further such embodiments, at least one of $R_1$, $R_4$, $R_9$, or $R_{12}$ is aryl, heteroaryl or $NR_aR_b$; wherein $R_a$ and $R_b$ are aryl or heteroaryl, which can be further substituted. In some further such embodiments, $R_1$ and $R_9$ are phenyl or $NR_aR_b$. In some further such embodiments, $R_a$ and $R_b$ are phenyl.

In some embodiments, the boron-nitrogen polyaromatic compound is a compound of Formula (II) or Formula (IV), and at least one of $R_8$, $R_{11}$, $R_{19}$, or $R_{22}$ is not hydrogen or deuterium. In some further such embodiments, at least one of $R_8$, $R_{11}$, $R_{19}$, or $R_{22}$ is aryl, heteroaryl or $NR_aR_b$; wherein $R_a$ and $R_b$ are aryl or heteroaryl, which can be further substituted. In some further such embodiments, $R_8$ and $R_{19}$ are phenyl or $NR_aR_b$. In some further such embodiments, $R_a$ and $R_b$ are phenyl.

In some embodiments, the boron-nitrogen polyaromatic compound is a compound of Formula (II), and at least one of $R_1$, $R_4$, $R_7$, $R_{12}$, $R_{15}$ or $R_{18}$ is not hydrogen or deuterium. In some further such embodiments, at least one of $R_1$, $R_4$, $R_7$, $R_{12}$, $R_{15}$ or $R_{18}$ is aryl, heteroaryl or $NR_aR_b$; wherein $R_a$ and $R_b$ are aryl or heteroaryl, which can be further substituted. In some further such embodiments, $R_1$ and $R_{12}$ are phenyl or $NR_aR_b$. In some further such embodiments, $R_a$ and $R_b$ are phenyl.

Boron-nitrogen polyaromatic compounds are provided, where the compounds are selected from the group consisting of:

Compound 0-1

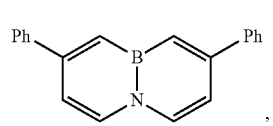

Compound 0-2

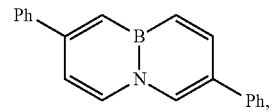

Compound 0-3

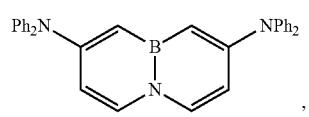

Compound 0-4

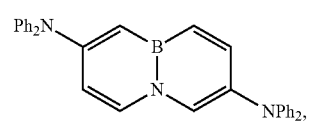

Compound 0-5

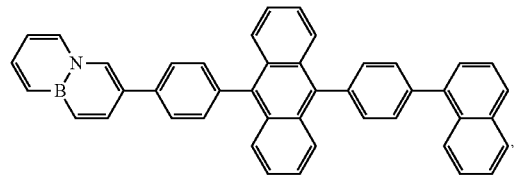

Compound 0-6

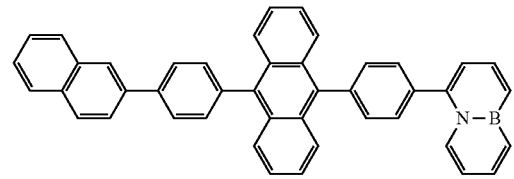

Compound 0-7

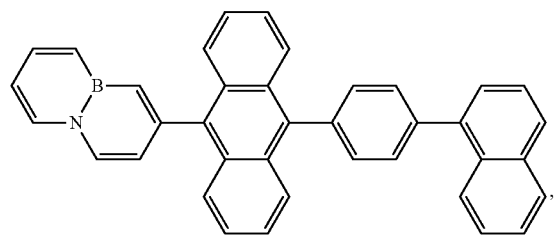

Compound 1-1-1

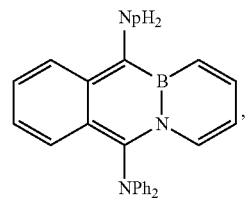

-continued
Compound 1-1-2
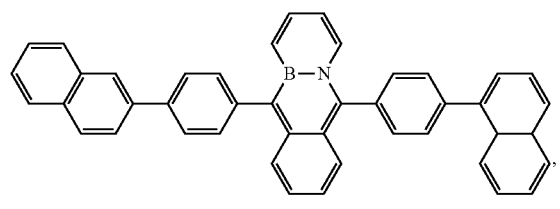
Compound 1-1-3
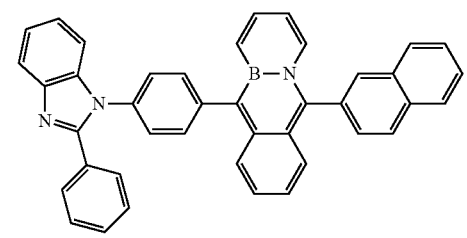
Compound 1-2-1
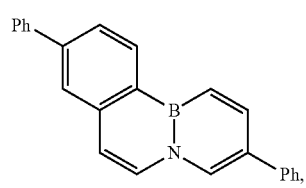
Compound 1-2-2
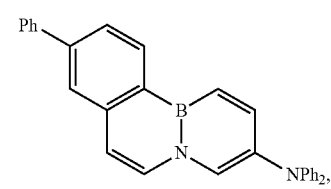
Compound 1-3-1
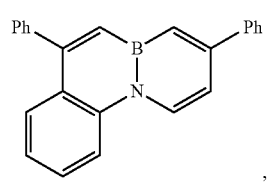
Compound 1-3-2
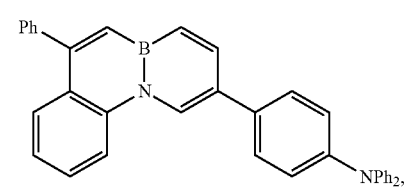
Compound 2-7-1
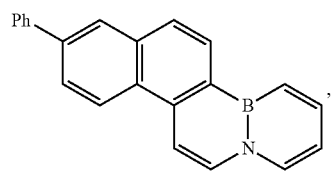
Compound 2-7-2
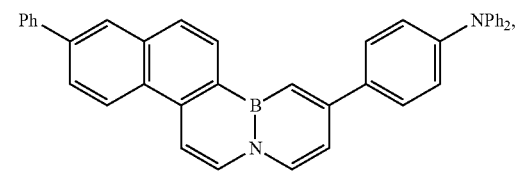
Compound 2-11-1
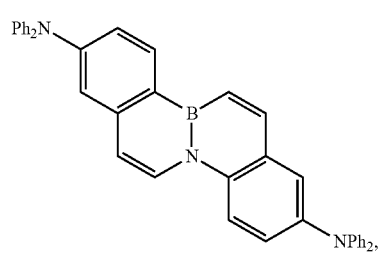
Compound 2-12-1
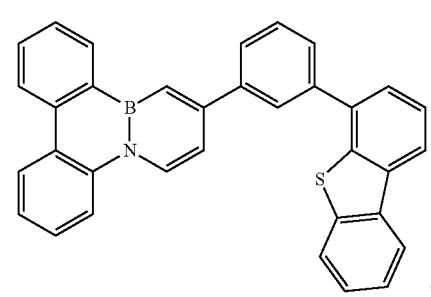
Compound 2-12-2
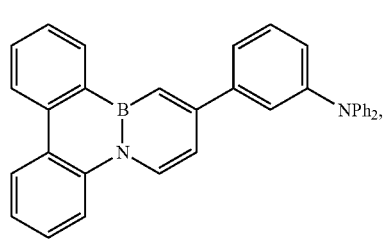
Compound 2-15-1
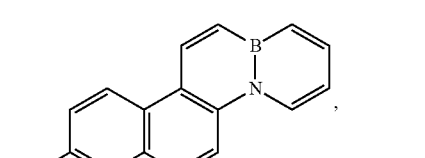
Compound 2-15-2
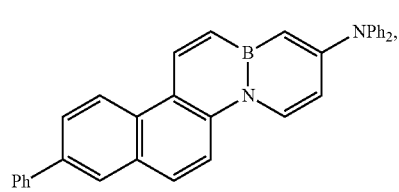
Compound 2-15-3
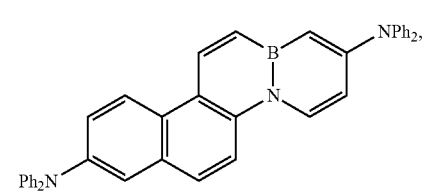

-continued
Compound 2-15-4
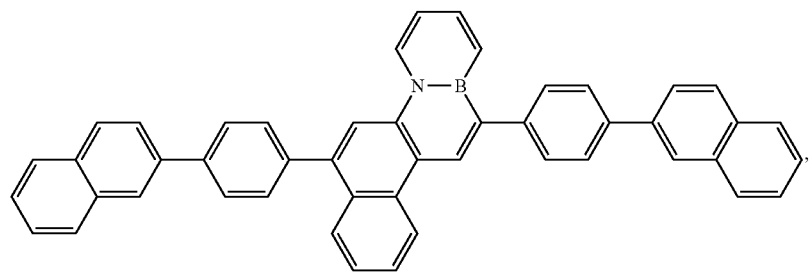
Compound 3-30-1
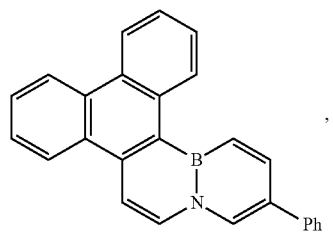
Compound 3-33-1
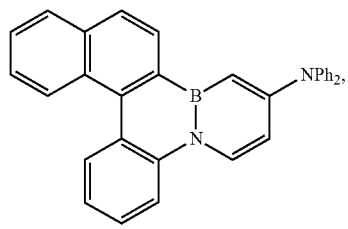
Compound 3-46-1
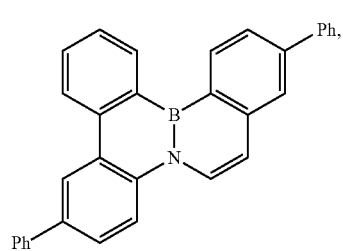
Compound 5-2-1
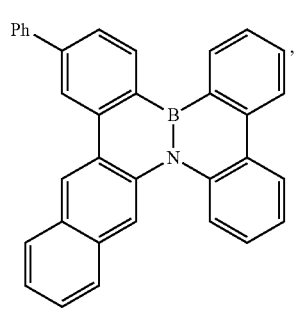
Compound 5-3-1
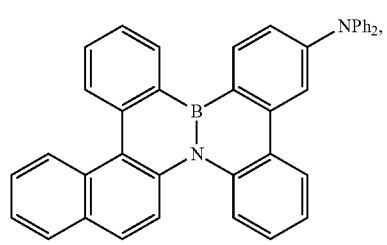
Compound 5-4-1
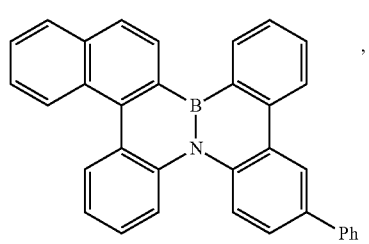
Compound 6-3-1
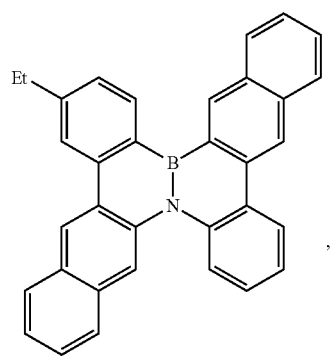
Compound 6-4-1
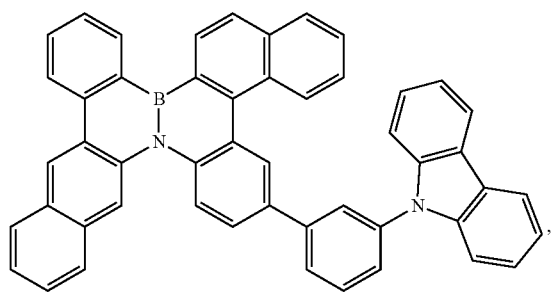

-continued
Compound 7-4-1
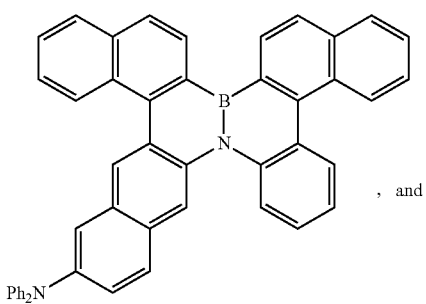
, and
Compound 8-4-1
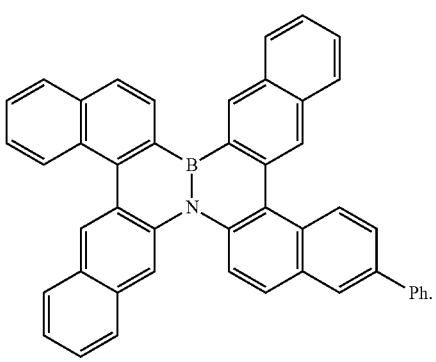
Boron-nitrogen polyaromatic compounds are provided, where the compounds are compounds of Formula (II) and are selected from the group consisting of:
Compound 4-1-1
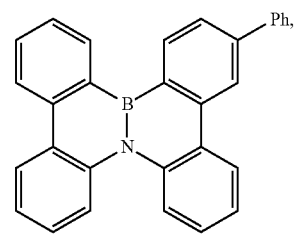
Compound 4-1-2
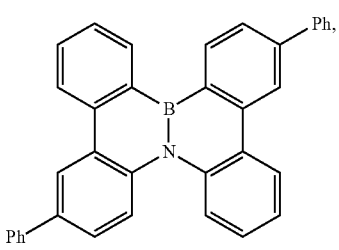
Compound 4-1-3
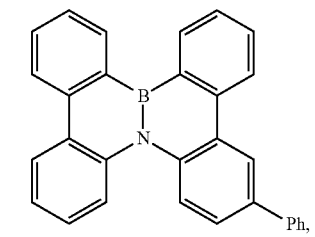
Compound 4-1-4
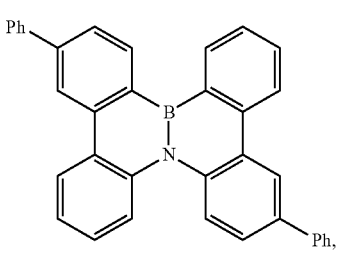
-continued
Compound 4-1-5
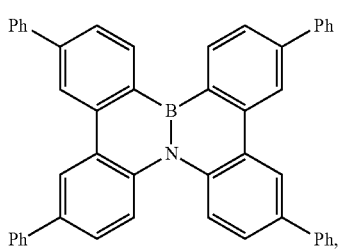
Compound 4-1-21
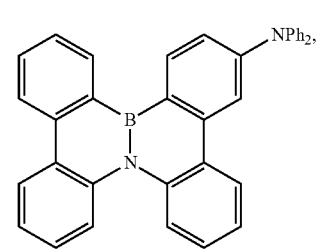
Compound 4-1-22
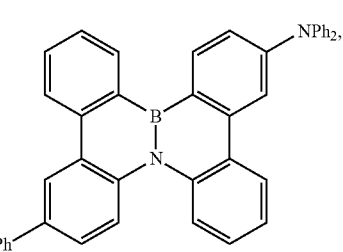
Compound 4-1-23
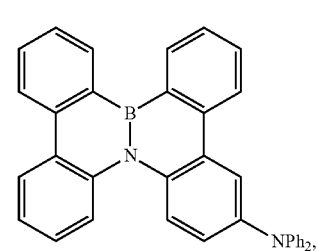
Compound 4-1-24
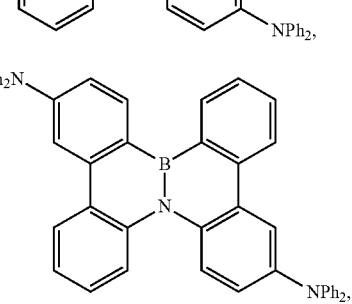

-continued

Compound 4-1-25

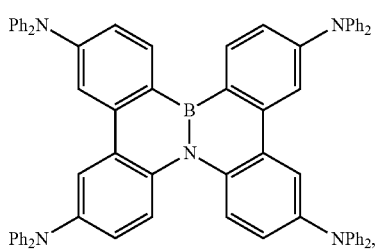

Compound 4-1-26

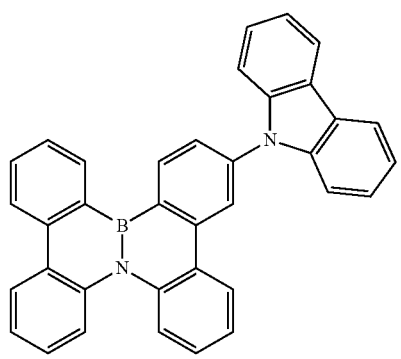
, and

Compound 4-1-27

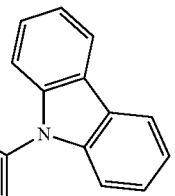

Boron-nitrogen polyaromatic compounds are provided, where the compound is a compound of Formula (II) and $R_1$ to $R_{16}$ have the values shown in the chart below. The references to S1, S2, etc., refer to the substituents identified above.

| Cmpd | $R_1$ | $R_2$ | $R_3$ | $R_4$ | $R_5$ | $R_6$ | $R_7$ | $R_8$ | $R_9$ | $R_{10}$ | $R_{11}$ | $R_{12}$ | $R_{13}$ | $R_{14}$ | $R_{15}$ | $R_{16}$ |
|---|---|---|---|---|---|---|---|---|---|---|---|---|---|---|---|---|
| 4-1-1 | H | H | H | H | S1 | H | H | H | H | H | H | H | H | H | H | H |
| 4-1-2 | H | H | H | H | S1 | H | H | H | H | H | H | H | S1 | H | H | H |
| 4-1-3 | H | H | H | H | H | H | H | S1 | H | H | H | H | H | H | H | H |
| 4-1-4 | H | H | H | H | H | H | H | S1 | H | H | H | H | H | H | H | S1 |
| 4-1-5 | H | H | H | H | S1 | H | H | S1 | H | H | H | H | S1 | H | H | S1 |
| 4-1-6 | H | H | H | H | S7 | H | H | H | H | H | H | H | H | H | H | H |
| 4-1-7 | H | H | H | H | S7 | H | H | H | H | H | H | H | S7 | H | H | H |
| 4-1-8 | H | H | H | H | H | H | H | S7 | H | H | H | H | H | H | H | H |
| 4-1-9 | H | H | H | H | H | H | H | S7 | H | H | H | H | H | H | H | S7 |
| 4-1-10 | H | H | H | H | S7 | H | H | S7 | H | H | H | H | S7 | H | H | S7 |
| 4-1-11 | H | H | H | H | S9 | H | H | H | H | H | H | H | H | H | H | H |
| 4-1-12 | H | H | H | H | S9 | H | H | H | H | H | H | H | S9 | H | H | H |
| 4-1-13 | H | H | H | H | H | H | H | S9 | H | H | H | H | H | H | H | H |
| 4-1-14 | H | H | H | H | H | H | H | S9 | H | H | H | H | H | H | H | S9 |
| 4-1-15 | H | H | H | H | S9 | H | H | S9 | H | H | H | H | S9 | H | H | S9 |
| 4-1-16 | H | H | H | H | S13 | H | H | H | H | H | H | H | H | H | H | H |
| 4-1-17 | H | H | H | H | S13 | H | H | H | H | H | H | H | S13 | H | H | H |
| 4-1-18 | H | H | H | H | H | H | H | S13 | H | H | H | H | H | H | H | H |
| 4-1-19 | H | H | H | H | H | H | H | S13 | H | H | H | H | H | H | H | S13 |
| 4-1-20 | H | H | H | H | S13 | H | H | S13 | H | H | H | H | S13 | H | H | S13 |
| 4-1-21 | H | H | H | H | S14 | H | H | H | H | H | H | H | H | H | H | H |
| 4-1-22 | H | H | H | H | S14 | H | H | H | H | H | H | H | S14 | H | H | H |
| 4-1-23 | H | H | H | H | H | H | H | S14 | H | H | H | H | H | H | H | H |
| 4-1-24 | H | H | H | H | H | H | H | S14 | H | H | H | H | H | H | H | S14 |
| 4-1-25 | H | H | H | H | S14 | H | H | S14 | H | H | H | H | S14 | H | H | S14 |
| 4-1-26 | H | H | H | H | S18 | H | H | H | H | H | H | H | H | H | H | H |
| 4-1-27 | H | H | H | H | S18 | H | H | H | H | H | H | H | S18 | H | H | H |
| 4-1-28 | H | H | H | H | H | H | H | S18 | H | H | H | H | H | H | H | H |
| 4-1-29 | H | H | H | H | H | H | H | S18 | H | H | H | H | H | H | H | S18 |
| 4-1-30 | H | H | H | H | S18 | H | H | S18 | H | H | H | H | S18 | H | H | S18 |
| 4-1-31 | H | H | H | H | S21 | H | H | H | H | H | H | H | H | H | H | H |
| 4-1-32 | H | H | H | H | S21 | H | H | H | H | H | H | H | S21 | H | H | H |
| 4-1-33 | H | H | H | H | H | H | H | S21 | H | H | H | H | H | H | H | H |
| 4-1-34 | H | H | H | H | H | H | H | S21 | H | H | H | H | H | H | H | S21 |
| 4-1-35 | H | H | H | H | S21 | H | H | S21 | H | H | H | H | S21 | H | H | S21 |
| 4-1-36 | H | H | H | H | S29 | H | H | H | H | H | H | H | H | H | H | H |
| 4-1-37 | H | H | H | H | S29 | H | H | H | H | H | H | H | S29 | H | H | H |
| 4-1-38 | H | H | H | H | H | H | H | S29 | H | H | H | H | H | H | H | H |
| 4-1-39 | H | H | H | H | H | H | H | S29 | H | H | H | H | H | H | H | S29 |
| 4-1-40 | H | H | H | H | S29 | H | H | S29 | H | H | H | H | S29 | H | H | S29 |
| 4-1-36 | H | H | H | H | S31 | H | H | H | H | H | H | H | H | H | H | H |
| 4-1-37 | H | H | H | H | S31 | H | H | H | H | H | H | H | S31 | H | H | H |
| 4-1-38 | H | H | H | H | H | H | H | S31 | H | H | H | H | H | H | H | H |
| 4-1-39 | H | H | H | H | H | H | H | S31 | H | H | H | H | H | H | H | S31 |
| 4-1-40 | H | H | H | H | S31 | H | H | S31 | H | H | H | H | S31 | H | H | S31 |

-continued

| Cmpd | R₁ | R₂ | R₃ | R₄ | R₅ | R₆ | R₇ | R₈ | R₉ | R₁₀ | R₁₁ | R₁₂ | R₁₃ | R₁₄ | R₁₅ | R₁₆ |
|---|---|---|---|---|---|---|---|---|---|---|---|---|---|---|---|---|
| 4-1-41 | H | H | H | H | S33 | H | H | H | H | H | H | H | H | H | H | H |
| 4-1-42 | H | H | H | H | S33 | H | H | H | H | H | H | H | S33 | H | H | H |
| 4-1-43 | H | H | H | H | H | H | H | S33 | H | H | H | H | H | H | H | H |
| 4-1-44 | H | H | H | H | H | H | H | S33 | H | H | H | H | H | H | H | S33 |
| 4-1-45 | H | H | H | H | S33 | H | H | S33 | H | H | H | H | S33 | H | H | S33 |
| 4-1-46 | H | H | H | H | S35 | H | H | H | H | H | H | H | H | H | H | H |
| 4-1-47 | H | H | H | H | S35 | H | H | H | H | H | H | H | S35 | H | H | H |
| 4-1-48 | H | H | H | H | H | H | H | S35 | H | H | H | H | H | H | H | H |
| 4-1-49 | H | H | H | H | H | H | H | S35 | H | H | H | H | H | H | H | S35 |
| 4-1-50 | H | H | H | H | S35 | H | H | S35 | H | H | H | H | S35 | H | H | S35 |
| 4-1-51 | H | H | H | H | S37 | H | H | H | H | H | H | H | H | H | H | H |
| 4-1-52 | H | H | H | H | S37 | H | H | H | H | H | H | H | S37 | H | H | H |
| 4-1-53 | H | H | H | H | H | H | H | S37 | H | H | H | H | H | H | H | H |
| 4-1-54 | H | H | H | H | H | H | H | S37 | H | H | H | H | H | H | H | S37 |
| 4-1-55 | H | H | H | H | S37 | H | H | S37 | H | H | H | H | S37 | H | H | S37 |
| 4-1-56 | H | H | H | H | S39 | H | H | H | H | H | H | H | H | H | H | H |
| 4-1-57 | H | H | H | H | S39 | H | H | H | H | H | H | H | S39 | H | H | H |
| 4-1-58 | H | H | H | H | H | H | H | S39 | H | H | H | H | H | H | H | H |
| 4-1-59 | H | H | H | H | H | H | H | S39 | H | H | H | H | H | H | H | S39 |
| 4-1-60 | H | H | H | H | S39 | H | H | S39 | H | H | H | H | S39 | H | H | S39 |
| 4-1-61 | H | H | H | H | S13 | H | H | H | H | H | H | H | H | H | H | H |
| 4-1-62 | H | H | H | H | S13 | H | H | H | H | H | H | H | S13 | H | H | H |
| 4-1-63 | H | H | H | H | H | H | H | S13 | H | H | H | H | H | H | H | H |
| 4-1-64 | H | H | H | H | H | H | H | S13 | H | H | H | H | H | H | H | S13 |
| 4-1-65 | H | H | H | H | S32 | H | H | H | H | H | H | H | H | H | H | H |
| 4-1-66 | H | H | H | H | H | H | H | S32 | H | H | H | H | H | H | H | H |
| 4-1-67 | H | H | H | H | S1 | H | H | H | H | H | H | H | S7 | H | H | H |
| 4-1-68 | H | H | H | H | S7 | H | H | H | H | H | H | H | S1 | H | H | H |
| 4-1-69 | H | H | H | H | S1 | H | H | H | H | H | H | H | S9 | H | H | H |
| 4-1-70 | H | H | H | H | S9 | H | H | H | H | H | H | H | S1 | H | H | H |
| 4-1-71 | H | H | H | H | S1 | H | H | H | H | H | H | H | S13 | H | H | H |
| 4-1-72 | H | H | H | H | S13 | H | H | H | H | H | H | H | S1 | H | H | H |
| 4-1-73 | H | H | H | H | S1 | H | H | H | H | H | H | H | S14 | H | H | H |
| 4-1-74 | H | H | H | H | S14 | H | H | H | H | H | H | H | S1 | H | H | H |
| 4-1-75 | H | H | H | H | S1 | H | H | H | H | H | H | H | S21 | H | H | H |
| 4-1-76 | H | H | H | H | S21 | H | H | H | H | H | H | H | S1 | H | H | H |
| 4-1-77 | H | H | H | H | S1 | H | H | H | H | H | H | H | S22 | H | H | H |
| 4-1-78 | H | H | H | H | S22 | H | H | H | H | H | H | H | S1 | H | H | H |
| 4-1-79 | H | H | H | H | S1 | H | H | H | H | H | H | H | S21 | H | H | H |
| 4-1-80 | H | H | H | H | S21 | H | H | H | H | H | H | H | S1 | H | H | H |
| 4-1-81 | H | H | H | H | S1 | H | H | H | H | H | H | H | S22 | H | H | H |
| 4-1-82 | H | H | H | H | S22 | H | H | H | H | H | H | H | S1 | H | H | H |
| 4-1-83 | H | H | H | H | S1 | H | H | H | H | H | H | H | S31 | H | H | H |
| 4-1-84 | H | H | H | H | S31 | H | H | H | H | H | H | H | S1 | H | H | H |
| 4-1-85 | H | H | H | H | S1 | H | H | H | H | H | H | H | S33 | H | H | H |
| 4-1-86 | H | H | H | H | S33 | H | H | H | H | H | H | H | S1 | H | H | H |
| 4-1-87 | H | H | H | H | S1 | H | H | H | H | H | H | H | S37 | H | H | H |
| 4-1-88 | H | H | H | H | S37 | H | H | H | H | H | H | H | S1 | H | H | H |
| 4-1-89 | H | H | H | H | S1 | H | H | H | H | H | H | H | S39 | H | H | H |
| 4-1-90 | H | H | H | H | S39 | H | H | H | H | H | H | H | S1 | H | H | H |

Boron-nitrogen polyaromatic compounds are provided, where the compounds are compounds of Formula (III) and are selected from the group consisting of:

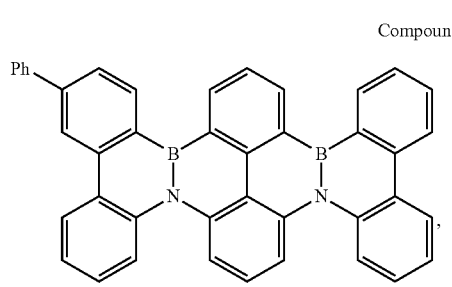

Compound 8-10-1

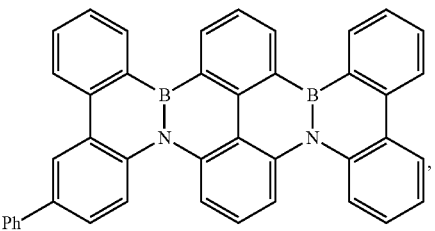

Compound 8-10-2

-continued
Compound 8-10-3
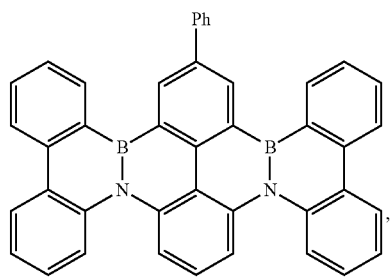
Compound 8-10-4
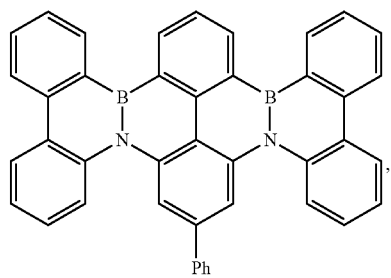
Compound 8-10-5
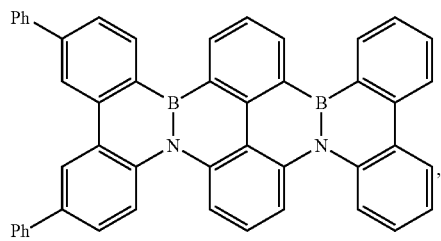
Compound 8-10-6
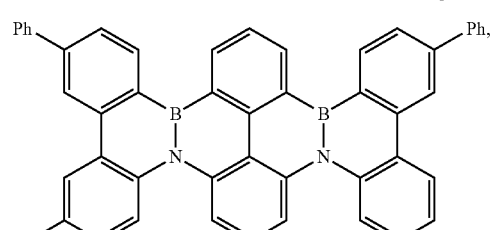
Compound 8-10-7
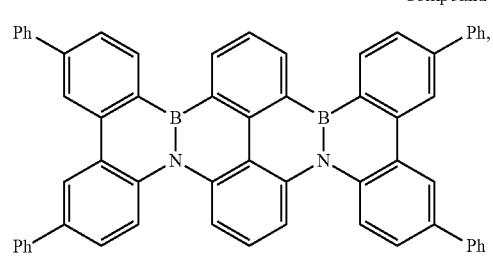
Compound 8-10-8
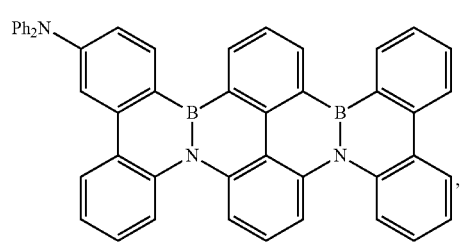
-continued
Compound 8-10-9
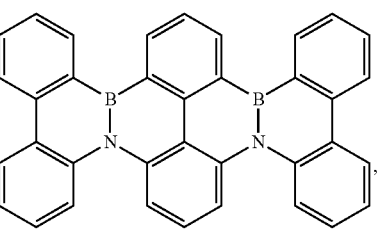
Compound 8-10-10
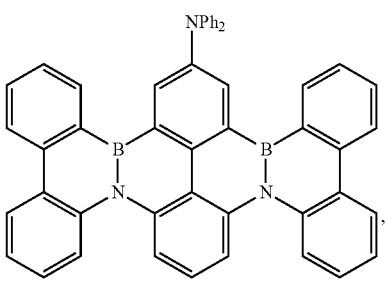
Compound 8-10-11
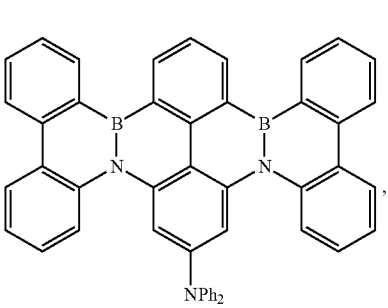
Compound 8-10-12
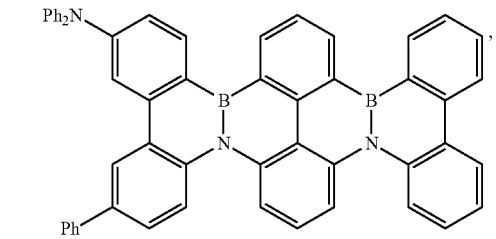
Compound 8-10-13
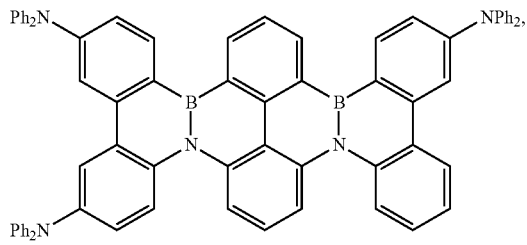
Compound 8-10-14
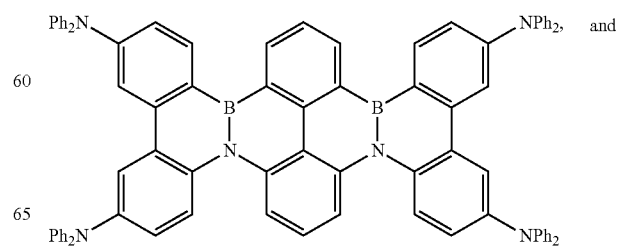
and -continued
Compound 8-10-15
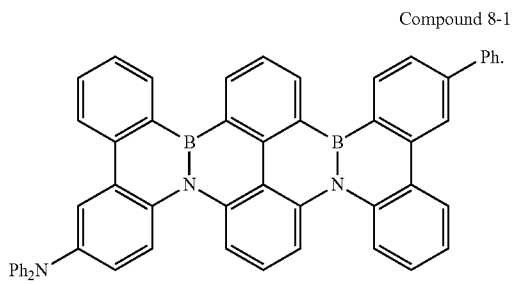
Boron-nitrogen polyaromatic compounds are provided, where the compounds are compounds of Formula (IV) and are selected from the group consisting of:
Compound 8-11-1
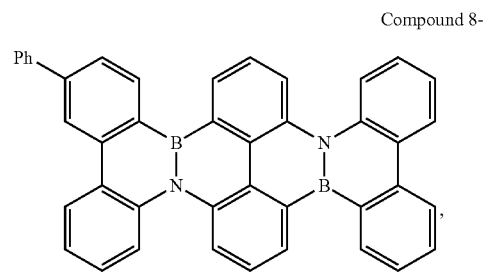
Compound 8-11-2
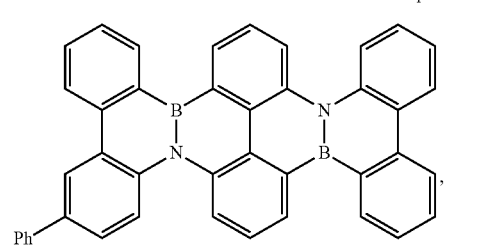
Compound 8-11-3
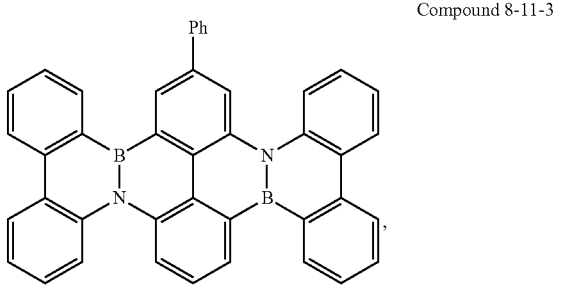
Compound 8-11-4
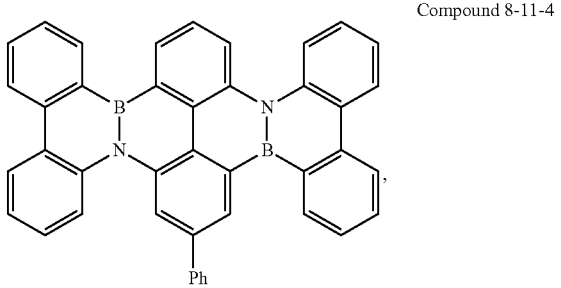
-continued
Compound 8-11-5
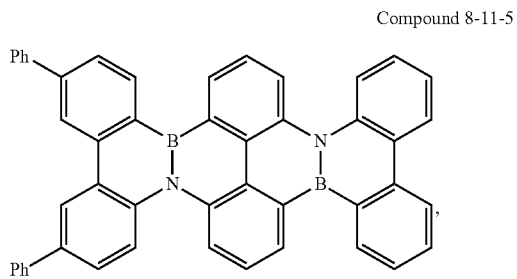
Compound 8-10-6
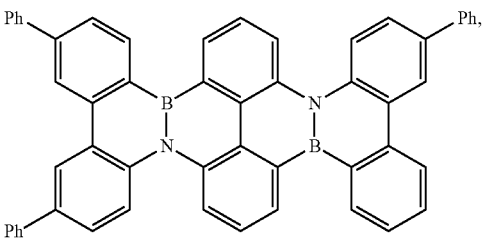
Compound 8-10-7
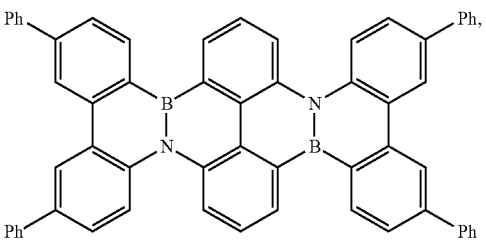
Compound 8-11-8
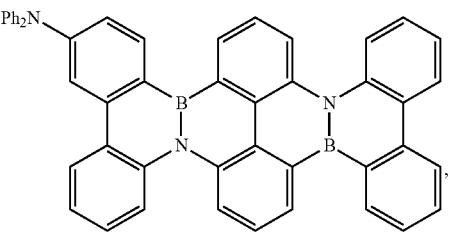
Compound 8-11-9
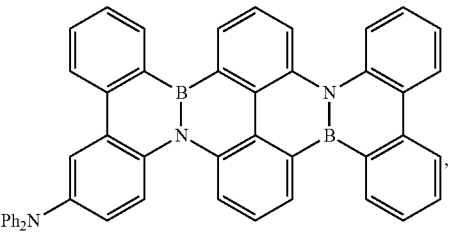
Compound 8-11-10
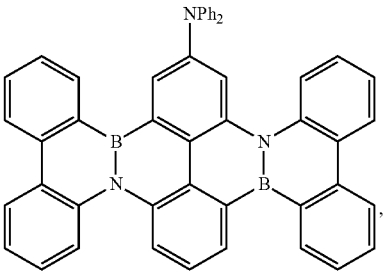

-continued

Compound 8-11-11

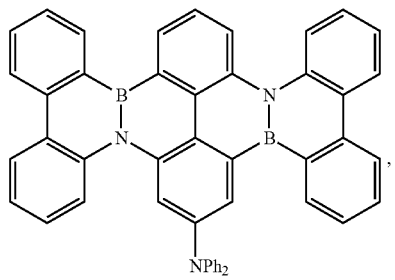

Compound 8-11-12

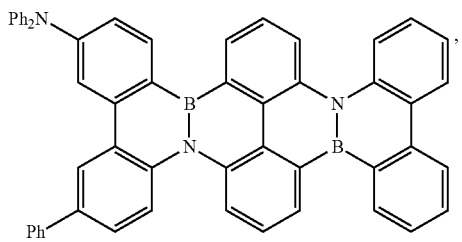

Compound 8-11-13

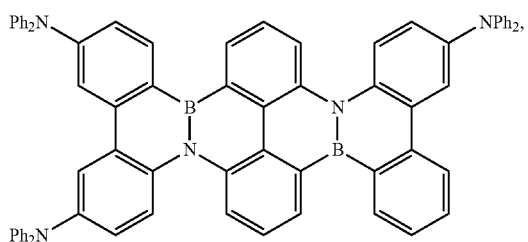

Compound 8-11-14
and

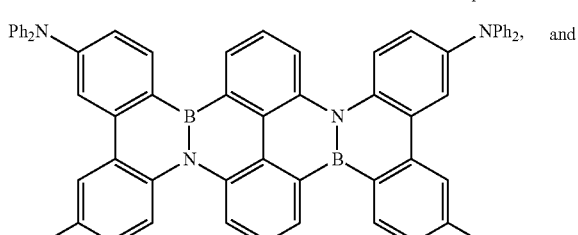

Compound 8-11-15

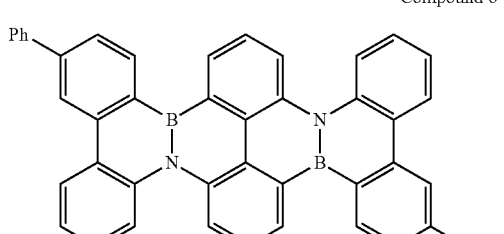

A device is also provided. The device may include an anode, a cathode, and an organic layer disposed between the anode and the cathode, where the organic layer comprises a boron-nitrogen polyaromatic compound of any of the foregoing embodiments.

The invention is not limited to any particular type of device. In some embodiments, the device is a consumer product. In some embodiments, the device is an organic light emitting device (OLED). In some embodiments, the device is a delayed fluorescence device. In other embodiments, the device comprises a lighting panel.

In some embodiments, the organic layer of the device is an emissive layer. In some such embodiments, the boron-nitrogen polyaromatic compound is an emissive dopant. In some other embodiments, the boron-nitrogen polyaromatic compound is a host.

In some embodiments, the organic layer of the device is a hole injecting layer or a hole transporting layer. In some other embodiments, the organic layer of the device is an electron injecting layer or an electron transporting layer. In some embodiments, the organic layer of the device is an exciton blocking layer.

Combination with Other Materials

The materials described herein as useful for a particular layer in an organic light emitting device may be used in combination with a wide variety of other materials present in the device. For example, compounds disclosed herein may be used in conjunction with a wide variety of hosts, transport layers, blocking layers, injection layers, electrodes and other layers that may be present. The materials described or referred to below are non-limiting examples of materials that may be useful in combination with the compounds disclosed herein, and one of skill in the art can readily consult the literature to identify other materials that may be useful in combination.

A hole injecting/transporting material to be used in the present invention is not particularly limited, and any compound may be used as long as the compound is typically used as a hole injecting/transporting material. Examples of the material include, but not limit to: a phthalocyanine or porphryin derivative; an aromatic amine derivative; an indolocarbazole derivative; a polymer containing fluorohydrocarbon; a polymer with conductivity dopants; a conducting polymer, such as PEDOT/PSS; a self-assembly monomer derived from compounds such as phosphonic acid and sliane derivatives; a metal oxide derivative, such as $MoO_x$; a p-type semiconducting organic compound, such as 1,4,5,8,9,12-Hexaazatriphenylenehexacarbonitrile; a metal complex, and a cross-linkable compounds.

Examples of aromatic amine derivatives used in HIL or HTL include, but not limit to the following general structures:

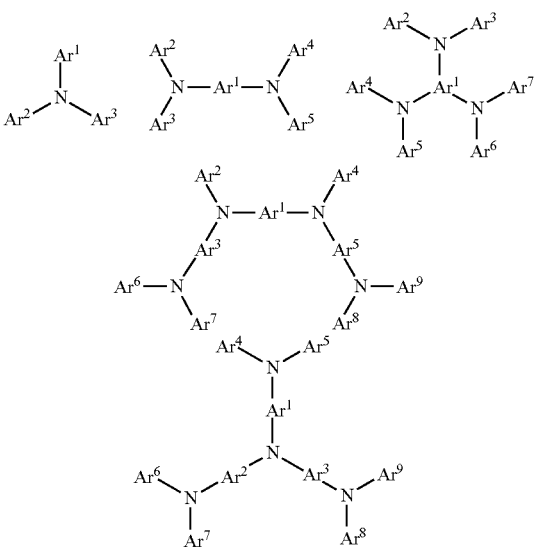

Each of $Ar^1$ to $Ar^9$ is selected from the group consisting aromatic hydrocarbon cyclic compounds such as benzene, biphenyl, triphenyl, triphenylene, naphthalene, anthracene, phenalene, phenanthrene, fluorene, pyrene, chrysene, perylene, azulene; group consisting aromatic heterocyclic compounds such as dibenzothiophene, dibenzofuran, dibenzoselenophene, furan, thiophene, benzofuran, benzothiophene, benzoselenophene, carbazole, indolocarbazole, pyridylindole, pyrrolodipyridine, pyrazole, imidazole, triazole, oxazole, thiazole, oxadiazole, oxatriazole, dioxazole, thiadiazole, pyridine, pyridazine, pyrimidine, pyrazine, triazine, oxazine, oxathiazine, oxadiazine, indole, benzimidazole, indazole, indoxazine, benzoxazole, benzisoxazole, benzothiazole, quinoline, isoquinoline, cinnoline, quinazoline, quinoxaline, naphthyridine, phthalazine, pteridine, xanthene, acridine, phenazine, phenothiazine, phenoxazine, benzofuropyridine, furodipyridine, benzothienopyridine, thienodipyridine, benzoselenophenopyridine, and selenophenodipyridine; and group consisting 2 to 10 cyclic structural units which are groups of the same type or different types selected from the aromatic hydrocarbon cyclic group and the aromatic heterocyclic group and are bonded to each other directly or via at least one of oxygen atom, nitrogen atom, sulfur atom, silicon atom, phosphorus atom, boron atom, chain structural unit and the aliphatic cyclic group. Wherein each Ar is further substituted by a substituent selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof.

In one aspect, $Ar^1$ to $Ar^9$ is independently selected from the group consisting of:

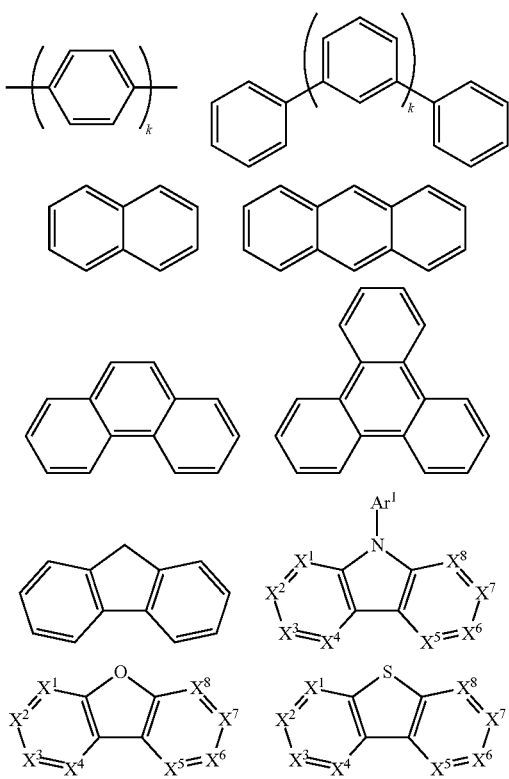

k is an integer from 1 to 20; $X^1$ to $X^8$ is C (including CH) or N; $Ar^1$ has the same group defined above.

Examples of metal complexes used in HIL or HTL include, but not limit to the following general formula:

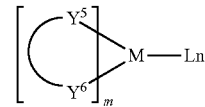

M is a metal, having an atomic weight greater than 40; $(Y^5—Y^6)$ is a bidentate ligand, $Y^5$ and $Y^6$ are independently selected from C, N, O, P, and S; L is an ancillary ligand; m is an integer value from 1 to the maximum number of ligands that may be attached to the metal; and m+n is the maximum number of ligands that may be attached to the metal.

In one aspect, $(Y^5—Y^6)$ is a 2-phenylpyridine derivative.
In another aspect, $(Y^5—Y^6)$ is a carbene ligand.
In another aspect, M is selected from Ir, Pt, Os, and Zn.
In a further aspect, the metal complex has a smallest oxidation potential in solution vs. $Fc^+/Fc$ couple less than about 0.6 V.

In addition to the host materials described above, the device may further comprise other host materials. Examples of such other host material are not particularly limited, and any metal complexes or organic compounds may be used as long as the triplet energy of the host is larger than that of the dopant. While the Table below categorizes host materials as preferred for devices that emit various colors, any host material may be used with any dopant so long as the triplet criteria is satisfied.

Examples of metal complexes used as host are preferred to have the following general formula:

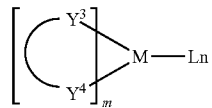

M is a metal; $(Y^3—Y^4)$ is a bidentate ligand, $Y^3$ and $Y^4$ are independently selected from C, N, O, P, and S; L is an ancillary ligand; m is an integer value from 1 to the maximum number of ligands that may be attached to the metal; and m+n is the maximum number of ligands that may be attached to the metal.

In one aspect, the metal complexes are:

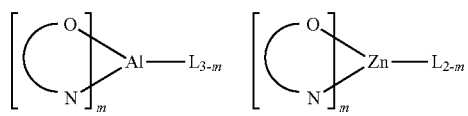

(O—N) is a bidentate ligand, having metal coordinated to atoms O and N.
In another aspect, M is selected from Ir and Pt.
In a further aspect, $(Y^3—Y^4)$ is a carbene ligand.

Examples of organic compounds used as host are selected from the group consisting aromatic hydrocarbon cyclic compounds such as benzene, biphenyl, triphenyl, triphenylene, naphthalene, anthracene, phenalene, phenanthrene, fluorene, pyrene, chrysene, perylene, azulene; group consisting aromatic heterocyclic compounds such as dibenzothiophene, dibenzofuran, dibenzoselenophene, furan, thiophene, benzofuran, benzothiophene, benzoselenophene, carbazole, indolocarbazole, pyridylindole, pyrrolodipyridine, pyrazole, imidazole, triazole, oxazole, thiazole, oxadiazole, oxatriazole, dioxazole, thiadiazole, pyridine, pyridazine, pyrimidine, pyrazine, triazine, oxazine, oxathiazine, oxadiazine, indole, benzimidazole, indazole, indoxazine, benzoxazole, benzisoxazole, benzothiazole, quinoline, isoquinoline, cinnoline, quinazoline, quinoxaline, naphthyridine, phthalazine, pteridine, xanthene, acridine, phenazine, phenothiazine, phenoxazine, benzofuropyridine, furodipyridine, benzothienopyridine, thienodipyridine, benzoselenophenopyridine, and selenophenodipyridine; and group consisting 2 to 10 cyclic structural units which are groups of the same type or different types selected from the aromatic hydrocarbon cyclic group and the aromatic heterocyclic group and are bonded to each other directly or via at least one of oxygen atom, nitrogen atome, sulfur atom, silicon atom, phosphorus atom, boron atom, chain structural unit and the aliphatic cyclic group. Wherein each group is further substituted by a substituent selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof.

In one aspect, host compound contains at least one of the following groups in the molecule:

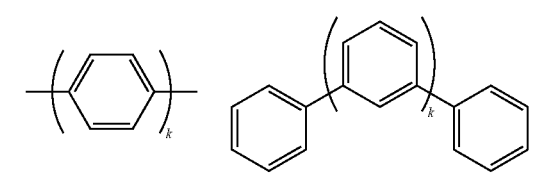

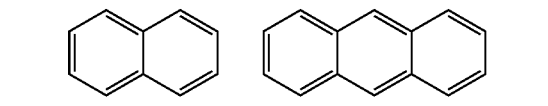

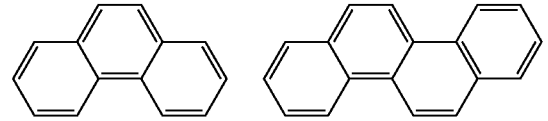

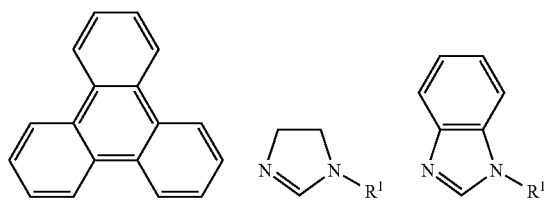

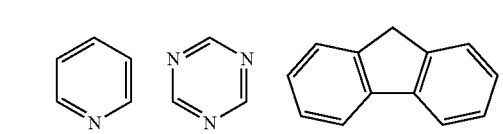

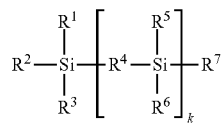

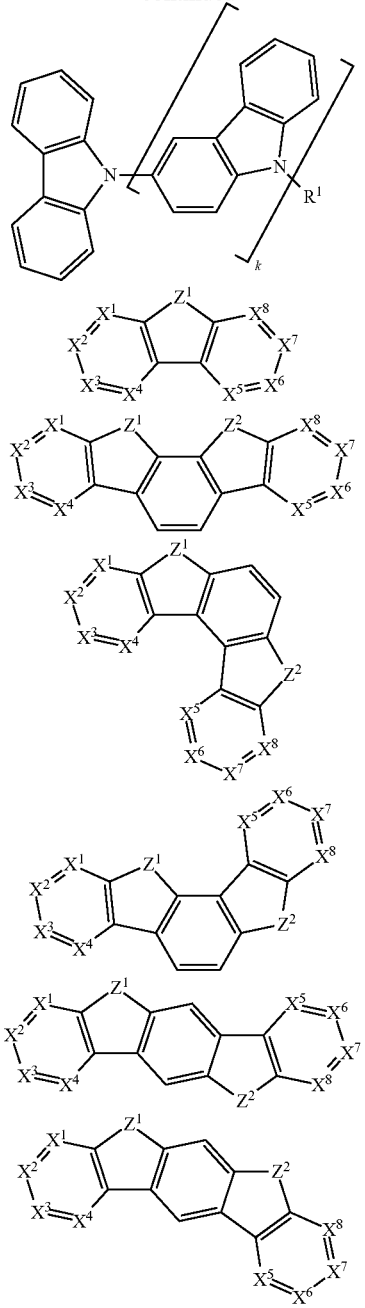

$R^1$ to $R^7$ is independently selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof, when it is aryl or heteroaryl, it has the similar definition as Ar's mentioned above; k is an integer from 0 to 20; $X^1$ to $X^8$ are selected from C (including CH) or N; and $Z^1$ and $Z^2$ are selected from $NR^1$, O, or S.

A hole blocking layer (HBL) may be used to reduce the number of holes and/or excitons that leave the emissive layer. The presence of such a blocking layer in a device may result in substantially higher efficiencies as compared to a similar device lacking a blocking layer. Also, a blocking layer may be used to confine emission to a desired region of an OLED.

In one aspect, compound used in HBL contains the same molecule or the same functional groups used as host described above.

In another aspect, compound used in HBL contains at least one of the following groups in the molecule:

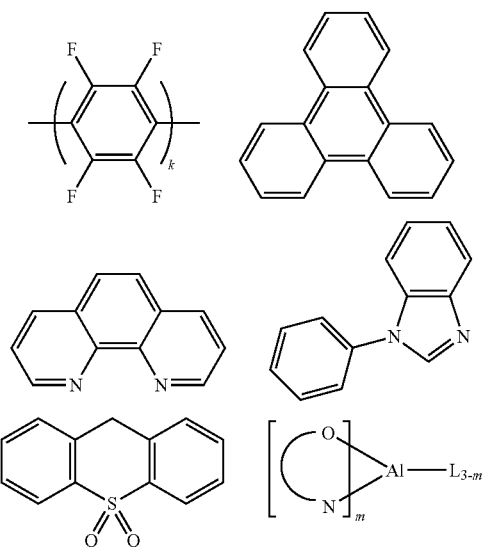

k is an integer from 0 to 20; L is an ancillary ligand, m is an integer from 1 to 3.

Electron transport layer (ETL) may include a material capable of transporting electrons. Electron transport layer may be intrinsic (undoped), or doped. Doping may be used to enhance conductivity. Examples of the ETL material are not particularly limited, and any metal complexes or organic compounds may be used as long as they are typically used to transport electrons.

In one aspect, compound used in ETL contains at least one of the following groups in the molecule:

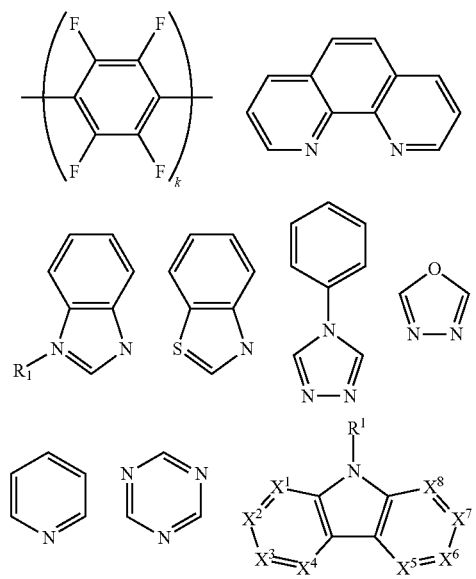

-continued

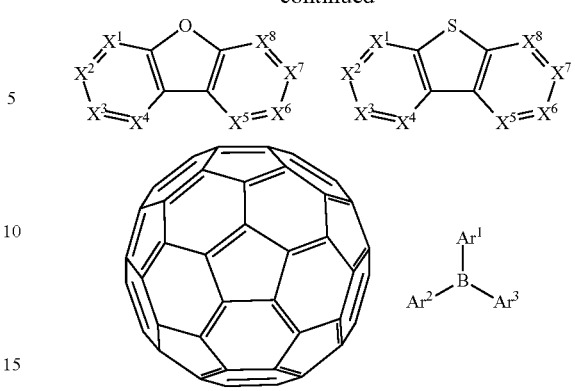

$R^1$ is selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof, when it is aryl or heteroaryl, it has the similar definition as Ar's mentioned above; $Ar^1$ to $Ar^3$ has the similar definition as Ar's mentioned above; k is an integer from 0 to 20; $X^1$ to $X^8$ is selected from C (including CH) or N.

In another aspect, the metal complexes used in ETL contains, but not limit to the following general formula:

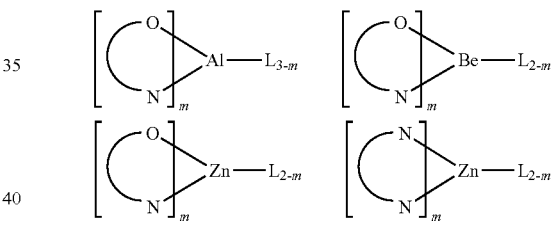

(O—N) or (N—N) is a bidentate ligand, having metal coordinated to atoms O, N or N, N; L is an ancillary ligand; m is an integer value from 1 to the maximum number of ligands that may be attached to the metal.

In any above-mentioned compounds used in each layer of the OLED device, the hydrogen atoms can be partially or fully deuterated. Thus, any specifically listed substituent, such as, without limitation, methyl, phenyl, pyridyl, etc. encompasses undeuterated, partially deuterated, and fully deuterated versions thereof. Similarly, classes of substituents such as, without limitation, alkyl, aryl, cycloalkyl, heteroaryl, etc. also encompass undeuterated, partially deuterated, and fully deuterated versions thereof.

In addition to and/or in combination with the materials disclosed herein, many hole injection materials, hole transporting materials, host materials, dopant materials, exiton/hole blocking layer materials, electron transporting and electron injecting materials may be used in an OLED. Non-limiting examples of the materials that may be used in an OLED in combination with materials disclosed herein are listed in Table 1 below. Table 1 lists non-limiting classes of materials, non-limiting examples of compounds for each class, and references that disclose the materials.

TABLE 1

| MATERIAL | EXAMPLES OF MATERIAL | PUBLICATIONS |
|---|---|---|
| Hole injection materials | | |
| Phthalocyanine and porphryin compounds | 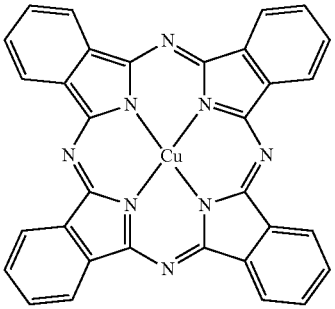 | Appl. Phys. Lett. 69, 2160 (1996) |
| Starburst triarylamines | 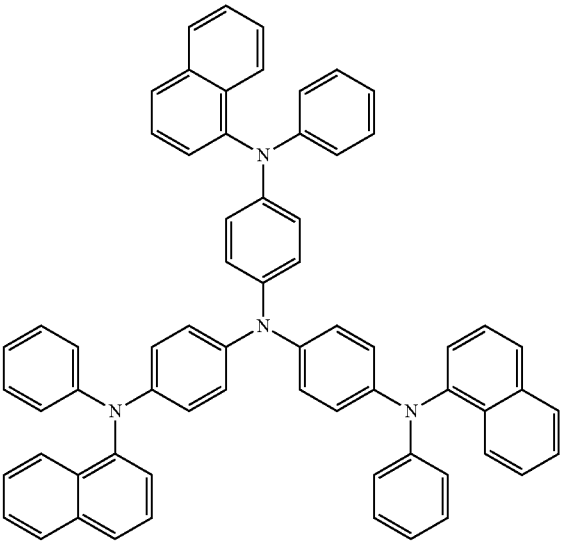 [SMILES: c1ccc(N(c2ccc(N(c3ccc(N(c4ccccc4)c4cccc5ccccc45)cc3)c3ccc(N(c4ccccc4)c4cccc5ccccc45)cc3)cc2)c2cccc3ccccc23)cc1] | J. Lumin. 72-74, 985 (1997) |
| $CF_x$ Fluorohydrocarbon polymer | $-\!\!-\!\![CH_xF_y]_n\!\!-\!\!-$ | Appl. Phys. Lett. 78, 673 (2001) |
| Conducting polymers (e.g., PEDOT:PSS, polyaniline, polypthiophene) | 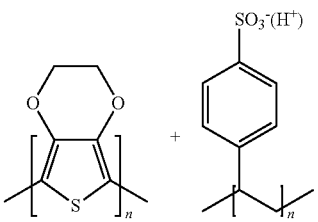 | Synth. Met. 87, 171 (1997)<br>WO2007002683 |
| Phosphonic acid and sliane SAMs | 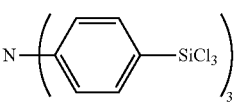 | US20030162053 |
| Triarylamine or polythiophene polymers with conductivity dopants | 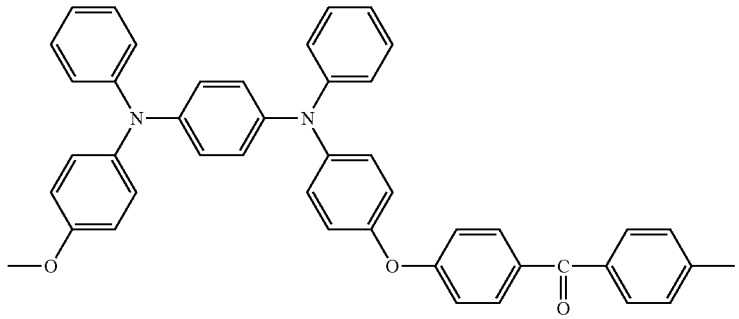 | EP1725079A1 |

TABLE 1-continued
| MATERIAL | EXAMPLES OF MATERIAL | PUBLICATIONS |
|---|---|---|
| | and 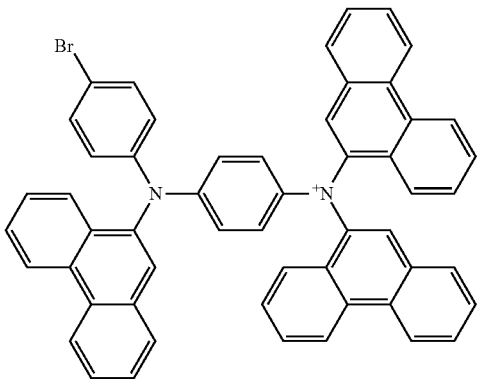 [SMILES: Brc1ccc(N(c2ccc([NH+](c3cc4ccccc4c4ccccc34)c3cc4ccccc4c4ccccc34)cc2)c2cc3ccccc3c3ccccc23)cc1] | |
| | 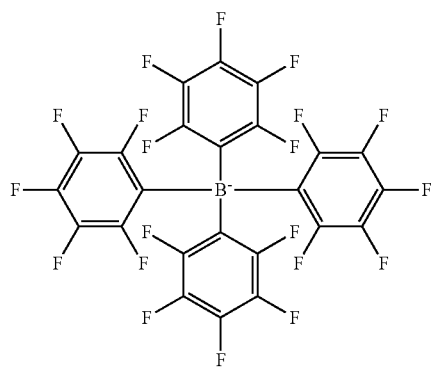 [SMILES: Fc1c(F)c(F)c([B-](c2c(F)c(F)c(F)c(F)c2F)(c2c(F)c(F)c(F)c(F)c2F)c2c(F)c(F)c(F)c(F)c2F)c(F)c1F] | |
| Organic compounds with conductive inorganic compounds, such as molybdenum and tungsten oxides | 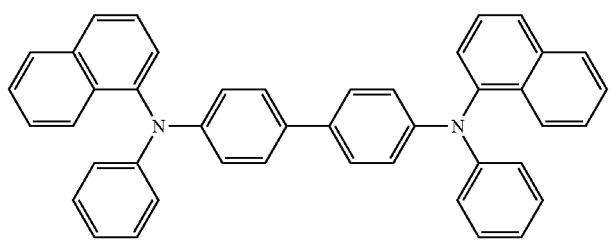 | US20050123751<br>SID Symposium Digest, 37, 923 (2006)<br>WO2009018009 |
| n-type semiconducting organic complexes | 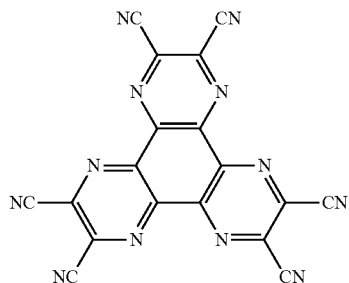 [SMILES: N#Cc1nc2c3nc(C#N)c(C#N)nc3c3nc(C#N)c(C#N)nc3c2nc1C#N] | US20020158242 |
| Metal organometallic complexes | 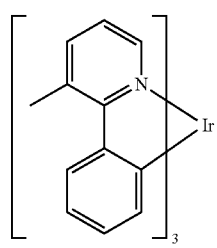 | US20060240279 |

TABLE 1-continued

| MATERIAL | EXAMPLES OF MATERIAL | PUBLICATIONS |
|---|---|---|
| Cross-linkable compounds | | US20080220265 |
| Polythiophene based polymers and copolymers | | WO 2011075644 EP2350216 |
| Hole transporting materials | | |
| Triarylamines (e.g., TPD, α-NPD) | | Appl. Phys. Lett. 51, 913 (1987) |
| | | US5061569 |

140
TABLE 1-continued
| MATERIAL | EXAMPLES OF MATERIAL | PUBLICATIONS |
|---|---|---|
| | 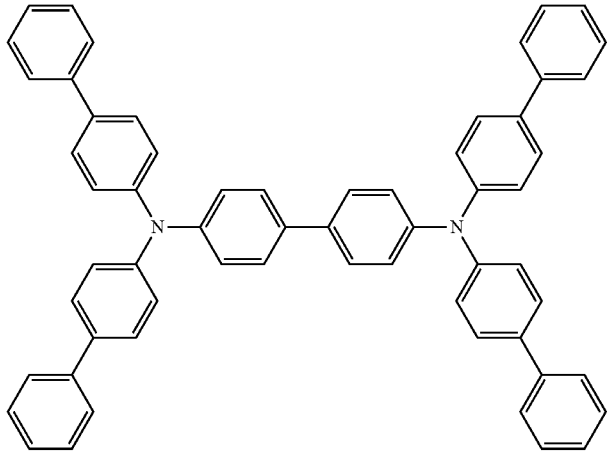 [SMILES: c1ccc(-c2ccc(N(c3ccc(-c4ccccc4)cc3)c3ccc(-c4ccc(N(c5ccc(-c6ccccc6)cc5)c5ccc(-c6ccccc6)cc5)cc4)cc3)cc2)cc1] | EP650955 |
| | 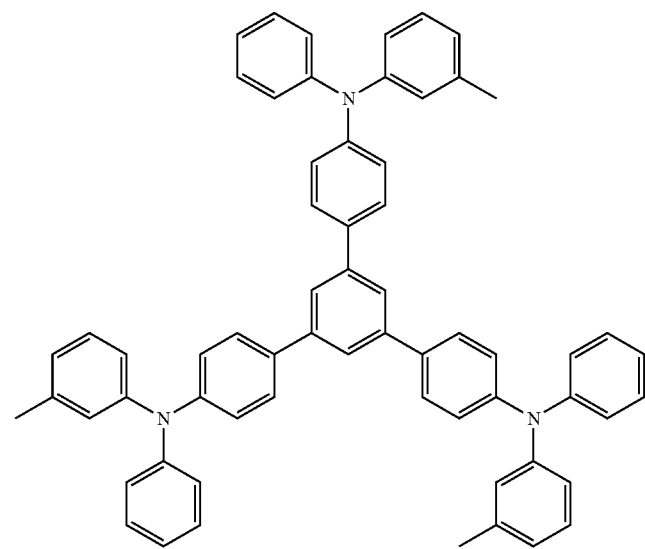 [SMILES: Cc1cccc(N(c2ccccc2)c2ccc(-c3cc(-c4ccc(N(c5ccccc5)c5cccc(C)c5)cc4)cc(-c4ccc(N(c5ccccc5)c5cccc(C)c5)cc4)c3)cc2)c1] | J. Mater. Chem. 3, 319 (1993) |
| | 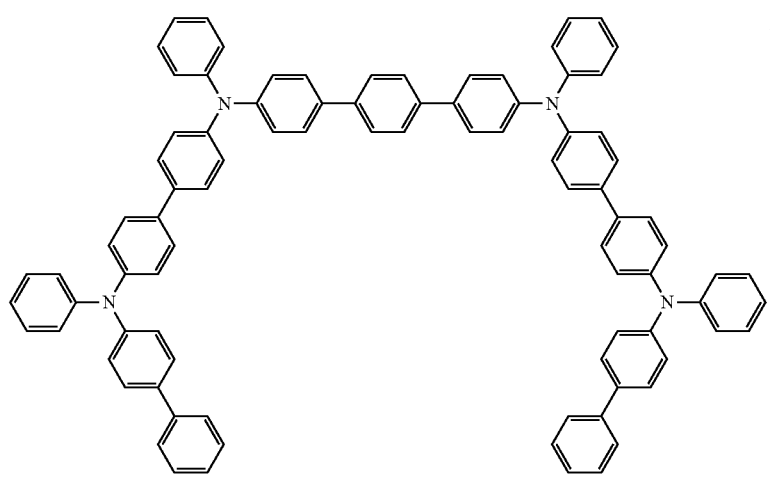 [SMILES: c1ccc(-c2ccc(N(c3ccccc3)c3ccc(-c4ccc(N(c5ccccc5)c5ccc(-c6ccc(-c7ccc(N(c8ccccc8)c8ccc(-c9ccc(N(c%10ccccc%10)c%10ccc(-c%11ccccc%11)cc%10)cc9)cc8)cc7)cc6)cc5)cc4)cc3)cc2)cc1] | Appl. Phys. Lett. 90, 183503 (2007) |

TABLE 1-continued

| MATERIAL | EXAMPLES OF MATERIAL | PUBLICATIONS |
| --- | --- | --- |
| | | Appl. Phys. Lett. 90, 183503 (2007) |
| Triaylamine on spirofluorene core | | Synth. Met. 91, 209 (1997) |
| Arylamine carbazole compounds | | Adv. Mater. 6, 677 (1994), US20080124572 |
| Triarylamine with (di)benzothiophene/(di)benzofuran | | US20070278938, US20080106190 US20110163302 |

TABLE 1-continued

| MATERIAL | EXAMPLES OF MATERIAL | PUBLICATIONS |
| --- | --- | --- |
| Indolocarbazoles | | Synth. Met. 111, 421 (2000) |
| Isoindole compounds | | Chem. Mater. 15, 3148 (2003) |
| Metal carbene complexes | | US20080018221 |

Phosphorescent OLED host materials
Red hosts

| | | |
| --- | --- | --- |
| Arylcarbazoles | | Appl. Phys. Lett. 78, 1622 (2001) |

TABLE 1-continued

| MATERIAL | EXAMPLES OF MATERIAL | PUBLICATIONS |
| --- | --- | --- |
| Metal 8-hydroxyquinolates (e.g., Alq$_3$, BAlq) | | Nature 395, 151 (1998) |
| | | US20060202194 |
| | | WO2005014551 |
| | | WO2006072002 |
| Metal phenoxybenzothiazole compounds | | Appl. Phys. Lett. 90, 123509 (2007) |
| Conjugated oligomers and polymers (e.g., polyfluorene) | | Org. Electron. 1, 15 (2000) |
| Aromatic fused rings | | WO2009066779, WO2009066778, WO2009063833, US20090045731, US20090045730, WO2009008311, US20090008605, US20090009065 |

TABLE 1-continued

| MATERIAL | EXAMPLES OF MATERIAL | PUBLICATIONS |
| --- | --- | --- |
| Zinc complexes | | WO2010056066 |
| Chrysene based compounds | | WO2011086863 |
| Green hosts | | |
| Arylcarbazoles | | Appl. Phys. Lett. 78, 1622 (2001) |
| | | US20030175553 |
| | | WO2001039234 |
| Aryltriphenylene compounds | | US20060280965 |

TABLE 1-continued
| MATERIAL | EXAMPLES OF MATERIAL | PUBLICATIONS |
|---|---|---|
| | 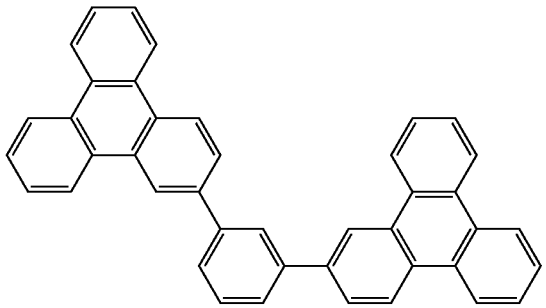 [SMILES: c1cc(-c2ccc3c4ccccc4c4ccccc4c3c2)cc(-c2ccc3c4ccccc4c4ccccc4c3c2)c1] | US20060280965 |
| | 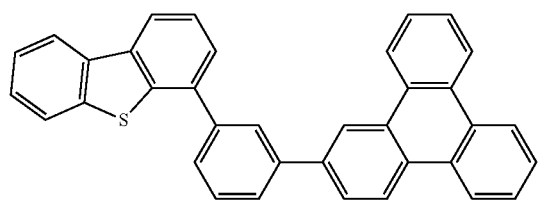 [SMILES: c1cc(-c2ccc3c4ccccc4c4ccccc4c3c2)cc(-c2cccc3c2sc2ccccc23)c1] | WO2009021126 |
| Poly-fused heteroaryl compounds | 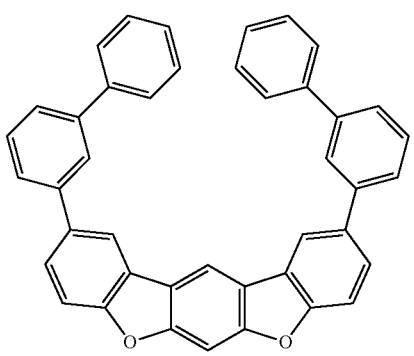 [SMILES: c1ccc(-c2cccc(-c3ccc4oc5cc6oc7ccc(-c8cccc(-c9ccccc9)c8)cc7c6cc5c4c3)c2)cc1] | US20090309488<br>US20090302743<br>US20100012931 |
| Donor acceptor type molecules | 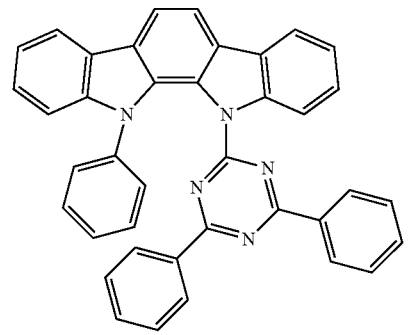 [SMILES: c1ccc(-c2nc(-c3ccccc3)nc(-n3c4ccccc4c4ccc5c6ccccc6n(-c6ccccc6)c5c43)n2)cc1] | WO2008056746 |
| | 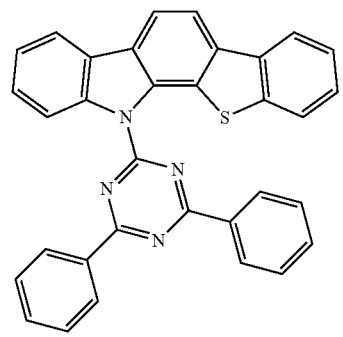 [SMILES: c1ccc(-c2nc(-c3ccccc3)nc(-n3c4ccccc4c4ccc5c6ccccc6sc5c43)n2)cc1] | WO2010107244 |

TABLE 1-continued

| MATERIAL | EXAMPLES OF MATERIAL | PUBLICATIONS |
|---|---|---|
| Aza-carbazole/DBT/DBF | | JP2008074939 |
| | | US20100187984 |
| Polymers (e.g., PVK) | | Appl. Phys. Lett. 77, 2280 (2000) |
| Spirofluorene compounds | | WO2004093207 |
| Metal phenoxybenzooxazole compounds | | WO2005089025 |

TABLE 1-continued
| MATERIAL | EXAMPLES OF MATERIAL | PUBLICATIONS |
|---|---|---|
| | 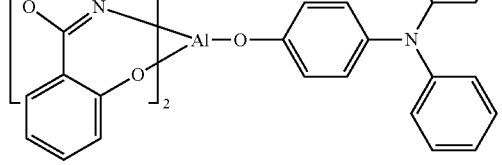 | WO2006132173 |
| | 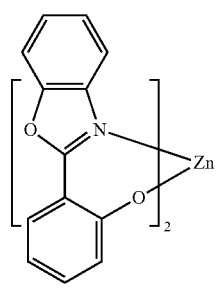 | JP200511610 |
| Spirofluorene-carbazole compounds | 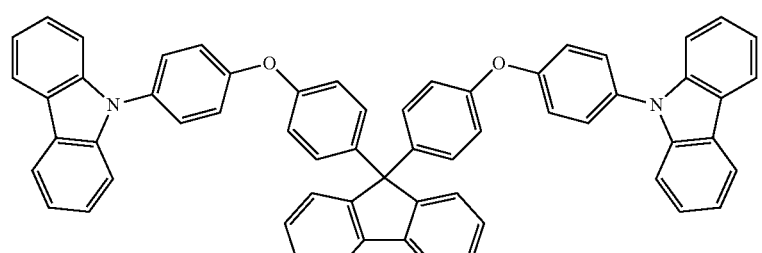 | JP2007254297 |
| | 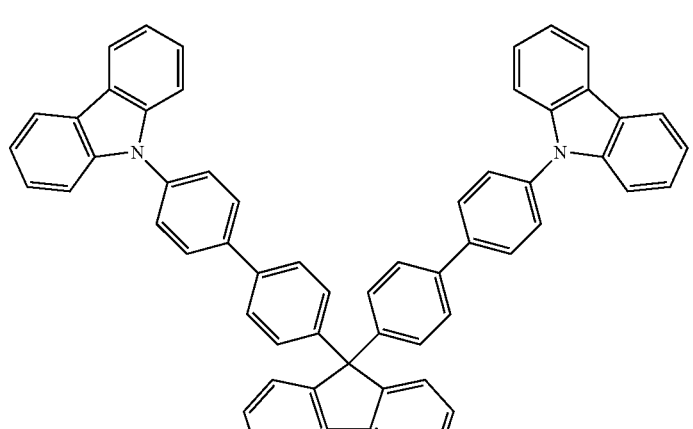 | JP2007254297 |
| Indolocabazoles | 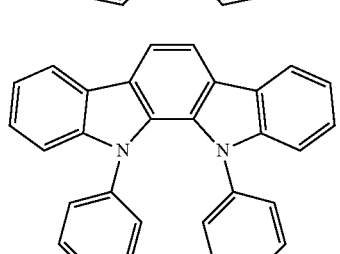 | WO2007063796 |

TABLE 1-continued
| MATERIAL | EXAMPLES OF MATERIAL | PUBLICATIONS |
|---|---|---|
| | 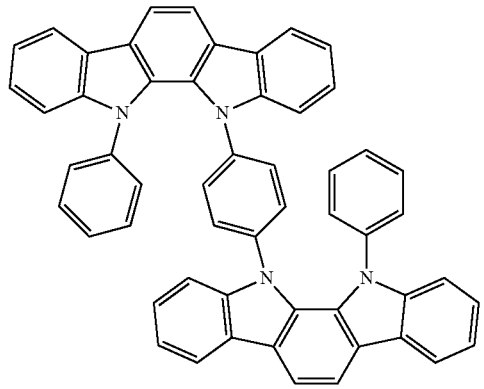 [SMILES: c1ccc(-n2c3ccccc3c3ccc4c5ccccc5n(-c5ccc(-n6c7ccccc7c7ccc8c9ccccc9n(-c9ccccc9)c8c76)cc5)c4c32)cc1] | WO2007063754 |
| 5-member ring electron deficient heterocycles (e.g., triazole, oxadiazole) | 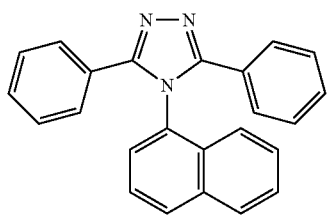 [SMILES: c1ccc(-c2nnc(-c3ccccc3)n2-c2cccc3ccccc23)cc1] | J. Appl. Phys. 90, 5048 (2001) |
| | 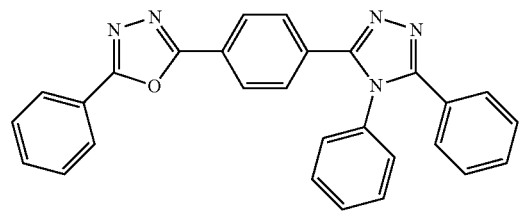 [SMILES: c1ccc(-c2nnc(-c3ccc(-c4nnc(-c5ccccc5)n4-c4ccccc4)cc3)o2)cc1] | WO2004107822 |
| Tetraphenylene complexes | 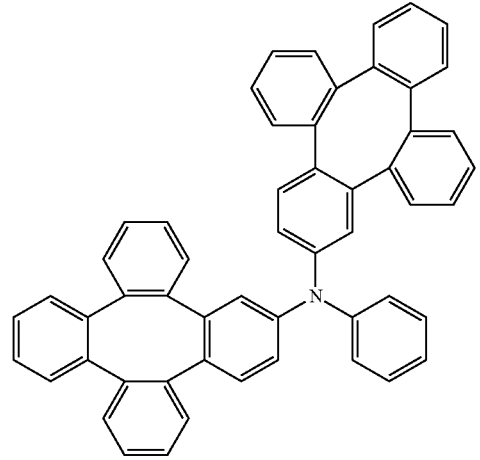 [SMILES: c1ccc(N(c2ccc3c(c2)-c2ccccc2-c2ccccc2-c2ccccc2-3)c2ccc3c(c2)-c2ccccc2-c2ccccc2-c2ccccc2-3)cc1] | US20050112407 |
| Metal phenoxypyridine compounds | 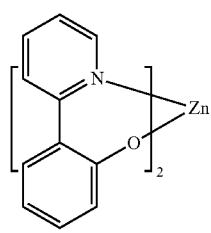 | WO2005030900 |

| MATERIAL | EXAMPLES OF MATERIAL | PUBLICATIONS |
|---|---|---|
| Metal coordination complexes (e.g., Zn, Al with N^N ligands) | 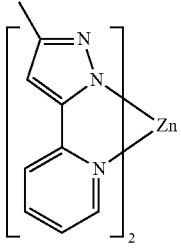 | US20040137268, US20040137267 |
| Blue hosts | | |
| Arylcarbazoles | 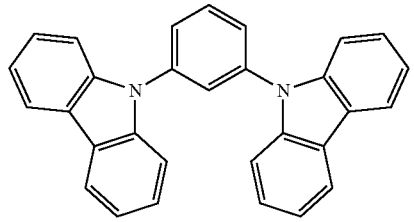 [SMILES: c1cc(-n2c3ccccc3c3ccccc32)cc(-n2c3ccccc3c3ccccc32)c1] | Appl. Phys. Lett, 82, 2422 (2003) |
|  | 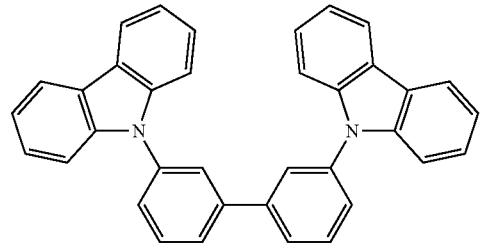 [SMILES: c1cc(-c2cccc(-n3c4ccccc4c4ccccc43)c2)cc(-n2c3ccccc3c3ccccc32)c1] | US20070190359 |
| Dibenzothiophene/Dibenzofuran-carbazole compounds | 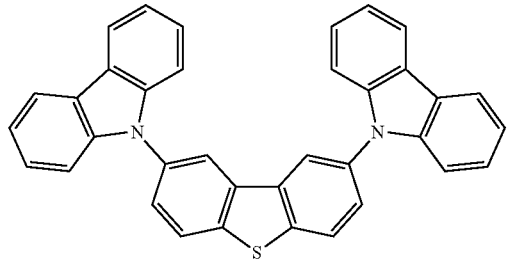 [SMILES: c1ccc2c(c1)c1ccccc1n2-c1ccc2sc3ccc(-n4c5ccccc5c5ccccc54)cc3c2c1] | WO2006114966, US20090167162 |
|  | 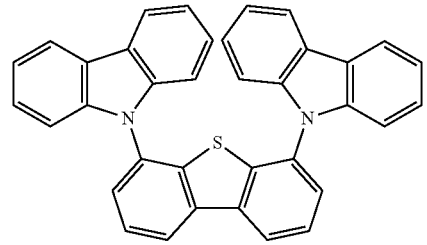 [SMILES: c1cc(-n2c3ccccc3c3ccccc32)c2sc3c(-n4c5ccccc5c5ccccc54)cccc3c2c1] | US20090167162 |
|  | 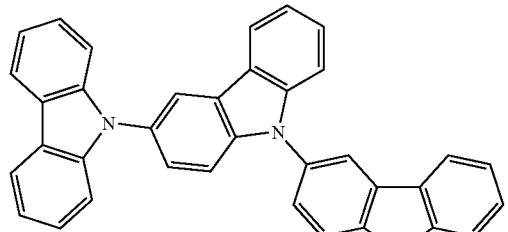 | WO2009086028 |

TABLE 1-continued
| MATERIAL | EXAMPLES OF MATERIAL | PUBLICATIONS |
|---|---|---|
| | 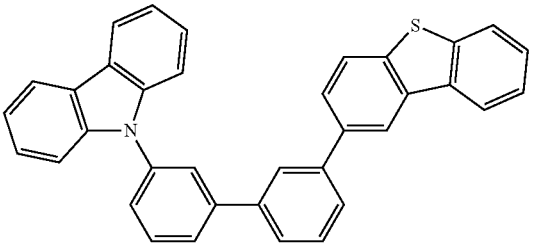 [SMILES: c1cc(-c2cccc(-n3c4ccccc4c4ccccc43)c2)cc(-c2ccc3sc4ccccc4c3c2)c1] | US20090030202, US20090017330 |
| | 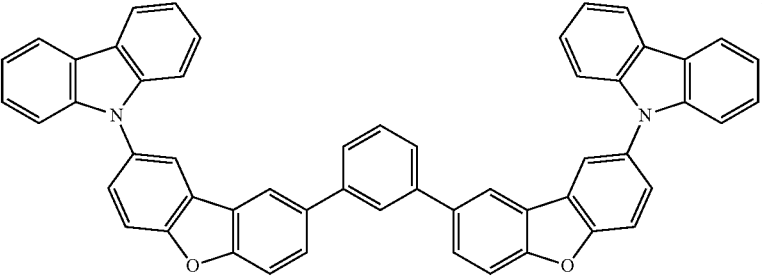 [SMILES: c1cc(-c2ccc3oc4ccc(-n5c6ccccc6c6ccccc65)cc4c3c2)cc(-c2ccc3oc4ccc(-n5c6ccccc6c6ccccc65)cc4c3c2)c1] | US20100084966 |
| Silicon aryl compounds | 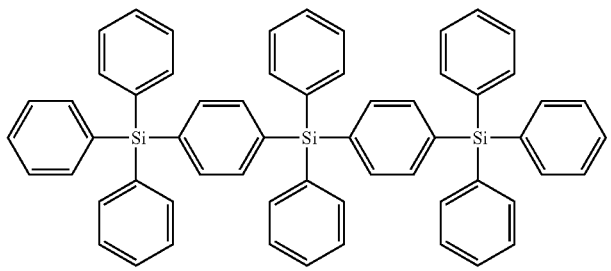 [SMILES: c1ccc([Si](c2ccccc2)(c2ccccc2)c2ccc([Si](c3ccccc3)(c3ccccc3)c3ccc([Si](c4ccccc4)(c4ccccc4)c4ccccc4)cc3)cc2)cc1] | US20050238919 |
| | 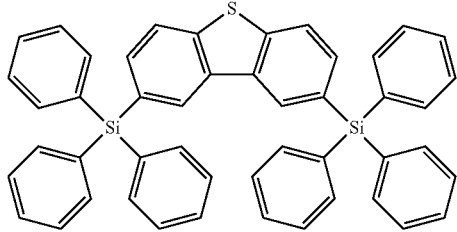 [SMILES: c1ccc([Si](c2ccccc2)(c2ccccc2)c2ccc3sc4ccc([Si](c5ccccc5)(c5ccccc5)c5ccccc5)cc4c3c2)cc1] | WO2009003898 |
| Silicon/Germanium aryl compounds | 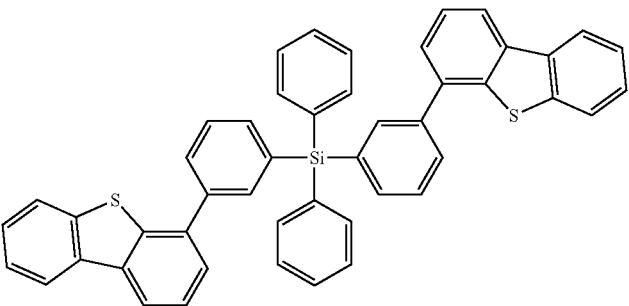 [SMILES: c1ccc([Si](c2ccccc2)(c2cccc(-c3cccc4c3sc3ccccc34)c2)c2cccc(-c3cccc4c3sc3ccccc34)c2)cc1] | EP2034538A |
| Aryl benzoyl ester | 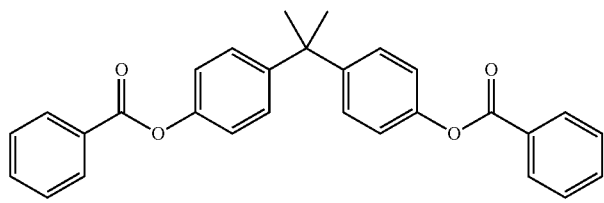 [SMILES: CC(C)(c1ccc(OC(=O)c2ccccc2)cc1)c1ccc(OC(=O)c2ccccc2)cc1] | WO2006100298 |

TABLE 1-continued
| MATERIAL | EXAMPLES OF MATERIAL | PUBLICATIONS |
| --- | --- | --- |
| Carbazole linked by non-conjugated groups | 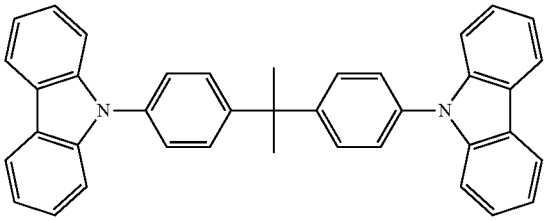 [SMILES: CC(C)(c1ccc(-n2c3ccccc3c3ccccc32)cc1)c1ccc(-n2c3ccccc3c3ccccc32)cc1] | US20040115476 |
| Aza-carbazoles | 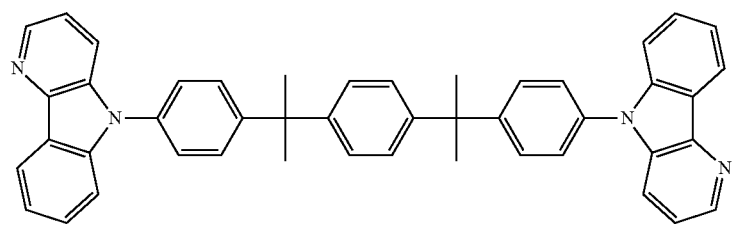 [SMILES: CC(C)(c1ccc(-n2c3ccccc3c3ncccc32)cc1)c1ccc(C(C)(C)c2ccc(-n3c4ccccc4c4ncccc43)cc2)cc1] | US20060121308 |
| High triplet metal organometallic complex | 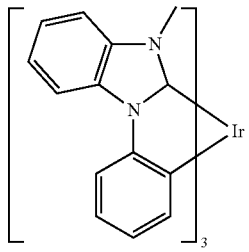 | US7154114 |
Phosphorescent dopants
Red dopants
| Heavy metal porphyrins (e.g., PtOEP) | 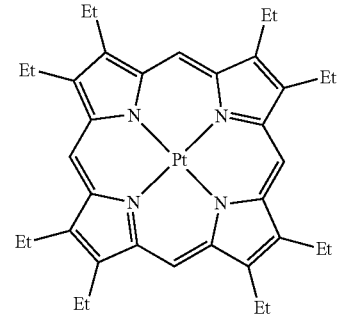 | Nature 395, 151 (1998) |
| --- | --- | --- |
| Iridium(III) organometallic complexes | 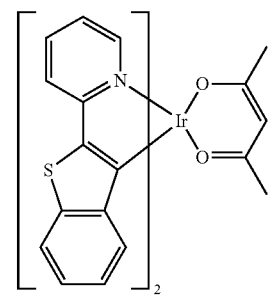 | Appl. Phys. Lett. 78, 1622 (2001) |

TABLE 1-continued

| MATERIAL | EXAMPLES OF MATERIAL | PUBLICATIONS |
|---|---|---|
| | | US2006835469 |
| | | US2006835469 |
| | | US20060202194 |
| | | US20060202194 |
| | | US20070087321 |

TABLE 1-continued
| MATERIAL | EXAMPLES OF MATERIAL | PUBLICATIONS |
|---|---|---|
| | 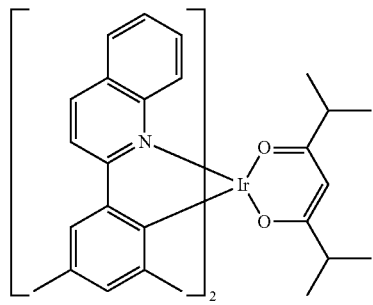 | US20080261076 US20100090591 |
| | 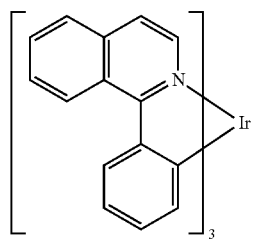 | US20070087321 |
| | 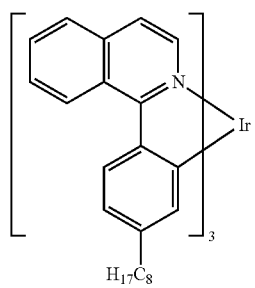 | Adv. Mater. 19, 739 (2007) |
| | 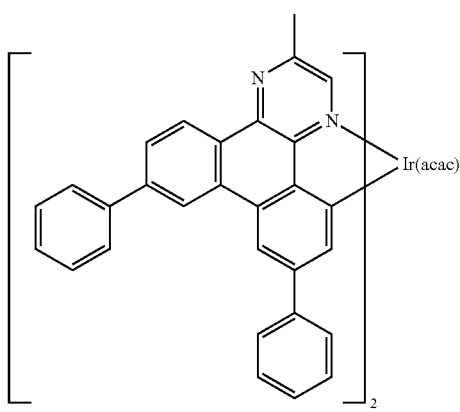 | WO2009100991 |
| | 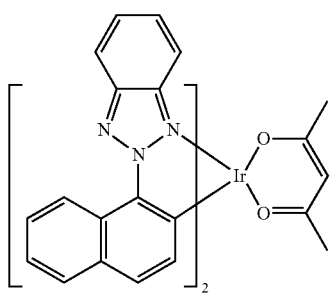 | WO2008101842 |

TABLE 1-continued
| MATERIAL | EXAMPLES OF MATERIAL | PUBLICATIONS |
|---|---|---|
| | 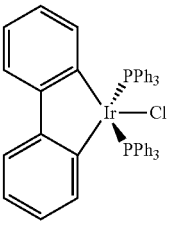 | US7232618 |
| Platinum(II) organometallic complexes | 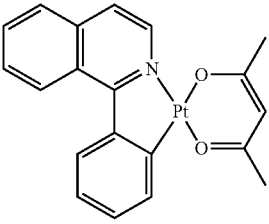 | WO2003040257 |
| | 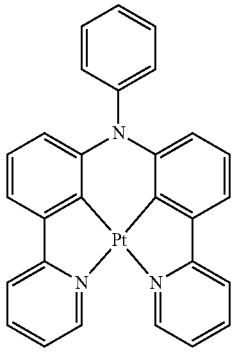 | US20070103060 |
| Osminum(III) complexes | 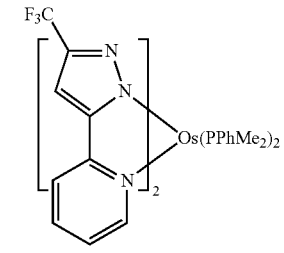 | Chem. Mater. 17, 3532 (2005) |
| Ruthenium(II) complexes | 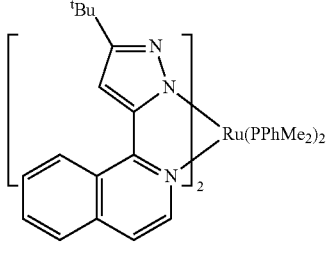 | Adv. Mater. 17, 1059 (2005) |
| Rhenium (I), (II), and (III) complexes | 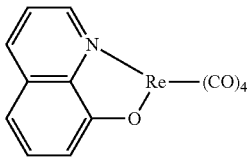 | US20050244673 |
Green dopants

TABLE 1-continued
| MATERIAL | EXAMPLES OF MATERIAL | PUBLICATIONS |
|---|---|---|
| Iridium(III) organometallic complexes | 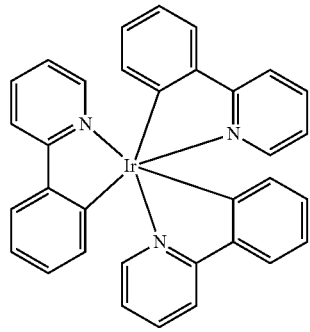<br>and its derivatives | Inorg. Chem. 40, 1704 (2001) |
| | 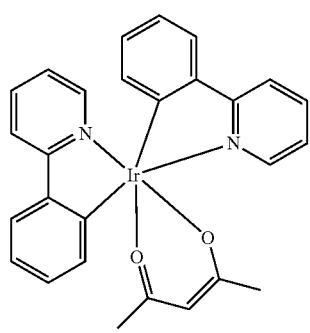 | US20020034656 |
| | 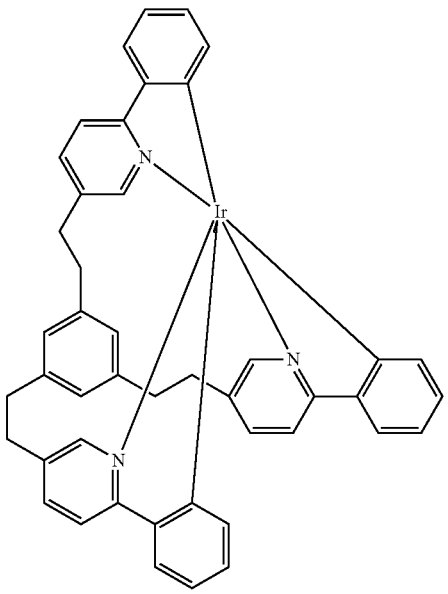 | US7332232 |

TABLE 1-continued
| MATERIAL | EXAMPLES OF MATERIAL | PUBLICATIONS |
|---|---|---|
| | 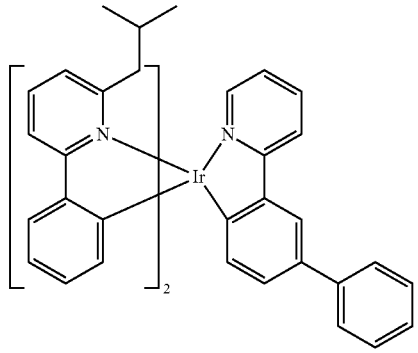 | US20090108737 |
| | 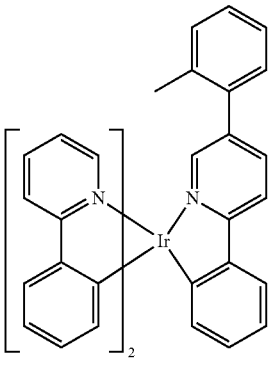 | WO2010028151 |
| | 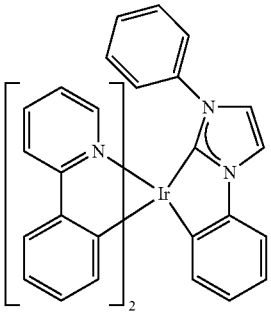 | EP1841834B |
| | 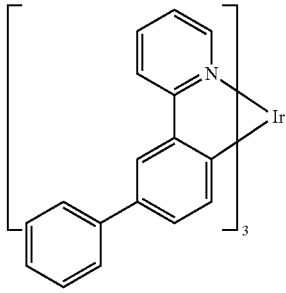 | US20060127696 |
| | 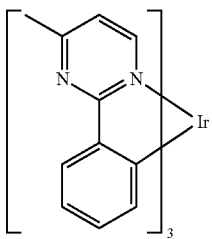 | US20090039776 |

TABLE 1-continued
| MATERIAL | EXAMPLES OF MATERIAL | PUBLICATIONS |
|---|---|---|
|  | 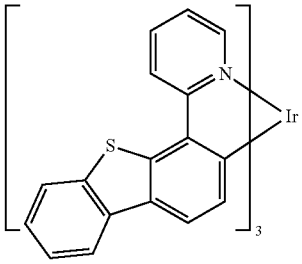 | US6921915 |
|  | 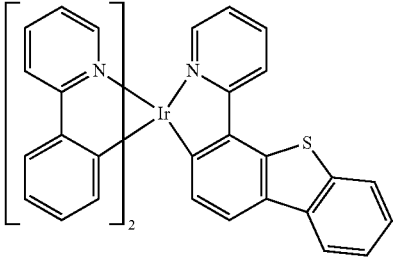 | US20100244004 |
|  | 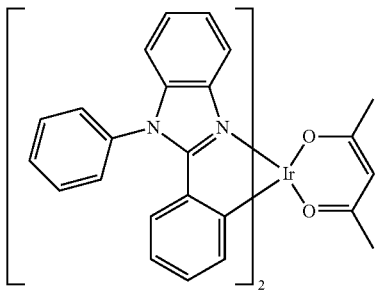 | US6687266 |
|  | 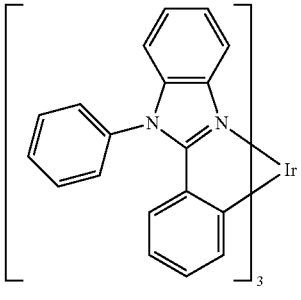 | Chem. Mater. 16, 2480 (2004) |
|  | 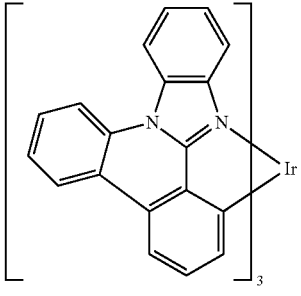 | US20070190359 |

TABLE 1-continued
| MATERIAL | EXAMPLES OF MATERIAL | PUBLICATIONS |
|---|---|---|
| | 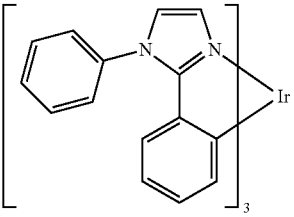 | US 20060008670<br>JP2007123392 |
| | 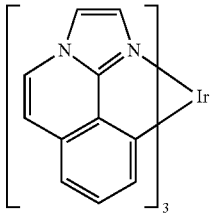 | WO2010086089,<br>WO2011044988 |
| | 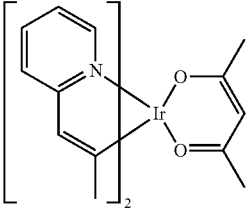 | Adv. Mater. 16, 2003<br>(2004) |
| | 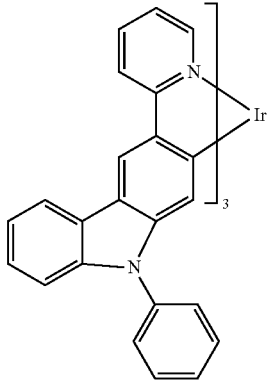 | Angew. Chem. Int. Ed.<br>2006, 45, 7800 |
| | 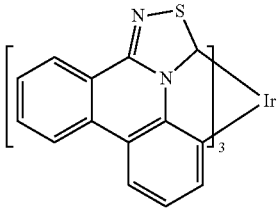 | WO2009050290 |
| | 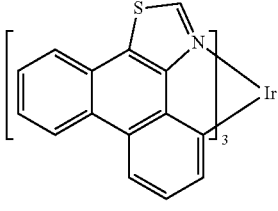 | US20090165846 |

TABLE 1-continued

| MATERIAL | EXAMPLES OF MATERIAL | PUBLICATIONS |
| --- | --- | --- |
| | | US20080015355 |
| | | US20010015432 |
| | | US20100295032 |
| Monomer for polymeric metal organometallic compounds | | US7250226, US7396598 |
| Pt(II) organometallic complexes, including polydentated ligands | | Appl. Phys. Lett. 86, 153505 (2005) |

TABLE 1-continued
| MATERIAL | EXAMPLES OF MATERIAL | PUBLICATIONS |
|---|---|---|
|  | 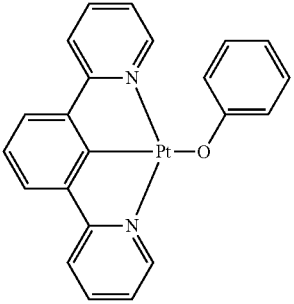 | Appl. Phys. Lett. 86, 153505 (2005) |
|  | 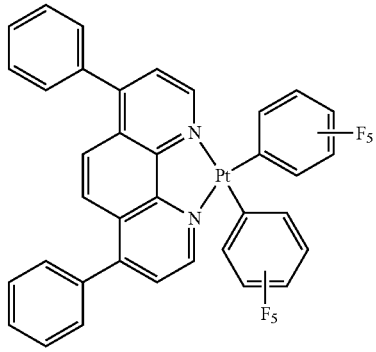 | Chem. Lett. 34, 592 (2005) |
|  | 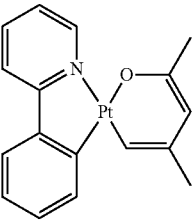 | WO2002015645 |
|  | 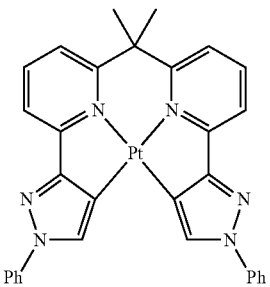 | US20060263635 |
|  | 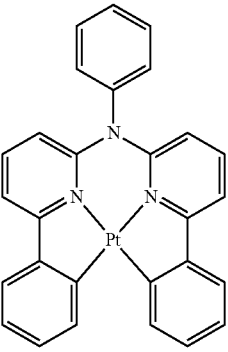 | US20060182992<br>US20070103060 |

| MATERIAL | EXAMPLES OF MATERIAL | PUBLICATIONS |
|---|---|---|
| Cu complexes | 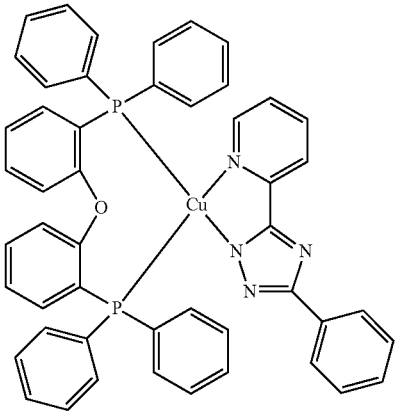 | WO2009000673 |
| | 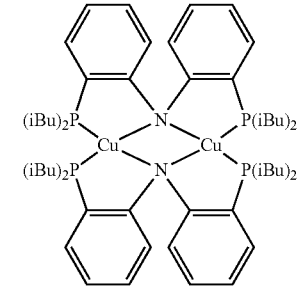 | US20070111026 |
| Gold complexes | 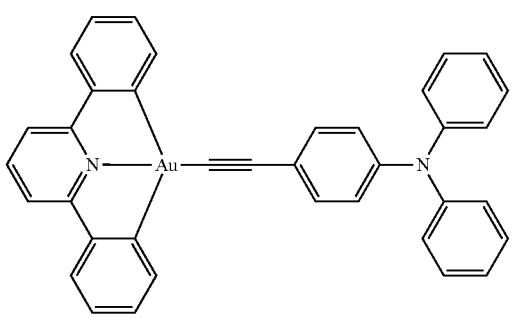 | Chem. Commun. 2906 (2005) |
| Rhenium(III) complexes | 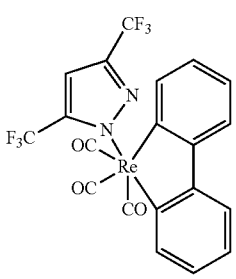 | Inorg. Chem. 42, 1248 (2003) |

TABLE 1-continued

| MATERIAL | EXAMPLES OF MATERIAL | PUBLICATIONS |
|---|---|---|
| Osmium(II) complexes | | US7279704 |
| Deuterated organometallic complexes | | US20030138657 |
| Organometallic complexes with two or more metal centers | | US20030152802 |
| | | US7090928 |
| Blue dopants | | |

TABLE 1-continued
| MATERIAL | EXAMPLES OF MATERIAL | PUBLICATIONS |
|---|---|---|
| Iridium(III) organometallic complexes | 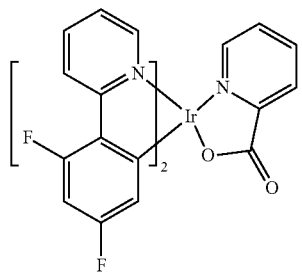 | WO2002002714 |
| | 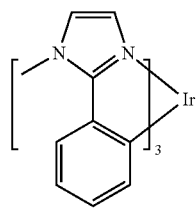 | WO2006009024 |
| | 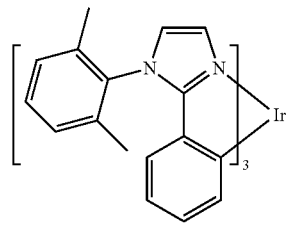 | US20060251923<br>US20110057559<br>US20110204333 |
| | 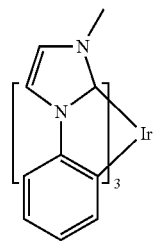 | US7393599,<br>WO2006056418,<br>US20050260441,<br>WO2005019373 |
| | 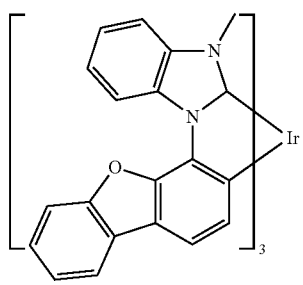 | US7534505 |
| | 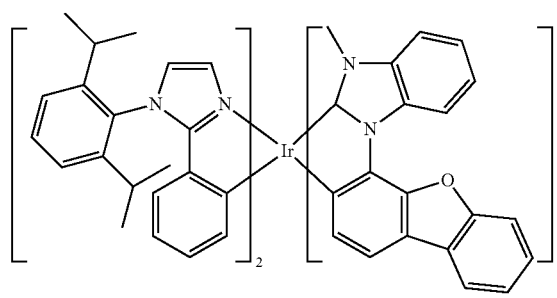 | WO2011051404 |

TABLE 1-continued

| MATERIAL | EXAMPLES OF MATERIAL | PUBLICATIONS |
|---|---|---|
| | | US7445855 |
| | | US20070190359, US20080297033 US20100148663 |
| | | US7338722 |
| | | US20020134984 |
| | | Angew. Chem. Int. Ed. 47, 1 (2008) |

TABLE 1-continued

| MATERIAL | EXAMPLES OF MATERIAL | PUBLICATIONS |
|---|---|---|
| | | Chem. Mater. 18, 5119 (2006) |
| | | Inorg. Chem. 46, 4308 (2007) |
| | | WO2005123873 |
| | | WO2005123873 |
| | | WO2007004380 |

TABLE 1-continued

| MATERIAL | EXAMPLES OF MATERIAL | PUBLICATIONS |
|---|---|---|
| | | WO2006082742 |
| Osmium(II) complexes | | US7279704 |
| | | Organometallics 23, 3745 (2004) |
| Gold complexes | | Appl. Phys. Lett. 74, 1361 (1999) |
| Platinum(II) complexes | | WO2006098120, WO2006103874 |

TABLE 1-continued

| MATERIAL | EXAMPLES OF MATERIAL | PUBLICATIONS |
|---|---|---|
| Pt tetradentate complexes with at least one metal-carbene bond | 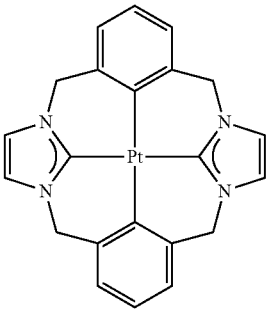 | US7655323 |

Exciton/hole blocking layer materials

| MATERIAL | EXAMPLES OF MATERIAL | PUBLICATIONS |
|---|---|---|
| Bathocuprine compounds (e.g., BCP, BPhen) | 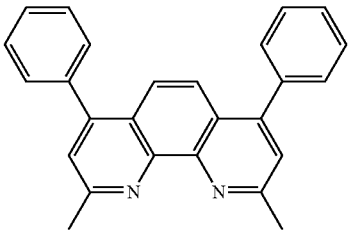 [SMILES: Cc1cc(-c2ccccc2)c2ccc3c(-c4ccccc4)cc(C)nc3c2n1] | Appl. Phys. Lett. 75, 4 (1999) |
|  | 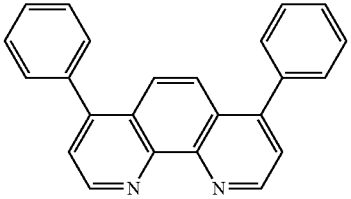 [SMILES: c1ccc(-c2ccnc3c2ccc2c(-c4ccccc4)ccnc23)cc1] | Appl. Phys. Lett. 79, 449 (2001) |
| Metal 8-hydroxyquinolates (e.g., BAlq) | 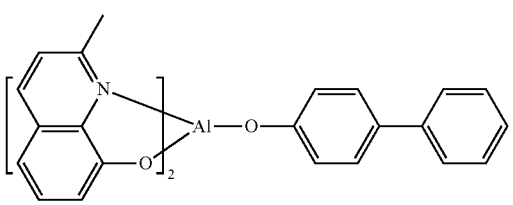 | Appl. Phys. Lett. 81, 162 (2002) |
| 5-member ring electron deficient heterocycles such as triazole, oxadiazole, imidazole, benzoimidazole | 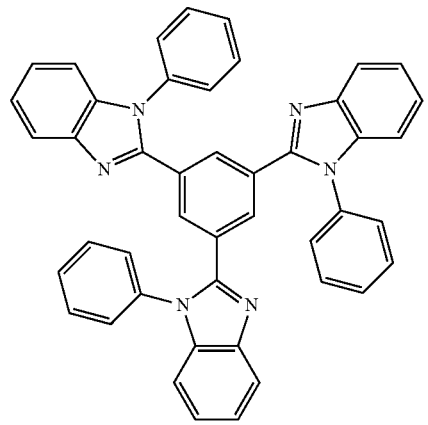 [SMILES: c1ccc(-n2c(-c3cc(-c4nc5ccccc5n4-c4ccccc4)cc(-c4nc5ccccc5n4-c4ccccc4)c3)nc3ccccc32)cc1] | Appl. Phys. Lett. 81, 162 (2002) |

TABLE 1-continued
| MATERIAL | EXAMPLES OF MATERIAL | PUBLICATIONS |
|---|---|---|
| Triphenylene compounds | 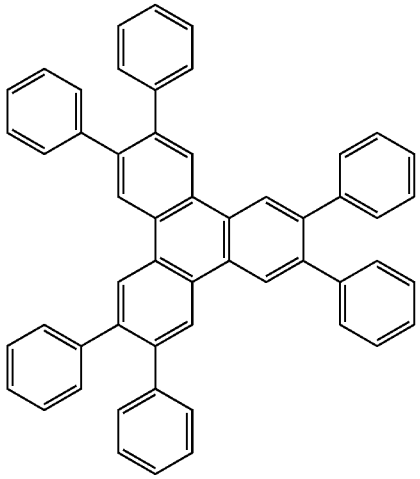 [SMILES: c1ccc(-c2cc3c4cc(-c5ccccc5)c(-c5ccccc5)cc4c4cc(-c5ccccc5)c(-c5ccccc5)cc4c3cc2-c2ccccc2)cc1] | US20050025993 |
| Fluorinated aromatic compounds | 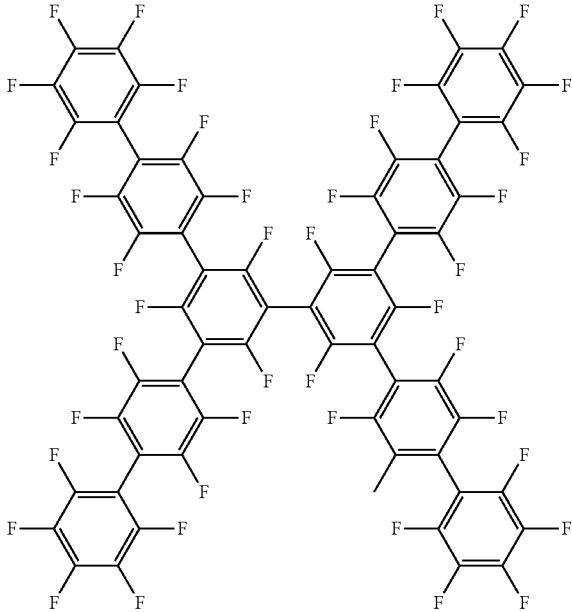 [SMILES: Cc1c(F)c(-c2c(F)c(-c3c(F)c(F)c(-c4c(F)c(F)c(F)c(F)c4F)c(F)c3F)c(F)c(-c3c(F)c(-c4c(F)c(F)c(-c5c(F)c(F)c(F)c(F)c5F)c(F)c4F)c(F)c(-c4c(F)c(F)c(-c5c(F)c(F)c(F)c(F)c5F)c(F)c4F)c3F)c2F)c(F)c(F)c1-c1c(F)c(F)c(F)c(F)c1F] | Appl. Phys. Lett. 79, 156 (2001) |
| Phenothiazine-S-oxide | 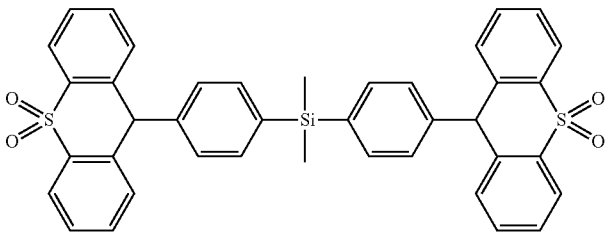 [SMILES: C[Si](C)(c1ccc(C2c3ccccc3S(=O)(=O)c3ccccc32)cc1)c1ccc(C2c3ccccc3S(=O)(=O)c3ccccc32)cc1] | WO2008132085 |
| Silylated five-membered nitrogen, oxygen, sulfur or phosphorus dibenzoheterocycles | 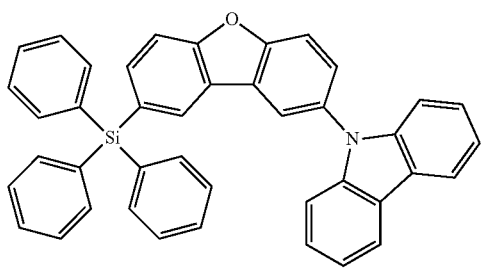 [SMILES: c1ccc([Si](c2ccccc2)(c2ccccc2)c2ccc3oc4ccc(-n5c6ccccc6c6ccccc65)cc4c3c2)cc1] | WO2010079051 |

TABLE 1-continued
| MATERIAL | EXAMPLES OF MATERIAL | PUBLICATIONS |
|---|---|---|
| Aza-carbazoles | 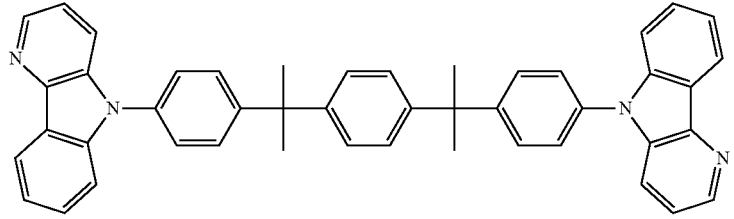 [SMILES: CC(C)(c1ccc(-n2c3ccccc3c3ncccc32)cc1)c1ccc(C(C)(C)c2ccc(-n3c4ccccc4c4ncccc43)cc2)cc1] | US20060121308 |
| Electron transporting materials | | |
| Anthracene-benzoimidazole compounds | 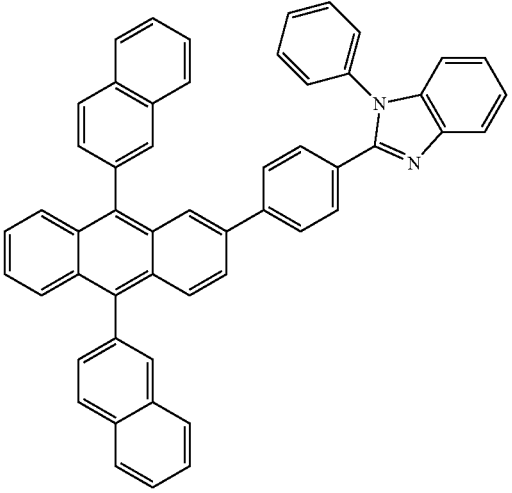 [SMILES: c1ccc(-n2c(-c3ccc(-c4ccc5c(-c6ccc7ccccc7c6)c6ccccc6c(-c6ccc7ccccc7c6)c5c4)cc3)nc3ccccc32)cc1] | WO2003060956 |
| | 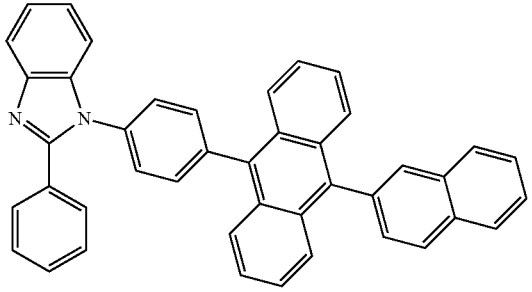 [SMILES: c1ccc(-c2nc3ccccc3n2-c2ccc(-c3c4ccccc4c(-c4ccc5ccccc5c4)c4ccccc34)cc2)cc1] | US20090179554 |
| Aza triphenylene derivatives | 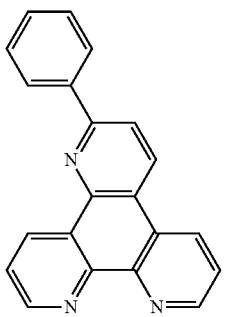 [SMILES: c1ccc(-c2ccc3c4cccnc4c4ncccc4c3n2)cc1] | US20090115316 |

TABLE 1-continued

| MATERIAL | EXAMPLES OF MATERIAL | PUBLICATIONS |
| --- | --- | --- |
| Anthracene-benzothiazole compounds | | Appl. Phys. Lett. 89, 063504 (2006) |
| Metal 8-hydroxyquinolates (e.g., Alq$_3$, Zrq$_4$) | | Appl. Phys. Lett. 51, 913 (1987)<br>US7230107 |
| Metal hydroxybenoquinolates | | Chem. Lett. 5, 905 (1993) |
| Bathocuprine compounds such as BCP, BPhen, etc. | | Appl. Phys. Lett. 91, 263503 (2007) |
| | | Appl. Phys. Lett. 79, 449 (2001) |
| 5-member ring electron deficient heterocycles (e.g., triazole, oxadiazole, imidazole, benzoimidazole) | | Appl. Phys. Lett. 74, 865 (1999) |

TABLE 1-continued

| MATERIAL | EXAMPLES OF MATERIAL | PUBLICATIONS |
|---|---|---|
| | | Appl. Phys. Lett. 55, 1489 (1989) |
| | | Jpn. J. Apply. Phys. 32, L917 (1993) |
| Silole compounds | | Org. Electron. 4, 113 (2003) |
| Arylborane compounds | | J. Am. Chem. Soc. 120, 9714 (1998) |
| Fluorinated aromatic compounds | | J. Am. Chem. Soc. 122, 1832 (2000) |
| Fullerene (e.g., C60) | | US20090101870 |

TABLE 1-continued

| MATERIAL | EXAMPLES OF MATERIAL | PUBLICATIONS |
|---|---|---|
| Triazine complexes | | US20040036077 |
| Zn (N^N) complexes | | US6528187 |

EXPERIMENTAL

Calculation of S1-T1 Gap

DFT calculations with the Gaussian software package at the B3LYP/cep-31g functional and basis set were carried out for five boron-nitrogen polyaromatic compounds. TABLE 2 below shows the calculated values for the HOMO and the LUMO, the HOMO-LUMO gap, the S1 and T1 energy levels, and the S1-T1 gap. The S1-T1 gap for the boron-nitrogen polyaromatic compounds generally ranged from about 0.4 eV to about 0.6 eV, which is much lower than the S1-T1 gap for corresponding benzenoid systems (about 1.0 eV).

TABLE 2

| Cmpd | Structure | HOMO (eV) | LUMO (eV) | HOMO-LUMO Gap (eV) | Calc. S1 (nm) | Calc. T1 (nm) | S1-T1 gap (eV) |
|---|---|---|---|---|---|---|---|
| 1 | 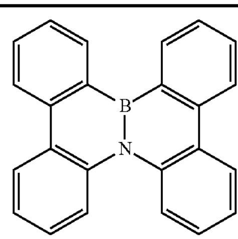 | −5.5 | −1.24 | −4.26 | 345 | 409 | 0.57 |
| 2 | 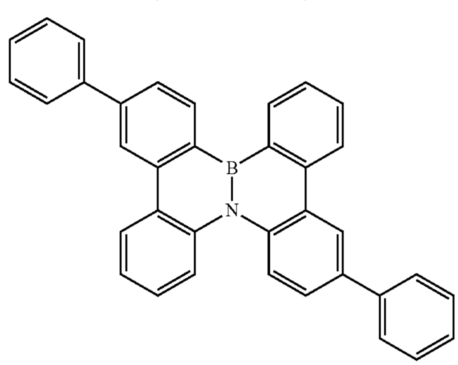 [SMILES: c1ccc(-c2ccc3c(c2)-c2ccccc2N2B3c3ccccc3-c3cc(-c4ccccc4)ccc32)cc1] | −5.39 | −1.41 | −3.98 | 380 | 430 | 0.38 |

TABLE 2-continued

| Cmpd | Structure | HOMO (eV) | LUMO (eV) | HOMO-LUMO Gap (eV) | Calc. S1 (nm) | Calc. T1 (nm) | S1-T1 gap (eV) |
|---|---|---|---|---|---|---|---|
| 3 | 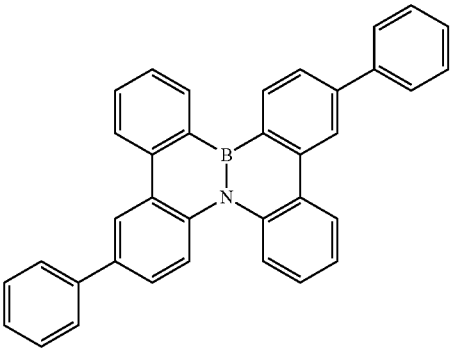 [SMILES: c1ccc(-c2ccc3c(c2)-c2ccccc2N2B3c3ccccc3-c3cc(-c4ccccc4)ccc32)cc1] | −5.39 | −1.41 | −3.98 | 380 | 431 | 0.39 |
| 4 | 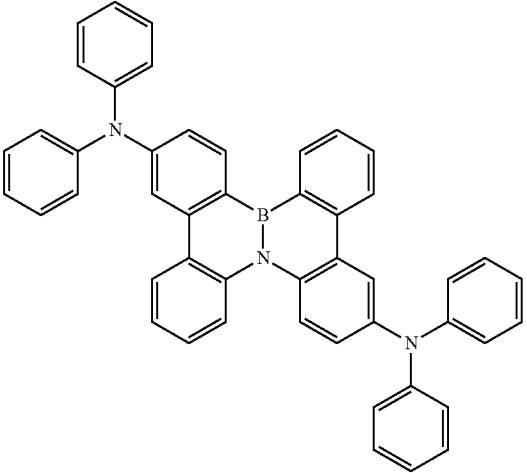 [SMILES: c1ccc(N(c2ccccc2)c2ccc3c(c2)-c2ccccc2N2B3c3ccccc3-c3cc(N(c4ccccc4)c4ccccc4)ccc32)cc1] | −4.77 | −1.19 | −3.58 | 399 | 458 | 0.40 |
| 5 | 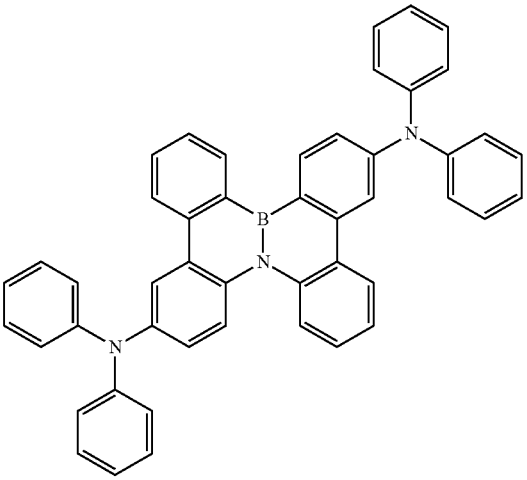 [SMILES: c1ccc(N(c2ccccc2)c2ccc3c(c2)-c2ccccc2N2B3c3ccccc3-c3cc(N(c4ccccc4)c4ccccc4)ccc32)cc1] | −4.76 | −1.2 | −3.55 | 401 | 459 | 0.39 |

Photoluminescence (PL) spectra were recorded for Compound 1 (shown in TABLE 2). FIG. 4 shows the PL spectra for Compound 1 in 2-MeTHF at room temperature (RT) and at 77 K, labeled as 1 and 2, respectively. The photoluminescence is strong at both temperatures. Based on the peak positions at 77 K, the S1-T1 gap is 0.25 eV. The PL efficiency at room temperature of a PMMA:Compound 1 thin film (100:5 by weight) is 18%. The PL spectrum for the thin film is labeled as 3 on FIG. 4. The aryl, heteroaryl, and/or amino analogs would be expected to show higher PL efficiency.

Synthetic Examples

Some of the boron-nitrogen polyaromatic compounds were synthesized as follows.

Synthesis of Compound 1.

Compound 1 can be synthesized using a method analogous to those described in Hatakeyama et al., *J. Am. Chem. Soc.*, vol. 133, pp. 18614-17(2011).

It is understood that the various embodiments described herein are by way of example only, and are not intended to limit the scope of the invention. For example, many of the materials and structures described herein may be substituted with other materials and structures without deviating from the spirit of the invention. The present invention as claimed may therefore include variations from the particular examples and preferred embodiments described herein, as will be apparent to one of skill in the art. It is understood that various theories as to why the invention works are not intended to be limiting.

I claim:

1. A compound comprising:
    a fused aromatic ring system comprising a [1,2]azaborino[1,2-a][1,2]azaborine

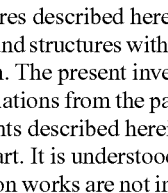

moiety;
    wherein the fused aromatic ring system is substituted by one or more substituents, R, that are not fused to the aromatic ring system, selected from the group consisting of deuterium, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof; wherein any two adjacent substituents, R, are optionally joined to form one or more non-aromatic rings; and
    wherein said fused aromatic ring system is selected from the group consisting of a first fused aromatic ring system group and a second fused aromatic ring system group, wherein the first fused aromatic system group is selected from the group consisting of:

Compound 2-7
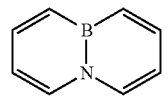,

Compound 2-8
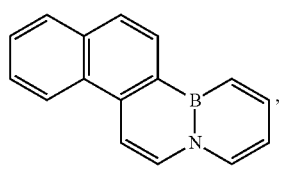,

Compound 2-9
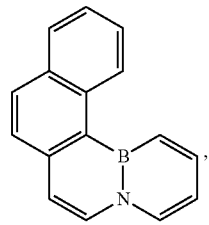,

Compound 2-13
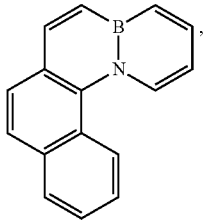,

Compound 2-14
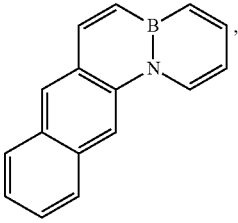,

Compound 2-15
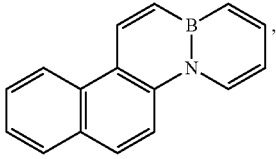,

Compound 3-27
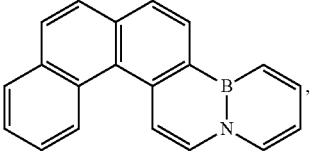,

Compound 3-28
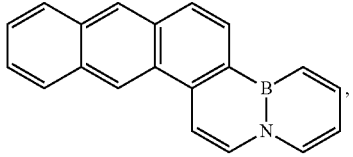,

Compound 3-29
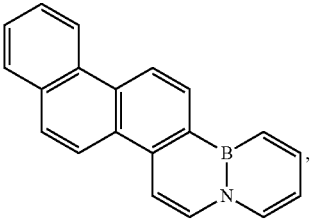,

Compound 3-30
Compound 3-31
Compound 3-32
Compound 3-33
Compound 3-34
Compound 3-35
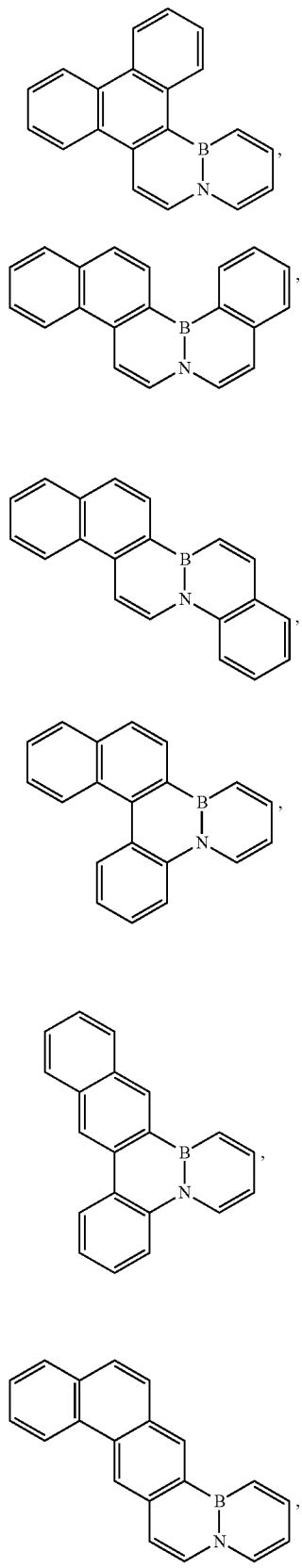
Compound 3-36
Compound 3-37
Compound 3-38
Compound 3-39
Compound 3-40
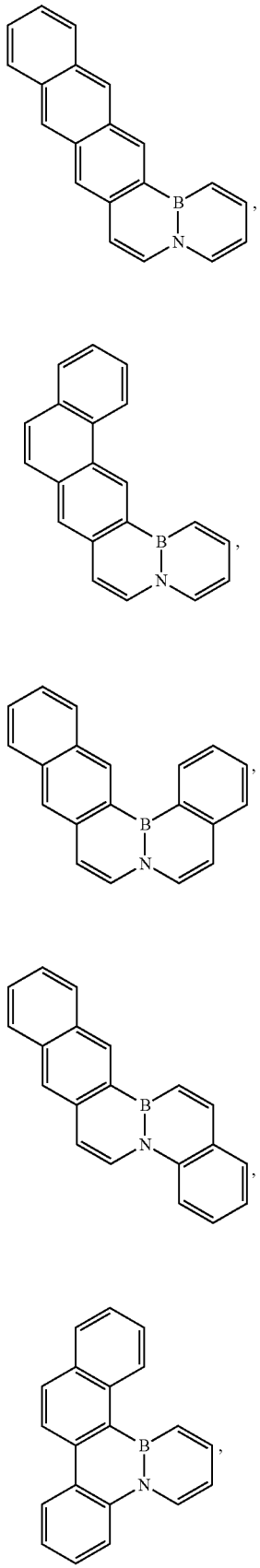

Compound 3-41
Compound 3-42
Compound 3-43
Compound 3-44
Compound 3-45
Compound 3-48
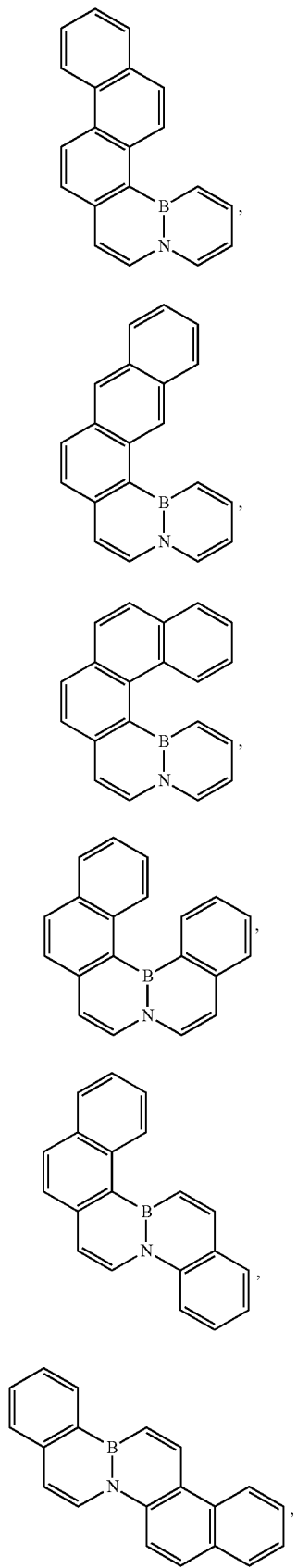
Compound 3-49
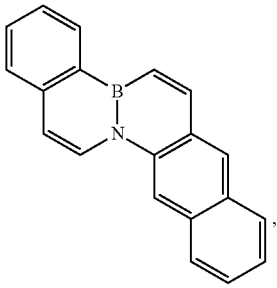
Compound 3-50
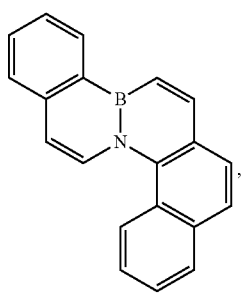
Compound 3-51
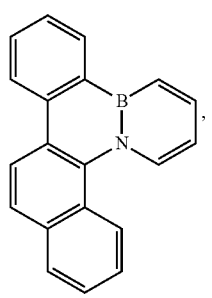
Compound 3-52
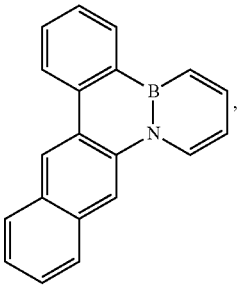
Compound 3-53
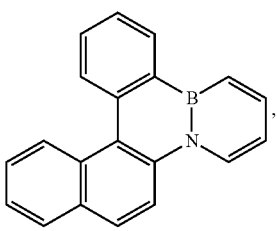
Compound 3-54

-continued
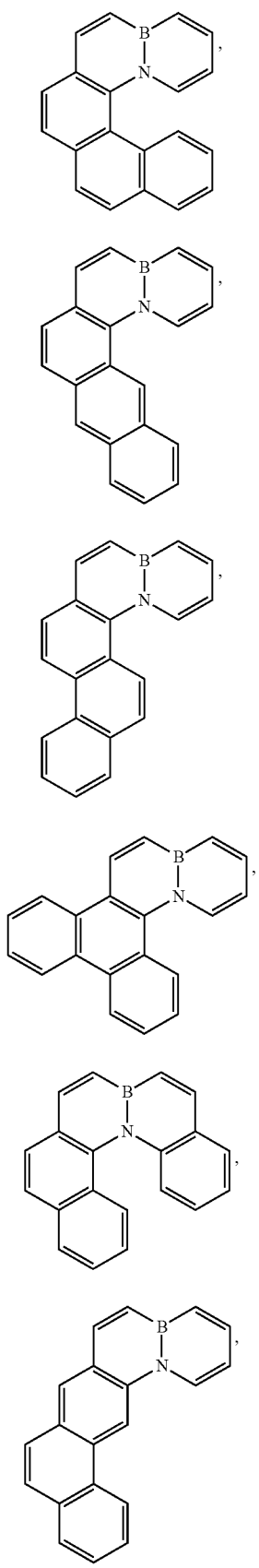
Compound 3-55
Compound 3-56
Compound 3-57
Compound 3-58
Compound 3-59
Compound 3-60
Compound 3-61
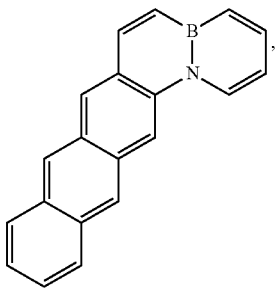
Compound 3-62
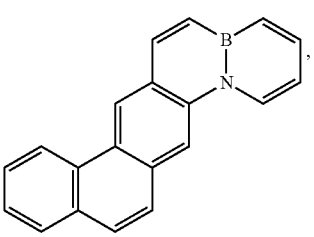
Compound 3-63
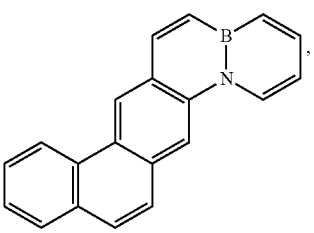
Compound 3-64
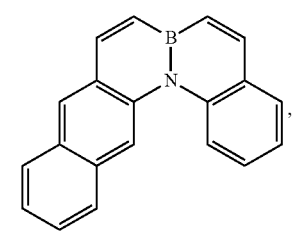
Compound 3-65
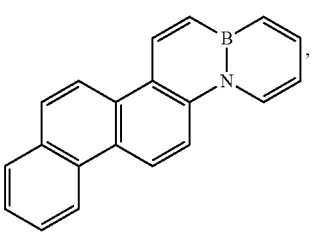
Compound 3-66
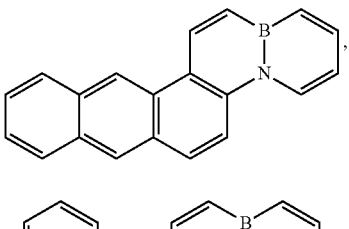
Compound 3-67
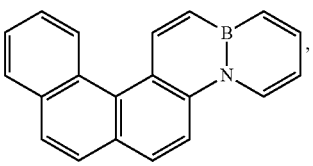

-continued
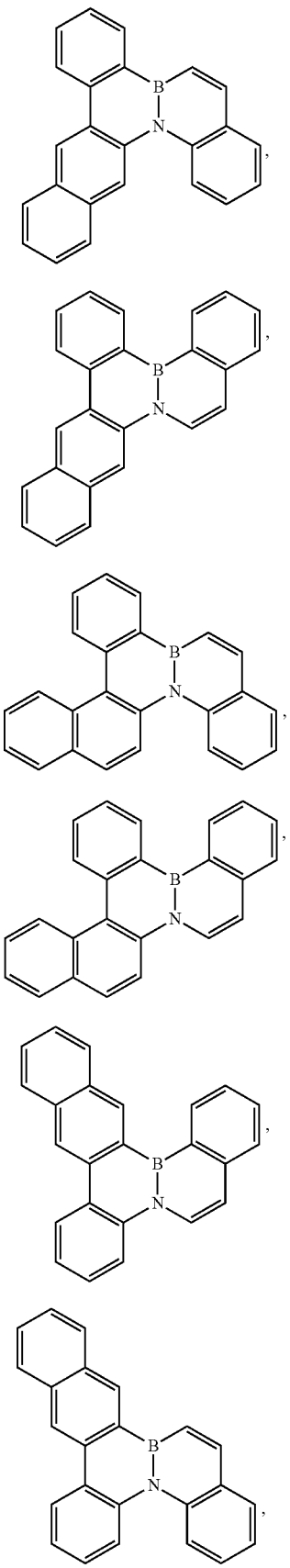
Compound 4-2
Compound 4-4
Compound 4-5
Compound 4-7
Compound 4-8
Compound 4-10
Compound 4-11
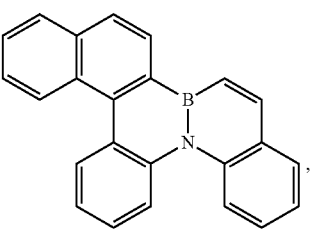
Compound 4-13
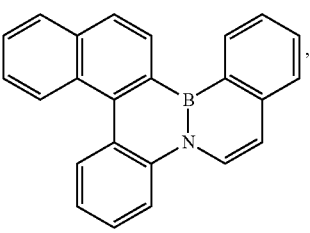
Compound 4-14
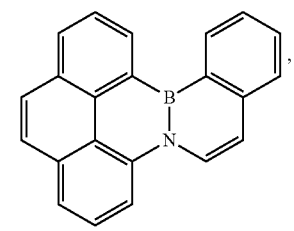
Compound 4-15
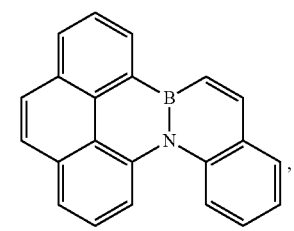
Compound 5-1
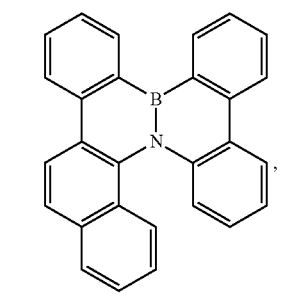
Compound 5-2
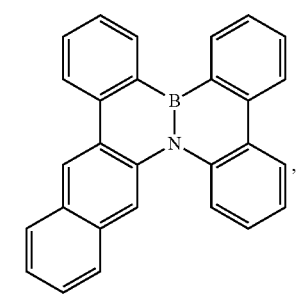

Compound 5-3
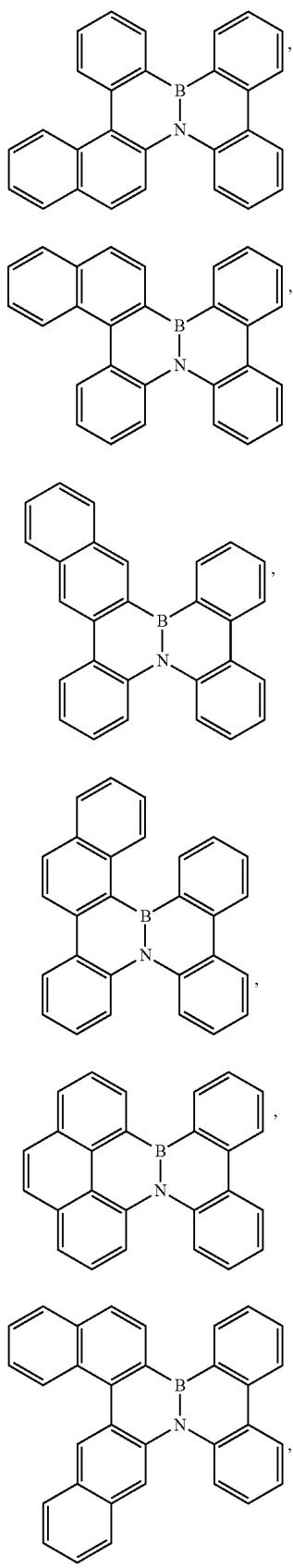
Compound 5-4
Compound 5-5
Compound 5-6
Compound 5-7
Compound 6-1
Compound 6-2
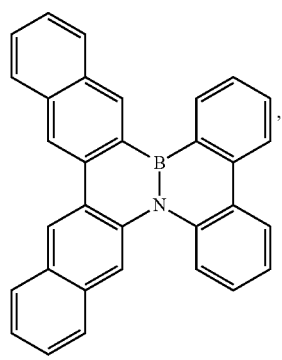
Compound 6-3
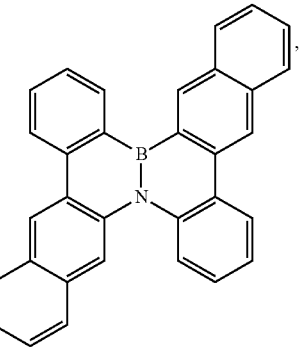
Compound 6-4
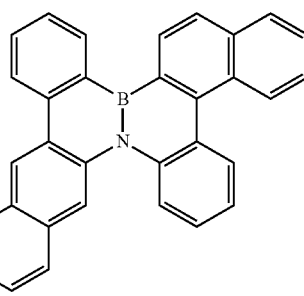
Compound 6-5
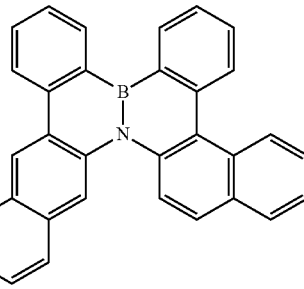
Compound 6-6
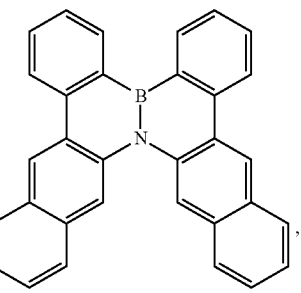

Compound 6-7
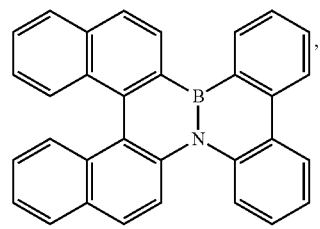
Compound 6-8
Compound 6-9
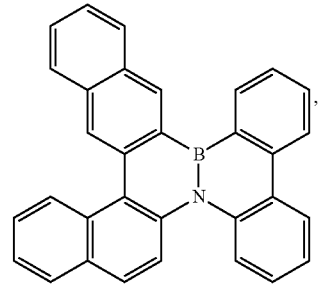
Compound 6-10
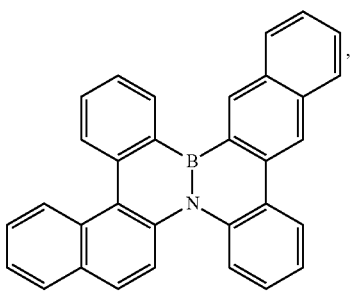
Compound 6-11
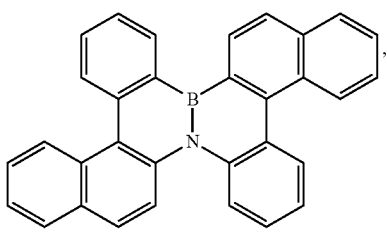
Compound 6-12
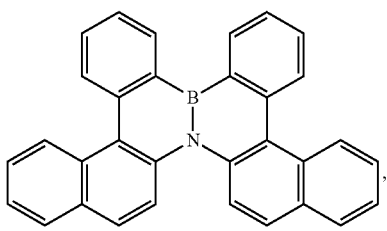
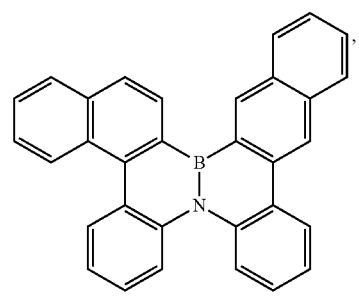
Compound 6-13
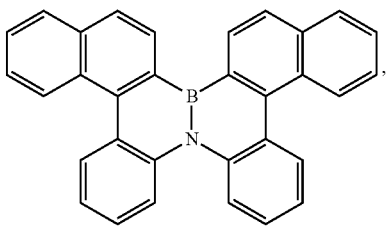
Compound 6-14
Compound 6-15
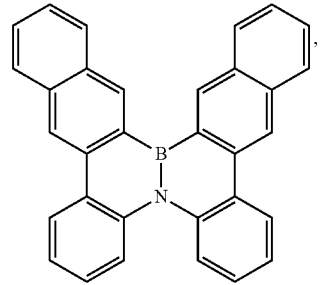
Compound 6-16
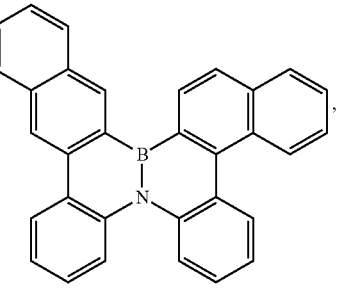
Compound 6-17
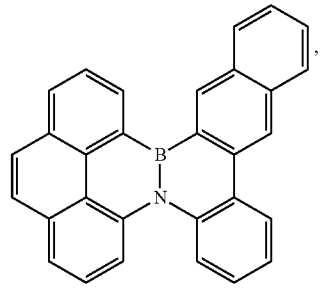
Compound 6-18
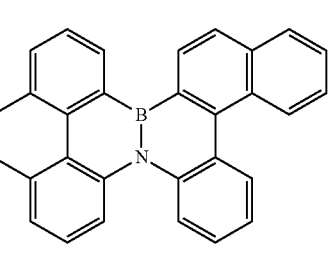
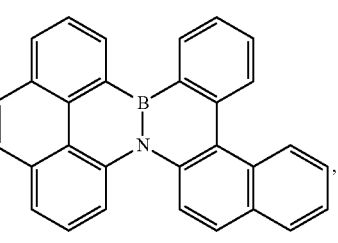

Compound 6-19
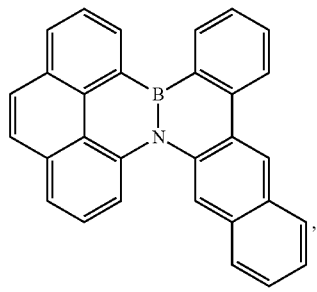
Compound 7-1
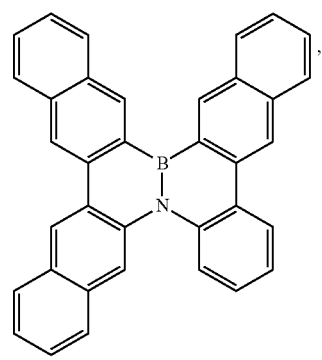
Compound 7-2
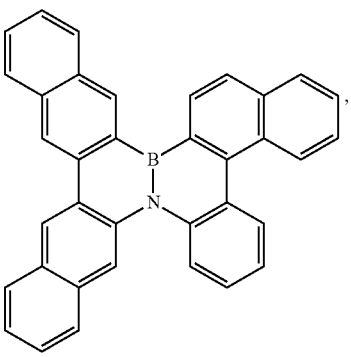
Compound 7-3
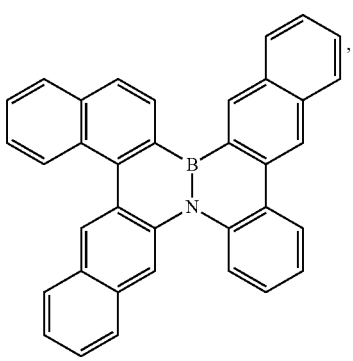
Compound 7-4
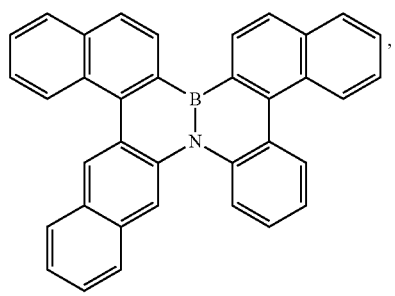
Compound 7-5
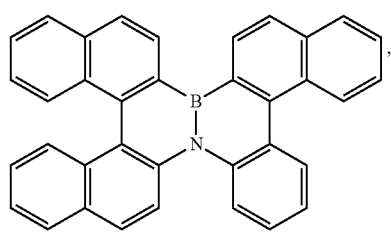
Compound 7-6
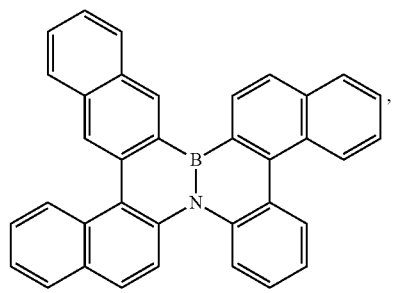
Compound 7-7
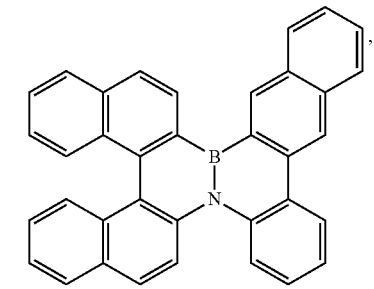
Compound 7-8
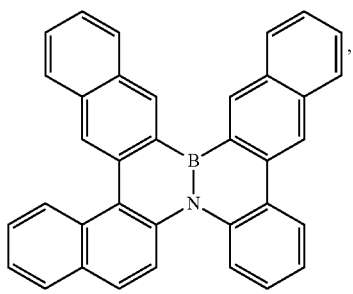

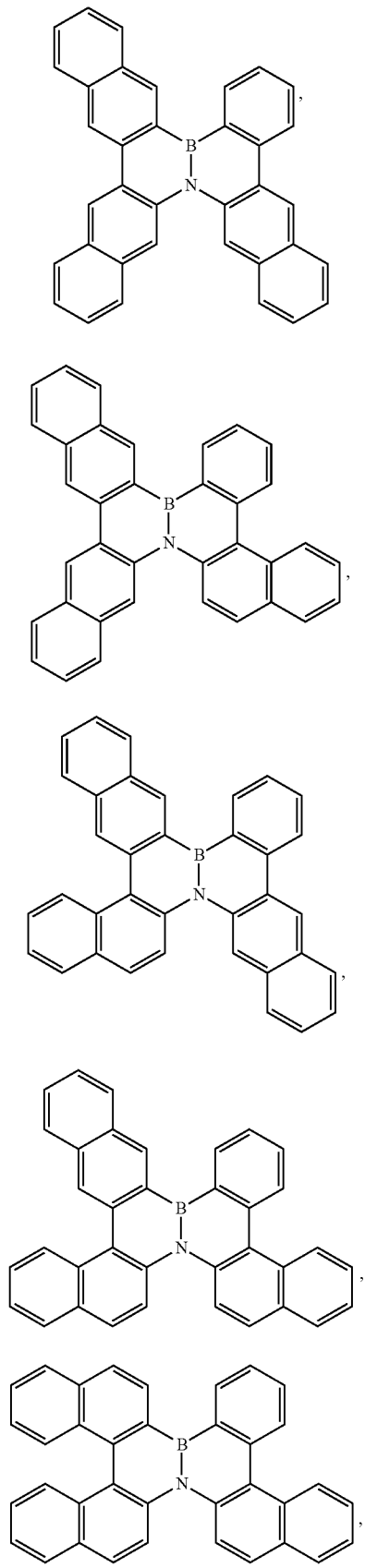
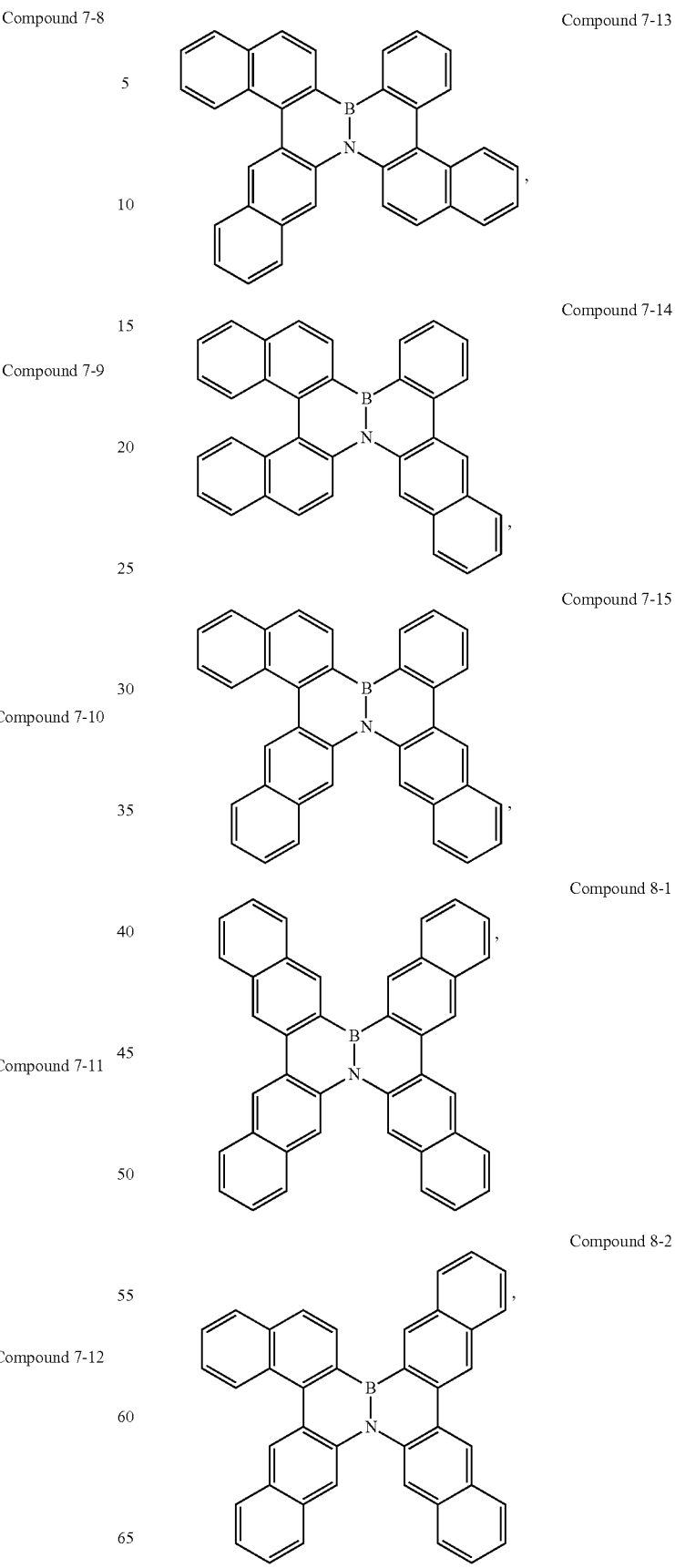

-continued
Compound 8-3
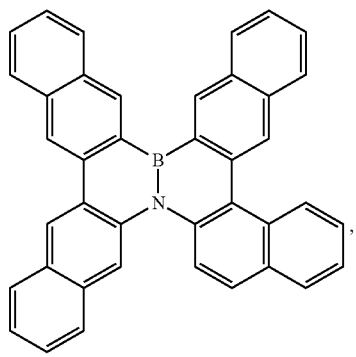
Compound 8-4
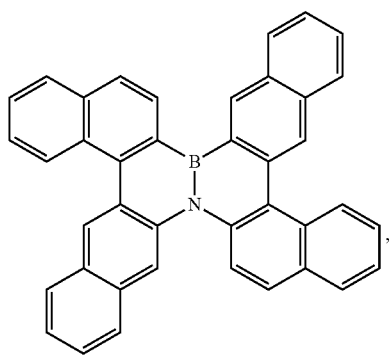
Compound 8-5
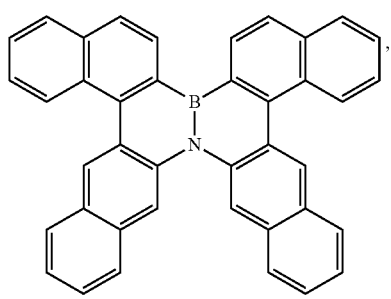
Compound 8-6
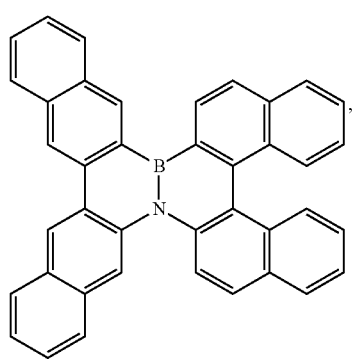
Compound 8-7
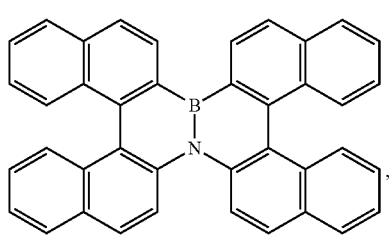
Compound 8-8
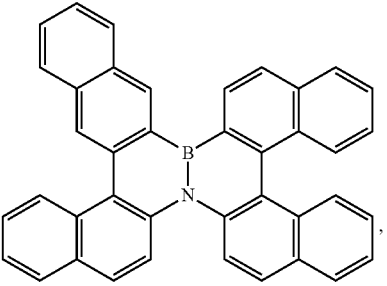
Compound 8-9
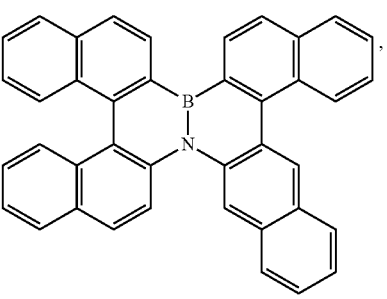
Compound 8-10
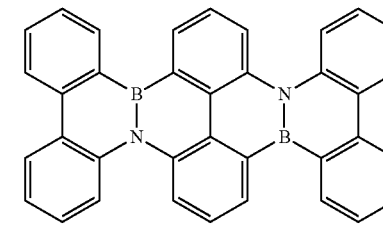
and
Compound 8-10'
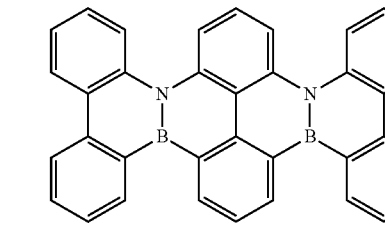
which is optionally fused to one or more aromatic rings; and
wherein the second fused aromatic ring system group selected from the group consisting of:
Compound 2-10
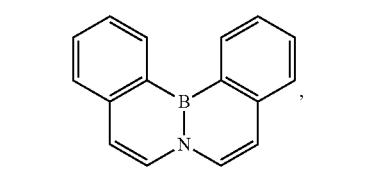

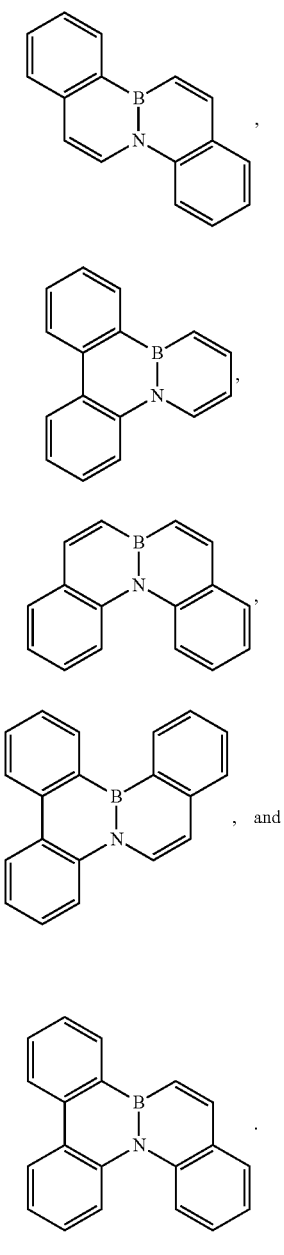
Compound 2-11,
Compound 2-12,
Compound 2-16,
Compound 3-46, and
Compound 3-47.
2. The compound of claim 1, wherein said fused aromatic ring system is selected from the group consisting of:
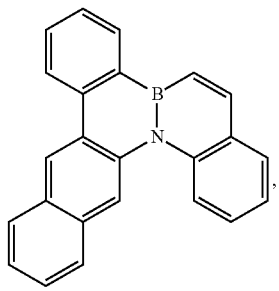
Compound 4-2,
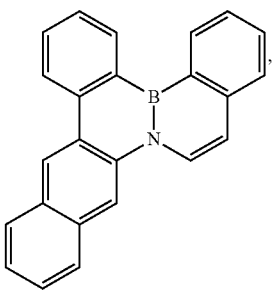
Compound 4-4,
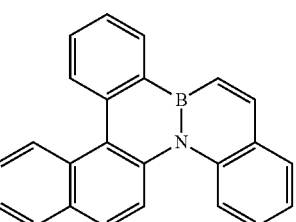
Compound 4-5,
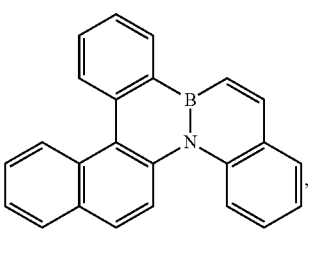
Compound 4-7,
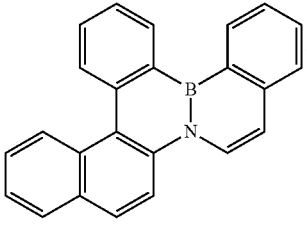
Compound 4-8,
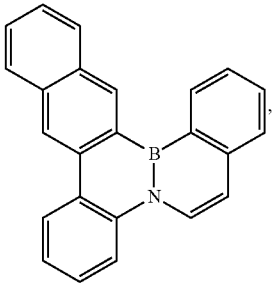
Compound 4-10,
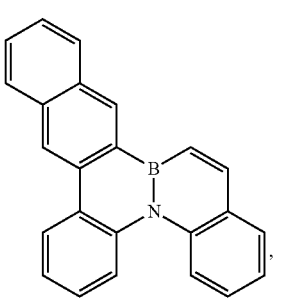
Compound 4-11, Compound 4-13
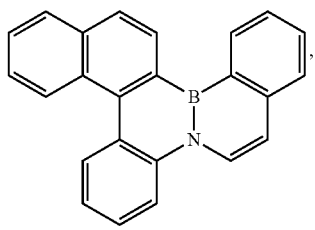
Compound 4-14
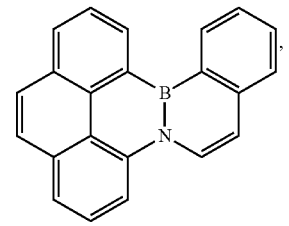
Compound 4-15
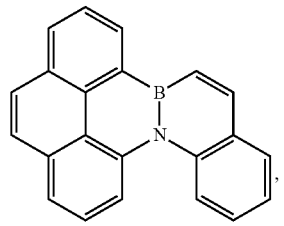
Compound 5-1
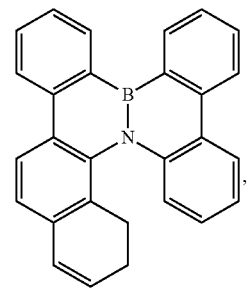
Compound 5-2
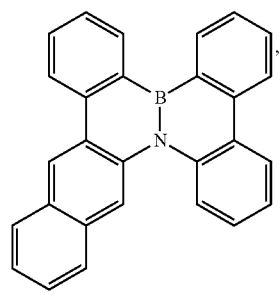
Compound 5-3
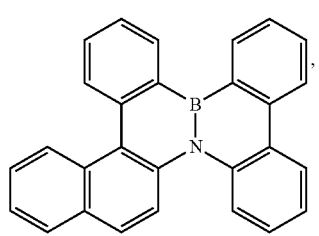
Compound 5-4
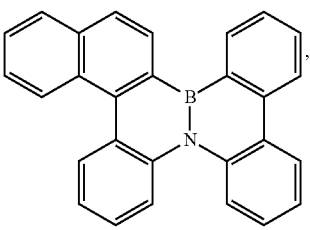
Compound 5-5
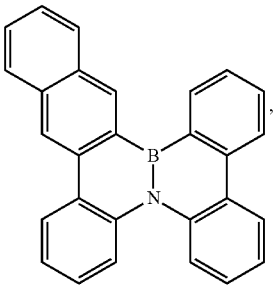
Compound 5-6
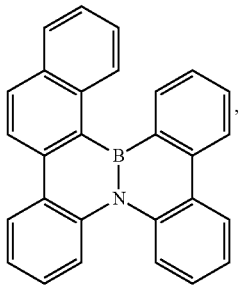
Compound 5-7
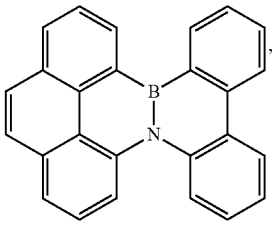
Compound 6-1
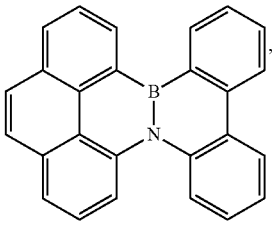

-continued
Compound 6-2
Compound 6-3
Compound 6-4
Compound 6-5
Compound 6-6
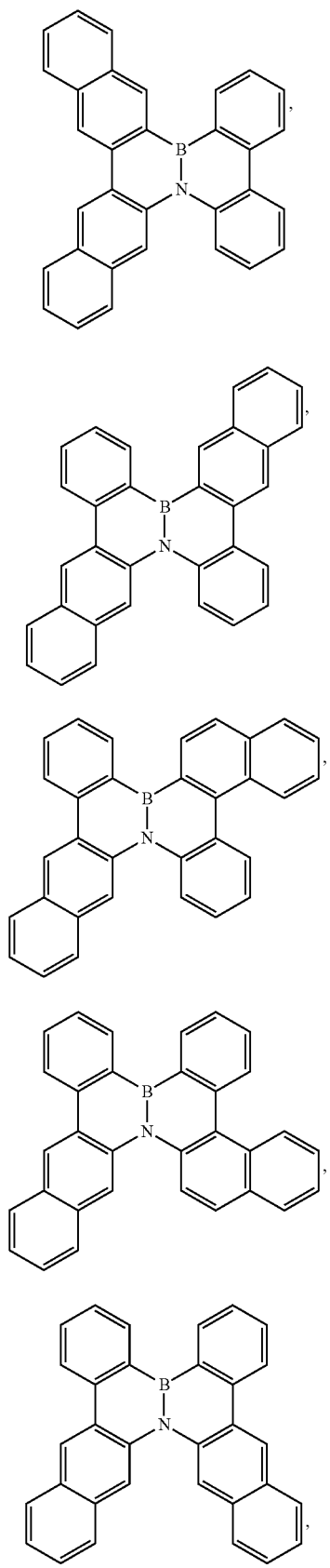
-continued
Compound 6-7
Compound 6-8
Compound 6-9
Compound 6-10
Compound 6-11
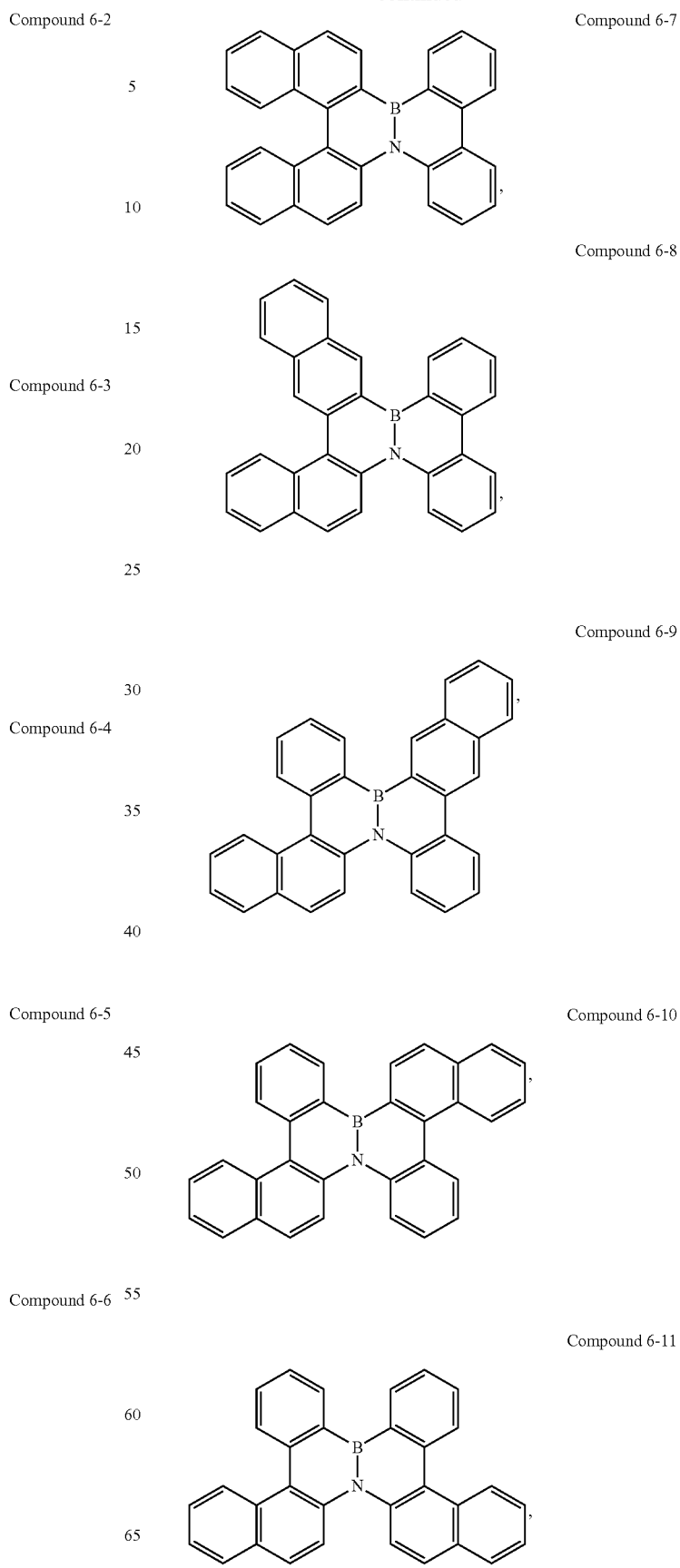

Compound 6-12
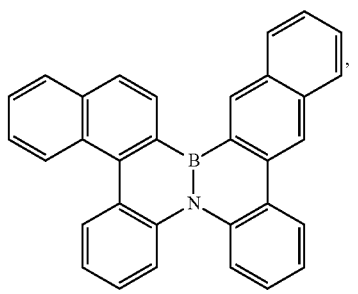
Compound 6-13
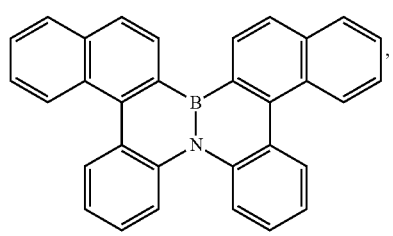
Compound 6-14
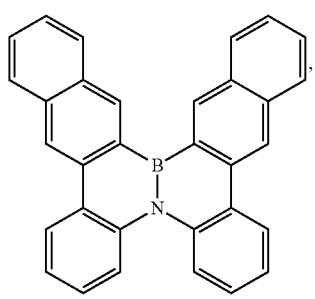
Compound 6-15
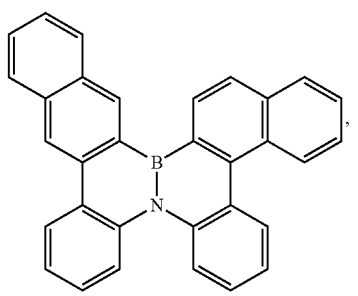
Compound 6-16
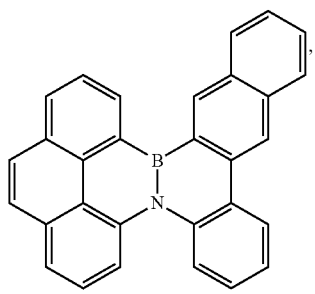
Compound 6-17
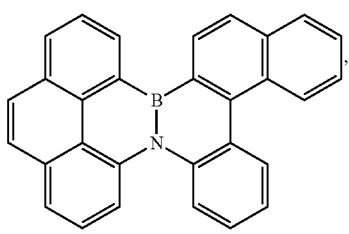
Compound 6-18
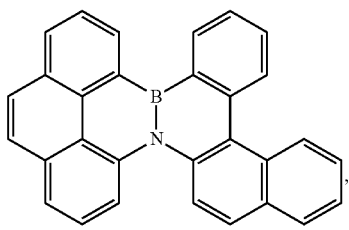
Compound 6-19
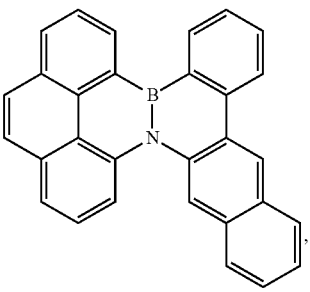
Compound 7-1
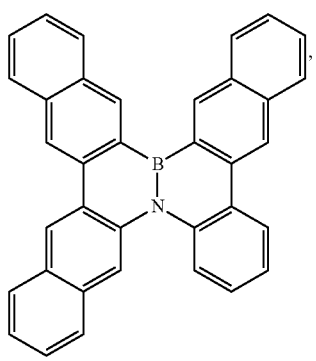
Compound 7-2
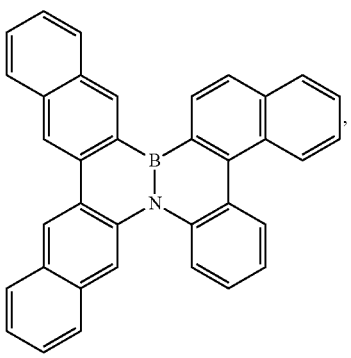

Compound 7-3
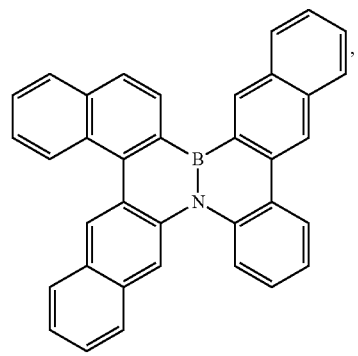
Compound 7-4
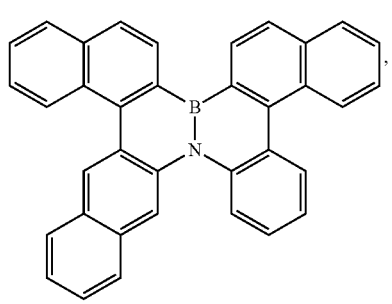
Compound 7-5
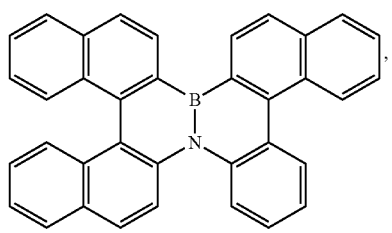
Compound 7-6
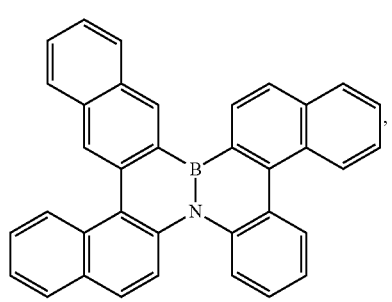
Compound 7-7
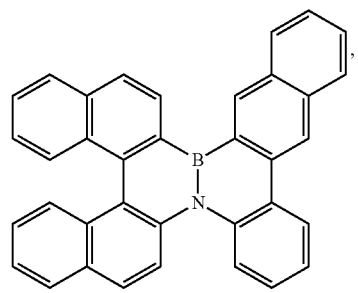
Compound 7-8
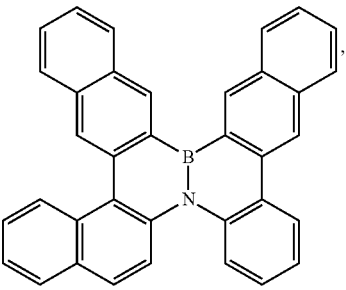
Compound 7-8
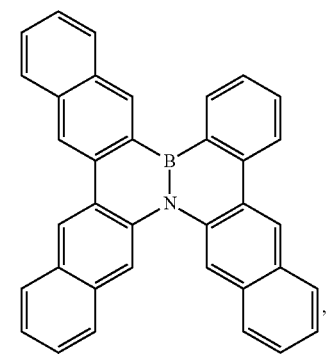
Compound 7-9
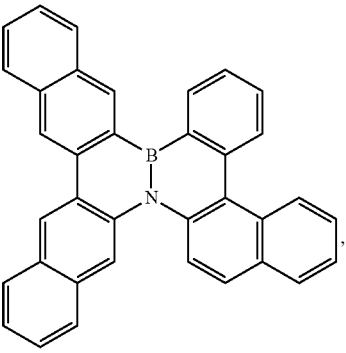
Compound 7-10
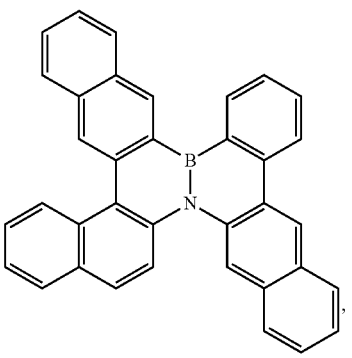

-continued
Compound 7-11
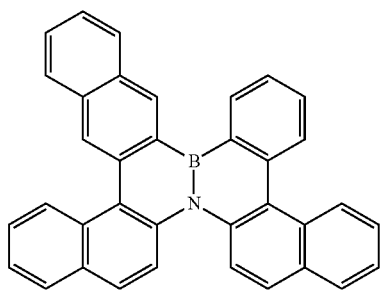
Compound 7-12
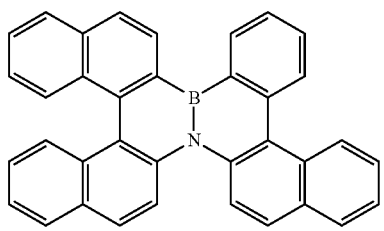
Compound 7-13
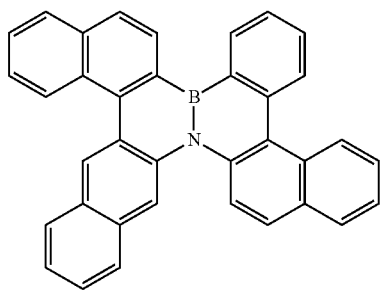
Compound 7-14
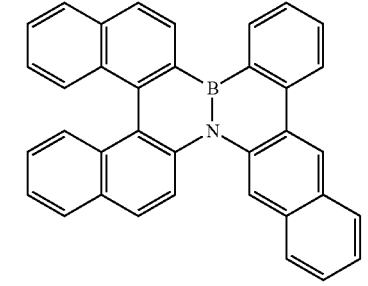
Compound 7-15
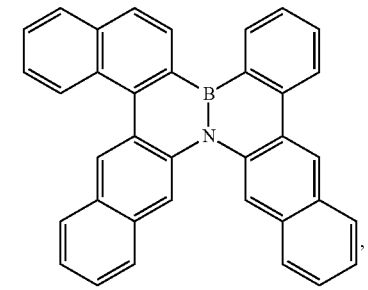
-continued
Compound 8-1
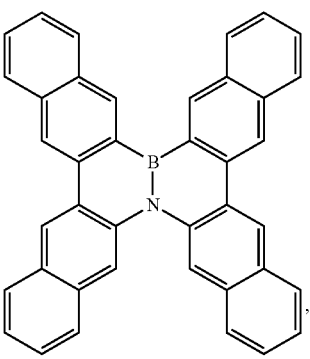
Compound 8-2
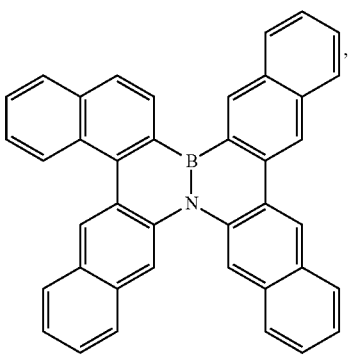
Compound 8-3
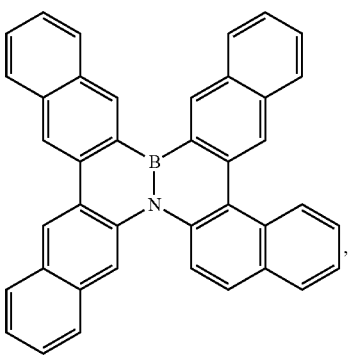
Compound 8-4
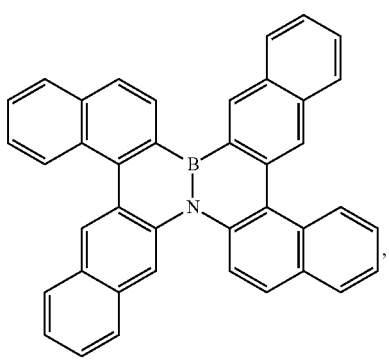

Compound 8-5
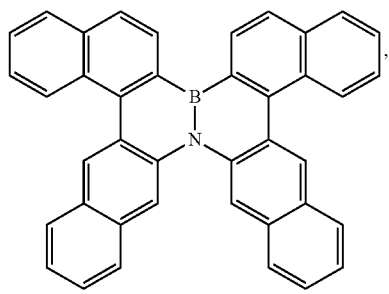

Compound 8-6
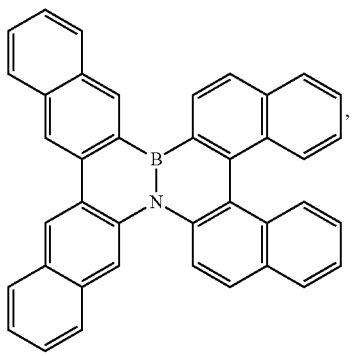

Compound 8-7
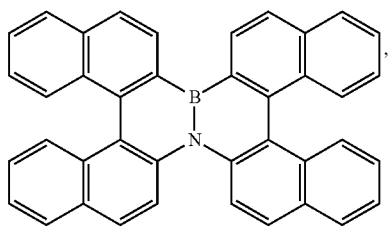

Compound 8-8
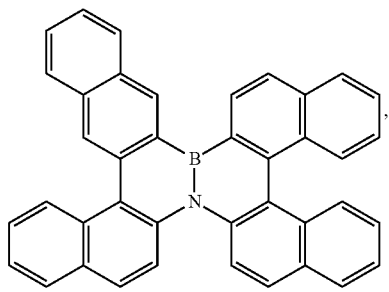

Compound 8-9
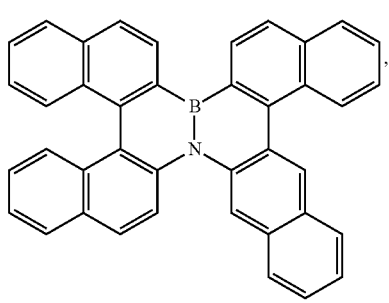

Compound 8-10
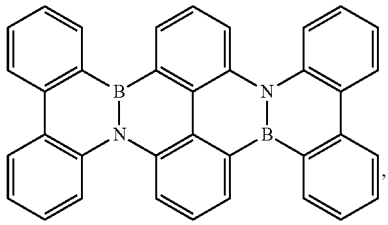
, and

Compound 8-10'
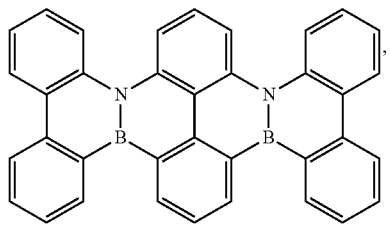
, wherein the fused aromatic ring system is substituted by one or more substituents, R, that are not fused to the aromatic ring system, selected from the group consisting of deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof; and wherein any two adjacent substituents, R, are optionally joined to form one or more non-aromatic rings.

3. The compound of claim 1, wherein R is selected from the group consisting of alkyl, cycloalkyl, amino, silyl, aryl, heteroaryl, and combinations thereof.

4. The compound of claim 1, wherein the compound is a compound of Formula (II), Formula (III), or Formula (IV):

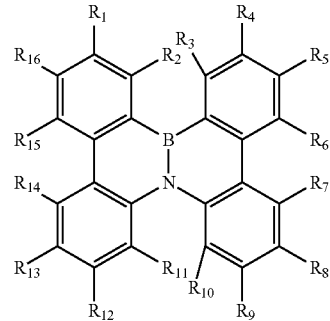

(II)

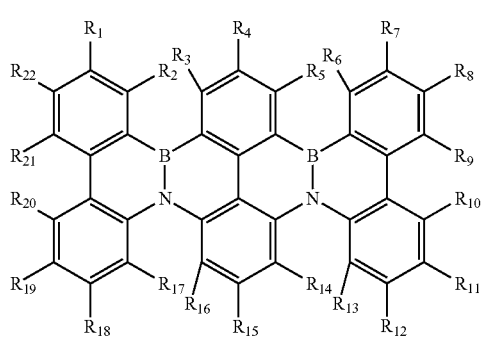

(III)

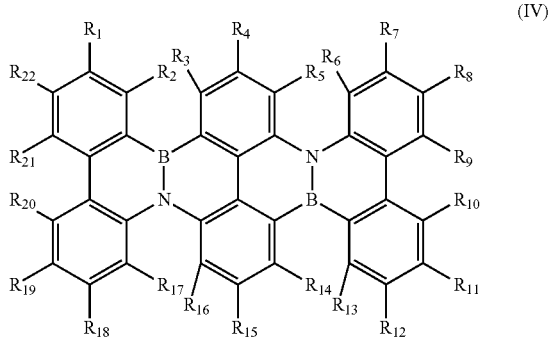

wherein $R_1$ to $R_{22}$ are each independently selected from the group consisting of hydrogen, deuterium, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof, wherein any two adjacent substituents are optionally joined to form a ring; and wherein at least one set of adjacent substituents is joined to form a ring.

5. The compound of claim 4, wherein each one of $R_1$ to $R_{22}$ that is not joined to an adjacent R to form a fused ring is independently selected from the group consisting of hydrogen, aryl, heteroaryl, and $NR_aR_b$; and wherein $R_a$ and $R_b$ are aryl or heteroaryl, which can be further substituted.

6. The compound of claim 4, wherein the compound is a compound of Formula (II) and at least one of $R_5$, $R_8$, $R_{13}$, or $R_{16}$ is not hydrogen or deuterium.

7. The compound of claim 4, wherein the compound is a compound of Formula (III) or Formula (IV), and at least one of $R_8$, $R_{11}$, $R_{19}$, or $R_{22}$ is not hydrogen or deuterium.

8. The compound of claim 4, wherein the compound is a compound of Formula (II) and at least one of $R_5$, $R_8$, $R_{13}$, or $R_{16}$ is aryl, heteroaryl or $NR_aR_b$; and wherein $R_a$ and $R_b$ are aryl or heteroaryl, which can be further substituted.

9. The compound of claim 4, wherein the compound is a compound of Formula (III) or Formula (IV) and at least one of $R_8$, $R_{11}$, $R_{19}$, or $R_{22}$ is aryl, heteroaryl or $NR_aR_b$; and wherein $R_a$ and $R_b$ are aryl or heteroaryl, which can be further substituted.

10. The compound of claim 4, wherein the compound is a compound of Formula (II) and at least one of $R_1$, $R_4$, $R_9$, or $R_{12}$ is not hydrogen or deuterium.

11. The compound of claim 4, wherein the compound is a compound of Formula (III) or Formula (IV), and at least one of $R_1$, $R_4$, $R_7$, $R_{12}$, $R_{15}$ or $R_{18}$ is not hydrogen or deuterium.

12. The compound of claim 4, wherein the compound is a compound of Formula (II) and at least one of $R_1$, $R_4$, $R_9$ or $R_{12}$ is aryl, heteroaryl or $NR_aR_b$; and wherein $R_a$ and $R_b$ are aryl or heteroaryl, which can be further substituted.

13. The compound of claim 4, wherein the compound is a compound of Formula (III) or Formula (IV), and at least one of $R_1$, $R_4$, $R_7$, $R_{12}$, $R_{15}$ or $R_{18}$ is aryl, heteroaryl or $NR_aR_b$; and wherein $R_a$ and $R_b$ are aryl or heteroaryl.

14. The compound of claim 8, wherein $R_5$ and $R_{13}$ are phenyl or $NR_aR_b$.

15. The compound of claim 14, wherein $R_5$ and $R_{13}$ are $NR_aR_b$, and $R_a$ and $R_b$ are phenyl.

16. The compound of claim 9, wherein $R_8$ and $R_{19}$ are phenyl or $NR_aR_b$.

17. The compound of claim 16, wherein $R_5$ and $R_{13}$ are $NR_aR_b$, and $R_a$ and $R_b$ are phenyl.

18. The compound of claim 12, wherein $R_1$ and $R_9$ are phenyl or $NR_aR_b$.

19. The compound of claim 18, wherein $R_5$ and $R_{13}$ are $NR_aR_b$, and $R_a$ and $R_b$ are phenyl.

20. A compound, having the structure of Formula (III) or Formula (IV):

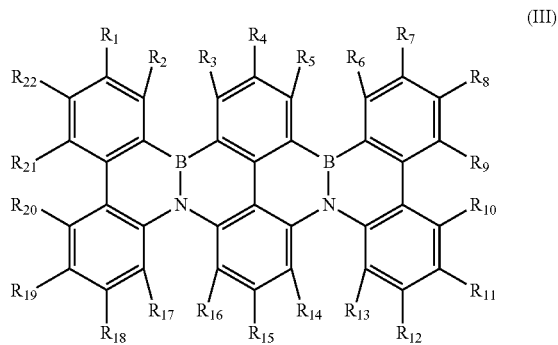

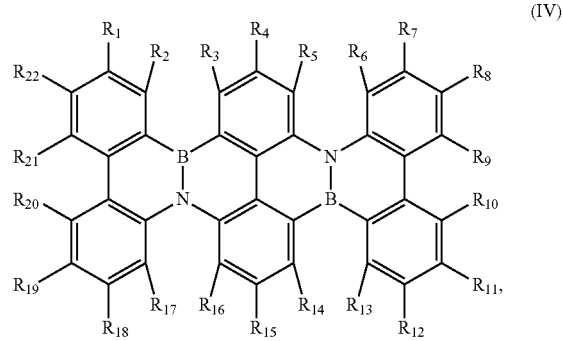

wherein $R_1$ to $R_{22}$ are each independently selected from the group consisting of hydrogen, deuterium, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof, wherein any two adjacent substituents are optionally joined to form an aromatic or non-aromatic ring, wherein at least one of $R_1$, $R_4$, $R_7$, $R_{12}$, $R_{15}$ or $R_{18}$ is aryl, heteroaryl or $NR_aR_b$, wherein $R_1$ and $R_{12}$ are phenyl or $NR_aR_b$, and wherein $R_a$ and $R_b$ are aryl or heteroaryl.

21. The compound of claim 20, wherein $R_5$ and $R_{13}$ are $NR_aR_b$, and $R_a$ and $R_b$ are phenyl.

22. The compound of claim 1, wherein the compound is selected from the group consisting of:
Compound 1-3-1
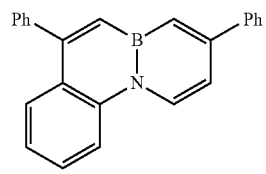
Compound 1-3-2
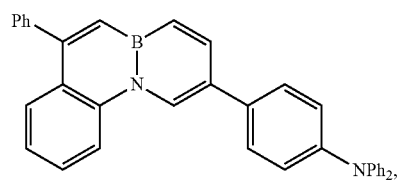
Compound 2-7-1
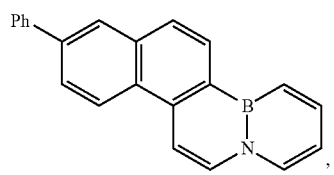
Compound 2-7-2
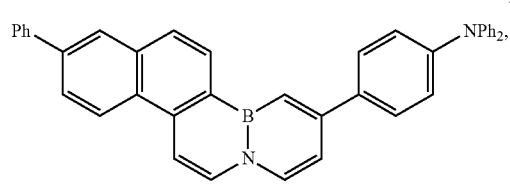
Compound 2-11-1
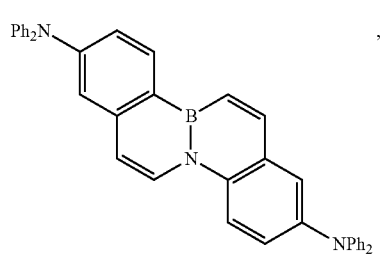
Compound 2-12-1
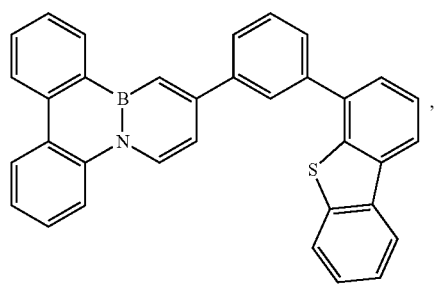
Compound 2-12-2
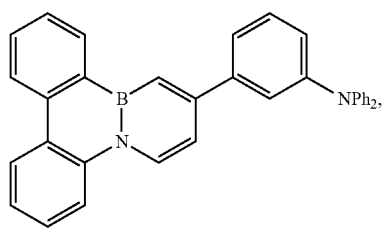
Compound 2-15-1
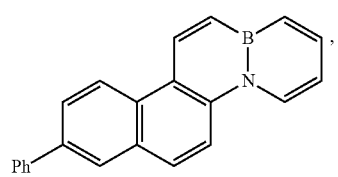
Compound 2-15-2
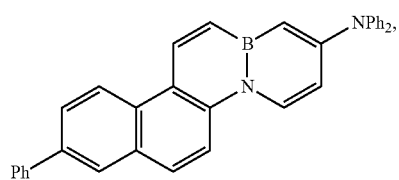
Compound 2-15-3
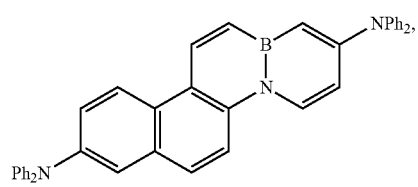
Compound 2-15-4
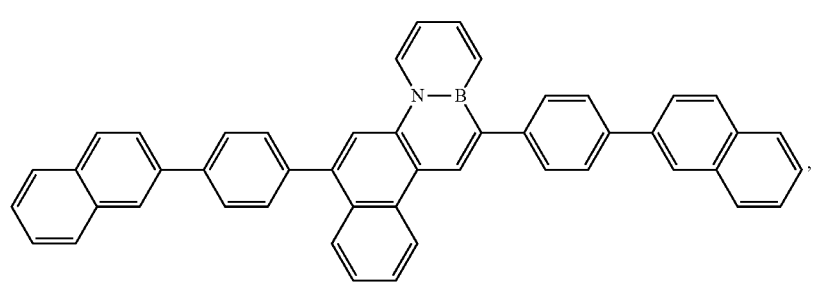

-continued
Compound 3-30-1
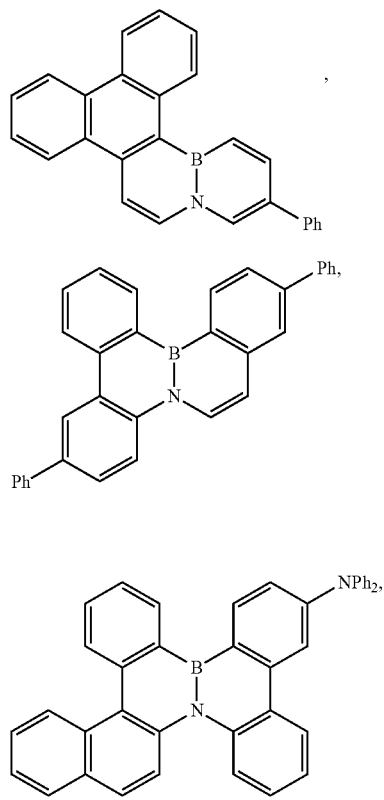
Compound 3-33-1
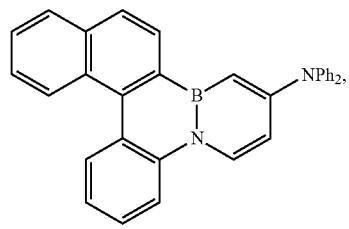
Compound 3-46-1
Compound 5-2-1
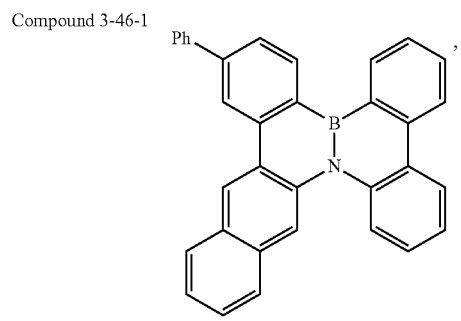
Compound 5-3-1
Compound 5-4-1
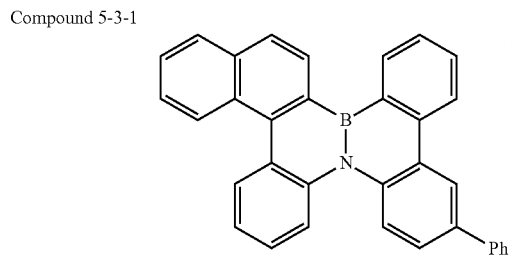
Compound 6-3-1
Compound 6-4-1
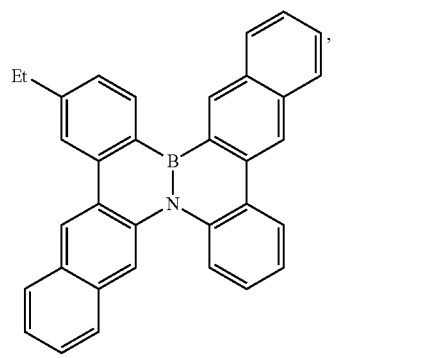
Compound 7-4-1
and
Compound 8-4-1
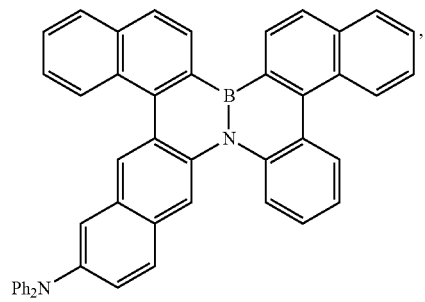
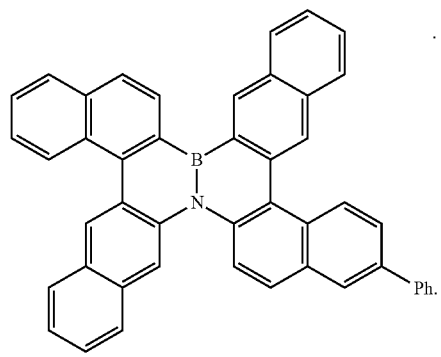

23. A device comprising an organic light emitting device, said organic light emitting device comprising:

an anode;

a cathode; and an organic layer, disposed between the anode and the cathode, comprising a compound that comprises:

a fused aromatic ring system comprising a [1,2]azaborino[1,2-a][1,2]azaborine

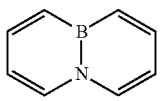

moiety;

wherein the fused aromatic ring system is substituted by one or more substituents, R, that are not fused to the aromatic ring system, selected from the group consisting of deuterium, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof;

wherein any two adjacent substituents, R, are optionally joined to form one or more non-aromatic rings; and wherein said fused aromatic ring system is selected from the group consisting of a first fused aromatic ring system group and a second fused aromatic ring system group, wherein the first fused aromatic ring system group is selected from the group consisting of:

Compound 2-7

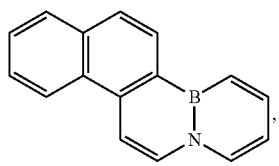

Compound 2-8

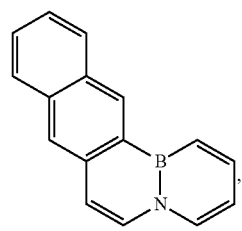

Compound 2-9

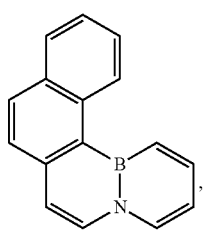

-continued

Compound 2-13

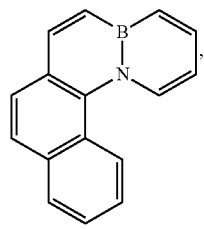

Compound 2-14

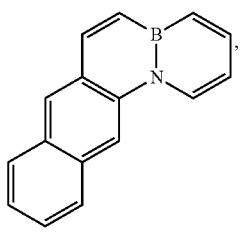

Compound 2-15

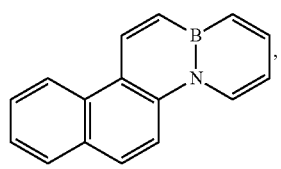

Compound 3-27

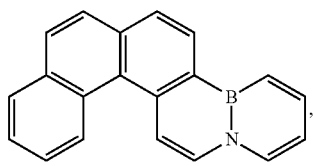

Compound 3-28

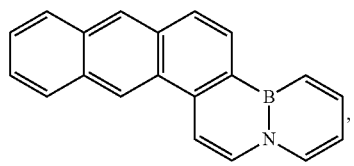

Compound 3-29

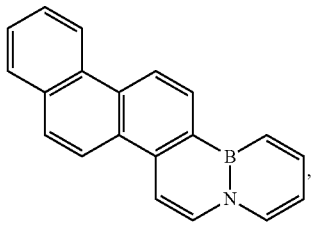

Compound 3-30

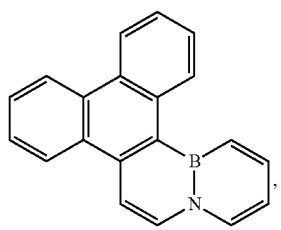

Compound 3-31

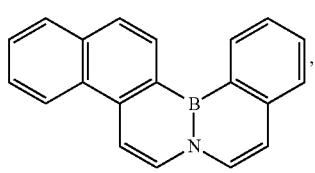

Compound 3-32
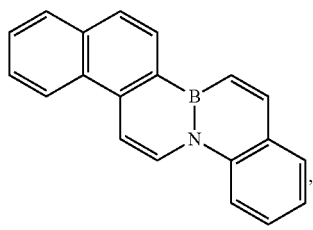
Compound 3-33
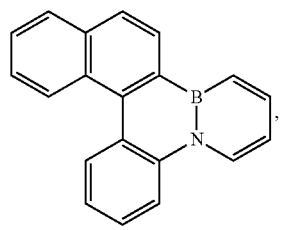
Compound 3-34
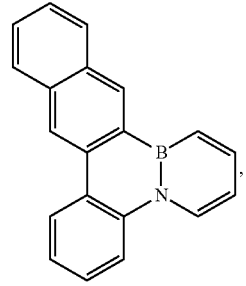
Compound 3-35
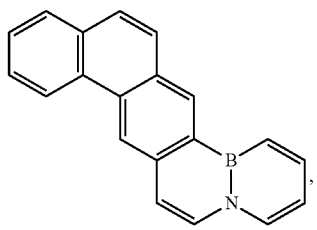
Compound 3-36
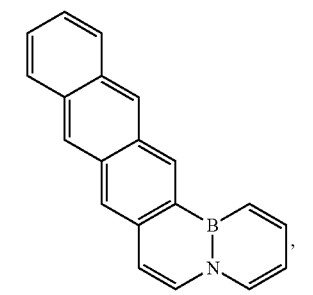
Compound 3-37
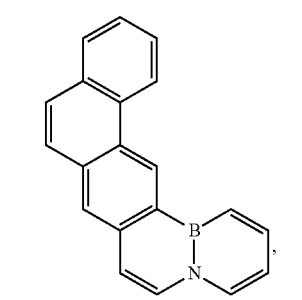
Compound 3-38
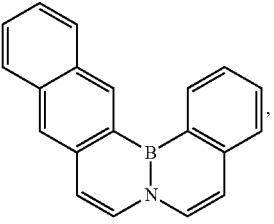
Compound 3-39
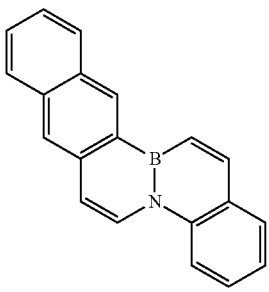
Compound 3-40
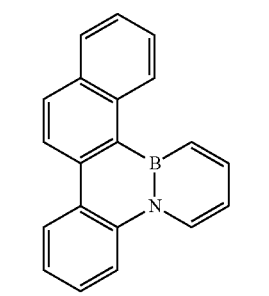
Compound 3-41
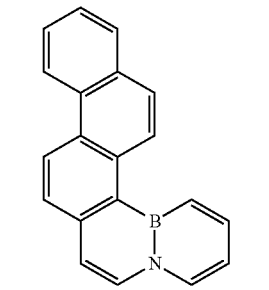
Compound 3-42
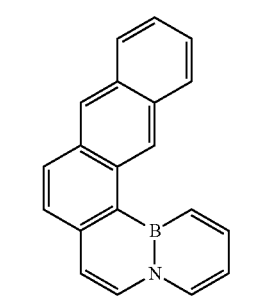
Compound 3-43
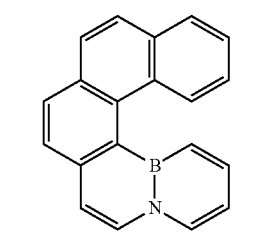

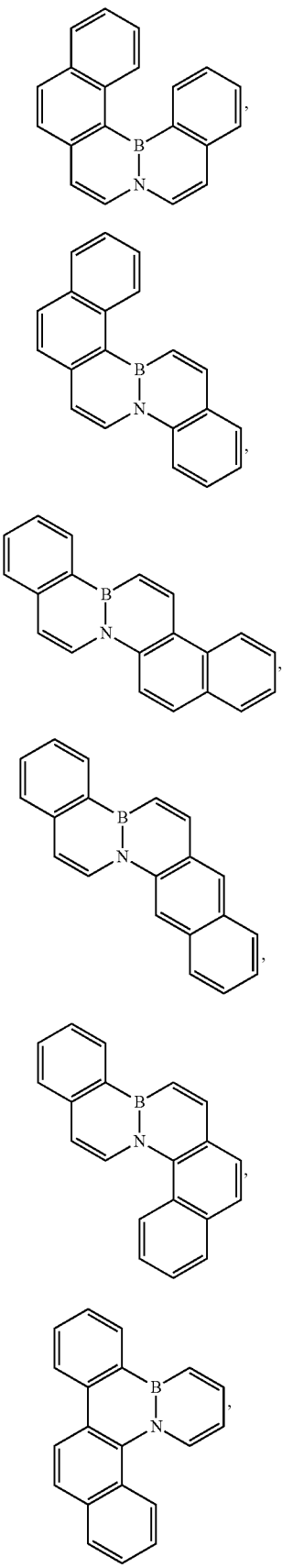
Compound 3-44
Compound 3-45
Compound 3-48
Compound 3-49
Compound 3-50
Compound 3-51
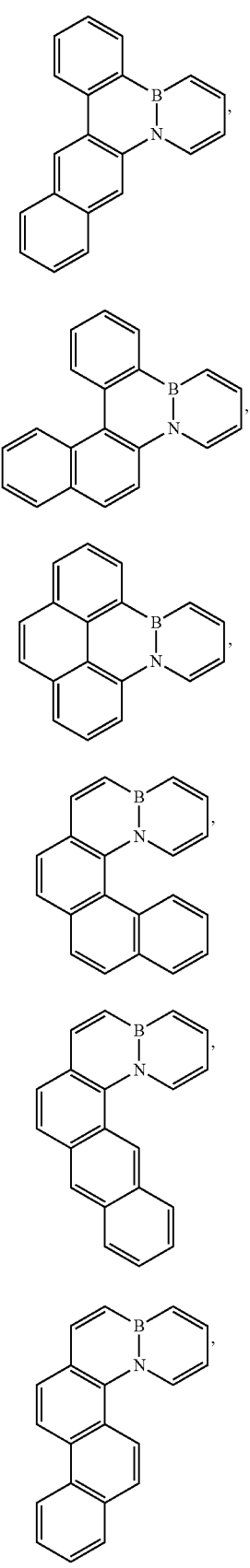
Compound 3-52
Compound 3-53
Compound 3-54
Compound 3-55
Compound 3-56
Compound 3-57

Compound 3-58
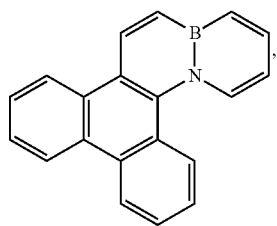
Compound 3-59
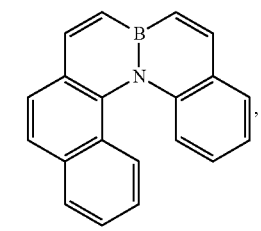
Compound 3-60
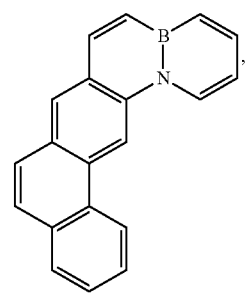
Compound 3-61
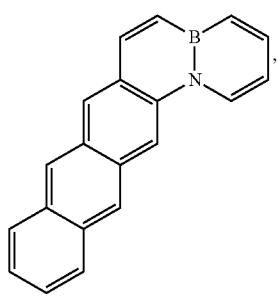
Compound 3-62
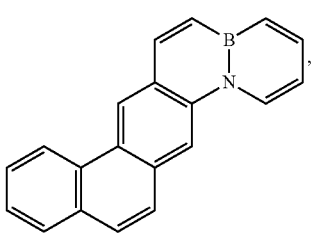
Compound 3-63
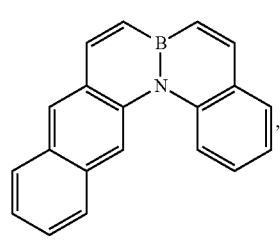
Compound 3-64
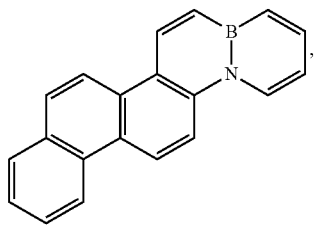
Compound 3-65
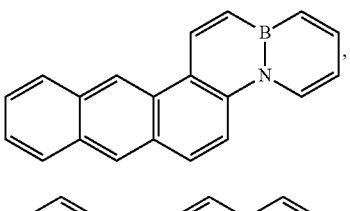
Compound 3-66
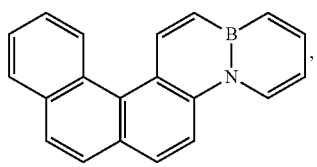
Compound 3-67
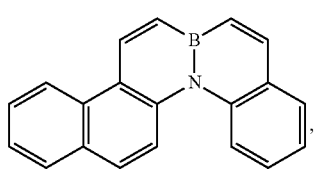
Compound 4-2
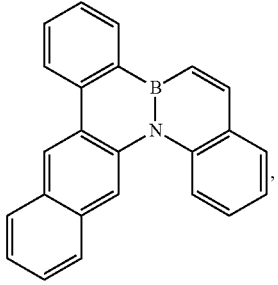
Compound 4-4
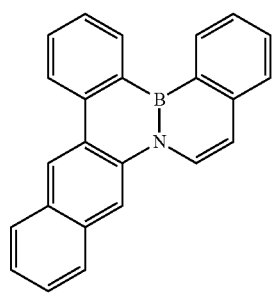
Compound 4-5
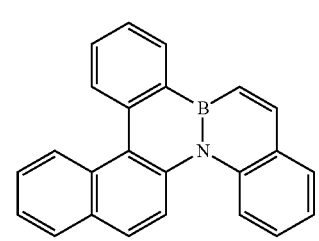

Compound 4-7
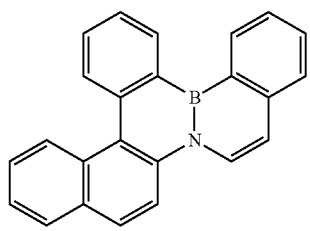
Compound 4-8
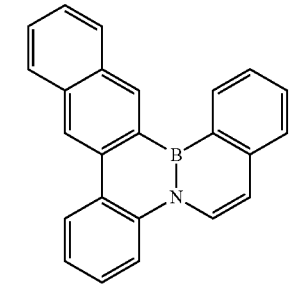
Compound 4-10
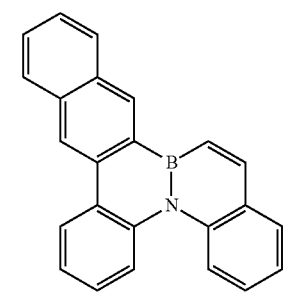
Compound 4-11
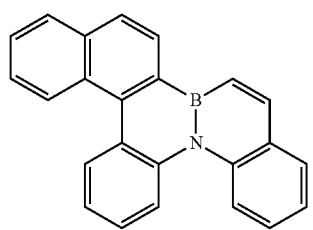
Compound 4-13
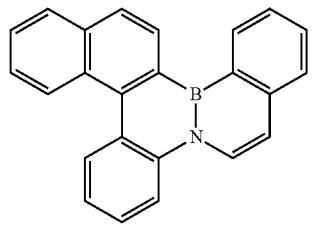
Compound 4-14
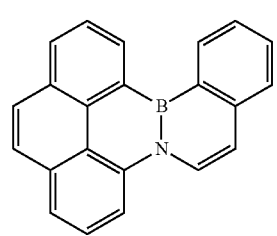
Compound 4-15
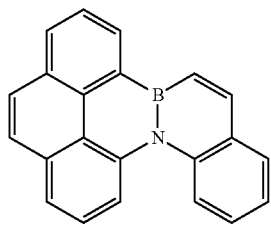
Compound 5-1
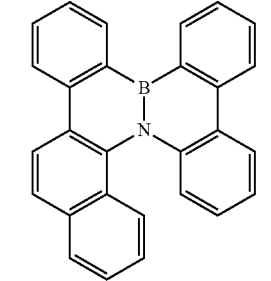
Compound 5-2
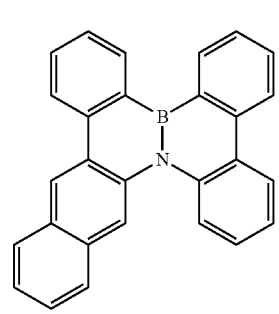
Compound 5-3
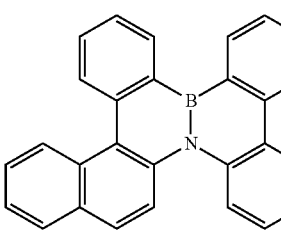
Compound 5-4
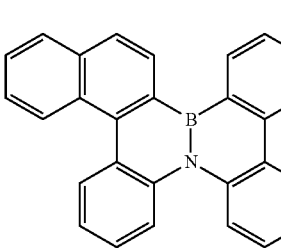
Compound 5-5
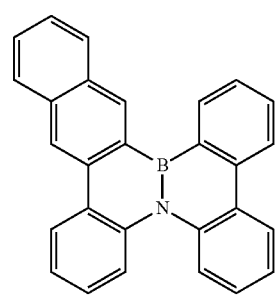

-continued
Compound 5-6
Compound 5-7
Compound 6-1
Compound 6-2
Compound 6-3
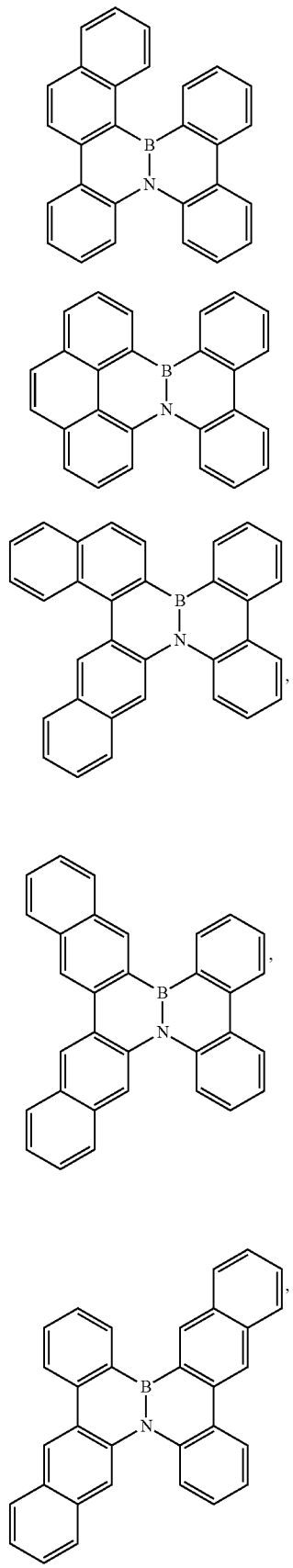
-continued
Compound 6-4
Compound 6-5
Compound 6-6
Compound 6-7
Compound 6-8
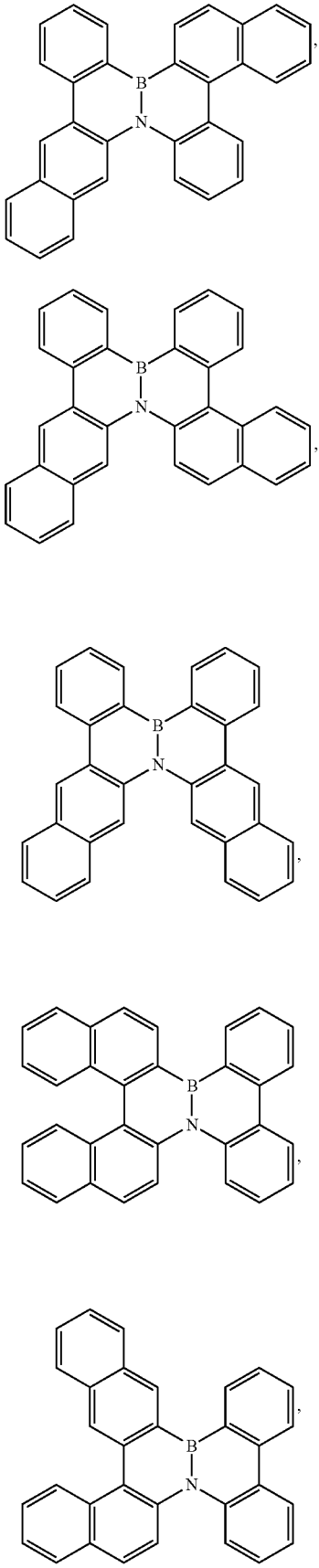

Compound 6-9
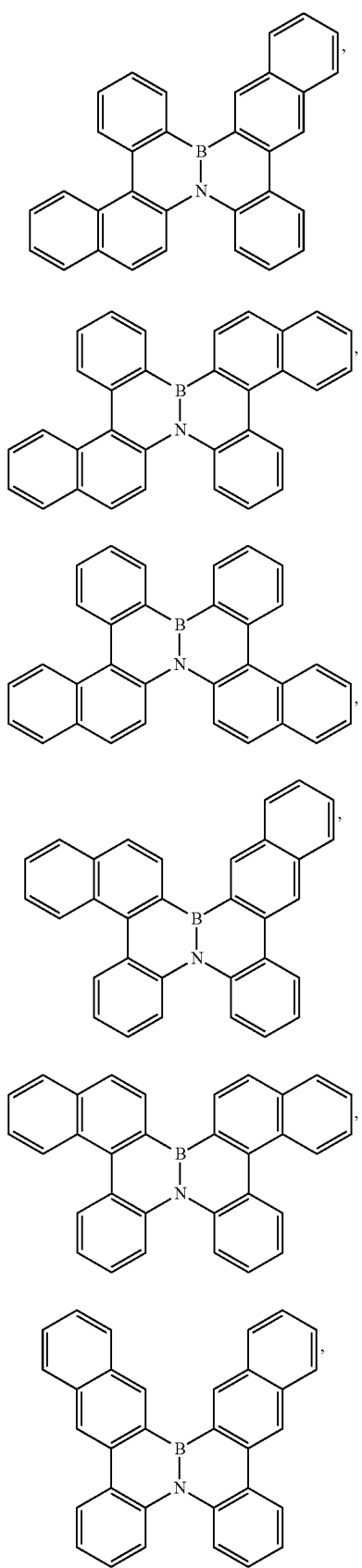
Compound 6-10
Compound 6-11
Compound 6-12
Compound 6-13
Compound 6-14
Compound 6-15
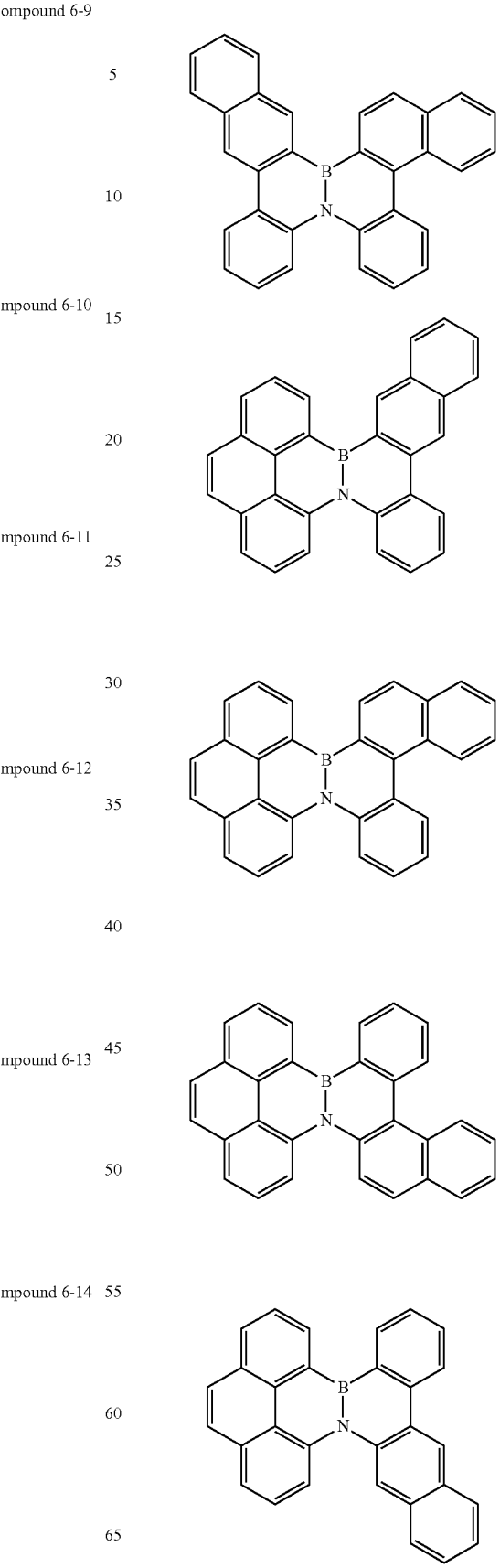
Compound 6-16
Compound 6-17
Compound 6-18
Compound 6-19

-continued
Compound 7-1
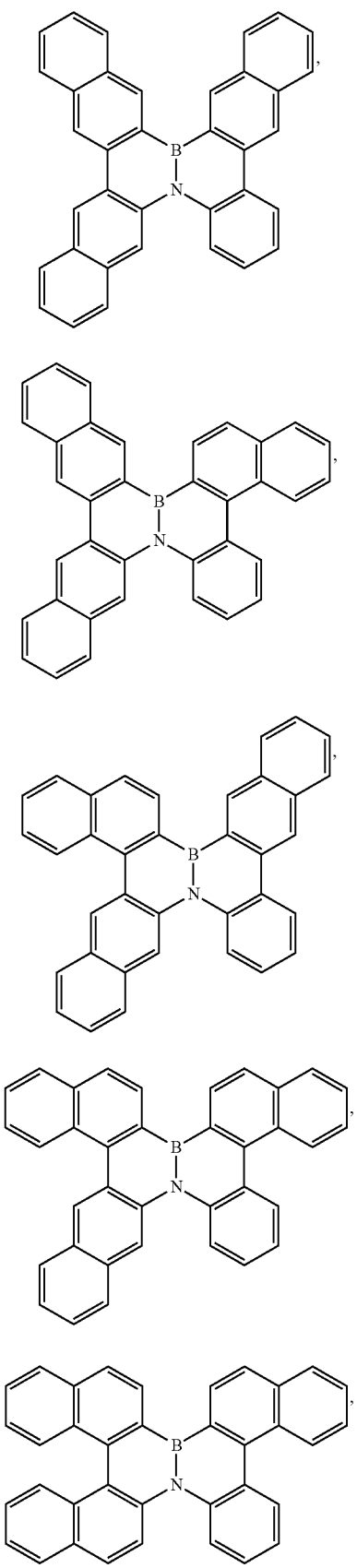
Compound 7-2
Compound 7-3
Compound 7-4
Compound 7-5
-continued
Compound 7-6
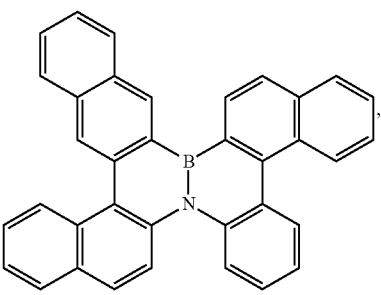
Compound 7-7
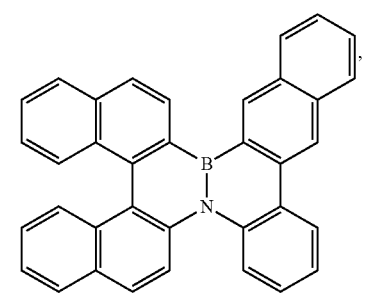
Compound 7-8
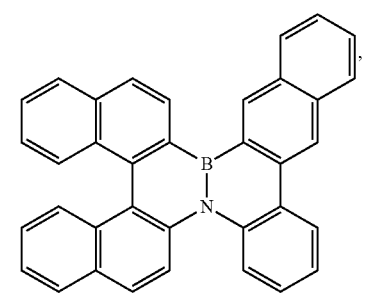
Compound 7-8
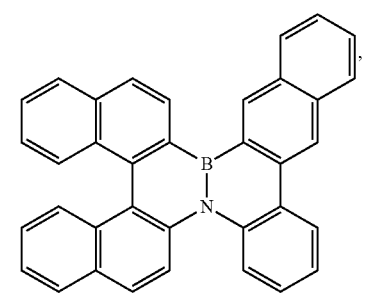
Compound 7-9
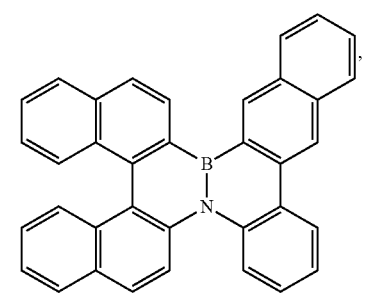

Compound 7-10
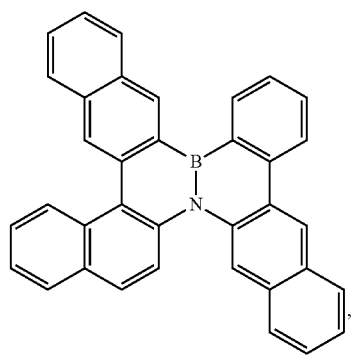
Compound 7-11
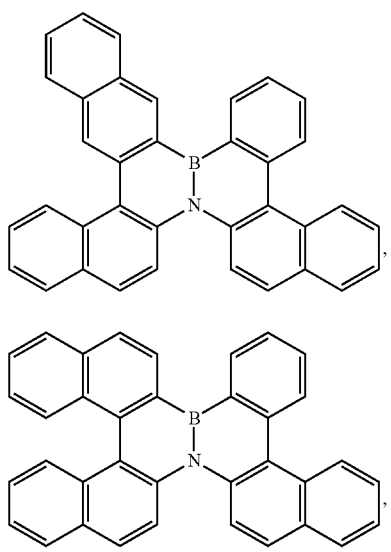
Compound 7-12
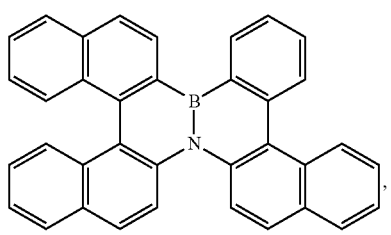
Compound 7-13
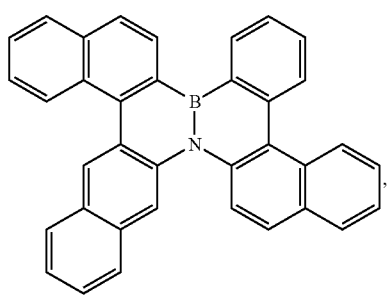
Compound 7-14
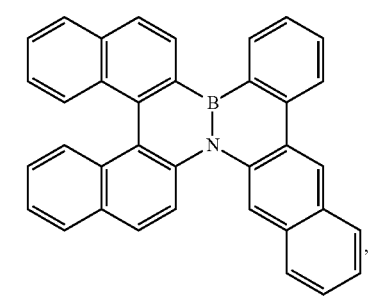
Compound 7-15
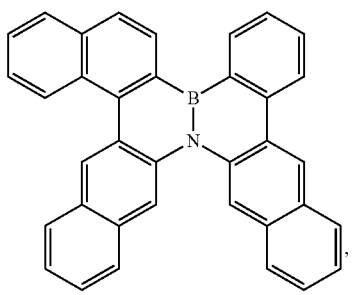
Compound 8-1
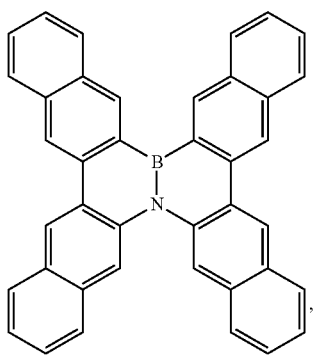
Compound 8-2
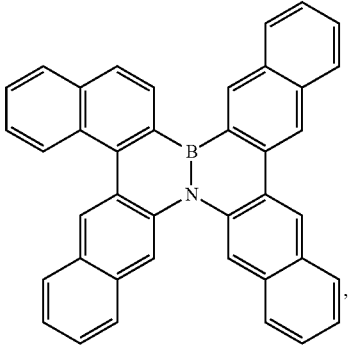
Compound 8-3
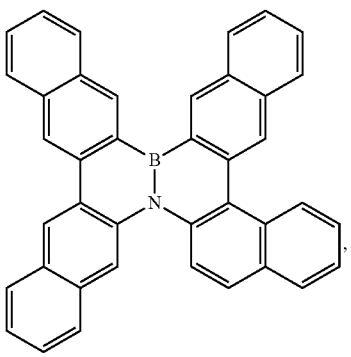

Compound 8-4
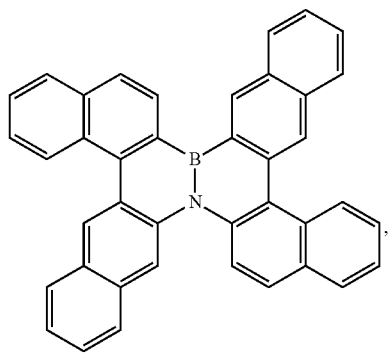
Compound 8-5
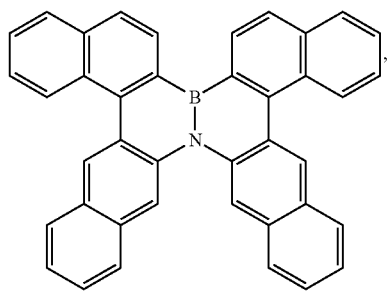
Compound 8-6
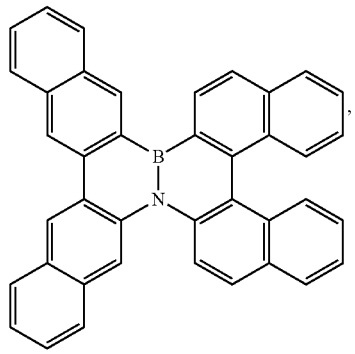
Compound 8-7
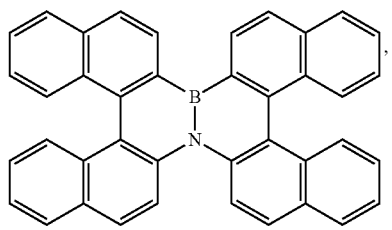
Compound 8-8
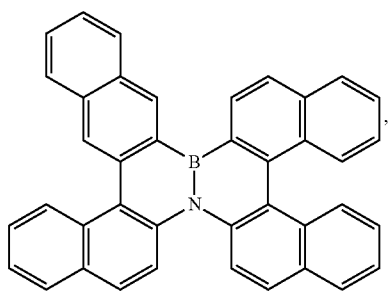
Compound 8-9
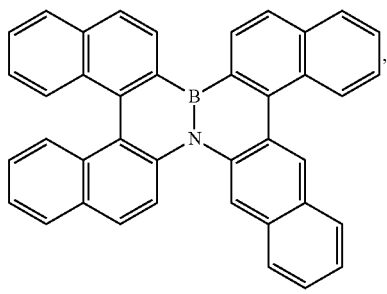
Compound 8-10
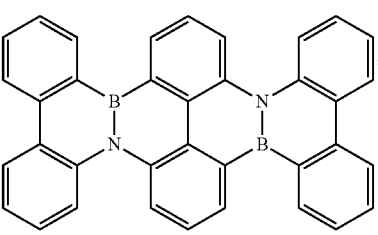
Compound 8-10'
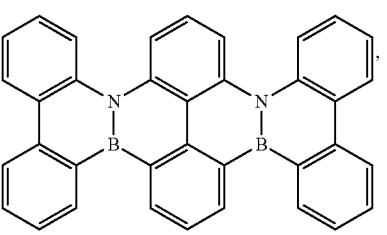
which is optionally fused to one or more aromatic rings; and
wherein the second fused aromatic ring system group selected from the group consisting of:
Compound 2-10
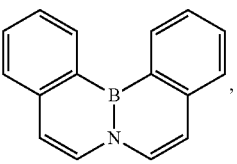
Compound 2-11
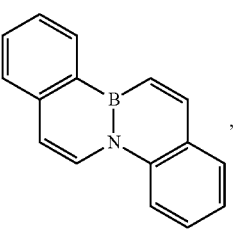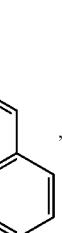
Compound 2-12
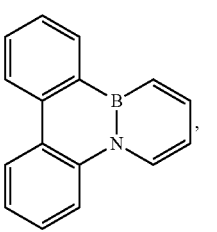

-continued

Compound 2-16

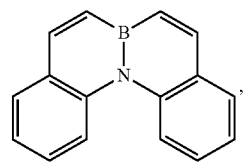

Compound 3-46

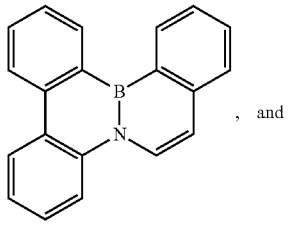
, and

Compound 3-47

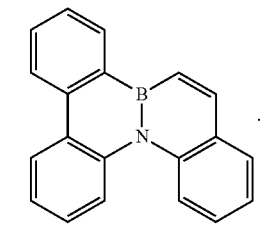

24. The device of claim 23, wherein the organic layer is an emissive layer and the compound of Formula (I) is an emissive dopant.

25. The device of claim 23, wherein the organic layer is an emissive layer and the compound of Formula (I) is a host.

26. The device of claim 23, wherein the organic layer is a hole injecting layer or a hole transporting layer.

27. The device of claim 23, wherein the organic layer is an electron injecting layer or an electron transporting layer.

28. The device of claim 23, wherein the organic layer is an exciton blocking layer.

29. The device of claim 23, wherein the device is adapted for emitting delayed fluorescence.

30. The device of claim 23, wherein the device is a consumer product comprising the organic light emitting device.

31. The device of claim 23, wherein the device is an second organic light-emitting device.

32. The device of claim 23, wherein the device comprises a lighting panel.

33. The compound of claim 1, wherein the

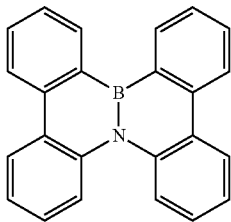 [SMILES: c1ccc2c(c1)B1c3ccccc3-c3ccccc3N1c1ccccc1-2]

[1,2]azaborino[1,2-a][1,2]azaborine is fused to one or more aromatic rings.

* * * * *